United States Patent
Kang et al.

(10) Patent No.: US 10,927,135 B2
(45) Date of Patent: Feb. 23, 2021

(54) METAL-FREE DIRECT ARYLATION OF DIALKYL PHOSPHONATES FOR THE SYNTHESIS OF MIXED ALKYL ARYL PHOSPHONATES

(71) Applicant: The Board of Regents of the Nevada System of Higher Education on Behalf of the University of Nevada, Las Vegas, Las Vegas, NV (US)

(72) Inventors: Jun Yong Kang, Las Vegas, NV (US); Hai Huang, Hong Kong (CN)

(73) Assignee: THE BOARD OF REGENTS OF THE NEVADA SYSTEM OF HIGHER EDUCATION ON BEHALF OF THE UNIVERSITY OF NEVADA, LAS VEGAS, Las Vegas, NV (US)

( * ) Notice: Subject to any disclaimer, the term of this patent is extended or adjusted under 35 U.S.C. 154(b) by 0 days.

(21) Appl. No.: 16/635,903

(22) PCT Filed: Aug. 3, 2018

(86) PCT No.: PCT/US2018/045224
§ 371 (c)(1),
(2) Date: Jan. 31, 2020

(87) PCT Pub. No.: WO2019/028391
PCT Pub. Date: Feb. 7, 2019

(65) Prior Publication Data
US 2020/0255461 A1    Aug. 13, 2020

Related U.S. Application Data

(60) Provisional application No. 62/610,825, filed on Dec. 27, 2017, provisional application No. 62/540,773, filed on Aug. 3, 2017.

(51) Int. Cl.
| | |
|---|---|
| *C07F 9/60* | (2006.01) |
| *C07F 9/12* | (2006.01) |
| *C07F 9/18* | (2006.01) |
| *C07J 51/00* | (2006.01) |
| *C07F 9/141* | (2006.01) |
| *C07F 9/40* | (2006.01) |
| *C07F 9/655* | (2006.01) |

(52) U.S. Cl.
CPC .................. *C07F 9/60* (2013.01); *C07F 9/12* (2013.01); *C07F 9/1414* (2013.01); *C07F 9/18* (2013.01); *C07F 9/4021* (2013.01); *C07F 9/4087* (2013.01); *C07F 9/65517* (2013.01); *C07F 9/65522* (2013.01); *C07J 51/00* (2013.01)

(58) Field of Classification Search
CPC .. C07F 9/60; C07F 9/12; C07F 9/1414; C07F 9/18; C07F 9/4021; C07F 9/4087; C07F 9/65517; C07F 9/65522; C07J 51/00
See application file for complete search history.

(56) References Cited

FOREIGN PATENT DOCUMENTS

WO    WO-2019/028391 A1    2/2019

OTHER PUBLICATIONS

Bargota et al. 'Structure-Activity Relationship on Human Serum Paraxonase (PON1) Using Substrate Analogues and Inhibitors', Biorganic and Medicinal Chemistry Letters, 2003, vol. 13, pp. 1623-1626.
Hirsch et al. '(3R,4S)-3,4,5-Trihydroxy-4-methylpentylphosphonic acid, an isosteric phosphonate analogue of 2-C-methyl-D-erythritol 4-phosphate, a key intermediate in the new pathway for isoprenoid biosynthesis', Tetrahedron Letters, 2004, vol. 45, pp. 519-521.
Pubchem 12067053 deposited on Feb. 7, 2007 (Feb. 7, 2007) p. 1-13. p. 3.
Pubchem 12735424 deposited on Feb. 8, 2007 (Feb. 8, 2007) p. 1-12. p. 4.
Pubchem 21853796 deposited on Dec. 5, 2007 (Dec. 5, 2007) p. 1-10. p. 3.
Pubchem 286944 deposited on Mar. 26, 2005 (Mar. 26, 2005) p. 1-14. p. 3.
Pubchem 57173183 deposited on Jun. 14, 2012 (Jun. 14, 2012) p. 1-11. p. 4.
Pubchem 67093206 deposited on Nov. 30, 2011 (Nov. 30, 2011) p. 1-11. p. 3.
Pubchem 99789 deposited on Mar. 26, 2005 (Mar. 26, 2005) p. 1-16. p. 3.
International Search Report and Written Opinion dated Oct. 23, 2018 by the International Searching Authority for International Application No. PCT/US2018/045224, filed on Aug. 3, 2018 and published as WO 2019/028391 on Feb. 7, 2019 (Applicant—The Board of Regents of the Nevada System of Higher Education on Behalf of the University of Nevada, Las Vegas) (8 Pages).
International Preliminary Report on Patentability dated Feb. 4, 2020 by the International Searching Authority for International Application No. PCT/US2018/045224, filed on Aug. 3, 2018 and published as WO 2019/028391 on Feb. 7, 2019 (Applicant—The Board of Regents of the Nevada System of Higher Education on Behalf of the University of Nevada, Las Vegas) (7 Pages).

*Primary Examiner* — Timothy R Rozof
(74) *Attorney, Agent, or Firm* — Ballard Spahr LLP

(57) ABSTRACT

Provided herein are phosphates, thiophosphates, phosphonates, and phosphinates, methods of making same, and methods of using these compounds and methods for the generation of pharmaceutically relevant phosphate, phosphonate, and phosphinate analogs. This abstract is intended as a scanning tool for purposes of searching in the particular art and is not intended to be limiting of the present invention.

13 Claims, 7 Drawing Sheets

METAL-FREE DIRECT ARYLATION OF DIALKYL PHOSPHONATES FOR THE SYNTHESIS OF MIXED ALKYL ARYL PHOSPHONATES

CROSS-REFERENCE TO RELATED APPLICATIONS

This application is a U.S. National Phase of International Application No. PCT/US2018/045224, filed on Aug. 3, 2018, which claims the benefit of U.S. Provisional Application No. 62/540,773, filed on Aug. 3, 2017 and U.S. Provisional Application No. 62/610,825, filed on Dec. 27, 2017, which are incorporated herein fully by reference in their entireties.

BACKGROUND

Organophosphonate compounds are ubiquitous structural motifs widely present in pharmaceuticals (Horsman and Zechel (2017) Chem. Rev. 117: 5704; Mucha et al. (2011) 54: 5955; McGrath et al. (2013) Nat. Rev. Microbiol. 11: 412), agrochemicals (Nowack (2003) Water Res. 37: 2533; Duke and Powles (2008) Pest Manage. Sci. 64: 319), and ligand scaffolds (Martin and Buchwald (2008) Acc. Chem. Res. 41: 1461), highlighting the significance of these structures. Among them, mixed alkyl aryl phosphonates have attracted significant attention in nucleoside phosphonate prodrugs (Pradere et al. (2014) Chem. Rev. 114: 9154; Thornton et al. (2016) J. Med. Chem. 59: 10400; Okon et al. (2017) J. Med. Chem. 60: 8131) and in coordination chemistry for the study of biological system A (FIG. 1; Park et al. (2016) ACS Catal. 6: 7458; Wieczorek et al. (2012) Organometallics 31: 2810; Galbiati et al. (2015) Bioconjugate Chem. 26: 680; Boersma et al. (2008) ChemBioChem 9: 1110). Mixed phosphonates show a wide range of biological activities such as phosphonate prodrugs of butyrophilin ligand B (Foust et al. (2017) ACS Med. Chem. Lett. 8: 914) and antibacterial reagent C (Kazuo et al. JP 48018461 B 19730606, 1973). They are also used as γ-glutamyl transpeptidase inhibitors D (Kamiyama et al. (2016) Bioorg. Med. Chem. 24: 5340; Nakajima et al. (2014) Bioorg. Med. Chem. 22: 1176) and esterase inhibitors E (Tramontano et al. (2000) Appl. Biochem. Biotechnol. 83: 233). Moreover, due to their unique structural properties of a hydrolysable P—O bond, mixed phosphonate units have been utilized as fluorogenic analogues to study biological mechanisms.

Current synthetic approaches toward mixed alkyl aryl phosphonates predominantly rely on stepwise processes involving substitution reaction of pre-generated alkyl phosphonochloridates with arenols (FIG. 2A) (Foust et al. (2017) ACS Med. Chem. Lett. 8: 914; Fukuto and Metcalf (1959) J. Am. Chem. Soc. 81: 372; Nowlan et al. (2006) J. Am. Chem. Soc. 128: 15892; Bera et al. (2016) ACS Catal. 6: 3575). These methods employ phosphonochloridates. In 2014, Feringa and co-workers (Fañanás-Mastral and Feringa (2014) J. Am. Chem. Soc. 136: 9894) disclosed an efficient copper-catalyzed direct arylation of dialkylphosphonates with diaryliodonium salts for the synthesis of mixed alkyl aryl phosphonates, which requires elevated reaction temperature and extra steps to prepare diaryliodonium salts (FIG. 2B). Therefore, a direct aryloxylation/alkyloxylation of dialkylphosphonates in one-pot using phenols/alcohols under mild reaction conditions is an ideal and step-economic strategy to generate mixed phosphonates. However, there are several challenges: (1) as compared to the reactive phosphonochloridates, P(O)—H (Wang et al. (2010) J. Org. Chem. 75: 3890; Atherton and Todd (1947) J. Chem. Soc. 674), and P(O)—OH compounds (Xiong et al. (2015) ACS Catal. 5: 537; Xiong et al. (2015) Tetrahedron 71: 9293; Keglevich et al. (2012) Org. Biomol. Chem. 10: 2011), the phosphonate moieties are chemically inert; and (2) for the mixed phosphonate synthesis, the reactivity and chemoselectivity must be carefully controlled to prevent dual substitution of the twin alkoxy groups.

Triflic anhydride (Tf$_2$O)-mediated activation of carbonyl compounds such as ketones, aldehydes, and amides as well as sulfoxides has emerged as a powerful synthetic tool in organic synthesis (Kaiser and Maulide (2016) J. Org. Chem. 81: 4421; Baraznenok et al. (2000) Tetrahedron 56: 3077; Chassaing et al. (2012) Tetrahedron 68: 7245; Shang et al. (2017) J. Am. Chem. Soc. 139: 4211; Eberhart and Procter (2013) Angew. Chem. Int. Ed. 52: 4008; Angew. Chem. 125: 4100; Kobatake et al. (2010) Angew. Chem. Int. Ed. 49: 2340; Angew. Chem. 122: 2390). Similarly, the activation of phosphorus compounds with P=O bond, especially phosphine oxides, was also achieved by Tf$_2$O (Hendrickson and Schwartzman (1975) Tetrahedron Letters 16: 277; McCauley (2012) Synlett 23: 2999). Recently, Miura and co-workers (Unoh et al. (2017) J. Am. Chem. Soc. 139: 6106) reported an elegant strategy for the activation of H-phosphine oxides. An electrophilic phosphorus species (P-species) generated from a diaryl phosphine oxide and Tf$_2$O reacts with an alkyne to form a reactive phosphirenium cation, which undergoes arylative ring-opening reaction to afford phosphinative cyclization product (FIG. 2C). Despite the demonstration of electrophilic P-species from the secondary arylphosphine oxides and Tf$_2$O at elevated temperature (Unoh et al. (2017) J. Am. Chem. Soc. 139: 6106; Yuan et al. (2018) Org. Biomol. Chem. 16: 30), the activation of dialkylphosphonates with Tf$_2$O at room temperature to generate electrophilic P-species remains undeveloped. Consequently, the development of direct functionalization strategies for accessing aryl phosphonates and mixed phosphonates that have good yields and functional group tolerance is highly desirable. These needs and others are met by the present invention.

SUMMARY

In accordance with the purpose(s) of the invention, as embodied and broadly described herein, the invention, in one aspect, relates to phosphates, thiophosphates, phosphonates, and phosphinates, methods of making same, and methods of using these compounds and methods for the generation of pharmaceutically relevant phosphate, phosphonate, and phosphinate analogs.

Disclosed are methods of making a compound having a structure represented by a formula:

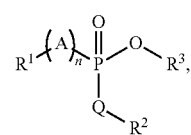

wherein n is 0 or 1; wherein A is selected from O, S, NR$^{20}$, and CHR$^{21}$; wherein R$^{20}$, when present, is selected from hydrogen and methyl; wherein R$^{21}$, when present, is selected from hydrogen and methyl; wherein Q is selected from O, S, and NR$^{22}$; wherein R$^{22}$, when present, is selected from hydrogen and C1-C8 alkyl; wherein R$^1$ is selected from C1-C8 alkyl, C2-C10 alkenyl, C1-C8 haloalkyl, C3-C6 cycloalkyl, —(C1-C4 alkyl)Ar$^1$, —(C2-C4 alkenyl)Ar$^1$, —(C2-C4 alkynyl)Ar$^1$, Ar$^1$, and a structure represented by a formula selected from:

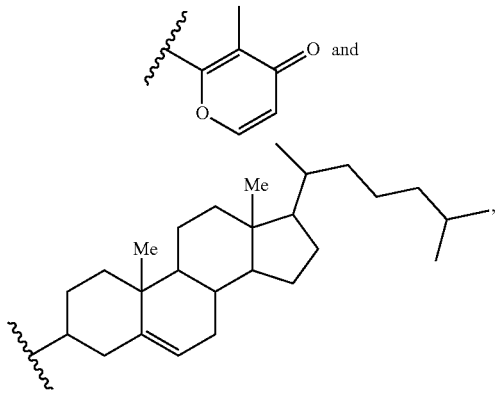

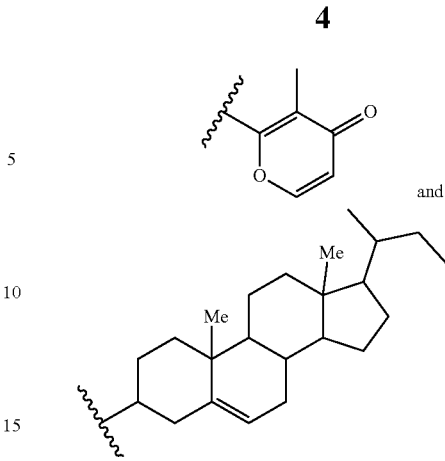

and wherein the C3-C6 cycloalkyl, when present, is substituted with 0 or 1 C1-C4 alkyl group; wherein Ar$^1$, when present, is selected from aryl and heteroaryl and is substituted with 0, 1, 2, or 3 groups independently selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO$_2$R$^{30}$, —CO$_2$R$^{30}$, —(C1-C4 alkyl)CO$_2$R$^{30}$, —(C2-C4 alkenyl)CO$_2$R$^{30}$, —(C=O)(C1-C4 alkyl), —(S=O)(C1-C4 alkyl), —SO$_2$(C1-C4 alkyl), —(C=O)NR$^{31a}$R$^{31b}$, —SO$_2$NR$^{31a}$R$^{31b}$, —O(C=O)NR$^{31a}$R$^{31b}$, —NHSO$_2$NR$^{31a}$R$^{31b}$, —NH(C=O)NR$^{31a}$R$^{31b}$, and —N=NR$^{32}$; wherein R$^{30}$, when present, is selected from hydrogen, C1-C8 alkyl, —(C1-C4 alkyl)phenyl, phenyl, and a structure represented by a formula:

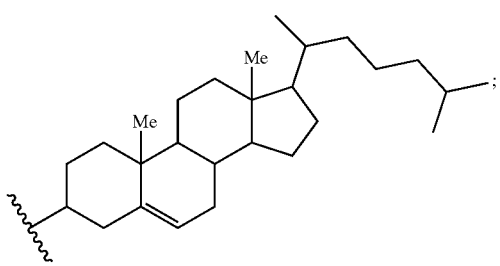 [SMILES: *C1CCC2(C)C(=CCC3C2CCC2(C)C(C(C)CCCC(C)C)CCC32)C1]

wherein each of R$^{31a}$ and R$^{31b}$, when present, is independently selected from hydrogen, C1-C8 alkyl, —(C1-C4 alkyl)phenyl, and phenyl; wherein R$^{32}$, when present, is selected from hydrogen, C1-C4 alkyl, and phenyl; or wherein each of R$^1$ and R$^{20}$, when present, are optionally covalently bonded together and, together with the intermediate carbon atoms, comprise a 3- to 6-membered heterocycloalkyl; wherein R$^2$ is selected from hydrogen, C1-C8 alkyl substituted with 0-1 phenyl groups, C2-C10 alkenyl, C1-C8 haloalkyl, C3-C6 cycloalkyl, —(C1-C4 alkyl)Ar$^2$, —(C2-C4 alkenyl)Ar$^2$, —(C2-C4 alkynyl)Ar$^2$, Ar$^2$, and a structure represented by a formula selected from:

and wherein the C3-C6 cycloalkyl, when present, is substituted with 0 or 1 C1-C4 alkyl groups; wherein Ar$^2$, when present, is selected from aryl and heteroaryl and is substituted with 0, 1, 2, or 3 groups independently selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO$_2$R$^{33}$, —CO$_2$R$^{33}$, —(C1-C4 alkyl)CO$_2$R$^{33}$, —(C2-C4 alkenyl)CO$_2$R$^{33}$, —(C=O)(C1-C4 alkyl), —(S=O)(C1-C4 alkyl), —SO$_2$(C1-C4 alkyl), —(C=O)NR$^{34a}$R$^{34b}$, —SO$_2$(C=S)NR$_2$NR$^{34a}$R$^{34b}$, —O(C=O)NR$^{34a}$R$^{34b}$, —NHSO$_2$NR$^{34a}$R$^{34b}$, —NH(C=O)NR$^{34a}$R$^{34b}$, and —N=NR$^{35}$; wherein R$^{33}$ when present, is selected from hydrogen, C1-C8 alkyl, —(C1-C4 alkyl)phenyl, phenyl, and a structure represented by a formula:

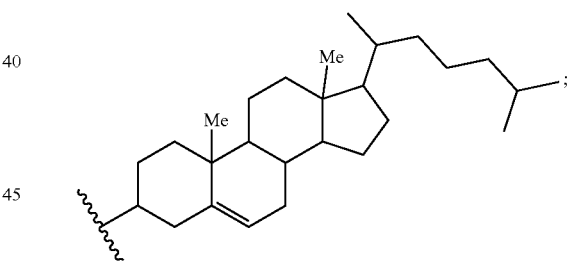

wherein each of R$^{34a}$ and R$^{34b}$, when present, is independently selected from hydrogen, C1-C8 alkyl, —(C1-C4 alkyl)phenyl, and phenyl; wherein R$^{35}$, when present, is selected from hydrogen, C1-C4 alkyl, and phenyl; and wherein R$^3$ is C1-C4 alkyl, or a salt thereof, the method comprising the step of reacting a phosphonate derivative having a structure represented by a formula:

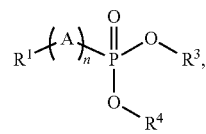

wherein R$^4$ is C1-C4 alkyl, provided that R$^2$ and R$^4$ are different, or a salt thereof, with a nucleophile having a structure represented by a formula:

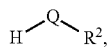

in the presence of an activating agent and a base.

Also disclosed are methods of making a compound having a structure represented by a formula:

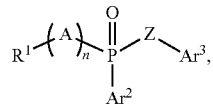

wherein n is 0 or 1; wherein A is selected from O, S, NR$^{20}$, and CHR$^{21}$; wherein R$^{20}$, when present, is selected from hydrogen and methyl; wherein R$^{21}$, when present, is selected from hydrogen and methyl; wherein Z is selected from O, S, and NR$^{23}$; wherein R$^{23}$, when present, is selected from hydrogen and methyl; wherein R$^1$ is selected from C1-C8 alkyl, C2-C10 alkenyl, C1-C8 haloalkyl, C3-C6 cycloalkyl, —(C1-C4 alkyl)Ar$^1$, —(C2-C4 alkenyl)Ar$^1$, —(C2-C4 alkynyl)Ar$^1$, Ar$^1$, and a structure represented by a formula selected from:

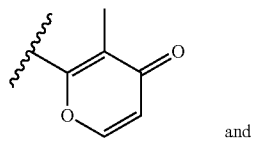

and

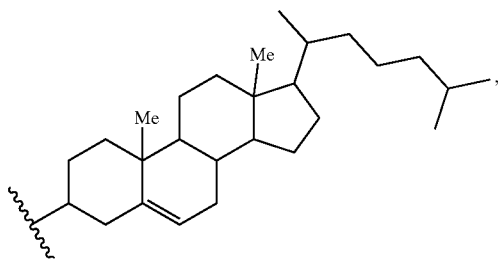 [SMILES: *C1CCC2(C)C(=CCC3C2CCC2(C)C(C(C)CCCC(C)C)CCC32)C1]

and wherein the C3-C6 cycloalkyl, when present, is substituted with 0 or 1 C1-C4 alkyl group; wherein Ar$^1$, when present, is selected from aryl and heteroaryl and is substituted with 0, 1, 2, or 3 groups independently selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO$_2$R$^{30}$, —CO$_2$R$^{30}$, —(C1-C4 alkyl)CO$_2$R$^{30}$, —(C2-C4 alkenyl)CO$_2$R$^{33}$, —(C=O)(C1-C4 alkyl), —(S=O)(C1-C4 alkyl), —SO$_2$(C1-C4 alkyl), —(C=O)NR$^{31a}$R$^{31b}$, —SO$_2$NR$^{31a}$R$^{31b}$, —O(C=O)NR$^{31a}$R$^{31b}$, —NHSO$_2$NR$^{31a}$R$^{31b}$, —NH(C=O)NR$^{31a}$R$^{31b}$, and —N=NR$^{32}$; wherein R$^{30}$, when present, is selected from hydrogen, C1-C8 alkyl, —(C1-C4 alkyl)phenyl, phenyl, and a structure represented by a formula:

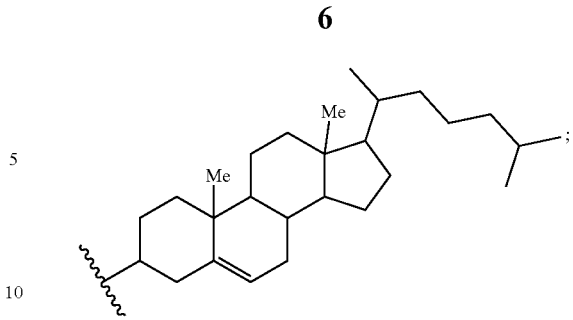

wherein each of R$^{31a}$ and R$^{31b}$, when present, is independently selected from hydrogen, C1-C8 alkyl, —(C1-C4 alkyl)phenyl, and phenyl; wherein R$^{32}$, when present, is selected from hydrogen, C1-C4 alkyl, and phenyl; or wherein each of R$^1$ and R$^{20}$, when present, are optionally covalently bonded together and, together with the intermediate carbon atoms, comprise a 3- to 6-membered heterocycloalkyl; wherein Ar$^2$ is selected from aryl and heteroaryl and is substituted with 0, 1, 2, or 3 groups independently selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl (C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO$_2$R$^{33}$, —CO$_2$R$^{33}$, —(C1-C4 alkyl)CO$_2$R$^{33}$, —(C2-C4 alkenyl)CO$_2$R$^{33}$, —(C=O)(C1-C4 alkyl), —(S=O)(C1-C4 alkyl), —SO$_2$(C1-C4 alkyl), —(C=O)NR$^{34a}$R$^{34b}$, —SO$_2$NR$^{34a}$R$^{34b}$, —O(C=O)NR$^{34a}$R$^{34b}$, —NHSO$_2$NR$^{34a}$R$^{34b}$, —NH(C=O)NR$^{34a}$R$^{34b}$, and —N=NR$^{35}$; wherein R$^{33}$, when present, is selected from hydrogen, C1-C8 alkyl, —(C1-C4 alkyl)phenyl, phenyl, and a structure represented by a formula:

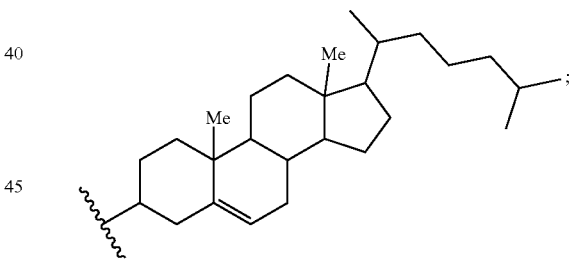

wherein each of R$^{34a}$ and R$^{34b}$, when present, is independently selected from hydrogen, C1-C8 alkyl, —(C1-C4 alkyl)phenyl, and phenyl; wherein R$^{35}$, when present, is selected from hydrogen, C1-C4 alkyl, and phenyl; wherein Ar$^4$ is selected from aryl and heteroaryl and is substituted with 0, 1, 2, or 3 groups independently selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO$_2$R$^{36}$, —CO$_2$R$^{36}$, —(C1-C4 alkyl)CO$_2$R$^{36}$, —(C2-C4 alkenyl)CO$_2$R$^{36}$, —(C=O)(C1-C4 alkyl), —(S=O)(C1-C4 alkyl), —SO$_2$(C1-C4 alkyl), —(C=O)NR$^{37a}$R$^{37b}$, —SO$_2$NR$^{37a}$R$^{37b}$, —O(C=O)NR$^{37a}$R$^{37b}$, —NHSO$_2$NR$^{37a}$R$^{37b}$, —NH(C=O)NR$^{37a}$R$^{37b}$, and —N=NR$^{38}$; wherein R$^{36}$, when present, is selected from hydrogen, C1-C8 alkyl, —(C1-C4 alkyl)phenyl, phenyl, and a structure represented by a formula:

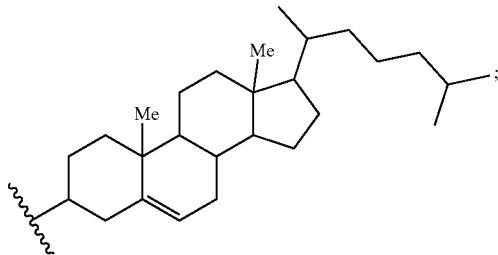 [SMILES: *C1CCC2(C)C(=CCC3C2CCC2(C)C(C(C)CCCC(C)C)CCC32)C1]

wherein each of $R^{37a}$ and $R^{37b}$, when present, is independently selected from hydrogen, C1-C8 alkyl, —(C1-C4 alkyl)phenyl, and phenyl; wherein $R^{38}$, when present, is selected from hydrogen, C1-C4 alkyl, and phenyl, or a salt thereof, the method comprising the step of reacting a phosphonate derivative having a structure represented by a formula:

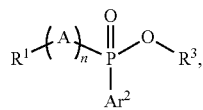

wherein $R^3$ is C1-C4 alkyl, or a salt thereof, with a nucleophile having a structure represented by a formula:

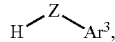

in the presence of an activating agent and a base.

Also disclosed are compounds having a structure represented by a formula:

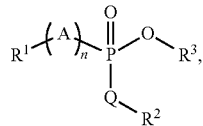

wherein n is 0 or 1; wherein A is selected from O, S, $NR^{20}$, and $CHR^{21}$; wherein $R^{20}$, when present, is selected from hydrogen and methyl; wherein $R^{21}$, when present, is selected from hydrogen and methyl; wherein Q is selected from O, S, and $NR^{22}$; wherein $R^{22}$, when present, is selected from hydrogen and C1-C8 alkyl; wherein $R^1$ is selected from C1-C8 alkyl, C2-C10 alkenyl, C1-C8 haloalkyl, C3-C6 cycloalkyl, —(C1-C4 alkyl)$Ar^1$, —(C2-C4 alkenyl)$Ar^1$, —(C2-C4 alkynyl)$Ar^1$, $Ar^1$, and a structure represented by a formula selected from:

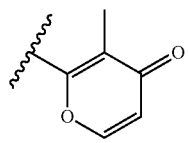

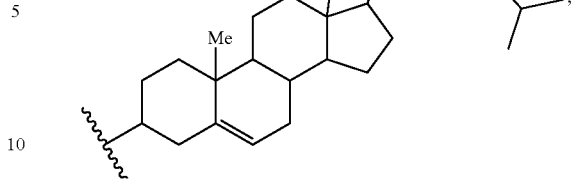

and wherein the C3-C6 cycloalkyl, when present, is substituted with 0 or 1 C1-C4 alkyl group; wherein $Ar^1$, when present, is selected from aryl and heteroaryl and is substituted with 0, 1, 2, or 3 groups independently selected from halogen, —$NO_2$, —CN, —OH, —SH, —$NH_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —$OCO_2R^{30}$, —$CO_2R^{30}$, —(C1-C4 alkyl)$CO_2R^{30}$, —(C2-C4 alkenyl)$CO_2R^{30}$, —(C=O)(C1-C4 alkyl), —(S=O)(C1-C4 alkyl), —$SO_2$(C1-C4 alkyl), —(C=O)$NR^{31a}R^{31b}$, —$SO_2NR^{31a}R^{31b}$, —O(C=O)$NR^{31a}R^{31b}$, —$NHSO_2NR^{31a}R^{31b}$, —NH(C=O)$NR^{31a}R^{31b}$, and —N=$NR^{32}$; wherein $R^{30}$, when present, is selected from hydrogen, C1-C8 alkyl, —(C1-C4 alkyl)phenyl, phenyl, and a structure represented by a formula:

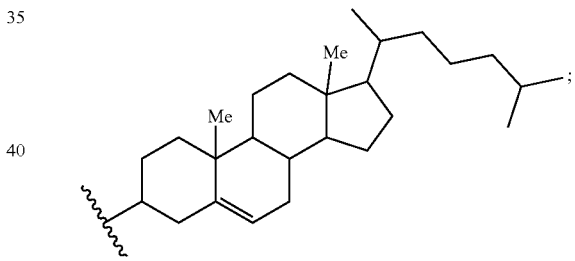

wherein each of $R^{31a}$ and $R^{31b}$, when present, is independently selected from hydrogen, C1-C8 alkyl, —(C1-C4 alkyl)phenyl, and phenyl; wherein $R^{32}$, when present, is selected from hydrogen, C1-C4 alkyl, and phenyl; or wherein each of $R^1$ and $R^{20}$, when present, are optionally covalently bonded together and, together with the intermediate carbon atoms, comprise a 3- to 6-membered heterocycloalkyl; wherein $R^2$ is selected from hydrogen, C1-C8 alkyl substituted with 0-1 phenyl groups, C2-C10 alkenyl, C1-C8 haloalkyl, C3-C6 cycloalkyl, —(C1-C4 alkyl)$Ar^2$, —(C2-C4 alkenyl)$Ar^2$, —(C2-C4 alkynyl)$Ar^2$, $Ar^2$, and a structure represented by a formula selected from:

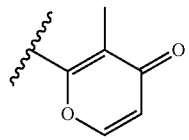

and

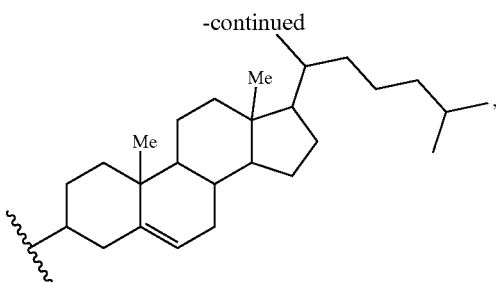

and wherein the C3-C6 cycloalkyl, when present, is substituted with 0 or 1 C1-C4 alkyl groups; wherein Ar², when present, is selected from aryl and heteroaryl and is substituted with 0, 1, 2, or 3 groups independently selected from halogen, —NO₂, —CN, —OH, —SH, —NH₂, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO₂R³³, —CO₂R³³, —(C1-C4 alkyl)CO₂R³³, —(C2-C4 alkenyl)CO₂R³³, —(C=O)(C1-C4 alkyl), —(S=O)(C1-C4 alkyl), —SO₂(C1-C4 alkyl), —(C=O) NR³⁴ᵃR³⁴ᵇ, —SO₂NR³⁴ᵃR³⁴ᵇ, —O(C=O)NR³⁴ᵃR³⁴ᵇ, —NHSO₂NR³⁴ᵃR³⁴ᵇ, —NH(C=O)NR³⁴ᵃR³⁴ᵇ, and —N=NR³⁵; wherein R³³ when present, is selected from hydrogen, C1-C8 alkyl, —(C1-C4 alkyl)phenyl, phenyl, and a structure represented by a formula:

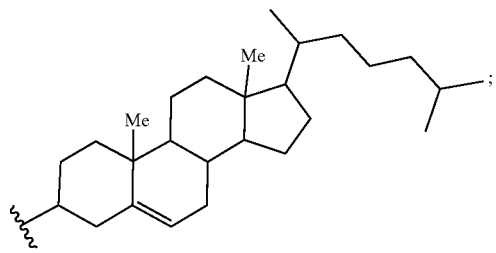 [SMILES: *C1CCC2(C)C(=CCC3C2CCC2(C)C(C(C)CCCC(C)C)CCC32)C1]

wherein each of R³⁴ᵃ and R³⁴ᵇ, when present, is independently selected from hydrogen, C1-C8 alkyl, —(C1-C4 alkyl)phenyl, and phenyl; wherein R³⁵, when present, is selected from hydrogen, C1-C4 alkyl, and phenyl; and wherein R³ is C1-C4 alkyl, or a salt thereof, the method comprising the step of reacting a phosphonate derivative having a structure represented by a formula:

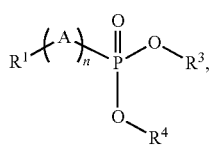

wherein R⁴ is C1-C4 alkyl, provided that R² and R⁴ are different, or a salt thereof, with a nucleophile having a structure represented by a formula:

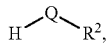

in the presence of an activating agent and a base.

Also disclosed are compounds having a structure represented by a formula:

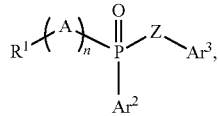

wherein n is 0 or 1; wherein A is selected from O, S, NR²⁰, and CHR²¹; wherein R²⁰, when present, is selected from hydrogen and methyl; wherein R²¹, when present, is selected from hydrogen and methyl; wherein Z is selected from O, S, and NR²³; wherein R²³, when present, is selected from hydrogen and methyl; wherein R¹ is selected from C1-C8 alkyl, C2-C10 alkenyl, C1-C8 haloalkyl, C3-C6 cycloalkyl, —(C1-C4 alkyl)Ar¹, —(C2-C4 alkenyl)Ar¹, —(C2-C4 alkynyl)Ar¹, Ar¹, and a structure represented by a formula selected from:

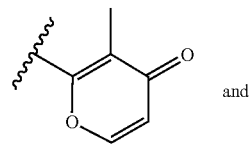

and

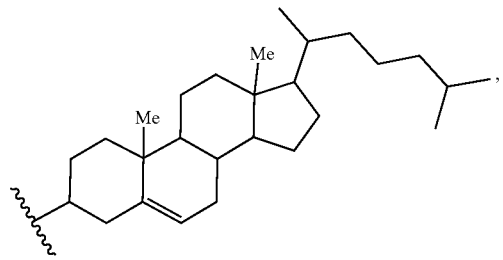 [SMILES: *C1CCC2(C)C(=CCC3C2CCC2(C)C(C(C)CCCC(C)C)CCC32)C1]

and wherein the C3-C6 cycloalkyl, when present, is substituted with 0 or 1 C1-C4 alkyl group; wherein Ar¹, when present, is selected from aryl and heteroaryl and is substituted with 0, 1, 2, or 3 groups independently selected from halogen, —NO₂, —CN, —OH, —SH, —NH₂, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO₂R³⁰, —CO₂R³⁰, —(C1-C4 alkyl)CO₂R³⁰, —(C2-C4 alkenyl)CO₂R³³, —(C=O)(C1-C4 alkyl), —(S=O)(C1-C4 alkyl), —SO₂(C1-C4 alkyl), —(C=O) NR³¹ᵃR³¹ᵇ, —SO₂NR³¹ᵃR³¹ᵇ, —O(C=O)NR³¹ᵃR³¹ᵇ, —NHSO₂NR³¹ᵃR³¹ᵇ, —NH(C=O)NR³¹ᵃR³¹ᵇ, and —N=NR³²; wherein R³⁰, when present, is selected from hydrogen, C1-C8 alkyl, —(C1-C4 alkyl)phenyl, phenyl, and a structure represented by a formula:

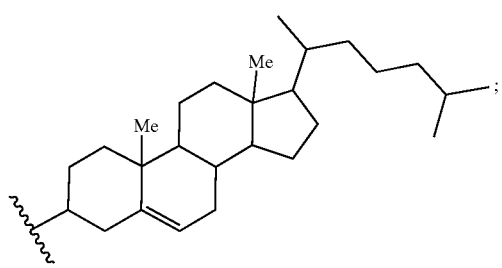 [SMILES: *C1CCC2(C)C(=CCC3C2CCC2(C)C(C(C)CCCC(C)C)CCC32)C1]

wherein each of $R^{31a}$ and $R^{31b}$, when present, is independently selected from hydrogen, C1-C8 alkyl, —(C1-C4 alkyl)phenyl, and phenyl; wherein $R^{32}$, when present, is selected from hydrogen, C1-C4 alkyl, and phenyl; or wherein each of $R^1$ and $R^{20}$, when present, are optionally covalently bonded together and, together with the intermediate carbon atoms, comprise a 3- to 6-membered heterocycloalkyl; wherein $Ar^2$ is selected from aryl and heteroaryl and is substituted with 0, 1, 2, or 3 groups independently selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl (C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO$_2$R$^{33}$, —CO$_2$R$^{33}$, —(C1-C4 alkyl)CO$_2$R$^{33}$, —(C2-C4 alkenyl)CO$_2$R$^{33}$, —(C=O) (C1-C4 alkyl), —(S=O)(C1-C4 alkyl), —SO$_2$(C1-C4 alkyl), —(C=O)NR$^{34a}$R$^{34b}$, —SO$_2$NR$^{34a}$R$^{34b}$, —O(C=O)NR$^{34a}$R$^{34b}$, —NHSO$_2$NR$^{34a}$R$^{34b}$, —NH(C=O)NR$^{34a}$R$^{34b}$, and —N=NR$^{35}$; wherein $R^{33}$, when present, is selected from hydrogen, C1-C8 alkyl, —(C1-C4 alkyl)phenyl, phenyl, and a structure represented by a formula:

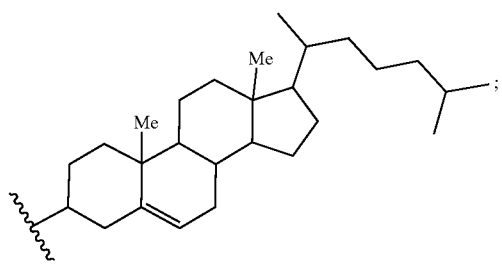 [SMILES: *C1CCC2(C)C(=CCC3C2CCC2(C)C(C(C)CCCC(C)C)CCC32)C1]

wherein each of $R^{34a}$ and $R^{34b}$, when present, is independently selected from hydrogen, C1-C8 alkyl, —(C1-C4 alkyl)phenyl, and phenyl; wherein $R^{35}$, when present, is selected from hydrogen, C1-C4 alkyl, and phenyl; wherein $Ar^4$ is selected from aryl and heteroaryl and is substituted with 0, 1, 2, or 3 groups independently selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO$_2$R$^{36}$, —CO$_2$R$^{36}$, —(C1-C4 alkyl)CO$_2$R$^{36}$, —(C2-C4 alkenyl)CO$_2$R$^{36}$, —(C=O)(C1-C4 alkyl), —(S=O)(C1-C4 alkyl), —SO$_2$(C1-C4 alkyl), —(C=O)NR$^{37a}$R$^{37b}$, —SO$_2$NR$^{37a}$R$^{37b}$, —O(C=O)NR$^{37a}$R$^{37b}$, —NHSO$_2$NR$^{37a}$R$^{37b}$, —NH(C=O)NR$^{37a}$R$^{37b}$, and —N=NR$^{38}$; wherein $R^{36}$, when present, is selected from hydrogen, C1-C8 alkyl, —(C1-C4 alkyl)phenyl, phenyl, and a structure represented by a formula:

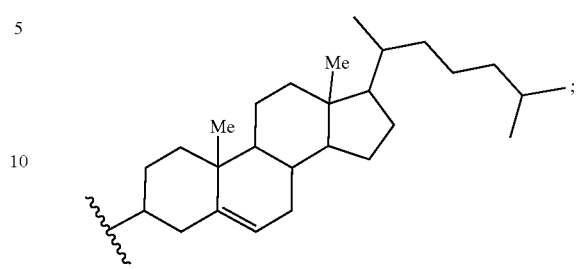

wherein each of $R^{37a}$ and $R^{37b}$, when present, is independently selected from hydrogen, C1-C8 alkyl, —(C1-C4 alkyl)phenyl, and phenyl; wherein $R^{38}$, when present, is selected from hydrogen, C1-C4 alkyl, and phenyl, or a salt thereof, the method comprising the step of reacting a phosphonate derivative having a structure represented by a formula:

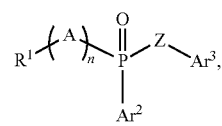

wherein $R^3$ is C1-C4 alkyl, or a salt thereof, with a nucleophile having a structure represented by a formula:

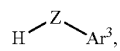

in the presence of an activating agent and a base.

Also disclosed are methods of using a disclosed compound.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE DRAWINGS

The accompanying figures, which are incorporated in and constitute a part of this specification, illustrate several aspects and together with the description serve to explain the principles of the invention.

Figure 1:
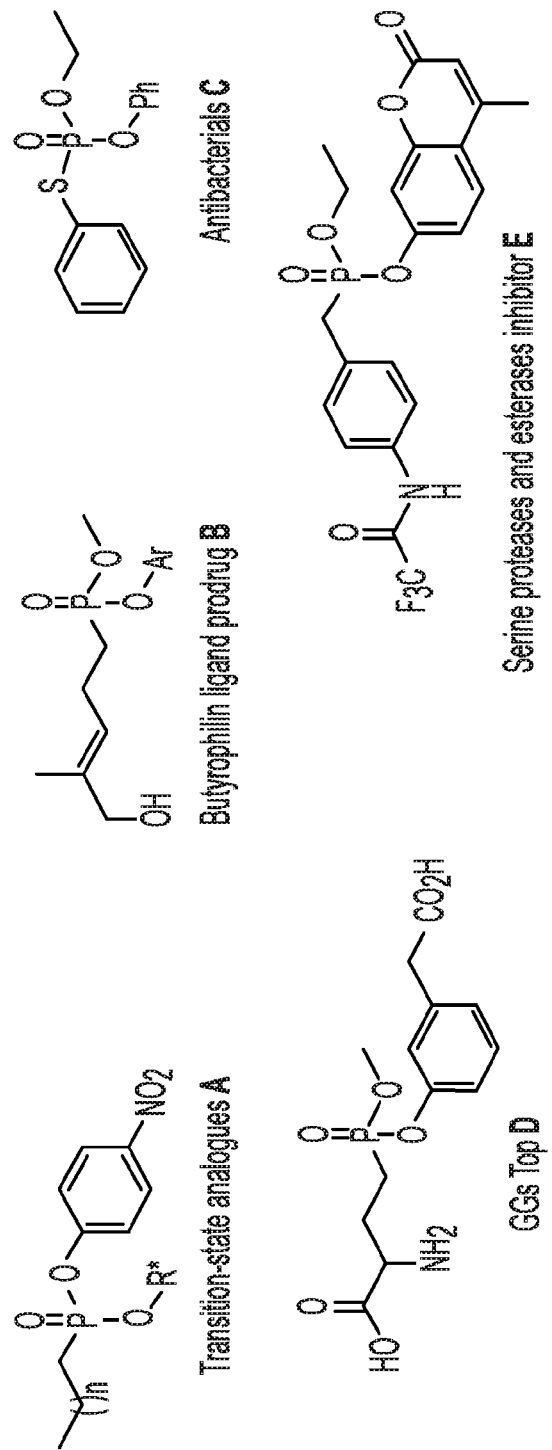
FIG. 1 shows representative examples of pharmaceutically-relevant mixed alkyl aryl phosphonates.
Figure 2A:
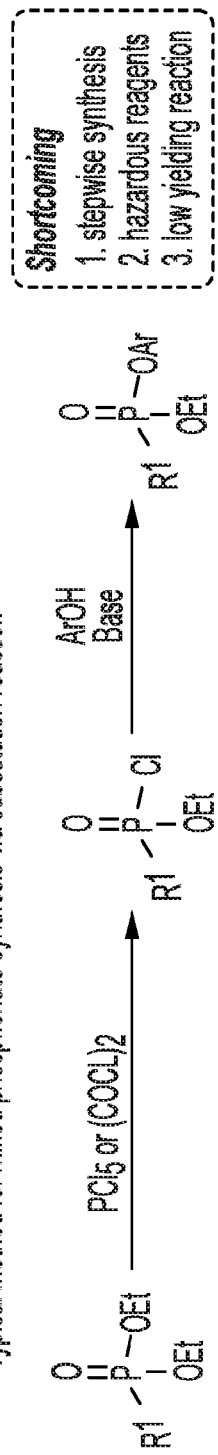
FIG. 2A-C show representative synthetic routes toward mixed phosphonates. Specifically, an exemplary method for the synthesis of mixed phosphonates via a substitution reaction (FIG. 2A), copper-catalyzed arylation of phosphonates (FIG. 2B), and Tf$_2$O-mediated electrophilic phosphination/cyclization of alkynes (FIG. 2C) is shown.
Figure 2B:
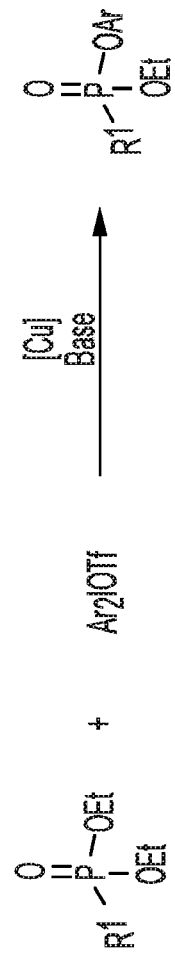
Figure 2C:
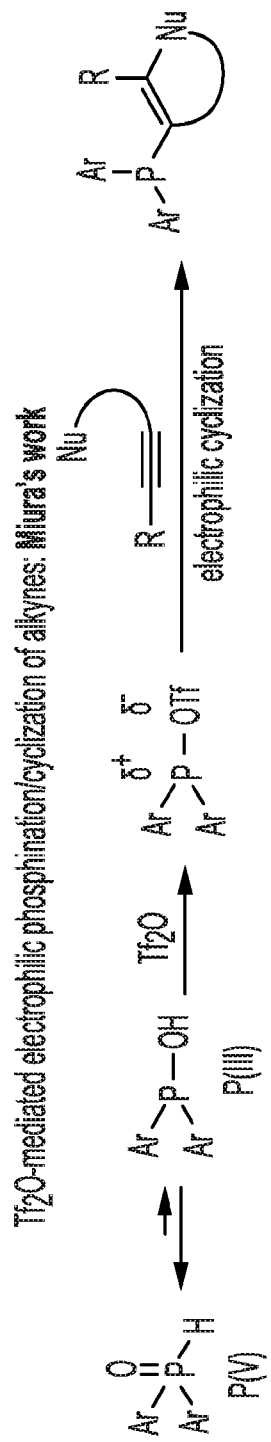

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

A. DEFINITIONS

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not.

It is appreciated that certain features of the disclosure, which are, for clarity, described in the context of separate aspects, can also be provided in combination in a single aspect. Conversely, various features of the disclosure which are, for brevity, described in the context of a single aspect, can also be provided separately or in any suitable subcombination.

For the terms "for example" and "such as," and grammatical equivalences thereof, the phrase "and without limitation" is understood to follow unless explicitly stated otherwise.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

All compounds, and salts thereof (e.g., pharmaceutically acceptable salts), can be found together with other substances such as water and solvents (e.g., hydrates and solvates).

Compounds provided herein also can include tautomeric forms. Tautomeric forms result from the swapping of a single bond with an adjacent double bond together with the concomitant migration of a proton. Tautomeric forms include prototropic tautomers that are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds provided herein can also include all isotopes of atoms occurring in the intermediates or final compounds. Isotopes include those atoms having the same atomic number but different mass numbers. For example, isotopes of hydrogen include hydrogen, tritium, and deuterium.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, or other problem or complication, commensurate with a reasonable benefit/risk ratio.

Also provided herein are pharmaceutically acceptable salts of the compounds described herein. As used herein, the term "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the compounds provided herein include the conventional non-toxic salts of the parent compound formed, for example, from non-toxic inorganic or organic acids. The pharmaceutically acceptable salts of the compounds provided herein can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. In various aspects, a non-aqueous media like ether, ethyl acetate, alcohols (e.g., methanol, ethanol, iso-propanol, or butanol) or acetonitrile (ACN) can be used. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977). Conventional methods for preparing salt forms are described, for example, in *Handbook of Pharmaceutical Salts. Properties, Selection, and Use,* Wiley-VCH, 2002.

In various aspects, the compounds provided herein, or salts thereof, are substantially isolated. By "substantially isolated" is meant that the compound is at least partially or substantially separated from the environment in which it was formed or detected. Partial separation can include, for example, a composition enriched in the compounds provided herein. Substantial separation can include compositions containing at least about 50%, at least about 60%, at least about 70%, at least about 80%, at least about 90%, at least about 95%, at least about 97%, or at least about 99% by weight of the compounds provided herein, or salt thereof. Methods for isolating compounds and their salts are routine in the art.

As used herein, chemical structures that contain one or more stereocenters depicted with dashed and bold bonds (i.e.,) are meant to indicate absolute stereochemistry of the stereocenter(s) present in the chemical structure. As used herein, bonds symbolized by a simple line do not indicate a stereo-preference. Unless otherwise indicated to the contrary, chemical structures, which include one or more stereocenters, illustrated herein without indicating absolute or relative stereochemistry encompass all possible stereoisomeric forms of the compound (e.g., diastereomers and enantiomers) and mixtures thereof. Structures with a single bold or dashed line, and at least one additional simple line, encompass a single enantiomeric series of all possible diastereomers.

Resolution of racemic mixtures of compounds can be carried out using appropriate methods. An exemplary method includes fractional recrystallization using a chiral resolving acid that is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid, or the various optically active camphorsulfonic acids such as camphorsulfonic acid. Other resolving agents suitable for fractional crystallization methods include stereoisomerically pure forms of methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent compositions can be determined by one skilled in the art.

The expressions "ambient temperature" and "room temperature" as used herein are understood in the art and refer generally to a temperature, e.g., a reaction temperature, that is about the temperature of the room in which the reaction is carried out, for example, a temperature from about 20° C. to about 30° C.

At various places in the present specification, divalent linking substituents are described. It is specifically intended that each divalent linking substituent include both the forward and backward forms of the linking substituent. For example, —NR(CR'R")$_n$— includes both —NR(CR'R")$_n$— and —(CR'R")$_n$NR—. Where the structure clearly requires a linking group, the Markush variables listed for that group are understood to be linking groups.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

As used herein, the phrase "optionally substituted" means unsubstituted or substituted. As used herein, the term "substituted" means that a hydrogen atom is removed and replaced by a substituent. It is to be understood that substitution at a given atom is limited by valency.

Throughout the definitions, the term "Cn-Cm" indicates a range that includes the endpoints, wherein n and m are integers and indicate the number of carbons. Examples include C1-C4, C1-C6, and the like.

As used herein, the term "Cn-Cm alkyl," employed alone or in combination with other terms, refers to a saturated hydrocarbon group that may be straight-chain or branched, having n to m carbons. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. In various aspects, the alkyl group contains from 1 to 6 carbon atoms, from 1 to 4 carbon atoms, from 1 to 3 carbon atoms, or 1 to 2 carbon atoms.

As used herein, "Cn-Cm alkenyl" refers to an alkyl group having one or more double carbon-carbon bonds and having n to m carbons. Example alkenyl groups include, but are not limited to, ethenyl, n-propenyl, isopropenyl, n-butenyl, sec-butenyl, and the like. In various aspects, the alkenyl moiety contains 2 to 6, 2 to 4, or 2 to 3 carbon atoms.

As used herein, "Cn-Cm alkynyl" refers to an alkyl group having one or more triple carbon-carbon bonds and having n to m carbons. Example alkynyl groups include, but are not limited to, ethynyl, propyn-1-yl, propyn-2-yl, and the like. In various aspects, the alkynyl moiety contains 2 to 6, 2 to 4, or 2 to 3 carbon atoms.

As used herein, the term "Cn-Cm alkylene," employed alone or in combination with other terms, refers to a divalent alkyl linking group having n to m carbons. Examples of alkylene groups include, but are not limited to, ethan-1,2-diyl, propan-1,3-diyl, propan-1,2-diyl, butan-1,4-diyl, butan-1,3-diyl, butan-1,2-diyl, 2-methyl-propan-1,3-diyl, and the like. In various aspects, the alkylene moiety contains 2 to 6, 2 to 4, 2 to 3, 1 to 6, 1 to 4, or 1 to 2 carbon atoms.

As used herein, the term "Cn-Cm alkoxy," employed alone or in combination with other terms, refers to a group of formula —O-alkyl, wherein the alkyl group has n to m carbons. Example alkoxy groups include methoxy, ethoxy, propoxy (e.g., n-propoxy and isopropoxy), tert-butoxy, and the like. In various aspects, the alkyl group has 1 to 6, 1 to 4, or 1 to 3 carbon atoms.

As used herein, the term "Cn-Cm alkylamino" refers to a group of formula —NH(alkyl), wherein the alkyl group has n to m carbon atoms. In various aspects, the alkyl group has 1 to 6, 1 to 4, or 1 to 3 carbon atoms.

As used herein, the term "Cn-Cm alkoxycarbonyl" refers to a group of formula —C(O)O-alkyl, wherein the alkyl group has n to m carbon atoms. In various aspects, the alkyl group has 1 to 6, 1 to 4, or 1 to 3 carbon atoms.

As used herein, the term "Cn-Cm alkylcarbonyl" refers to a group of formula —C(O)-alkyl, wherein the alkyl group has n to m carbon atoms. In various aspects, the alkyl group has 1 to 6, 1 to 4, or 1 to 3 carbon atoms.

As used herein, the term "Cn-Cm alkylcarbonylamino" refers to a group of formula —NHC(O)-alkyl, wherein the alkyl group has n to m carbon atoms. In various aspects, the alkyl group has 1 to 6, 1 to 4, or 1 to 3 carbon atoms.

As used herein, the term "Cn-Cm alkylsulfonylamino" refers to a group of formula —NHS(O)$_2$-alkyl, wherein the alkyl group has n to m carbon atoms. In various aspects, the alkyl group has 1 to 6, 1 to 4, or 1 to 3 carbon atoms.

As used herein, the term "aminosulfonyl" refers to a group of formula —S(O)$_2$NH$_2$.

As used herein, the term "Cn-Cm alkylaminosulfonyl" refers to a group of formula —S(O)$_2$NH(alkyl), wherein the alkyl group has n to m carbon atoms. In various aspects, the alkyl group has 1 to 6, 1 to 4, or 1 to 3 carbon atoms.

As used herein, the term "di(Cn-Cm alkyl)aminosulfonyl" refers to a group of formula —S(O)$_2$N(alkyl)$_2$, wherein each alkyl group independently has n to m carbon atoms. In various aspects, each alkyl group has, independently, 1 to 6, 1 to 4, or 1 to 3 carbon atoms.

As used herein, the term "aminosulfonylamino" refers to a group of formula —NHS(O)$_2$NH$_2$.

As used herein, the term "Cn-Cm alkylaminosulfonylamino" refers to a group of formula —NHS(O)$_2$NH(alkyl), wherein the alkyl group has n to m carbon atoms. In various aspects, the alkyl group has 1 to 6, 1 to 4, or 1 to 3 carbon atoms.

As used herein, the term "di(Cn-Cm alkyl)aminosulfonylamino" refers to a group of formula —NHS(O)$_2$N(alkyl)$_2$, wherein each alkyl group independently has n to m carbon atoms. In various aspects, each alkyl group has, independently, 1 to 6, 1 to 4, or 1 to 3 carbon atoms.

As used herein, the term "aminocarbonylamino," employed alone or in combination with other terms, refers to a group of formula —NHC(O)NH$_2$.

As used herein, the term "Cn-Cm alkylaminocarbonylamino" refers to a group of formula —NHC(O)NH(alkyl), wherein the alkyl group has n to m carbon atoms. In various aspects, the alkyl group has 1 to 6, 1 to 4, or 1 to 3 carbon atoms.

As used herein, the term "di(Cn-Cm alkyl)aminocarbonylamino" refers to a group of formula —NHC(O)N(alkyl)$_2$, wherein each alkyl group independently has n to m carbon atoms. In various aspects, each alkyl group has, independently, 1 to 6, 1 to 4, or 1 to 3 carbon atoms.

As used herein, the term "Cn-Cm alkylcarbamoyl" refers to a group of formula —C(O)—NH(alkyl), wherein the alkyl group has n to m carbon atoms. In various aspects, the alkyl group has 1 to 6, 1 to 4, or 1 to 3 carbon atoms.

As used herein, the term "thio" refers to a group of formula —SH.

As used herein, the term "Cn-Cm alkylthio" refers to a group of formula —S-alkyl, wherein the alkyl group has n to m carbon atoms. In various aspects, the alkyl group has 1 to 6, 1 to 4, or 1 to 3 carbon atoms.

As used herein, the term "Cn-Cm alkylsulfinyl" refers to a group of formula —S(O)-alkyl, wherein the alkyl group has n to m carbon atoms. In various aspects, the alkyl group has 1 to 6, 1 to 4, or 1 to 3 carbon atoms.

As used herein, the term "Cn-Cm alkylsulfonyl" refers to a group of formula —S(O)$_2$-alkyl, wherein the alkyl group has n to m carbon atoms. In various aspects, the alkyl group has 1 to 6, 1 to 4, or 1 to 3 carbon atoms.

As used herein, the term "amino" refers to a group of formula —NH$_2$.

As used herein, the term "carbamyl" to a group of formula —C(O)NH$_2$.

As used herein, the term "carbonyl," employed alone or in combination with other terms, refers to a —C(=O)— group, which may also be written as C(O).

As used herein, the term "carboxy" refers to a group of formula —C(O)OH.

As used herein, the term "(Cn-Cm)(Cn-Cm)amino" refers to a group of formula —N(alkyl)$_2$, wherein the two alkyl groups each has, independently, n to m carbon atoms. In various aspects, each alkyl group independently has 1 to 6, 1 to 4, or 1 to 3 carbon atoms.

As used herein, the term "di(Cn-Cm-alkyl)carbamyl" refers to a group of formula —C(O)N(alkyl)$_2$, wherein the two alkyl groups each has, independently, n to m carbon atoms. In various aspects, each alkyl group independently has 1 to 6, 1 to 4, or 1 to 3 carbon atoms.

As used herein, "halo" refers to F, Cl, Br, or I. In various aspects, the halo group is F or Cl.

As used herein, "Cn-Cm haloalkoxy" refers to a group of formula —O-haloalkyl having n to m carbon atoms. An example haloalkoxy group is $OCF_3$. In various aspects, the haloalkoxy group is fluorinated only. In various aspects, the alkyl group has 1 to 6, 1 to 4, or 1 to 3 carbon atoms.

As used herein, the term "Cn-Cm haloalkyl," employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In various aspects, the haloalkyl group is fluorinated only. In various aspects, the alkyl group has 1 to 6, 1 to 4, or 1 to 3 carbon atoms.

As used herein, the term "amine base" refers to a mono-substituted amine group (i.e., primary amine base), di-substituted amine group (i.e., secondary amine base), or a tri-substituted amine group (i.e., tertiary amine base). Example mono-substituted amine bases include methyl amine, ethyl amine, propyl amine, butyl amine, and the like. Example di-substituted amine bases include dimethylamine, diethylamine, dipropylamine, dibutylamine, pyrrolidine, piperidine, azepane, morpholine, and the like. In various aspects, the tertiary amine has the formula $N(R')_3$, wherein each R' is independently $C_{1-6}$ alkyl, 3-10 member cycloalkyl, 4-10 membered heterocycloalkyl, 1-10 membered heteroaryl, and 5-10 membered aryl, wherein the 3-10 member cycloalkyl, 4-10 membered heterocycloalkyl, 1-10 membered heteroaryl, and 5-10 membered aryl are optionally substituted by 1, 2, 3, 4, 5, or 6 $C_{1-6}$ alkyl groups. Example tertiary amine bases include trimethylamine, triethylamine, tripropylamine, triisopropylamine, tributylamine, tri-tert-butylamine, N,N-dimethylethanamine, N-ethyl-N-methylpropan-2-amine, N-ethyl-N-isopropylpropan-2-amine, morpholine, N-methylmorpholine, and the like. In various aspects, the term "tertiary amine base" refers to a group of formula $N(R)_3$, wherein each R is independently a linear or branched $C_{1-6}$ alkyl group.

As used herein, "cycloalkyl" refers to non-aromatic cyclic hydrocarbons including cyclized alkyl and/or alkenyl groups. Cycloalkyl groups can include mono- or polycyclics (e.g., having 2, 3 or 4 fused rings) groups and spirocycles. Cycloalkyl groups can have 3, 4, 5, 6, 7, 8, 9, or 10 ring-forming carbons ($C_{3-10}$). Ring-forming carbon atoms of a cycloalkyl group can be optionally substituted by oxo or sulfido (e.g., C(O) or C(S)). Cycloalkyl groups also include cycloalkylidenes. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, and the like. In various aspects, cycloalkyl is cyclopropyl, cyclobutyl, cyclopentyl, cyclohexyl, cyclopentyl, or adamantyl. In various aspects, the cycloalkyl has 6-10 ring-forming carbon atoms. In various aspects, cycloalkyl is cyclohexyl or adamantyl. Also included in the definition of cycloalkyl are moieties that have one or more aromatic rings fused (i.e., having a bond in common with) to the cycloalkyl ring, for example, benzo or thienyl derivatives of cyclopentane, cyclohexane, and the like. A cycloalkyl group containing a fused aromatic ring can be attached through any ring-forming atom including a ring-forming atom of the fused aromatic ring.

As used herein, "heterocycloalkyl" refers to non-aromatic monocyclic or polycyclic heterocycles having one or more ring-forming heteroatoms selected from O, N, or S. Included in heterocycloalkyl are monocyclic 4-, 5-, 6-, and 7-membered heterocycloalkyl groups. Heterocycloalkyl groups can also include spirocycles. Example heterocycloalkyl groups include pyrrolidin-2-one, 1,3-isoxazolidin-2-one, pyranyl, tetrahydropuran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, benzazapene, and the like. Ring-forming carbon atoms and heteroatoms of a heterocycloalkyl group can be optionally substituted by oxo or sulfido (e.g., C(O), S(O), C(S), or $S(O)_2$, etc.). The heterocycloalkyl group can be attached through a ring-forming carbon atom or a ring-forming heteroatom. In various aspects, the heterocycloalkyl group contains 0 to 3 double bonds. In various aspects, the heterocycloalkyl group contains 0 to 2 double bonds. Also included in the definition of heterocycloalkyl are moieties that have one or more aromatic rings fused (i.e., having a bond in common with) to the cycloalkyl ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring. In various aspects, the heterocycloalkyl has 4-10, 4-7 or 4-6 ring atoms with 1 or 2 heteroatoms independently selected from nitrogen, oxygen, or sulfur and having one or more oxidized ring members.

As used herein, the term "aryl," employed alone or in combination with other terms, refers to an aromatic hydrocarbon group, which may be monocyclic or polycyclic (e.g., having 2, 3 or 4 fused rings). The term "$C_{n-m}$ aryl" refers to an aryl group having from n to m ring carbon atoms. Aryl groups include, e.g., phenyl, naphthyl, anthracenyl, phenanthrenyl, indanyl, indenyl, and the like. In various aspects, aryl groups have from 6 to about 20 carbon atoms, from 6 to about 15 carbon atoms, or from 6 to about 10 carbon atoms. In various aspects, the aryl group is a substituted or unsubstituted phenyl.

As used herein, "heteroaryl" refers to a monocyclic or polycyclic aromatic heterocycle having at least one heteroatom ring member selected from sulfur, oxygen, and nitrogen. In various aspects, the heteroaryl ring has 1, 2, 3, or 4 heteroatom ring members independently selected from nitrogen, sulfur and oxygen. In various aspects, any ring-forming N in a heteroaryl moiety can be an N-oxide. In various aspects, the heteroaryl has 5-10 ring atoms and 1, 2, 3 or 4 heteroatom ring members independently selected from nitrogen, sulfur and oxygen. In various aspects, the heteroaryl has 5-6 ring atoms and 1 or 2 heteroatom ring members independently selected from nitrogen, sulfur and oxygen. In various aspects, the heteroaryl is a five-membered or six-membered heteroaryl ring. A five-membered heteroaryl ring is a heteroaryl with a ring having five ring atoms wherein one or more (e.g., 1, 2, or 3) ring atoms are independently selected from N, O, and S. Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl. A six-membered heteroaryl ring is a heteroaryl with a ring having six ring atoms wherein one or more (e.g., 1, 2, or 3) ring atoms are independently selected from N, O, and S. Exemplary six-membered ring heteroaryls are pyridyl, pyrazinyl, pyrimidinyl, triazinyl and pyridazinyl.

At certain places, the definitions or aspects refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas an azetidin-3-yl ring is attached at the 3-position.

As used herein, the term "electron withdrawing group" (EWG), employed alone or in combination with other terms, refers to an atom or group of atoms substituted onto a π-system (e.g., substituted onto an aryl or heteroaryl ring) that draws electron density away from the r-system through induction (e.g., withdrawing electron density about a σ-bond) or resonance (e.g., withdrawing electron density about a π-bond or π-system). Example electron withdrawing groups include, but are not limited to, halo groups (e.g., fluoro, chloro, bromo, iodo), nitriles (e.g., —CN), carbonyl groups (e.g., aldehydes, ketones, carboxylic acids, acid chlorides, esters, and the like), nitro groups (e.g., —NO$_2$), haloalkyl groups (e.g., —CH$_2$F, —CHF$_2$, —CF$_3$, and the like), alkenyl groups (e.g., vinyl), alkynyl groups (e.g., ethynyl), sulfonyl groups (e.g., S(O)R, S(O)$_2$R), sulfonate groups (e.g., —SO$_3$H), and sulfonamide groups (e.g., S(O)N(R)$_2$, S(O)$_2$N(R)$_2$). In various aspects, the electron withdrawing group is selected from the group consisting of halo, C2-C6 alkenyl, C2-C6 alkynyl, C1-C3 haloalkyl, CN, NO$_2$, C(=O)OR$^{a1}$, C(=O)R$^{b1}$, C(=O)NR$^{c1}$R$^{d1}$, C(=O)SR$^{e1}$, —NR$^{c1}$S(O)R$^{e1}$, —NR$^{c1}$S(O)$_2$R$^{e1}$, S(=O)R$^{e1}$, S(=O)$_2$R$^{e1}$, S(=O)NR$^{c1}$R$^{d1}$, S(=O)$_2$NR$^{c1}$R$^{d1}$, and P(O)(OR$^{a1}$)$_2$. In various aspects, the electron withdrawing group is selected from the group consisting of C(=O)OR$^{a1}$, C(=O)R$^{b1}$, C(=O)NR$^{c1}$R$^{d1}$, C(=O)SR$^{e1}$, S(=O)R$^{e1}$, S(=O)$_2$R$^{e1}$, S(=O)NR$^{c1}$R$^{d1}$, and S(=O)$_2$NR$^{c1}$R$^{d1}$. In various aspects, the electron withdrawing group is C(=O)OR$^{a1}$. In various aspects, the electron withdrawing group is C(=O)OR$^{a1}$, wherein R$^{a1}$ is C$_{1-6}$ alkyl or (C$_{6-10}$ aryl)-C$_{1-3}$ alkylene. In various aspects, the electron withdrawing group is an ester.

As used herein, the term "phosphonate derivative" means an organophosphorous compound in which the phosphorous atom is attached to at least three oxygen atoms. Thus, examples of phosphonate derivatives include, but are not limited to, compounds having a structure represented by a formula:

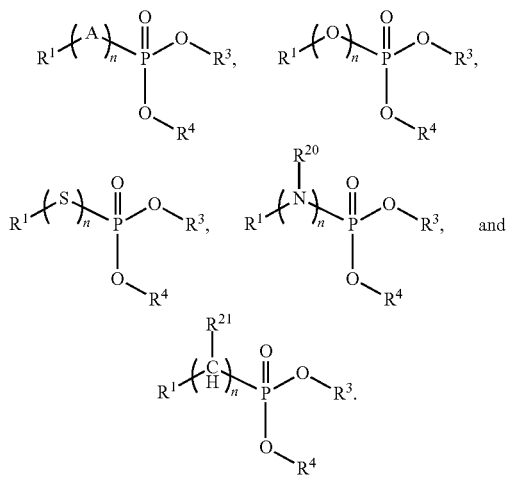

As used herein, the term "phosphinate derivative" means an organophosphorous compound in which the phosphorous atom is attached to at least two oxygen atoms. Thus, examples of phosphinate derivatives include, but are not limited to, compounds having a structure represented by a formula:

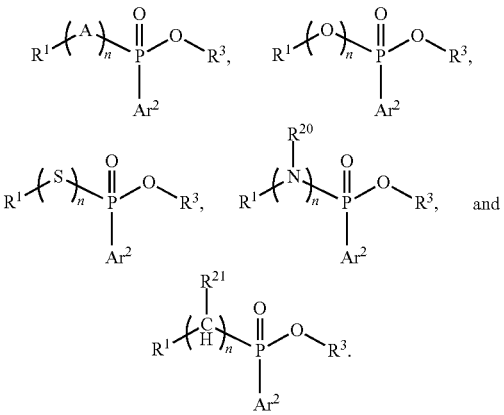

Preparation of the compounds described herein can involve a reaction in the presence of an acid or a base. Example acids can be inorganic or organic acids and include, but are not limited to, strong and weak acids. Example acids include, but are not limited to, hydrochloric acid, hydrobromic acid, sulfuric acid, phosphoric acid, p-toluenesulfonic acid, 4-nitrobenzoic acid, methanesulfonic acid, benzenesulfonic acid, trifluoroacetic acid, and nitric acid. Example weak acids include, but are not limited to, acetic acid, propionic acid, butanoic acid, benzoic acid, tartaric acid, pentanoic acid, hexanoic acid, heptanoic acid, octanoic acid, nonanoic acid, and decanoic acid. Example bases include, without limitation, lithium hydroxide, sodium hydroxide, potassium hydroxide, lithium carbonate, sodium carbonate, potassium carbonate, sodium bicarbonate, and amine bases. Example strong bases include, but are not limited to, hydroxide, alkoxides, metal amides, metal hydrides, metal dialkylamides and arylamines, wherein; alkoxides include lithium, sodium and potassium salts of methyl, ethyl and t-butyl oxides; metal amides include sodium amide, potassium amide and lithium amide; metal hydrides include sodium hydride, potassium hydride and lithium hydride; and metal dialkylamides include lithium, sodium, and potassium salts of methyl, ethyl, n-propyl, iso-propyl, n-butyl, t-butyl, trimethylsilyl and cyclohexyl substituted amides (e.g., lithium N-isopropylcyclohexylamide).

The following abbreviations may be used herein: AcOH (acetic acid); aq. (aqueous); atm. (atmosphere(s)); Br$_2$ (bromine); Bn (benzyl); calc. (calculated); d (doublet); dd (doublet of doublets); DCM (dichloromethane); DMF (N,N-dimethylformamide); Et (ethyl); Et$_2$O (diethyl ether); EtOAc (ethyl acetate); EtOH (ethanol); EWG (electron withdrawing group); g (gram(s)); h (hour(s)); H$_2$ (hydrogen gas); HCl (hydrochloric acid/hydrogen choride); HPLC (high performance liquid chromatography); H$_2$SO$_4$ (sulfuric acid); Hz (hertz); I$_2$ (iodine); IPA (isopropyl alcohol); J (coupling constant); KOH (potassium hydroxide); K$_3$PO$_4$ (potassium phosphate); LCMS (liquid chromatography-mass spectrometry); LiICA (lithium N-isopropylcyclohexylamide); m (multiplet); M (molar); MS (Mass spectrometry); Me (methyl); MeCN (acetonitrile); MeOH (methanol); mg (milligram(s)); min. (minutes(s)); mL (milliliter(s)); mmol (millimole(s)); N (normal); NaBH$_3$CN (sodium cyanoborohydride); NHP (N-heterocyclic phosphine); NHP—Cl (N-heterocyclic phosphine chloride); $Na_2CO_3$ (sodium carbonate); $NaHCO_3$ (sodium bicarbonate); NaOH (sodium hydroxide); $Na_2SO_4$ (sodium sulfate); nM (nanomolar); NMR (nuclear magnetic resonance spectroscopy); $PCl_3$ (trichlorophosphine); PMP (4-methoxyphenyl); RP-HPLC (reverse phase high performance liquid chromatography); t (triplet or tertiary); t-Bu (tert-butyl); TEA (triethylamine); TFA (trifluoroacetic acid); THF (tetrahydrofuran); TLC (thin layer chromatography); g (microgram(s)); μL (microliter(s)); M (micromolar); wt % (weight percent).

B. COMPOUNDS

In one aspect, the invention relates to phosphates, thiophosphates, phosphonates, and phosphinates useful in, for example, the synthesis of pharmaceuticals, agrochemicals, and ligand scaffolds. The use of the disclosed compounds in the synthesis of other pharmaceutically active compounds is also envisioned.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Structure

In one aspect, disclosed are compounds having a structure represented by a formula:

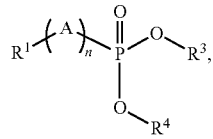

wherein n is 0 or 1; wherein A is selected from O, S, $NR^{20}$, and $CHR^{21}$; wherein $R^{20}$, when present, is selected from hydrogen and methyl; wherein $R^{21}$, when present, is selected from hydrogen and methyl; wherein Q is selected from O, S, and $NR^{22}$; wherein $R^{22}$, when present, is selected from hydrogen and C1-C8 alkyl; wherein $R^1$ is selected from C1-C8 alkyl, C2-C10 alkenyl, C1-C8 haloalkyl, C3-C6 cycloalkyl, —(C1-C4 alkyl)$Ar^1$, —(C2-C4 alkenyl)$Ar^1$, —(C2-C4 alkynyl)$Ar^1$, $Ar^1$, and a structure represented by a formula selected from:

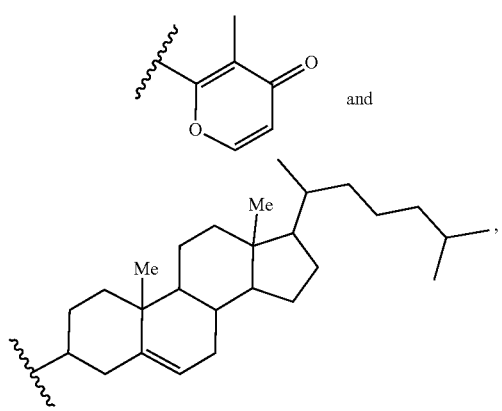

and wherein the C3-C6 cycloalkyl, when present, is substituted with 0 or 1 C1-C4 alkyl group; wherein $Ar^1$, when present, is selected from aryl and heteroaryl and is substituted with 0, 1, 2, or 3 groups independently selected from halogen, —$NO_2$, —CN, —OH, —SH, —$NH_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —$OCO_2R^{30}$, —$CO_2R^{30}$, —(C1-C4 alkyl)$CO_2R^{30}$, —(C2-C4 alkenyl)$CO_2R^{30}$, —(C=O)(C1-C4 alkyl), —(S=O)(C1-C4 alkyl), —$SO_2$(C1-C4 alkyl), —(C=O)$NR^{31a}R^{31b}$, —$SO_2NR^{31a}R^{31b}$, —O(C=O)$NR^{31a}R^{31b}$, —$NHSO_2NR^{31a}R^{31b}$, —NH(C=O)$NR^{31a}R^{31b}$, and —N=$NR^{32}$; wherein $R^{30}$, when present, is selected from hydrogen, C1-C8 alkyl, —(C1-C4 alkyl)phenyl, phenyl, and a structure represented by a formula:

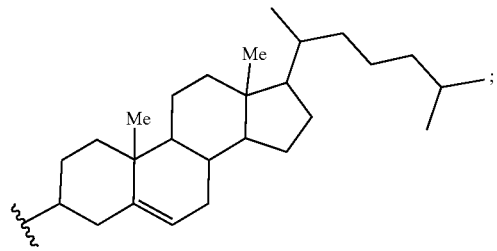 [SMILES: *C1CCC2(C)C(=CCC3C2CCC2(C)C(C(C)CCCC(C)C)CCC32)C1]

wherein each of $R^{31a}$ and $R^{31b}$, when present, is independently selected from hydrogen, C1-C8 alkyl, —(C1-C4 alkyl)phenyl, and phenyl; wherein $R^{32}$, when present, is selected from hydrogen, C1-C4 alkyl, and phenyl; or wherein each of $R^1$ and $R^{20}$, when present, are optionally covalently bonded together and, together with the intermediate carbon atoms, comprise a 3- to 6-membered heterocycloalkyl; wherein $R^2$ is selected from hydrogen, C1-C8 alkyl substituted with 0-1 phenyl groups, C2-C10 alkenyl, C1-C8 haloalkyl, C3-C6 cycloalkyl, —(C1-C4 alkyl)$Ar^2$, —(C2-C4 alkenyl)$Ar^2$, —(C2-C4 alkynyl)$Ar^2$, $Ar^2$, and a structure represented by a formula selected from:

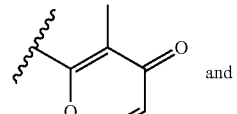
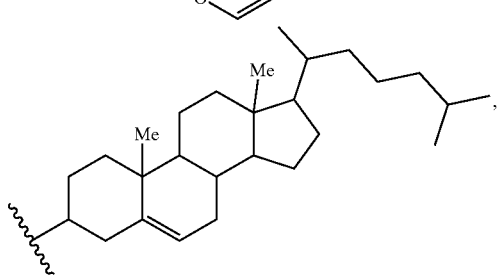

and wherein the C3-C6 cycloalkyl, when present, is substituted with 0 or 1 C1-C4 alkyl groups; wherein $Ar^2$, when present, is selected from aryl and heteroaryl and is substituted with 0, 1, 2, or 3 groups independently selected from halogen, —$NO_2$, —CN, —OH, —SH, —$NH_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO$_2$R$^{33}$, —CO$_2$R$^{33}$, —(C1-C4 alkyl)CO$_2$R$^{33}$, —(C2-C4 alkenyl)CO$_2$R$^{33}$, —(C=O)(C1-C4 alkyl), —(S=O)(C1-C4 alkyl), —SO$_2$(C1-C4 alkyl), —(C=O)NR$^{34a}$R$^{34b}$, —SO$_2$NR$^{34a}$R$^{34b}$, —O(C=O)NR$^{34a}$R$^{34b}$, —NHSO$_2$NR$^{34a}$R$^{34b}$, —NH(C=O)NR$^{34a}$R$^{34b}$, and —N=NR$^{35}$; wherein R$^{33}$ when present, is selected from hydrogen, C1-C8 alkyl, —(C1-C4 alkyl)phenyl, phenyl, and a structure represented by a formula:

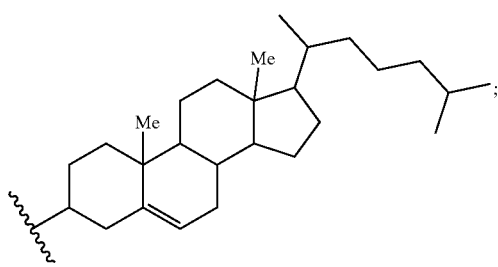 [SMILES: *C1CCC2(C)C(=CCC3C2CCC2(C)C(C(C)CCCC(C)C)CCC32)C1]

wherein each of R$^{34a}$ and R$^{34b}$, when present, is independently selected from hydrogen, C1-C8 alkyl, —(C1-C4 alkyl)phenyl, and phenyl; wherein R$^{35}$, when present, is selected from hydrogen, C1-C4 alkyl, and phenyl; and wherein R$^{3}$ is C1-C4 alkyl, or a salt thereof, the method comprising the step of reacting a phosphonate derivative having a structure represented by a formula:

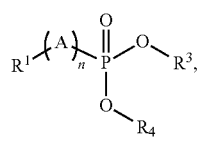

wherein R$^{4}$ is C1-C4 alkyl, provided that R$^{2}$ and R$^{4}$ are different, or a salt thereof, with a nucleophile having a structure represented by a formula:

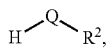

in the presence of an activating agent and a base.

In one aspect, disclosed are compounds having a structure represented by a formula:

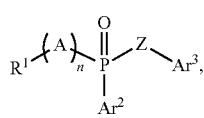

wherein n is 0 or 1; wherein A is selected from O, S, NR$^{20}$, and CHR$^{21}$; wherein R$^{20}$, when present, is selected from hydrogen and methyl; wherein R$^{21}$, when present, is selected from hydrogen and methyl; wherein Z is selected from O, S, and NR$^{23}$; wherein R$^{23}$, when present, is selected from hydrogen and methyl; wherein R$^{1}$ is selected from C1-C8 alkyl, C2-C10 alkenyl, C1-C8 haloalkyl, C3-C6 cycloalkyl, —(C1-C4 alkyl)Ar$^{1}$, —(C2-C4 alkenyl)Ar$^{1}$, —(C2-C4 alkynyl)Ar$^{1}$, Ar$^{1}$, and a structure represented by a formula selected from:

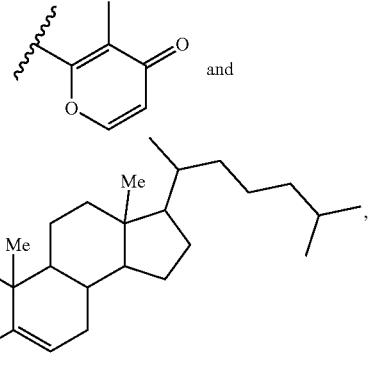

and wherein the C3-C6 cycloalkyl, when present, is substituted with 0 or 1 C1-C4 alkyl group; wherein Ar$^{1}$, when present, is selected from aryl and heteroaryl and is substituted with 0, 1, 2, or 3 groups independently selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO$_2$R$^{30}$, —CO$_2$R$^{30}$, —(C1-C4 alkyl)CO$_2$R$^{30}$, —(C2-C4 alkenyl)CO$_2$R$^{33}$, —(C=O)(C1-C4 alkyl), —(S=O)(C1-C4 alkyl), —SO$_2$(C1-C4 alkyl), —(C=O)NR$^{31a}$R$^{31b}$, —SO$_2$NR$^{31a}$R$^{31b}$, —O(C=O)NR$^{31a}$R$^{31b}$, —NHSO$_2$NR$^{31a}$R$^{31b}$, —NH(C=O)NR$^{31a}$R$^{31b}$, and —N=NR$^{32}$; wherein R$^{30}$, when present, is selected from hydrogen, C1-C8 alkyl, —(C1-C4 alkyl)phenyl, phenyl, and a structure represented by a formula:

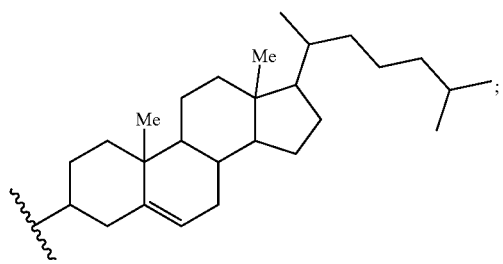 [SMILES: *C1CCC2(C)C(=CCC3C2CCC2(C)C(C(C)CCCC(C)C)CCC32)C1]

wherein each of R$^{31a}$ and R$^{31b}$, when present, is independently selected from hydrogen, C1-C8 alkyl, —(C1-C4 alkyl)phenyl, and phenyl; wherein R$^{32}$, when present, is selected from hydrogen, C1-C4 alkyl, and phenyl; or wherein each of R$^{1}$ and R$^{20}$, when present, are optionally covalently bonded together and, together with the intermediate carbon atoms, comprise a 3- to 6-membered heterocycloalkyl; wherein Ar$^{2}$ is selected from aryl and heteroaryl and is substituted with 0, 1, 2, or 3 groups independently selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO$_2$R$^{33}$, —CO$_2$R$^{33}$, —(C1-C4 alkyl)CO$_2$R$^{33}$, —(C2-C4 alkenyl)CO$_2$R$^{33}$, —(C=O)(C1-C4 alkyl), —(S=O)(C1-C4 alkyl), —SO$_2$(C1-C4 alkyl), —(C=O)NR$^{34a}$R$^{34b}$, —SO$_2$NR$^{34a}$R$^{34b}$, —O(C=O)NR$^{34a}$R$^{34b}$, —NHSO$_2$NR$^{34a}$R$^{34b}$, —NH(C=O)NR$^{34a}$R$^{34b}$, and —N=NR$^{35}$; wherein R$^{33}$, when present, is selected from hydrogen, C1-C8 alkyl, —(C1-C4 alkyl)phenyl, phenyl, and a structure represented by a formula:

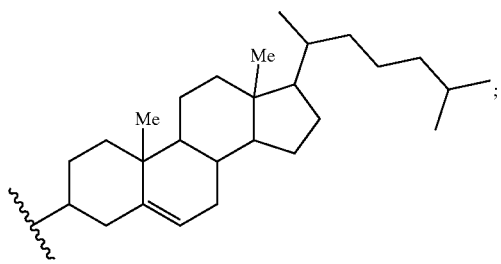 [SMILES: *C1CCC2(C)C(=CCC3C2CCC2(C)C(C(C)CCCC(C)C)CCC32)C1]

wherein each of R$^{34a}$ and R$^{34b}$, when present, is independently selected from hydrogen, C1-C8 alkyl, —(C1-C4 alkyl)phenyl, and phenyl; wherein R$^{35}$, when present, is selected from hydrogen, C1-C4 alkyl, and phenyl; wherein Ar$^4$ is selected from aryl and heteroaryl and is substituted with 0, 1, 2, or 3 groups independently selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO$_2$R$^{36}$, —CO$_2$R$^{36}$, —(C1-C4 alkyl)CO$_2$R$^{36}$, —(C2-C4 alkenyl)CO$_2$R$^{36}$, —(C=O)(C1-C4 alkyl), —(S=O)(C1-C4 alkyl), —SO$_2$(C1-C4 alkyl), —(C=O)NR$^{37a}$R$^{37b}$, —SO$_2$NR$^{37a}$R$^{37b}$, —O(C=O)NR$^{37a}$R$^{37b}$, —NHSO$_2$NR$^{37a}$R$^{37b}$, —NH(C=O)NR$^{37a}$R$^{37b}$, and —N=NR$^{38}$; wherein R$^{36}$, when present, is selected from hydrogen, C1-C8 alkyl, —(C1-C4 alkyl)phenyl, phenyl, and a structure represented by a formula:

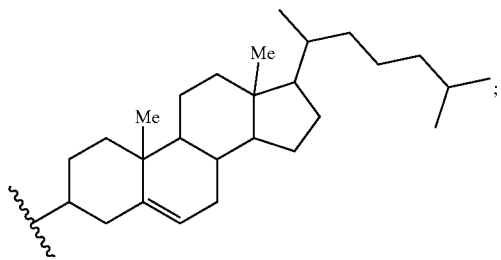 [SMILES: *C1CCC2(C)C(=CCC3C2CCC2(C)C(C(C)CCCC(C)C)CCC32)C1]

wherein each of R$^{37a}$ and R$^{37b}$, when present, is independently selected from hydrogen, C1-C8 alkyl, —(C1-C4 alkyl)phenyl, and phenyl; wherein R$^{38}$, when present, is selected from hydrogen, C1-C4 alkyl, and phenyl, or a salt thereof, the method comprising the step of reacting a phosphinate derivative having a structure represented by a formula:

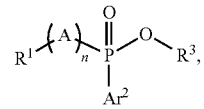

wherein R$^3$ is C1-C4 alkyl, or a salt thereof, with a nucleophile having a structure represented by a formula:

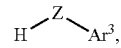

in the presence of an activating agent and a base.

In a further aspect, the compound has a structure represented by a formula:

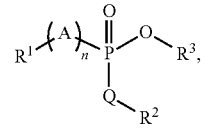

wherein n is 0 or 1; wherein A is selected from O, S, and CHR$^{21}$; wherein R$^{21}$, when present, is selected from hydrogen and methyl; wherein Q is selected from O, S, and NR$^{22}$; wherein R$^{22}$, when present, is selected from hydrogen and C1-C8 alkyl; wherein R$^1$ is selected from —(C1-C4 alkyl)Ar$^1$ and Ar$^1$; wherein Ar$^1$, when present, is selected from aryl and heteroaryl and is substituted with 0, 1, 2, or 3 groups independently selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO$_2$R$^{30}$, —CO$_2$R$^{30}$, —(C1-C4 alkyl)CO$_2$R$^{30}$, —(C2-C4 alkenyl)CO$_2$R$^{30}$, —(C=O)(C1-C4 alkyl), —(S=O)(C1-C4 alkyl), —SO$_2$(C1-C4 alkyl), —(C=O)NR$^{31a}$R$^{31b}$, —SO$_2$NR$^{31a}$R$^{31b}$, —O(C=O)NR$^{31a}$R$^{31b}$, —NHSO$_2$NR$^{31a}$R$^{31b}$, —NH(C=O)NR$^{31a}$R$^{31b}$, and —N=NR$^{32}$; wherein R$^{30}$, when present, is selected from hydrogen, C1-C8 alkyl, —(C1-C4 alkyl)phenyl, phenyl, and a structure represented by a formula:

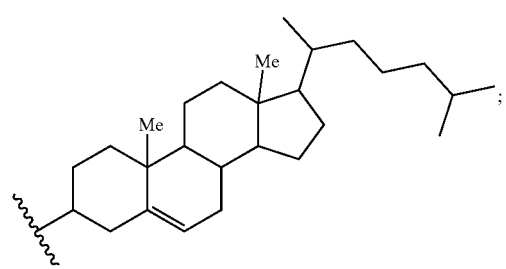 [SMILES: *C1CCC2(C)C(=CCC3C2CCC2(C)C(C(C)CCCC(C)C)CCC32)C1]

wherein each of R$^{31a}$ and R$^{31b}$, when present, is independently selected from hydrogen, C1-C8 alkyl, —(C1-C4 alkyl)phenyl, and phenyl; wherein R$^{32}$, when present, is selected from hydrogen, C1-C4 alkyl, and phenyl; wherein R$^2$ is selected from —(C1-C4 alkyl)Ar$^2$ and Ar$^2$; wherein Ar$^2$, when present, is selected from aryl and heteroaryl and is substituted with 0, 1, 2, or 3 groups independently selected from halogen, —NO₂, —CN, —OH, —SH, —NH₂, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4) (C1-C4) dialkylamino, C3-C7 cycloalkyl, C6-C10 aryl, —O(C2-C4 alkenyl), —OCO₂R³³, —CO₂R³³, —(C1-C4 alkyl)CO₂R³³, —(C2-C4 alkenyl)CO₂R³³, —(C=O)(C1-C4 alkyl), —(S=O)(C1-C4 alkyl), —SO₂(C1-C4 alkyl), —(C=O)NR³⁴ᵃR³⁴ᵇ, —SO₂NR³⁴ᵃR³⁴ᵇ, —O(C=O) NR³⁴ᵃR³⁴ᵇ, —NHSO₂NR³⁴ᵃR³⁴ᵇ, —NH(C=O)NR³⁴ᵃR³⁴ᵇ, and —N=NR³⁵; wherein R³³, when present, is selected from hydrogen, C1-C8 alkyl, —(C1-C4 alkyl)phenyl, phenyl, and a structure represented by a formula:

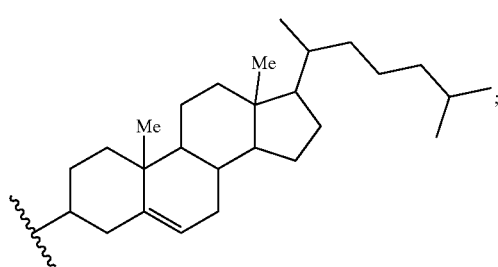 [SMILES: *C1CCC2(C)C(=CCC3C2CCC2(C)C(C(C)CCCC(C)C)CCC32)C1]

wherein each of R³⁴ᵃ and R³⁴ᵇ, when present, is independently selected from hydrogen, C1-C8 alkyl, —(C1-C4 alkyl)phenyl, and phenyl; wherein R³⁵, when present, is selected from hydrogen, C1-C4 alkyl, and phenyl; and wherein R³ is C1-C4 alkyl.

In a further aspect, the compound has a structure represented by a formula:

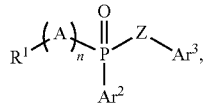

wherein n is 0 or 1; wherein A is selected from O, S, and CHR²¹; wherein R²¹, when present, is selected from hydrogen and methyl; wherein Z is selected from O, S, and NR²³; wherein R²³, when present, is selected from hydrogen and methyl; wherein R¹ is selected from —(C1-C4 alkyl)Ar¹ and Ar¹; wherein Ar², when present, is selected from aryl and heteroaryl and is substituted with 0, 1, 2, or 3 groups independently selected from halogen, —NO₂, —CN, —OH, —SH, —NH₂, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO₂R³⁰, —CO₂R³⁰, —(C1-C4 alkyl)CO₂R³⁰, —(C2-C4 alkenyl)CO₂R³³, —(C=O)(C1-C4 alkyl), —(S=O)(C1-C4 alkyl), —SO₂(C1-C4 alkyl), —(C=O)NR³¹ᵃR³¹ᵇ, —SO₂NR³¹ᵃR³¹ᵇ, —O(C=O)NR³¹ᵃR³¹ᵇ, —NHSO₂NR³¹ᵃR³¹ᵇ, —NH(C=O)NR³¹ᵃR³¹ᵇ, and —N=NR³²; wherein R³⁰, when present, is selected from hydrogen, C1-C8 alkyl, —(C1-C4 alkyl)phenyl, phenyl, and a structure represented by a formula:

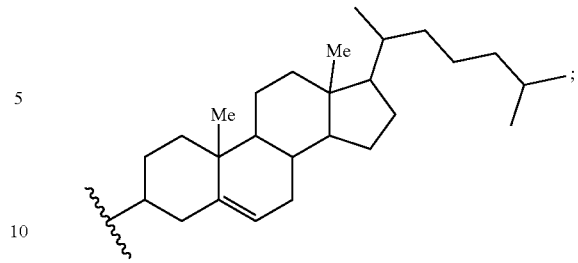

wherein each of R³¹ᵃ and R³¹ᵇ, when present, is independently selected from hydrogen, C1-C8 alkyl, —(C1-C4 alkyl)phenyl, and phenyl; wherein R³², when present, is selected from hydrogen, C1-C4 alkyl, and phenyl; wherein Ar², when present, is selected from aryl and heteroaryl and is substituted with 0, 1, 2, or 3 groups independently selected from halogen, —NO₂, —CN, —OH, —SH, —NH₂, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4) (C1-C4) dialkylamino, C3-C7 cycloalkyl, C6-C10 aryl, —O(C2-C4 alkenyl), —OCO₂R³³, —CO₂R³³, —(C1-C4 alkyl)CO₂R³³, —(C2-C4 alkenyl)CO₂R³³, —(C=O)(C1-C4 alkyl), —(S=O)(C1-C4 alkyl), —SO₂(C1-C4 alkyl), —(C=O)NR³⁴ᵃR³⁴ᵇ, —SO₂NR³⁴ᵃR³⁴ᵇ, —O(C=O) NR³⁴ᵃR³⁴ᵇ, —NHSO₂NR³⁴ᵃR³⁴ᵇ, —NH(C=O)NR³⁴ᵃR³⁴ᵇ, and —N=NR³⁵; wherein R³³, when present, is selected from hydrogen, C1-C8 alkyl, —(C1-C4 alkyl)phenyl, phenyl, and a structure represented by a formula:

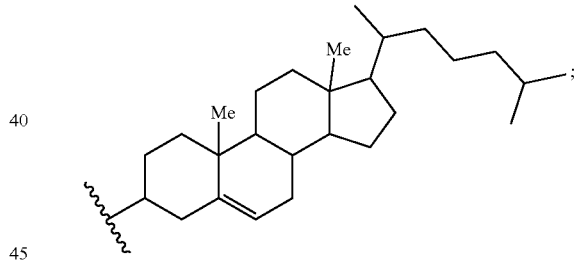

wherein each of R³⁴ᵃ and R³⁴ᵇ, when present, is independently selected from hydrogen, C1-C8 alkyl, —(C1-C4 alkyl)phenyl, and phenyl; wherein R³⁵, when present, is selected from hydrogen, C1-C4 alkyl, and phenyl; and wherein Ar³ is selected from aryl and heteroaryl and is substituted with 0, 1, 2, or 3 groups independently selected from halogen, —NO₂, —CN, —OH, —SH, —NH₂, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4) (C1-C4) dialkylamino, C3-C7 cycloalkyl, C6-C10 aryl, —O(C2-C4 alkenyl), —OCO₂R³⁶, —CO₂R³⁶, —(C1-C4 alkyl)CO₂R³⁶, —(C2-C4 alkenyl)CO₂R³⁶, —(C=O)(C1-C4 alkyl), —(S=O)(C1-C4 alkyl), —SO₂(C1-C4 alkyl), —(C=O)NR³⁷ᵃR³⁷ᵇ, —SO₂NR³⁷ᵃR³⁷ᵇ, —O(C=O) NR³⁷ᵃR³⁷ᵇ, —NHSO₂NR³⁷ᵃR³⁷ᵇ, —NH(C=O)NR³⁷ᵃR³⁷ᵇ, and —N=NR³⁸; wherein R³⁶, when present, is selected from hydrogen, C1-C8 alkyl, —(C1-C4 alkyl)phenyl, phenyl, and a structure represented by a formula:

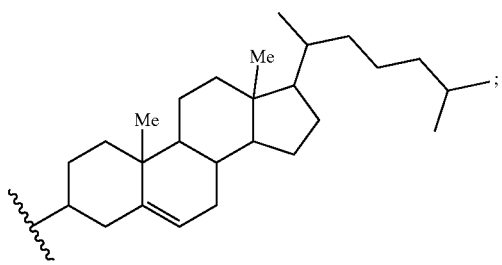 [SMILES: *C1CCC2(C)C(=CCC3C2CCC2(C)C(C(C)CCCC(C)C)CCC32)C1]

wherein each of $R^{37a}$ and $R^{37b}$, when present, is independently selected from hydrogen, C1-C8 alkyl, —(C1-C4 alkyl)phenyl, and phenyl; wherein $R^{38}$, when present, is selected from hydrogen, C1-C4 alkyl, and phenyl.

In a further aspect, the compound has a structure represented by a formula:

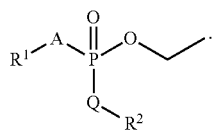

In a further aspect, the compound has a structure represented by a formula:

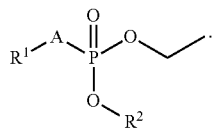

In a further aspect, the compound has a structure represented by a formula:

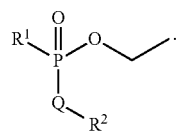

In a further aspect, the compound has a structure represented by a formula:

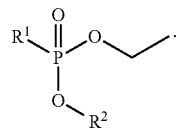

In a further aspect, the compound has a structure represented by a formula:

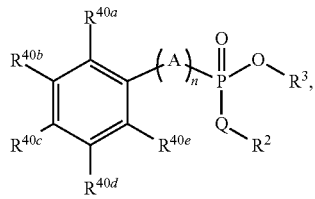

wherein each of $R^{40a}$, $R^{40b}$, $R^{40c}$, $R^{40d}$, and $R^{40e}$ is independently selected from hydrogen, halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO$_2$R$^{30}$, —CO$_2$R$^{30}$, —(C1-C4 alkyl)CO$_2$R$^{30}$, —(C2-C4 alkenyl)CO$_2$R$^{30}$, —(C=O)(C1-C4 alkyl), —(S=O)(C1-C4 alkyl), —SO$_2$(C1-C4 alkyl), —(C=O)NR$^{31a}$R$^{31b}$, —SO$_2$NR$^{31a}$R$^{31b}$, —O(C=O)NR$^{31a}$R$^{31b}$, —NHSO$_2$NR$^{31a}$R$^{31b}$, —NH(C=O)NR$^{31a}$R$^{31b}$, and —N=NR$^{32}$.

In a further aspect, the compound has a structure represented by a formula:

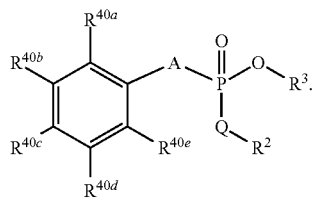

In a further aspect, the compound has a structure represented by a formula:

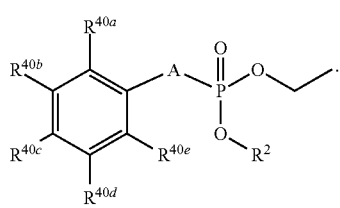

In a further aspect, the compound has a structure represented by a formula:

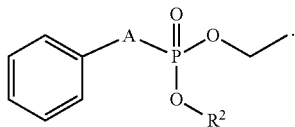

In a further aspect, the compound has a structure represented by a formula:

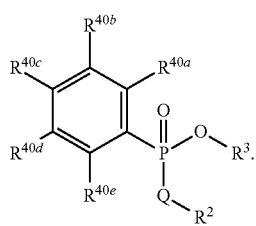

In a further aspect, the compound has a structure represented by a formula:

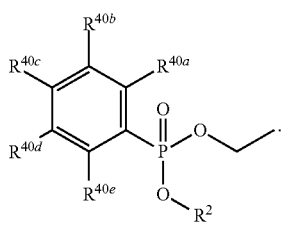

In a further aspect, the compound has a structure represented by a formula:

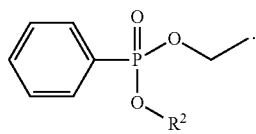

In a further aspect, the compound has a structure represented by a formula:

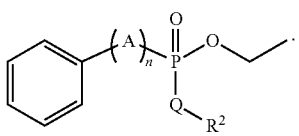

In a further aspect, the compound has a structure represented by a formula:

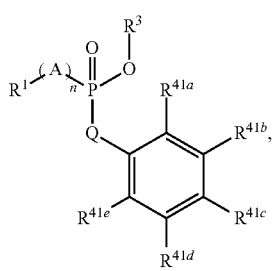

wherein each of $R^{41a}$, $R^{41b}$, $R^{41c}$, $R^{41d}$, and $R^{41e}$ is independently selected from hydrogen, halogen, —$NO_2$, —CN, —OH, —SH, —$NH_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —$OCO_2R^{33}$, —$CO_2R^{33}$, —(C1-C4 alkyl)$CO_2R^{33}$, —(C2-C4 alkenyl)$CO_2R^{33}$, —(C=O)(C1-C4 alkyl), —(S=O)(C1-C4 alkyl), —$SO_2$(C1-C4 alkyl), —(C=O)$NR^{34a}R^{34b}$, —$SO_2NR^{34a}R^{34b}$, —O(C=O)$NR^{34a}R^{34b}$, —$NHSO_2NR^{34a}R^{34b}$, —NH(C=O)$NR^{34a}R^{34b}$, and —N=$NR^{35}$.

In a further aspect, the compound has a structure represented by a formula:

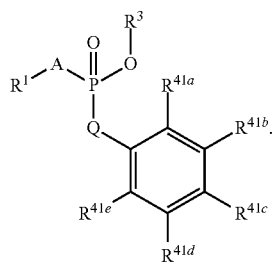

In a further aspect, the compound has a structure represented by a formula:

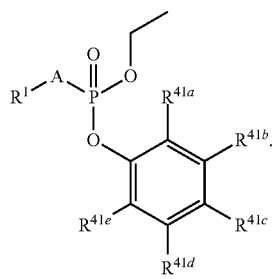

In a further aspect, the compound has a structure represented by a formula:

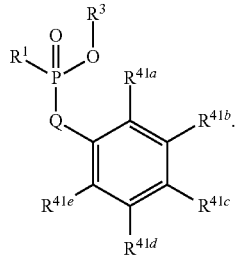

In a further aspect, the compound has a structure represented by a formula:

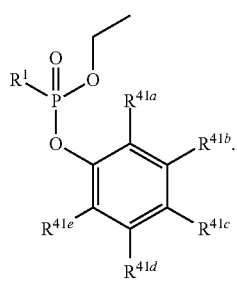

In a further aspect, the compound has a structure represented by a formula:

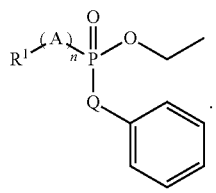

In a further aspect, the compound has a structure represented by a formula:

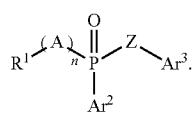

In a further aspect, the compound has a structure represented by a formula:

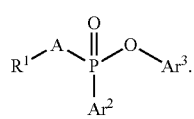

In a further aspect, the compound has a structure represented by a formula:

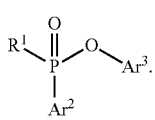

In a further aspect, the compound has a structure represented by a formula:

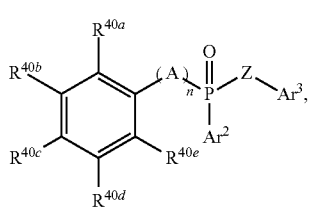

wherein each of $R^{40a}$, $R^{40b}$, $R^{40c}$, $R^{40d}$, and $R^{40e}$ is independently selected from hydrogen, halogen, —$NO_2$, —CN, —OH, —SH, —$NH_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —$OCO_2R^{30}$, —$CO_2R^{30}$, —(C1-C4 alkyl)$CO_2R^{30}$, —(C2-C4 alkenyl)$CO_2R^{30}$, —(C=O)(C1-C4 alkyl), —(S=O)(C1-C4 alkyl), —$SO_2$(C1-C4 alkyl), —(C=O)$NR^{31a}R^{31b}$, —$SO_2NR^{31a}R^{31b}$, —O(C=O)$NR^{31a}R^{31b}$, —$NHSO_2NR^{31a}R^{31b}$, —NH(C=O)$NR^{31a}R^{31b}$, and —N=$NR^{32}$.

In a further aspect, the compound has a structure represented by a formula:

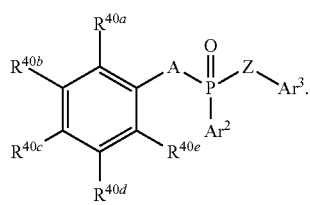

In a further aspect, the compound has a structure represented by a formula:

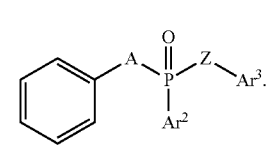

In a further aspect, the compound has a structure represented by a formula:

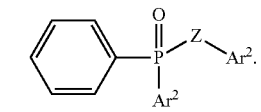

In a further aspect, the compound has a structure represented by a formula:

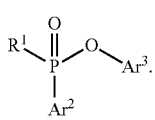

In a further aspect, the compound has a structure represented by a formula:

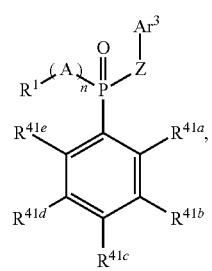

wherein each of $R^{41a}$, $R^{41b}$, $R^{41c}$, $R^{41d}$, and $R^{41e}$ is independently selected from hydrogen, halogen, —$NO_2$, —CN, —OH, —SH, —$NH_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO$_2$R$^{33}$, —CO$_2$R$^{33}$, —(C1-C4 alkyl)CO$_2$R$^{33}$, —(C2-C4 alkenyl) CO$_2$R$^{33}$, —(C=O)(C1-C4 alkyl), —(S=O)(C1-C4 alkyl), —SO$_2$(C1-C4 alkyl), —(C=O)NR$^{34a}$R$^{34b}$, —SO$_2$NR$^{34a}$R$^{34b}$, —O(C=O)NR$^{34a}$R$^{34b}$, —NHSO$_2$NR$^{34a}$R$^{34b}$, —NH(C=O)NR$^{34a}$R$^{34b}$, and —N=NR$^{35}$.

In a further aspect, the compound has a structure represented by a formula:

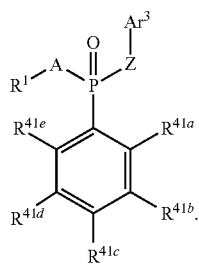

In a further aspect, the compound has a structure represented by a formula:

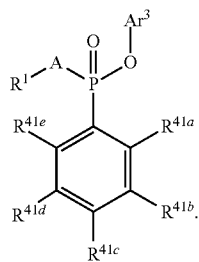

In a further aspect, the compound has a structure represented by a formula:

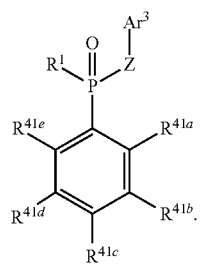

In a further aspect, the compound has a structure represented by a formula:

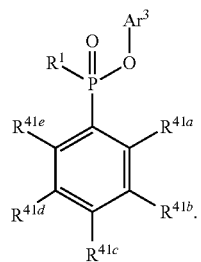

In a further aspect, the compound is selected from:

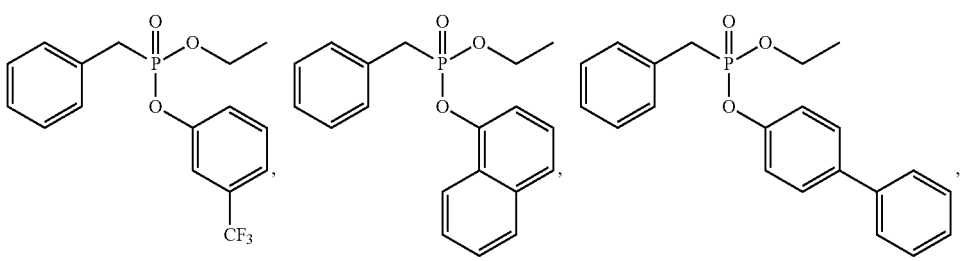

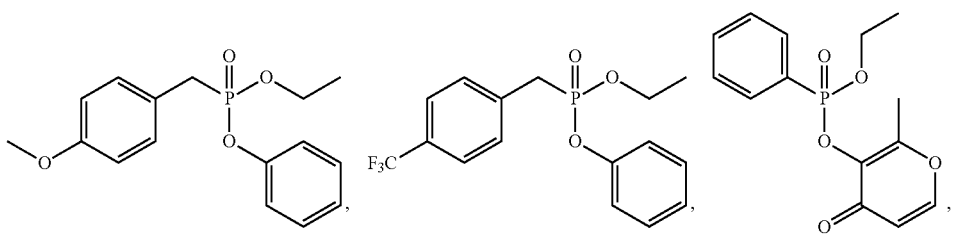

-continued
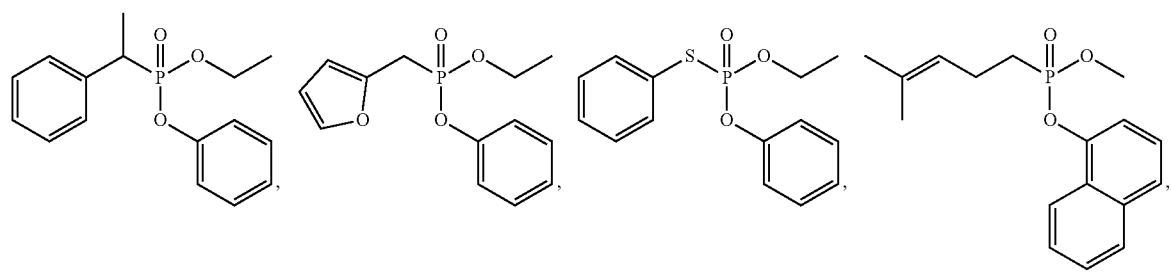
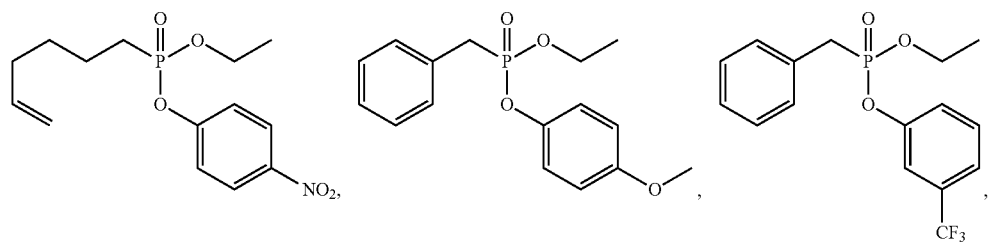
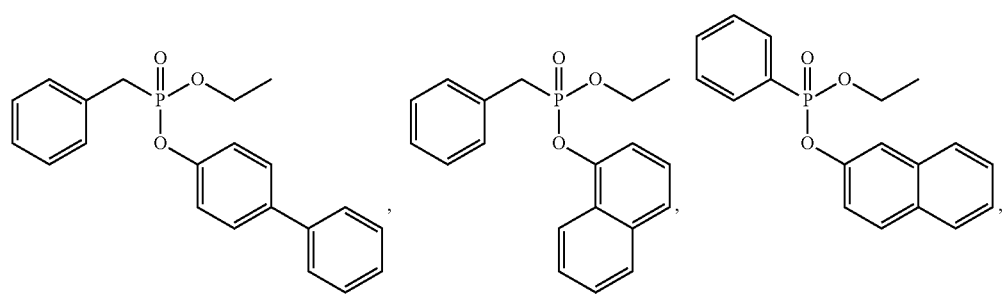
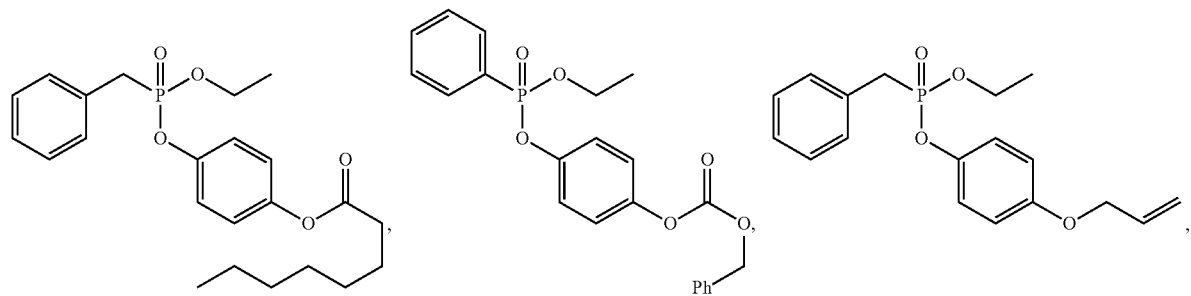
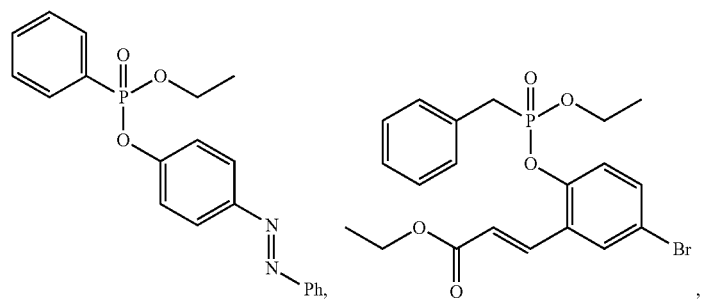

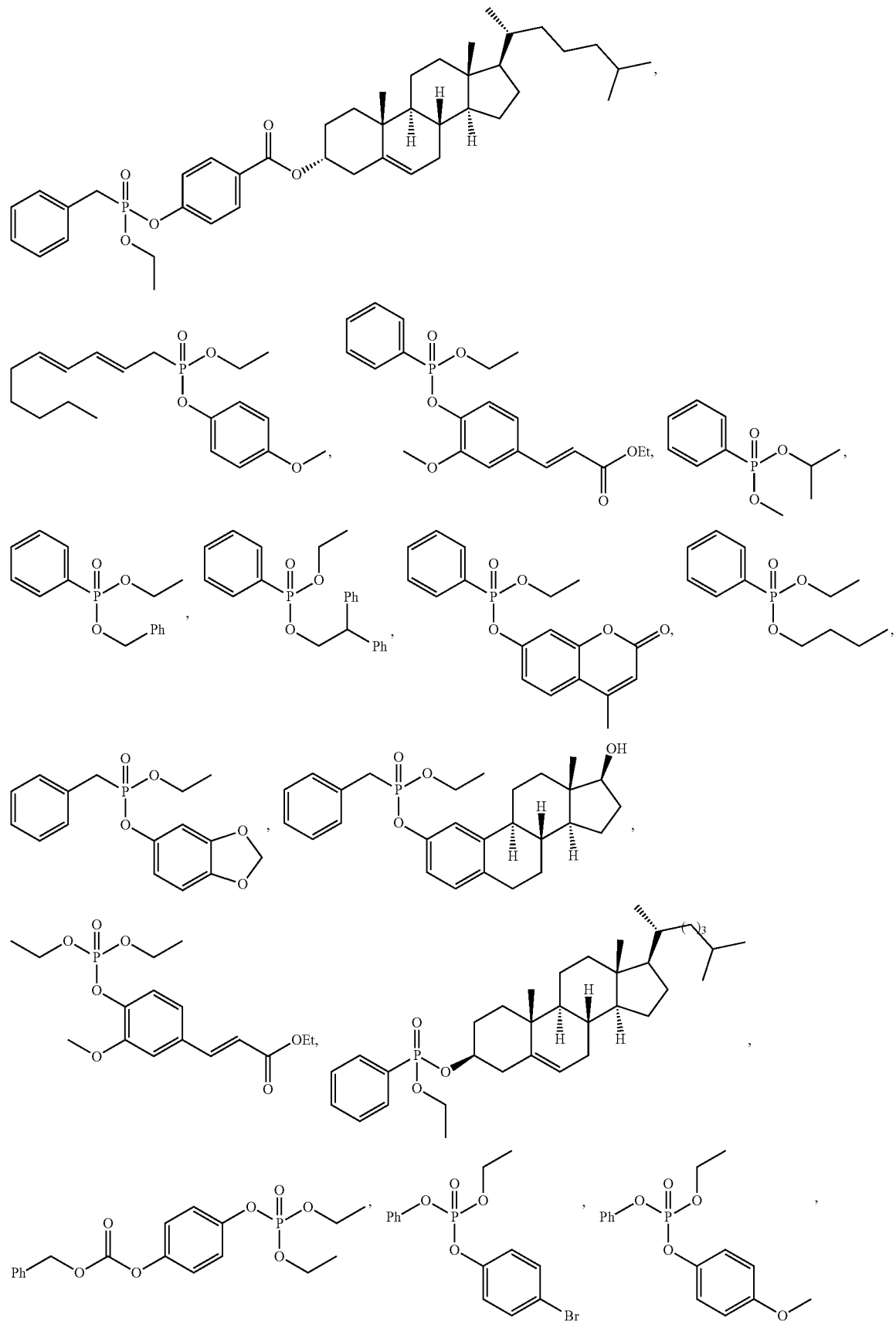

-continued
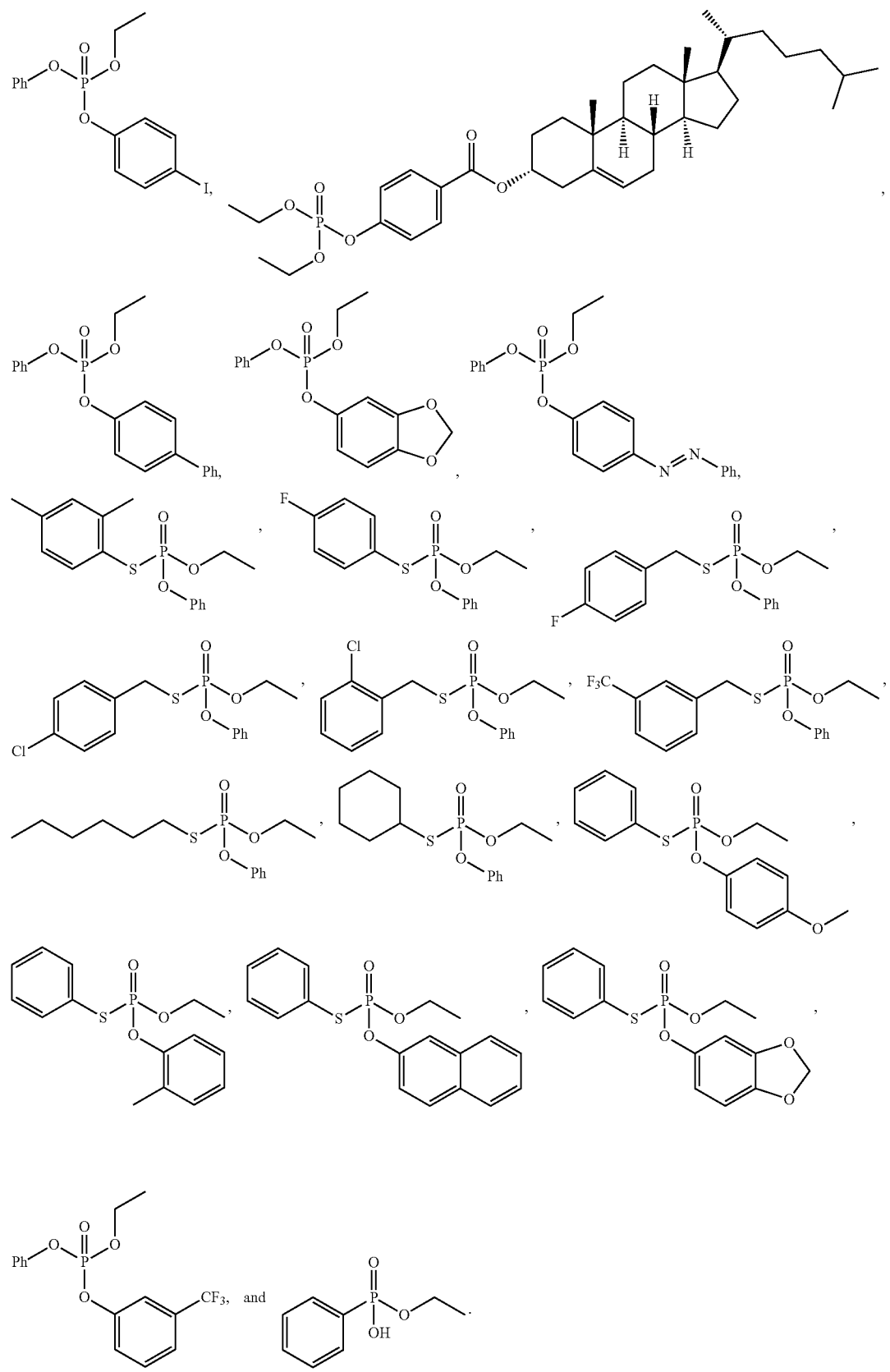

In a further aspect, the compound is selected from:
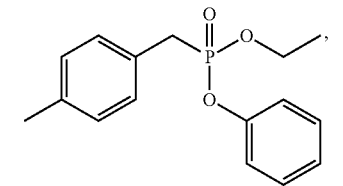
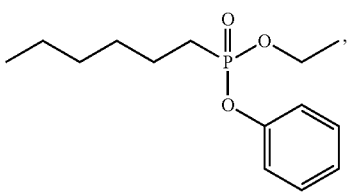
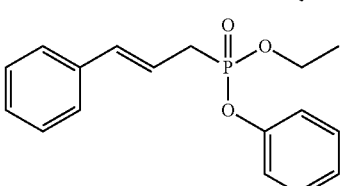
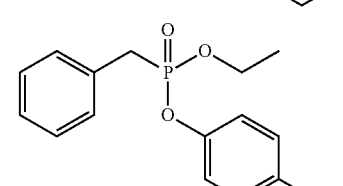
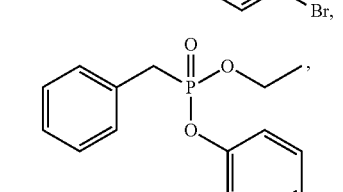
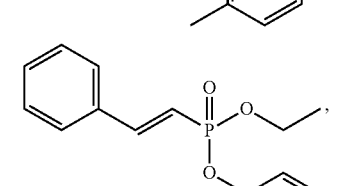
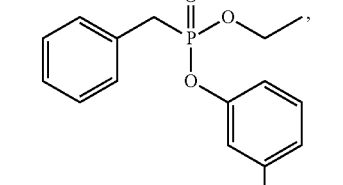
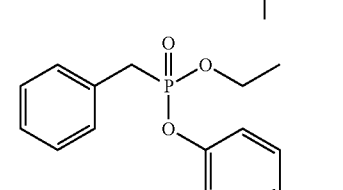
-continued
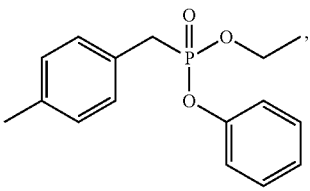
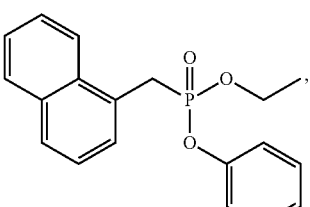
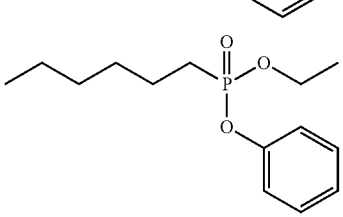
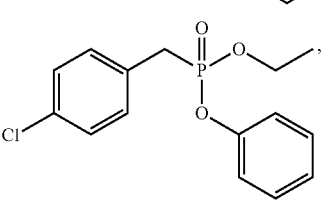
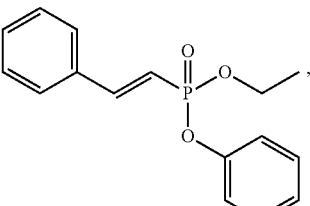
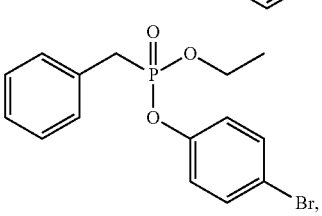
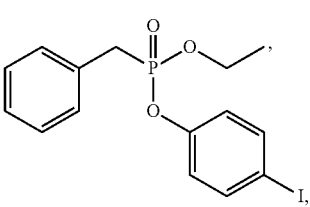
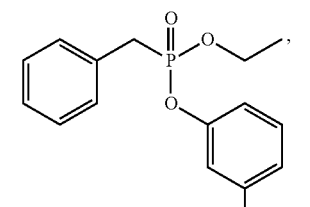

-continued

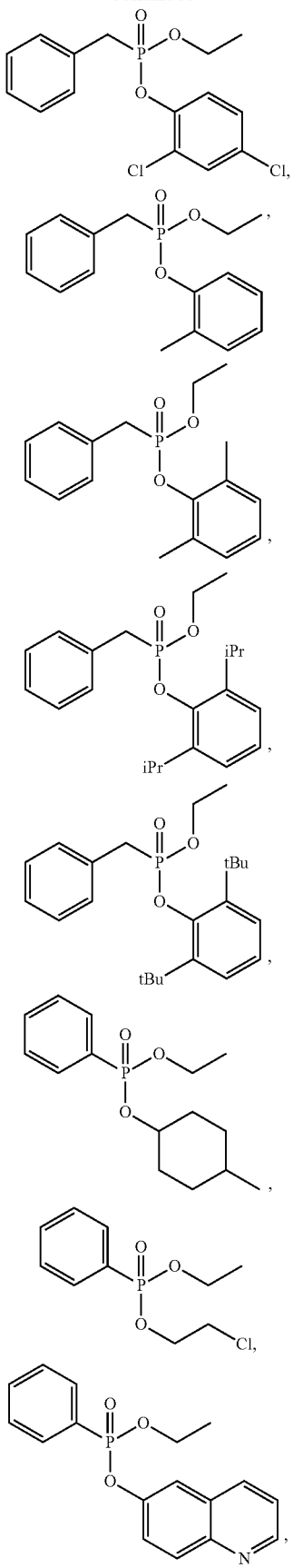

-continued

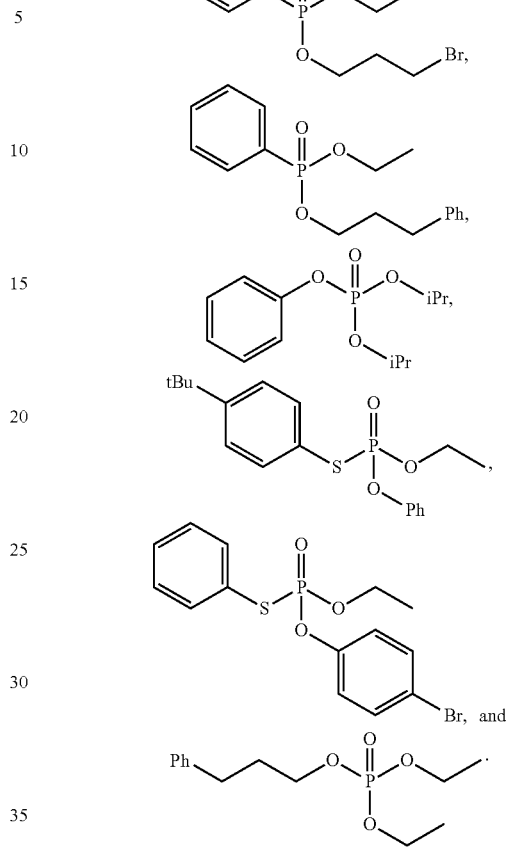

In one aspect, n is 0 or 1. In a further aspect, n is 0. In a still further aspect, n is 1.

a. A Groups

In one aspect, wherein A is selected from O, S, NR$^{20}$, and CHR$^{21}$. In a further aspect, A is selected from O, S, NH, N(CH$_3$), CH$_2$, and CH(CH$_3$).

In a further aspect, A is selected from O, S, and NR$^{20}$. In a still further aspect, A is selected from O and NR$^{20}$. In yet a further aspect, A is selected from S and NR$^{20}$. In an even further aspect, A is selected from O and S.

In a further aspect, A is selected from O, S, and CHR$^{21}$. In a still further aspect, A is selected from O and CHR$^{21}$. In yet a further aspect, A is selected from S and CHR$^{21}$.

In a further aspect, A is O. In a still further aspect, A is S.

In a further aspect, A is selected from NR$^{20}$ and CHR$^{21}$. In a still further aspect, A is selected from NH, N(CH$_3$), CH$_2$, and CH(CH$_3$). In yet a further aspect, A is selected from NH and CH$_2$. In an even further aspect, A is selected from N(CH$_3$) and CH(CH$_3$).

In a further aspect, A is NR$^{20}$. In a still further aspect, A is CHR$^{21}$.

b. Q Groups

In one aspect, wherein Q is selected from O, S, and NR$^{22}$. In a further aspect, Q is selected from O, S, NH, and N(CH$_3$).

In a further aspect, Q is selected from O and NR$^{22}$. In yet a further aspect, Q is selected from S and NR$^{22}$. In an even further aspect, Q is selected from O and S.

In a further aspect, Q is O. In a still further aspect, Q is S.

In a further aspect, Q is NR²².

c. Z Groups

In one aspect, Z is selected from O, S, and NR²³. In a further aspect, Z is selected from O, S, NH, and N(CH₃).

In a further aspect, Z is selected from O and NR²³. In yet a further aspect, Z is selected from S and NR²³. In an even further aspect, Z is selected from O and S.

In a further aspect, Z is O. In a still further aspect, Z is S. In a further aspect, Z is NR²³.

d. R¹ Groups

In one aspect, R¹ is selected from C1-C8 alkyl, C2-C10 alkenyl, C1-C8 haloalkyl, C3-C6 cycloalkyl, —(C1-C4 alkyl)Ar¹, —(C2-C4 alkenyl)Ar¹, —(C2-C4 alkynyl)Ar¹, Ar¹, and a structure represented by a formula selected from:

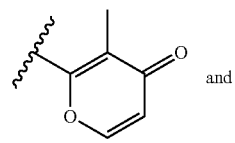
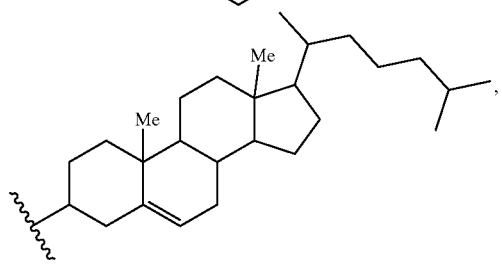

and wherein the C3-C6 cycloalkyl, when present, is substituted with 0 or 1 C1-C4 alkyl group. In a further aspect, R¹ is selected from C1-C4 alkyl, C2-C4 alkenyl, C1-C4 haloalkyl, C3-C6 cycloalkyl, —(C1-C4 alkyl)Ar¹, —(C2-C4 alkenyl)Ar¹, —(C2-C4 alkynyl)Ar¹, Ar¹, and a structure represented by a formula selected from:

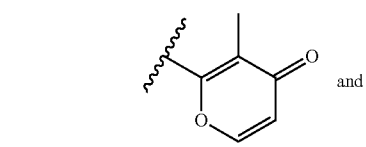
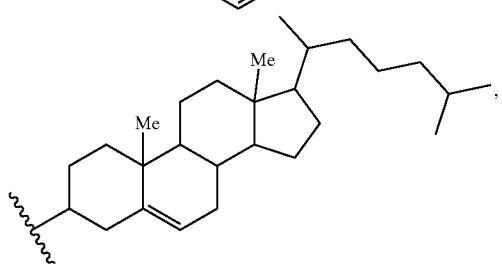

and wherein the C3-C6 cycloalkyl, when present, is substituted with 0 or 1 C1-C4 alkyl group.

In one aspect, each of R¹ and R²⁰, when present, are optionally covalently bonded together and, together with the intermediate carbon atoms, comprise a 3- to 6-membered heterocycloalkyl.

In a further aspect, R¹ is selected from —(C1-C4 alkyl)Ar¹, —(C2-C4 alkenyl)Ar¹, —(C2-C4 alkynyl)Ar¹, Ar¹, and a structure represented by a formula selected from:

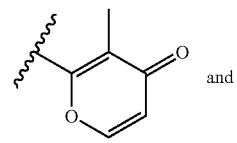
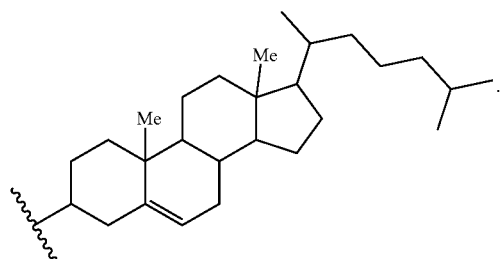

In a further aspect, R¹ is selected from —(C1-C4 alkyl)Ar¹, —(C2-C4 alkenyl)Ar¹, —(C2-C4 alkynyl)Ar¹, and Ar¹. In a still further aspect, R¹ is selected from —CH₂Ar¹, —CH₂CH₂Ar¹, —CH(CH₃)Ar¹, —CH=CHAr¹, —CH=CHCH₂Ar¹, —(C2-C3 alkynyl)Ar¹, and Ar¹. In yet a further aspect, R¹ is selected from —CH₂Ar¹, —CH=CHAr¹, —(C2 alkynyl)Ar¹, and Ar¹.

In a further aspect, R¹ is selected from —(C1-C4 alkyl)Ar¹ and Ar¹.

In a further aspect, R¹ is Ar¹. In a still further aspect, R¹ is —(C2-C4 alkynyl)Ar¹. In yet a further aspect, selected from R¹ is —(C2-C4 alkenyl)Ar¹. In an even further aspect, R¹ is —(C1-C4 alkyl)Ar¹.

In a further aspect, R¹ is a structure represented by a formula selected from:

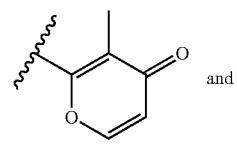
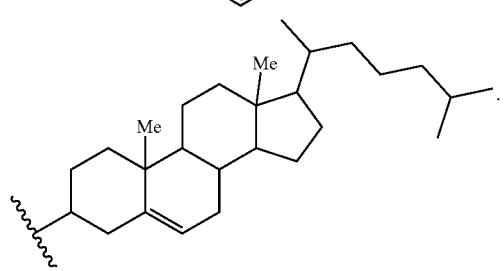

In a further aspect, R¹ is a structure represented by a formula:

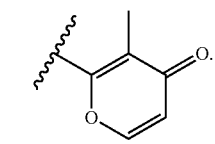 [SMILES: *c1occc(=O)c1C]

In a further aspect, R¹ is a structure represented by a formula:

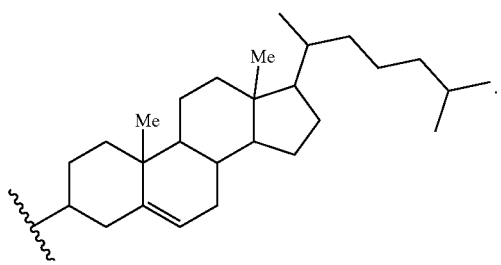 [SMILES: *C1CCC2(C)C(=CCC3C2CCC2(C)C(C(C)CCCC(C)C)CCC32)C1]

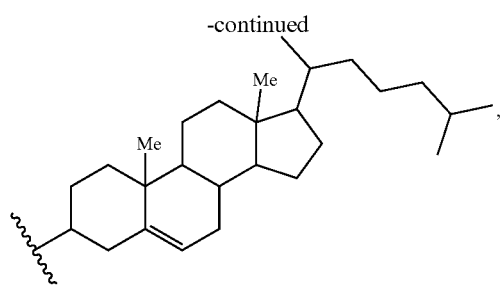

-continued

In a further aspect, R¹ is selected from C1-C8 alkyl, C2-C10 alkenyl, C1-C8 haloalkyl, and C3-C6 cycloalkyl. In a still further aspect, R¹ is selected from C1-C4 alkyl, C2-C4 alkenyl, C1-C4 haloalkyl, and C3-C6 cycloalkyl. In yet a further aspect, R¹ is selected from methyl, ethyl, n-propyl, isopropyl, ethenyl, propenyl, —CH₂F, —CHF₂, —CF₃, —CH₂CH₂F, —CH₂CH₂CH₂F, —CH(CH₃)CH₂F, —CH₂Cl, —CHCl₂, —CCl₃, —CH₂CH₂Cl, —CH₂CH₂CH₂Cl, —CH(CH₃)CH₂Cl, cyclopropyl, cyclobutyl, cyclopentyl, and cyclohexyl. In an even further aspect, R¹ is selected from methyl, ethyl, ethenyl, —CH₂F, —CHF₂, —CF₃, —CH₂CH₂F, —CH₂Cl, —CHCl₂, —CCl₃, —CH₂CH₂Cl, cyclopropyl, cyclobutyl, and cyclopentyl. In a still further aspect, R¹ is selected from methyl, —CH₂F, —CHF₂, —CF₃, —CH₂Cl, —CHCl₂, —CCl₃, cyclopropyl, and cyclobutyl.

In a further aspect, R¹ is selected from C1-C8 alkyl, C2-C10 alkenyl, and C1-C8 haloalkyl. In a still further aspect, R¹ is selected from C1-C4 alkyl, C2-C4 alkenyl, and C1-C4 haloalkyl. In yet a further aspect, R¹ is selected from methyl, ethyl, n-propyl, isopropyl, ethenyl, propenyl, —CH₂F, —CHF₂, —CF₃, —CH₂CH₂F, —CH₂CH₂CH₂F, —CH(CH₃)CH₂F, —CH₂Cl, —CHCl₂, —CC₃, —CH₂CH₂Cl, —CH₂CH₂CH₂Cl, and —CH(CH₃)CH₂Cl. In an even further aspect, R¹ is selected from methyl, ethyl, ethenyl, —CH₂F, —CHF₂, —CF₃, —CH₂CH₂F, —CH₂Cl, —CHCl₂, —CCl₃, and —CH₂CH₂Cl. In a still further aspect, R¹ is selected from methyl, —CH₂F, —CHF₂, —CF₃, —CH₂Cl, —CHCl₂, and —CCl₃.

In a further aspect, R¹ is C3-C6 cycloalkyl substituted with 0 or 1 C1-C4 alkyl group. In a still further aspect, R¹ is C3-C6 cycloalkyl substituted with 1 C1-C4 alkyl group. In yet a further aspect, R¹ is C3-C6 cycloalkyl substituted with 1 methyl group. In an even further aspect, R¹ is unsubstituted C3-C6 cycloalkyl.

e. R² Groups

In one aspect, R² is selected from hydrogen, C1-C8 alkyl substituted with 0-1 phenyl groups, C2-C10 alkenyl, C1-C8 haloalkyl, C3-C6 cycloalkyl, —(C1-C4 alkyl)Ar², —(C2-C4 alkenyl)Ar², —(C2-C4 alkynyl)Ar², Ar², and a structure represented by a formula selected from:

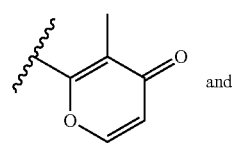

and and wherein the C3-C6 cycloalkyl, when present, is substituted with 0 or 1 C1-C4 alkyl group. In a further aspect, R² is selected from hydrogen, C1-C4 alkyl, C2-C4 alkenyl, C1-C4 haloalkyl, C3-C6 cycloalkyl, —(C1-C4 alkyl)Ar², —(C2-C4 alkenyl)Ar², —(C2-C4 alkynyl)Ar², Ar², and a structure represented by a formula selected from:

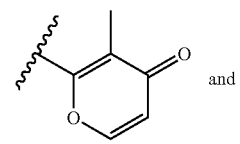

and

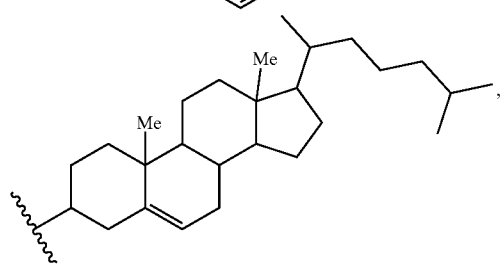

and wherein the C3-C6 cycloalkyl, when present, is substituted with 0 or 1 C1-C4 alkyl group.

In a further aspect, R² is selected from C1-C8 alkyl substituted with 0-1 phenyl groups, C2-C10 alkenyl, C1-C8 haloalkyl, C3-C6 cycloalkyl, —(C1-C4 alkyl)Ar², —(C2-C4 alkenyl)Ar², —(C2-C4 alkynyl)Ar², Ar², and a structure represented by a formula selected from:

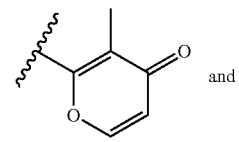

and

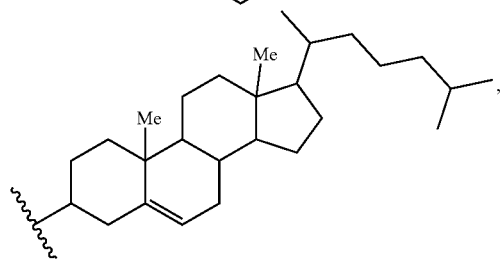

and wherein the C3-C6 cycloalkyl, when present, is substituted with 0 or 1 C1-C4 alkyl group.

In a further aspect, R² is hydrogen.

In a further aspect, R² is selected from —(C1-C4 alkyl)Ar², —(C2-C4 alkenyl)Ar², —(C2-C4 alkynyl)Ar², Ar², and a structure represented by a formula selected from:

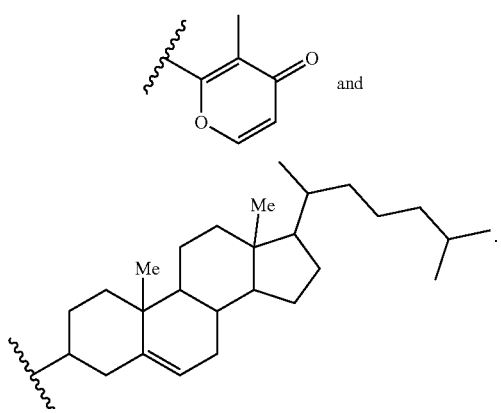

In a further aspect, $R^2$ is selected from —(C1-C4 alkyl)$Ar^2$, —(C2-C4 alkenyl)$Ar^2$, —(C2-C4 alkynyl)$Ar^2$, and $Ar^2$. In a still further aspect, $R^2$ is selected from —$CH_2Ar^2$, —$CH_2CH_2Ar^2$, —$CH(CH_3)Ar^2$, —CH=$CHAr^2$, —CH=$CHCH_2Ar^2$, —(C2-C3 alkynyl)$Ar^2$, and $Ar^2$. In yet a further aspect, $R^2$ is selected from —$CH_2Ar^2$, —CH=$CHAr^2$, —(C2 alkynyl)$Ar^2$, and $Ar^2$.

In a further aspect, $R^2$ is selected from —(C1-C4 alkyl)$Ar^2$ and $Ar^2$.

In a further aspect, $R^2$ is $Ar^2$. In a still further aspect, $R^2$ is —(C2-C4 alkynyl)$Ar^2$. In yet a further aspect, selected from $R^2$ is —(C2-C4 alkenyl)$Ar^2$. In an even further aspect, $R^2$ is —(C1-C4 alkyl)$Ar^2$.

In a further aspect, $R^2$ is a structure represented by a formula selected from:

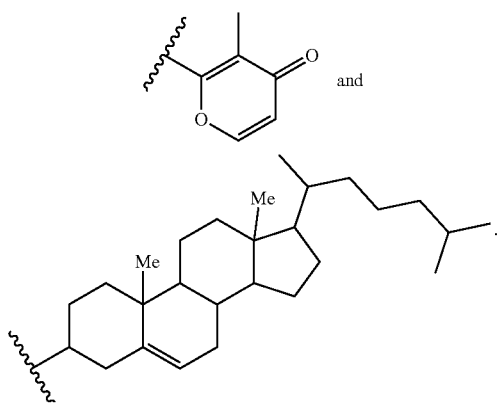

In a further aspect, $R^2$ is a structure represented by a formula:

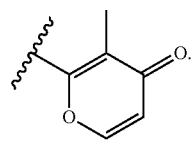 [SMILES: *c1occc(=O)c1C]

In a further aspect, $R^2$ is a structure represented by a formula:

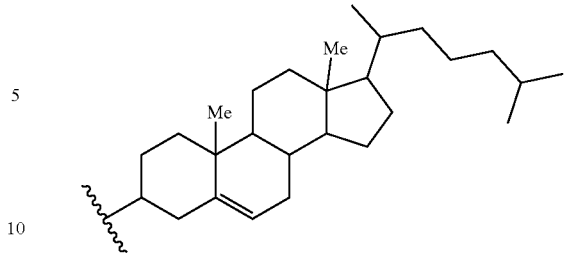

In a further aspect, $R^2$ is selected from C1-C8 alkyl, C2-C10 alkenyl, C1-C8 haloalkyl, and C3-C6 cycloalkyl. In a still further aspect, $R^2$ is selected from C1-C4 alkyl, C2-C4 alkenyl, C1-C4 haloalkyl, and C3-C6 cycloalkyl. In yet a further aspect, $R^2$ is selected from methyl, ethyl, n-propyl, isopropyl, ethenyl, propenyl, —$CH_2F$, —$CHF_2$, —$CF_3$, —$CH_2CH_2F$, —$CH_2CH_2CH_2F$, —$CH(CH_3)CH_2F$, —$CH_2Cl$, —$CHCl_2$, —$CCl_3$, —$CH_2CH_2Cl$, —$CH_2CH_2CH_2Cl$, —$CH(CH_3)CH_2Cl$, cyclopropyl, cyclobutyl, cyclopentyl, and cyclohexyl. In an even further aspect, $R^2$ is selected from methyl, ethyl, ethenyl, —$CH_2F$, —$CHF_2$, —$CF_3$, —$CH_2CH_2F$, —$CH_2Cl$, —$CHCl_2$, —$CCl_3$, —$CH_2CH_2Cl$, cyclopropyl, cyclobutyl, and cyclopentyl. In a still further aspect, $R^2$ is selected from methyl, —$CH_2F$, —$CHF_2$, —$CF_3$, —$CH_2Cl$, —$CHCl_2$, —$CCl_3$, cyclopropyl, and cyclobutyl.

In a further aspect, $R^2$ is selected from C1-C8 alkyl, C2-C10 alkenyl, and C1-C8 haloalkyl. In a still further aspect, $R^2$ is selected from C1-C4 alkyl, C2-C4 alkenyl, and C1-C4 haloalkyl. In yet a further aspect, $R^2$ is selected from methyl, ethyl, n-propyl, isopropyl, ethenyl, propenyl, —$CH_2F$, —$CHF_2$, —$CF_3$, —$CH_2CH_2F$, —$CH_2CH_2CH_2F$, —$CH(CH_3)CH_2F$, —$CH_2Cl$, —$CHCl_2$, —$CCl_3$, —$CH_2CH_2Cl$, —$CH_2CH_2CH_2Cl$, and —$CH(CH_3)CH_2Cl$. In an even further aspect, $R^2$ is selected from methyl, ethyl, ethenyl, —$CH_2F$, —$CHF_2$, —$CF_3$, —$CH_2CH_2F$, —$CH_2Cl$, —$CHCl_2$, —$CCl_3$, and —$CH_2CH_2Cl$. In a still further aspect, $R^2$ is selected from methyl, —$CH_2F$, —$CHF_2$, —$CF_3$, —$CH_2Cl$, —$CHCl_2$, and —$CCl_3$.

In a further aspect, $R^2$ is C3-C6 cycloalkyl substituted with 0 or 1 C1-C4 alkyl group. In a still further aspect, $R^2$ is C3-C6 cycloalkyl substituted with 1 C1-C4 alkyl group. In yet a further aspect, $R^2$ is C3-C6 cycloalkyl substituted with 1 methyl group. In an even further aspect, $R^2$ is unsubstituted C3-C6 cycloalkyl.

In a further aspect, $R^2$ is C1-C8 alkyl substituted with 0-1 phenyl groups. In a still further aspect, $R^2$ is C1-C8 alkyl substituted with 1 phenyl group. In yet a further aspect, $R^2$ is C1-C8 alkyl substituted with 0 phenyl groups.

f. $R^3$ Groups

In one aspect, $R^3$ is C1-C4 alkyl. In a further aspect, $R^3$ is selected from methyl, ethyl, n-propyl, and isopropyl. In a still further aspect, $R^3$ is selected from n-butyl, isobutyl, sec-butyl, and tert-butyl. In yet a further aspect, $R^3$ is selected from n-propyl and isopropyl. In an even further aspect, $R^3$ is ethyl. In a still further aspect, $R^3$ is methyl.

g. $R^4$ Groups

In one aspect, $R^4$ is C1-C4 alkyl. In a further aspect, $R^4$ is selected from methyl, ethyl, n-propyl, and isopropyl. In a still further aspect, $R^4$ is selected from n-butyl, isobutyl, sec-butyl, and tert-butyl. In yet a further aspect, $R^4$ is selected from n-propyl and isopropyl. In an even further aspect, $R^4$ is ethyl. In a still further aspect, $R^4$ is methyl.

h. $R^{20}$ Groups

In one aspect, $R^{20}$, when present, is selected from hydrogen and methyl. In a further aspect, $R^{20}$, when present, is hydrogen. In a still further aspect, $R^{20}$, when present, is methyl.

In one aspect, each of $R^1$ and $R^{20}$, when present, are optionally covalently bonded together and, together with the intermediate carbon atoms, comprise a 3- to 6-membered heterocycloalkyl. In a further aspect, each of $R^1$ and $R^{20}$, when present, are optionally covalently bonded together and, together with the intermediate carbon atoms, comprise a 4- to 6-membered heterocycloalkyl. In a still further aspect, each of $R^1$ and $R^{20}$, when present, are optionally covalently bonded together and, together with the intermediate carbon atoms, comprise a 5- to 6-membered heterocycloalkyl. In yet a further aspect, each of $R^1$ and $R^{20}$, when present, are optionally covalently bonded together and, together with the intermediate carbon atoms, comprise a 6-membered heterocycloalkyl.

i. $R^{21}$ Groups

In one aspect, $R^{21}$, when present, is selected from hydrogen and methyl. In a further aspect, $R^{21}$, when present, is hydrogen. In a still further aspect, $R^{21}$, when present, is methyl.

j. $R^{22}$ Groups

In one aspect, $R^{22}$, when present, is selected from hydrogen and C1-C8 alkyl. In a further aspect, $R^{22}$, when present, is selected from hydrogen and C1-C4 alkyl. In a still further aspect, $R^{22}$, when present, is hydrogen.

In a further aspect, $R^{22}$, when present, is C1-C8 alkyl. In a still further aspect, $R^{22}$, when present, is C1-C4 alkyl. In yet a further aspect, $R^{22}$, when present, is selected from methyl, ethyl, n-propyl, and isopropyl. In an even further aspect, $R^{22}$, when present, is selected from methyl and ethyl. In a still further aspect, $R^{22}$, when present, is ethyl. In yet a further aspect, $R^{22}$, when present, is methyl.

In a further aspect, $R^{22}$, when present, is selected from hydrogen, methyl, ethyl, n-propyl, isopropyl, n-butyl, isobutyl, sec-butyl, and tert-butyl. In a still further aspect, $R^{22}$, when present, is selected from hydrogen, methyl, ethyl, n-propyl, and isopropyl. In yet a further aspect, $R^{22}$, when present, is selected from hydrogen, methyl, and ethyl. In an even further aspect, $R^{22}$, when present, is selected from hydrogen and ethyl. In a still further aspect, $R^{22}$, when present, is selected from hydrogen and methyl.

k. $R^{23}$ Groups

In one aspect, $R^{23}$, when present, is selected from hydrogen and methyl. In a further aspect, $R^{23}$, when present, is hydrogen. In a still further aspect, $R^{23}$, when present, is methyl.

l. $R^{30}$ Groups

In one aspect, $R^{30}$, when present, is selected from hydrogen, C1-C8 alkyl, —(C1-C4 alkyl)phenyl, phenyl, and a structure represented by a formula:

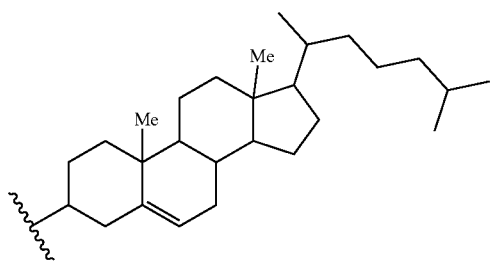

In a further aspect, $R^{30}$, when present, is selected from hydrogen, C1-C4 alkyl, —(C1-C4 alkyl)phenyl, phenyl, and a structure represented by a formula:

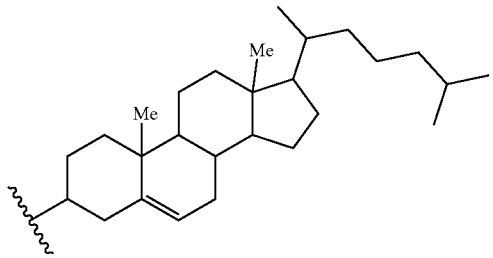

In a further aspect, $R^{30}$, when present, is a structure represented by a formula:

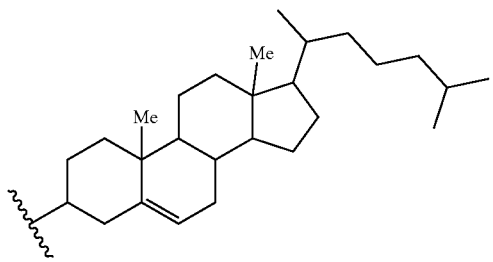

In a further aspect, $R^{30}$, when present, is selected from hydrogen, C1-C8 alkyl, —(C1-C4 alkyl)phenyl, and phenyl. In a still further aspect, $R^{30}$, when present, is selected from hydrogen, C1-C4 alkyl, —(C1-C4 alkyl)phenyl, and phenyl. In yet a further aspect, $R^{30}$ when present, is selected from hydrogen, methyl, ethyl, n-propyl, isopropyl, —(CH$_2$)phenyl, —(CH(CH$_3$))phenyl, and phenyl. In an even further aspect, $R^{30}$, when present, is selected from hydrogen, methyl, ethyl, —(CH$_2$)phenyl, —(CH(CH$_3$))phenyl, and phenyl. In a still further aspect, $R^{30}$, when present, is selected from hydrogen, methyl, —(CH$_2$)phenyl, —(CH(CH$_3$))phenyl, and phenyl.

In a further aspect, $R^{30}$, when present, is selected from —(C1-C4 alkyl)phenyl and phenyl. In a still further aspect, $R^{30}$, when present, is selected from —(CH$_2$)phenyl, —(CH(CH$_3$))phenyl, and phenyl. In an even further aspect, $R^{30}$, when present, is —(CH$_2$)phenyl. In a still further aspect, $R^{30}$, when present, is —(CH(CH$_3$))phenyl. In yet a further aspect, $R^{30}$, when present, is phenyl.

In a further aspect, $R^{30}$, when present, is selected from hydrogen and C1-C8 alkyl. In a still further aspect, $R^{30}$, when present, is selected from hydrogen and C1-C4 alkyl. In yet a further aspect, $R^{30}$, when present, is selected from hydrogen, methyl, ethyl, n-propyl, and isopropyl. In an even further aspect, $R^{30}$, when present, is selected from hydrogen, methyl, and ethyl. In a still further aspect, $R^{30}$, when present, is selected from hydrogen and ethyl. In yet a further aspect, $R^{30}$, when present, is selected from hydrogen and methyl.

In a further aspect, $R^{30}$, when present, is C1-C8 alkyl. In a still further aspect, $R^{30}$ when present, is C1-C4 alkyl. In yet a further aspect, $R^{30}$, when present, is selected from methyl, ethyl, n-propyl, and isopropyl. In an even further aspect, $R^{30}$, when present, is selected from methyl and ethyl. In a still further aspect, $R^{30}$, when present, is ethyl. In yet a further aspect, $R^{30}$, when present, is methyl.

In a further aspect, $R^{30}$, when present, is hydrogen.

m. $R^{31a}$ and $R^{31b}$ Groups

In one aspect, each of $R^{31a}$ and $R^{31b}$, when present, is independently selected from hydrogen, C1-C8 alkyl, —(C1-C4 alkyl)phenyl, and phenyl. In a further aspect, each of $R^{31a}$ and $R^{31b}$, when present, is selected from hydrogen, C1-C4 alkyl, —(C1-C4 alkyl)phenyl, and phenyl.

In a further aspect, each of $R^{31a}$ and $R^{31b}$, when present, is selected from hydrogen, C1-C8 alkyl, —(C1-C4 alkyl)phenyl, and phenyl. In a still further aspect, each of $R^{31a}$ and $R^{31b}$, when present, is selected from hydrogen, C1-C4 alkyl, —(C1-C4 alkyl)phenyl, and phenyl. In yet a further aspect, each of $R^{31a}$ and $R^{31b}$, when present, is selected from hydrogen, methyl, ethyl, n-propyl, isopropyl, —(CH$_2$)phenyl, —(CH(CH$_3$))phenyl, and phenyl. In an even further aspect, each of $R^{31a}$ and $R^{31b}$, when present, is selected from hydrogen, methyl, ethyl, —(CH$_2$)phenyl, —(CH(CH$_3$))phenyl, and phenyl. In a still further aspect, each of $R^{31a}$ and $R^{31b}$, when present, is selected from hydrogen, methyl, —(CH$_2$)phenyl, —(CH(CH$_3$))phenyl, and phenyl.

In a further aspect, each of $R^{31a}$ and $R^{31b}$, when present, is selected from —(C1-C4 alkyl)phenyl and phenyl. In a still further aspect, each of $R^{31a}$ and $R^{31b}$, when present, is selected from —(CH$_2$)phenyl, —(CH(CH$_3$))phenyl, and phenyl. In an even further aspect, each of $R^{31a}$ and $R^{31b}$, when present, is —(CH$_2$)phenyl. In a still further aspect, each of $R^{31a}$ and $R^{31b}$, when present, is —(CH(CH$_3$))phenyl. In yet a further aspect, each of $R^{31a}$ and $R^{31b}$, when present, is phenyl.

In a further aspect, each of $R^{31a}$ and $R^{31b}$, when present, is selected from hydrogen and C1-C8 alkyl. In a still further aspect, each of $R^{31a}$ and $R^{31b}$, when present, is selected from hydrogen and C1-C4 alkyl. In yet a further aspect, each of $R^{31a}$ and $R^{31b}$, when present, is selected from hydrogen, methyl, ethyl, n-propyl, and isopropyl. In an even further aspect, each of $R^{31a}$ and $R^{31b}$, when present, is selected from hydrogen, methyl, and ethyl. In a still further aspect, each of $R^{31a}$ and $R^{31b}$, when present, is selected from hydrogen and ethyl. In yet a further aspect, each of $R^{31a}$ and $R^{31b}$, when present, is selected from hydrogen and methyl.

In a further aspect, each of $R^{31a}$ and $R^{31b}$, when present, is C1-C8 alkyl. In a still further aspect, each of $R^{31a}$ and $R^{31b}$, when present, is C1-C4 alkyl. In yet a further aspect, each of $R^{31a}$ and $R^{31b}$, when present, is selected from methyl, ethyl, n-propyl, and isopropyl. In an even further aspect, each of $R^{31a}$ and $R^{31b}$, when present, is selected from methyl and ethyl. In a still further aspect, each of $R^{31a}$ and $R^{31b}$, when present, is ethyl. In yet a further aspect, each of $R^{31a}$ and $R^{31b}$, when present, is methyl.

In a further aspect, each of $R^{31a}$ and $R^{31b}$, when present, is hydrogen.

n. $R^{32}$ Groups

In one aspect, $R^{32}$, when present, is selected from hydrogen, C1-C4 alkyl, and phenyl. In a further aspect, $R^{32}$, when present, is hydrogen.

In a further aspect, $R^{32}$, when present, is selected from hydrogen, methyl, ethyl, n-propyl, isopropyl, and phenyl. In a still further aspect, $R^{32}$, when present, is selected from hydrogen, methyl, ethyl, and phenyl. In yet a further aspect, $R^{32}$, when present, is selected from hydrogen, methyl, and phenyl.

In a further aspect, $R^{32}$, when present, is selected from hydrogen and C1-C4 alkyl. In a still further aspect, $R^{32}$, when present, is selected from hydrogen, methyl, ethyl, n-propyl, and isopropyl. In yet a further aspect, $R^{32}$, when present, is selected from hydrogen, methyl, and ethyl. In an even further aspect, $R^{32}$, when present, is selected from hydrogen and ethyl. In a still further aspect, $R^{32}$, when present, is selected from hydrogen and methyl.

In a further aspect, $R^{32}$, when present, is phenyl.

o. $R^{33}$ Groups

In one aspect, $R^{33}$, when present, is selected from hydrogen, C1-C8 alkyl, —(C1-C4 alkyl)phenyl, phenyl, and a structure represented by a formula:

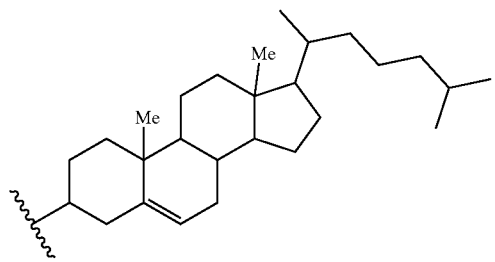

In a further aspect, $R^{33}$, when present, is selected from hydrogen, C1-C4 alkyl, —(C1-C4 alkyl)phenyl, phenyl, and a structure represented by a formula:

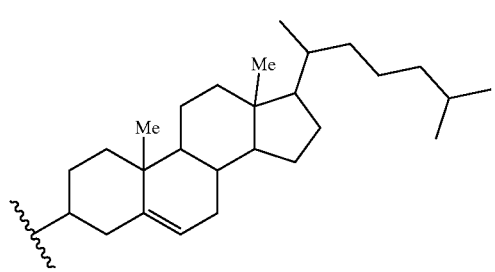

In a further aspect, $R^{33}$, when present, is a structure represented by a formula:

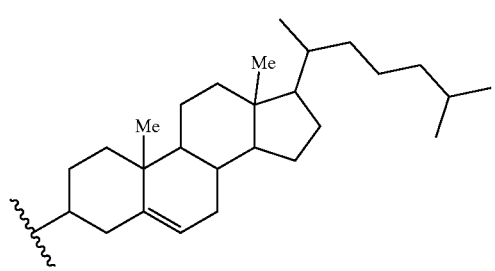

In a further aspect, $R^{33}$, when present, is selected from hydrogen, C1-C8 alkyl, —(C1-C4 alkyl)phenyl, and phenyl. In a still further aspect, $R^{33}$, when present, is selected from hydrogen, C1-C4 alkyl, —(C1-C4 alkyl)phenyl, and phenyl. In yet a further aspect, $R^{33}$ when present, is selected from hydrogen, methyl, ethyl, n-propyl, isopropyl, —(CH$_2$)phenyl, —(CH(CH$_3$))phenyl, and phenyl. In an even further aspect, $R^{33}$, when present, is selected from hydrogen, methyl, ethyl, —(CH$_2$)phenyl, —(CH(CH$_3$))phenyl, and phenyl. In a still further aspect, $R^{33}$, when present, is selected from hydrogen, methyl, —(CH$_2$)phenyl, —(CH(CH$_3$))phenyl, and phenyl.

In a further aspect, $R^{33}$, when present, is selected from —(C1-C4 alkyl)phenyl and phenyl. In a still further aspect, $R^{33}$, when present, is selected from —(CH$_2$)phenyl, —(CH (CH$_3$))phenyl, and phenyl. In an even further aspect, R$^{33}$, when present, is —(CH$_2$)phenyl. In a still further aspect, R$^{33}$, when present, is —(CH(CH$_3$))phenyl. In yet a further aspect, R$^{33}$, when present, is phenyl.

In a further aspect, R$^{33}$, when present, is selected from hydrogen and C1-C8 alkyl. In a still further aspect, R$^{33}$, when present, is selected from hydrogen and C1-C4 alkyl. In yet a further aspect, R$^{33}$, when present, is selected from hydrogen, methyl, ethyl, n-propyl, and isopropyl. In an even further aspect, R$^{33}$, when present, is selected from hydrogen, methyl, and ethyl. In a still further aspect, R$^{33}$, when present, is selected from hydrogen and ethyl. In yet a further aspect, R$^{33}$, when present, is selected from hydrogen and methyl.

In a further aspect, R$^{33}$, when present, is C1-C8 alkyl. In a still further aspect, R$^{33}$, when present, is C1-C4 alkyl. In yet a further aspect, R$^{33}$, when present, is selected from methyl, ethyl, n-propyl, and isopropyl. In an even further aspect, R$^{33}$, when present, is selected from methyl and ethyl. In a still further aspect, R$^{33}$, when present, is ethyl. In yet a further aspect, R$^{33}$, when present, is methyl.

In a further aspect, R$^{33}$, when present, is hydrogen.

p. R$^{34a}$ and R$^{34b}$ Groups

In one aspect, each of R$^{34a}$ and R$^{34b}$, when present, is independently selected from hydrogen, C1-C8 alkyl, —(C1-C4 alkyl)phenyl, and phenyl. In a further aspect, each of R$^{34a}$ and R$^{34b}$, when present, is selected from hydrogen, C1-C4 alkyl, —(C1-C4 alkyl)phenyl, and phenyl.

In a further aspect, each of R$^{34a}$ and R$^{34b}$, when present, is selected from hydrogen, C1-C8 alkyl, —(C1-C4 alkyl)phenyl, and phenyl. In a still further aspect, each of R$^{34a}$ and R$^{34b}$, when present, is selected from hydrogen, C1-C4 alkyl, —(C1-C4 alkyl)phenyl, and phenyl. In yet a further aspect, each of R$^{34a}$ and R$^{34b}$, when present, is selected from hydrogen, methyl, ethyl, n-propyl, isopropyl, —(CH$_2$)phenyl, —(CH(CH$_3$))phenyl, and phenyl. In an even further aspect, each of R$^{34a}$ and R$^{34b}$, when present, is selected from hydrogen, methyl, ethyl, —(CH$_2$)phenyl, —(CH(CH$_3$))phenyl, and phenyl. In a still further aspect, each of R$^{34a}$ and R$^{34b}$, when present, is selected from hydrogen, methyl, —(CH$_2$)phenyl, —(CH(CH$_3$))phenyl, and phenyl.

In a further aspect, each of R$^{34a}$ and R$^{34b}$, when present, is selected from —(C1-C4 alkyl)phenyl and phenyl. In a still further aspect, each of R$^{34a}$ and R$^{34b}$, when present, is selected from —(CH$_2$)phenyl, —(CH(CH$_3$))phenyl, and phenyl. In an even further aspect, each of R$^{34a}$ and R$^{34b}$, when present, is —(CH$_2$)phenyl. In a still further aspect, each of R$^{34a}$ and R$^{34b}$, when present, is —(CH(CH$_3$)) phenyl. In yet a further aspect, each of R$^{34a}$ and R$^{34b}$, when present, is phenyl.

In a further aspect, each of R$^{34a}$ and R$^{34b}$, when present, is selected from hydrogen and C1-C8 alkyl. In a still further aspect, each of R$^{34a}$ and R$^{34b}$, when present, is selected from hydrogen and C1-C4 alkyl. In yet a further aspect, each of R$^{34a}$ and R$^{34b}$, when present, is selected from hydrogen, methyl, ethyl, n-propyl, and isopropyl. In an even further aspect, each of R$^{34a}$ and R$^{34b}$, when present, is selected from hydrogen, methyl, and ethyl. In a still further aspect, each of R$^{34a}$ and R$^{34b}$, when present, is selected from hydrogen and ethyl. In yet a further aspect, each of R$^{34a}$ and R$^{34b}$, when present, is selected from hydrogen and methyl.

In a further aspect, each of R$^{34a}$ and R$^{34b}$, when present, is C1-C8 alkyl. In a still further aspect, each of R$^{34a}$ and R$^{34b}$, when present, is C1-C4 alkyl. In yet a further aspect, each of R$^{34a}$ and R$^{34b}$, when present, is selected from methyl, ethyl, n-propyl, and isopropyl. In an even further aspect, each of R$^{34a}$ and R$^{34b}$, when present, is selected from methyl and ethyl. In a still further aspect, each of R$^{34a}$ and R$^{34b}$, when present, is ethyl. In yet a further aspect, each of R$^{34a}$ and R$^{34b}$, when present, is methyl.

In a further aspect, each of R$^{34a}$ and R$^{34b}$, when present, is hydrogen.

q. R$^{35}$ Groups

In one aspect, R$^{35}$, when present, is selected from hydrogen, C1-C4 alkyl, and phenyl. In a further aspect, R$^{35}$, when present, is hydrogen.

In a further aspect, R$^{35}$, when present, is selected from hydrogen, methyl, ethyl, n-propyl, isopropyl, and phenyl. In a still further aspect, R$^{35}$, when present, is selected from hydrogen, methyl, ethyl, and phenyl. In yet a further aspect, R$^{35}$, when present, is selected from hydrogen, methyl, and phenyl.

In a further aspect, R$^{35}$, when present, is selected from hydrogen and C1-C4 alkyl. In a still further aspect, R$^{35}$, when present, is selected from hydrogen, methyl, ethyl, n-propyl, and isopropyl. In yet a further aspect, R$^{35}$, when present, is selected from hydrogen, methyl, and ethyl. In an even further aspect, R$^{35}$, when present, is selected from hydrogen and ethyl. In a still further aspect, R$^{35}$, when present, is selected from hydrogen and methyl.

In a further aspect, R$^{35}$, when present, is phenyl.

r. R$^{36}$ Groups

In one aspect, R$^{36}$, when present, is selected from hydrogen, C1-C8 alkyl, —(C1-C4 alkyl)phenyl, phenyl, and a structure represented by a formula:

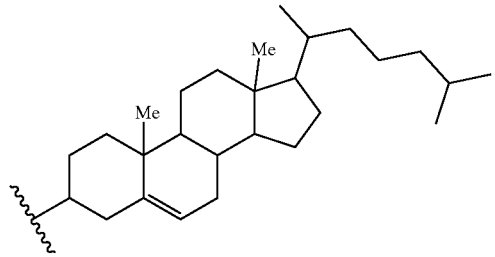

In a further aspect, R$^{36}$, when present, is selected from hydrogen, C1-C4 alkyl, —(C1-C4 alkyl)phenyl, phenyl, and a structure represented by a formula:

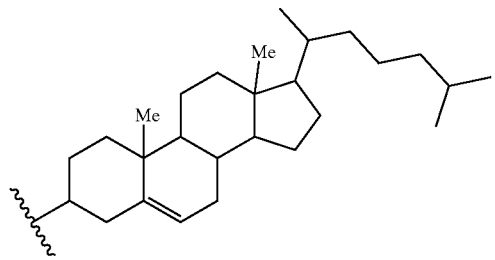

In a further aspect, R$^{36}$, when present, is a structure represented by a formula:

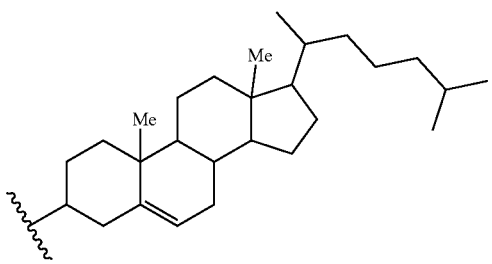

In a further aspect, $R^{36}$, when present, is selected from hydrogen, C1-C8 alkyl, —(C1-C4 alkyl)phenyl, and phenyl. In a still further aspect, $R^{36}$, when present, is selected from hydrogen, C1-C4 alkyl, —(C1-C4 alkyl)phenyl, and phenyl. In yet a further aspect, $R^{36}$ when present, is selected from hydrogen, methyl, ethyl, n-propyl, isopropyl, —(CH$_2$)phenyl, —(CH(CH$_3$))phenyl, and phenyl. In an even further aspect, $R^{36}$, when present, is selected from hydrogen, methyl, ethyl, —(CH$_2$)phenyl, —(CH(CH$_3$))phenyl, and phenyl. In a still further aspect, $R^{36}$, when present, is selected from hydrogen, methyl, —(CH$_2$)phenyl, —(CH(CH$_3$))phenyl, and phenyl.

In a further aspect, $R^{36}$, when present, is selected from —(C1-C4 alkyl)phenyl and phenyl. In a still further aspect, $R^{36}$, when present, is selected from —(CH$_2$)phenyl, —(CH(CH$_3$))phenyl, and phenyl. In an even further aspect, $R^{36}$, when present, is —(CH$_2$)phenyl. In a still further aspect, $R^{36}$, when present, is —(CH(CH$_3$))phenyl. In yet a further aspect, $R^{36}$, when present, is phenyl.

In a further aspect, $R^{36}$, when present, is selected from hydrogen and C1-C8 alkyl. In a still further aspect, $R^{36}$, when present, is selected from hydrogen and C1-C4 alkyl. In yet a further aspect, $R^{36}$, when present, is selected from hydrogen, methyl, ethyl, n-propyl, and isopropyl. In an even further aspect, $R^{36}$, when present, is selected from hydrogen, methyl, and ethyl. In a still further aspect, $R^{36}$, when present, is selected from hydrogen and ethyl. In yet a further aspect, $R^{36}$, when present, is selected from hydrogen and methyl.

In a further aspect, $R^{36}$, when present, is C1-C8 alkyl. In a still further aspect, $R^{36}$ when present, is C1-C4 alkyl. In yet a further aspect, $R^{36}$, when present, is selected from methyl, ethyl, n-propyl, and isopropyl. In an even further aspect, $R^{36}$, when present, is selected from methyl and ethyl. In a still further aspect, $R^{36}$, when present, is ethyl. In yet a further aspect, $R^{36}$, when present, is methyl.

In a further aspect, $R^{36}$, when present, is hydrogen.

s. $R^{37a}$ and $R^{37b}$ Groups

In one aspect, each of $R^{37a}$ and $R^{37b}$, when present, is independently selected from hydrogen, C1-C8 alkyl, —(C1-C4 alkyl)phenyl, and phenyl. In a further aspect, each of $R^{37a}$ and $R^{37b}$, when present, is selected from hydrogen, C1-C4 alkyl, —(C1-C4 alkyl)phenyl, and phenyl.

In a further aspect, each of $R^{37a}$ and $R^{37b}$, when present, is selected from hydrogen, C1-C8 alkyl, —(C1-C4 alkyl)phenyl, and phenyl. In a still further aspect, each of $R^{37a}$ and $R^{37b}$, when present, is selected from hydrogen, C1-C4 alkyl, —(C1-C4 alkyl)phenyl, and phenyl. In yet a further aspect, each of $R^{37a}$ and $R^{37b}$, when present, is selected from hydrogen, methyl, ethyl, n-propyl, isopropyl, —(CH$_2$)phenyl, —(CH(CH$_3$))phenyl, and phenyl. In an even further aspect, each of $R^{37a}$ and $R^{37b}$, when present, is selected from hydrogen, methyl, ethyl, —(CH$_2$)phenyl, —(CH(CH$_3$))phenyl, and phenyl. In a still further aspect, each of $R^{37a}$ and $R^{37b}$, when present, is selected from hydrogen, methyl, —(CH$_2$)phenyl, —(CH(CH$_3$))phenyl, and phenyl.

In a further aspect, each of $R^{37a}$ and $R^{37b}$, when present, is selected from —(C1-C4 alkyl)phenyl and phenyl. In a still further aspect, each of $R^{37a}$ and $R^{37b}$, when present, is selected from —(CH$_2$)phenyl, —(CH(CH$_3$))phenyl, and phenyl. In an even further aspect, each of $R^{37a}$ and $R^{37b}$, when present, is —(CH$_2$)phenyl. In a still further aspect, each of $R^{37a}$ and $R^{37b}$, when present, is —(CH(CH$_3$))phenyl. In yet a further aspect, each of $R^{37a}$ and $R^{37b}$, when present, is phenyl.

In a further aspect, each of $R^{37a}$ and $R^{37b}$, when present, is selected from hydrogen and C1-C8 alkyl. In a still further aspect, each of $R^{37a}$ and $R^{37b}$, when present, is selected from hydrogen and C1-C4 alkyl. In yet a further aspect, each of $R^{37a}$ and $R^{37b}$, when present, is selected from hydrogen, methyl, ethyl, n-propyl, and isopropyl. In an even further aspect, each of $R^{37a}$ and $R^{37b}$, when present, is selected from hydrogen, methyl, and ethyl. In a still further aspect, each of $R^{37a}$ and $R^{37b}$, when present, is selected from hydrogen and ethyl. In yet a further aspect, each of $R^{37a}$ and $R^{37b}$, when present, is selected from hydrogen and methyl.

In a further aspect, each of $R^{37a}$ and $R^{37b}$, when present, is C1-C8 alkyl. In a still further aspect, each of $R^{37a}$ and $R^{37b}$, when present, is C1-C4 alkyl. In yet a further aspect, each of $R^{37a}$ and $R^{37b}$, when present, is selected from methyl, ethyl, n-propyl, and isopropyl. In an even further aspect, each of $R^{37a}$ and $R^{37b}$, when present, is selected from methyl and ethyl. In a still further aspect, each of $R^{37a}$ and $R^{37b}$, when present, is ethyl. In yet a further aspect, each of $R^{37a}$ and $R^{37b}$, when present, is methyl.

In a further aspect, each of $R^{37a}$ and $R^{37b}$, when present, is hydrogen.

t. $R^{38}$ Groups

In one aspect, $R^{38}$, when present, is selected from hydrogen, C1-C4 alkyl, and phenyl. In a further aspect, $R^{38}$, when present, is hydrogen.

In a further aspect, $R^{38}$, when present, is selected from hydrogen, methyl, ethyl, n-propyl, isopropyl, and phenyl. In a still further aspect, $R^{38}$, when present, is selected from hydrogen, methyl, ethyl, and phenyl. In yet a further aspect, $R^{38}$, when present, is selected from hydrogen, methyl, and phenyl.

In a further aspect, $R^{38}$, when present, is selected from hydrogen and C1-C4 alkyl. In a still further aspect, $R^{38}$, when present, is selected from hydrogen, methyl, ethyl, n-propyl, and isopropyl. In yet a further aspect, $R^{38}$, when present, is selected from hydrogen, methyl, and ethyl. In an even further aspect, $R^{38}$, when present, is selected from hydrogen and ethyl. In a still further aspect, $R^{38}$, when present, is selected from hydrogen and methyl.

In a further aspect, $R^{38}$, when present, is phenyl.

u. $R^{40a}$, $R^{40b}$, $R^{40c}$, $R^{40d}$, and $R^{40e}$ Groups

In one aspect, each of $R^{40a}$, $R^{40b}$, $R^{40c}$, $R^{40d}$, and $R^{40e}$ is independently selected from hydrogen, halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO$_2$R$^{30}$, —CO$_2$R$^{30}$, —(C1-C4 alkyl)CO$_2$R$^{30}$, —(C2-C4 alkenyl)CO$_2$R$^{30}$, —(C=O)(C1-C4 alkyl), —(S=O)(C1-C4 alkyl), —SO$_2$(C1-C4 alkyl), —(C=O)NR$^{31a}$R$^{31b}$SO$_2$NR$^{31a}$R$^{31b}$, —O(C=O)NR$^{31a}$R$^{31b}$, —NHSO$_2$NR$^{31a}$R$^{31b}$, —NH(C=O)NR$^{31a}$R$^{31b}$, and —N=NR$^{32}$.

In a further aspect, each of $R^{40a}$, $R^{40b}$, $R^{40c}$, $R^{40d}$, and $R^{40e}$ is independently selected from hydrogen, —O(C2-C4 alkenyl), —OCO$_2$R$^{30}$, —(C1-C4 alkyl)CO$_2$R$^{30}$, —(C2-C4 alkenyl)CO$_2$R$^{30}$, and —N=NR$^{32}$.

In a further aspect, each of $R^{40a}$, $R^{40b}$, $R^{40c}$, $R^{40d}$, and $R^{40e}$ is independently selected from hydrogen, —F, —Cl, —NO$_2$, —CN, —OH, —SH, —NH$_2$, methyl, ethyl, propyl, ethenyl, propenyl, ethynyl, propynyl, —CH$_2$F, —CHF$_2$, —CF$_3$, —CH$_2$CH$_2$F, —CH$_2$Cl, —CHCl$_2$, —CCl$_3$, —CH$_2$CH$_2$Cl, —CH$_2$CN, —CH$_2$CH$_2$CN, —CH$_2$OH, —CH$_2$CH$_2$OH, —OCH$_2$F, —OCHF$_2$, —OCF$_3$, —OCH$_3$, —OCH$_2$CH$_3$, —SCH$_3$, —SCH$_2$CH$_3$, —CH$_2$OCH$_3$, —CH$_2$CH$_2$OCH$_2$CH$_3$, —CH$_2$NH$_2$, —CH$_2$CH$_2$NH$_2$, —NHCH$_3$, —NHCH$_2$CH$_3$, —N(CH$_3$)$_2$, —NH(CH$_2$CH$_3$)$_2$, cyclopropyl, cyclobutyl, cyclopentyl, phenyl, —(C=O)CH$_3$, —(C=O)CH$_2$CH$_3$, —(S=O)CH$_3$, —(S=O)CH$_2$CH$_3$, —SO$_2$CH$_3$, —SO$_2$CH$_2$CH$_3$, —CO$_2$CH$_3$, —CO$_2$CH$_2$CH$_3$, —(C=O)NH$_2$, —(C=O)NHCH$_3$, —(C=O)N(CH$_3$)$_2$, —SO$_2$NH$_2$, —SO$_2$NHCH$_3$, —SO$_2$N(CH$_3$)$_2$, —O(C=O)NH$_2$, —O(C=O)NHCH$_3$, —O(C=O)N(CH$_3$)$_2$, —NHSO$_2$NH$_2$, —NHSO$_2$NHCH$_3$, —NHSO$_2$N(CH$_3$)$_2$, —NH(C=O)NH$_2$, —NH(C=O)NHCH$_3$, and —NH(C=O)N(CH$_3$)$_2$. In a still further aspect, each of $R^{40a}$, $R^{40b}$, $R^{40c}$, $R^{40d}$, and $R^{40e}$ is independently selected from hydrogen, —F, —Cl, —NO$_2$, —CN, —OH, —SH, —NH$_2$, methyl, ethyl, ethenyl, ethynyl, —CH$_2$F, —CHF$_2$, —CF$_3$, —CH$_2$Cl, —CHCl$_2$, —CCl$_3$, —CH$_2$CN, —CH$_2$OH, —OCH$_2$F, —OCHF$_2$, —OCF$_3$, —OCH$_3$, —SCH$_3$, —CH$_2$OCH$_3$, —CH$_2$NH$_2$, —NHCH$_3$, —N(CH$_3$)$_2$, cyclopropyl, cyclobutyl, phenyl, —(C=O)CH$_3$, —(S=O)CH$_3$, —SO$_2$CH$_3$, —CO$_2$CH$_3$, —(C=O)NH$_2$, —(C=O)NHCH$_3$, —(C=O)N(CH$_3$)$_2$, —SO$_2$NH$_2$, —SO$_2$NHCH$_3$, —SO$_2$N(CH$_3$)$_2$, —O(C=O)NH$_2$, —O(C=O)NHCH$_3$, —O(C=O)N(CH$_3$)$_2$, —NHSO$_2$NH$_2$, —NHSO$_2$NHCH$_3$, —NHSO$_2$N(CH$_3$)$_2$, —NH(C=O)NH$_2$, —NH(C=O)NHCH$_3$, and —NH(C=O)N(CH$_3$)$_2$. In yet a further aspect, each of $R^{40a}$, $R^{40b}$, $R^{40c}$, $R^{40d}$, and $R^{40e}$ is independently selected from hydrogen, —F, —Cl, —NO$_2$, —CN, —OH, —SH, —NH$_2$, methyl, —CH$_2$F, —CHF$_2$, —CF$_3$, —CH$_2$Cl, —CHCl$_2$, —CCl$_3$, —CH$_2$CN, —CH$_2$OH, —OCH$_2$F, —OCHF$_2$, —OCF$_3$, —OCH$_3$, —SCH$_3$, —CH$_2$OCH$_3$, —CH$_2$NH$_2$, —NHCH$_3$, —N(CH$_3$)$_2$, cyclopropyl, phenyl, —(C=O)CH$_3$, —(S=O)CH$_3$, —SO$_2$CH$_3$, —CO$_2$CH$_3$, —(C=O)NH$_2$, —(C=O)NHCH$_3$, —(C=O)N(CH$_3$)$_2$, —SO$_2$NH$_2$, —SO$_2$NHCH$_3$, —SO$_2$N(CH$_3$)$_2$, —O(C=O)NH$_2$, —O(C=O)NHCH$_3$, —O(C=O)N(CH$_3$)$_2$, —NHSO$_2$NH$_2$, —NHSO$_2$NHCH$_3$, —NHSO$_2$N(CH$_3$)$_2$, —NH(C=O)NH$_2$, —NH(C=O)NHCH$_3$, and —NH(C=O)N(CH$_3$)$_2$.

In a further aspect, each of $R^{40a}$, $R^{40b}$, $R^{40c}$, $R^{40d}$, and $R^{40e}$ is independently selected from hydrogen and C6-C10 aryl. In a still further aspect, each of $R^{40a}$, $R^{40b}$, $R^{40c}$, $R^{40d}$, and $R^{40e}$ is independently selected from hydrogen and phenyl.

In a further aspect, each of $R^{40a}$, $R^{40b}$, $R^{40c}$, $R^{40d}$, and $R^{40e}$ is independently selected from hydrogen, halogen, —NO$_2$, —CN, —OH, —SH, —NH$_2$, C1-C4 alkyl, C1-C4 haloalkyl, C1-C4 alkoxy, C1-C4 thioalkyl, C1-C4 alkyl(C1-C4 alkoxy), C1-C4 alkylamino, and (C1-C4)(C1-C4) dialkylamino. In a further aspect, each of $R^{40a}$, $R^{40b}$, $R^{40c}$, $R^{40d}$, and $R^{40e}$ is independently selected from hydrogen, —F, —Cl, —NO$_2$, —CN, —OH, —SH, —NH$_2$, methyl, ethyl, propyl, —CH$_2$F, —CHF$_2$, —CF$_3$, —CH$_2$CH$_2$F, —CH$_2$Cl, —CHCl$_2$, —CCl$_3$, —CH$_2$CH$_2$Cl, —OCH$_3$, —OCH$_2$CH$_3$, —SCH$_3$, —SCH$_2$CH$_3$, —CH$_2$OCH$_3$, —CH$_2$CH$_2$OCH$_2$CH$_3$, —NHCH$_3$, —NHCH$_2$CH$_3$, —N(CH$_3$)$_2$, and —NH(CH$_2$CH$_3$)$_2$. In a still further aspect, each of $R^{40a}$, $R^{40b}$, $R^{40c}$, $R^{40d}$, and $R^{40e}$ is independently selected from hydrogen, —F, —Cl, —NO$_2$, —CN, —OH, —SH, —NH$_2$, methyl, ethyl, —CH$_2$F, —CHF$_2$, —CF$_3$, —CH$_2$Cl, —CHCl$_2$, —CCl$_3$, —OCH$_3$, —SCH$_3$, —CH$_2$OCH$_3$, —NHCH$_3$, and —N(CH$_3$)$_2$. In yet a further aspect, each of $R^{40a}$, $R^{40b}$, $R^{40c}$, $R^{40d}$ and $R^{40e}$ is independently selected from hydrogen, —F, —Cl, —NO$_2$, —CN, —OH, —SH, —NH$_2$, methyl, —CH$_2$F, —CHF$_2$, —CF$_3$, —CH$_2$Cl, —CHCl$_2$, —CCl$_3$, —OCH$_3$, —SCH$_3$, —CH$_2$OCH$_3$, —NHCH$_3$, and —N(CH$_3$)$_2$.

In a further aspect, each of $R^{40a}$, $R^{40b}$, $R^{40c}$, $R^{40d}$, and $R^{40e}$ is independently selected from hydrogen, halogen, —NO$_2$, —CN, —OH, —SH, —NH$_2$, C1-C4 alkyl, C1-C4 haloalkyl, and C1-C4 alkoxy. In a further aspect, each of $R^{40a}$, $R^{40b}$, $R^{40c}$, $R^{40d}$, and $R^{40e}$ is independently selected from hydrogen, —F, —Cl, —NO$_2$, —CN, —OH, —SH, —NH$_2$, methyl, ethyl, propyl, —CH$_2$F, —CHF$_2$, —CF$_3$, —CH$_2$CH$_2$F, —CH$_2$Cl, —CHCl$_2$, —CCl$_3$, —CH$_2$CH$_2$Cl, —OCH$_3$, and —OCH$_2$CH$_3$. In a still further aspect, each of $R^{40a}$, $R^{40b}$, $R^{40c}$, $R^{40d}$, and $R^{40e}$ is independently selected from hydrogen, —F, —Cl, —NO$_2$, —CN, —OH, —SH, —NH$_2$, methyl, ethyl, —CH$_2$F, —CHF$_2$, —CF$_3$, —CH$_2$Cl, —CHCl$_2$, —CCl$_3$, and —OCH$_3$. In yet a further aspect, each of $R^{40a}$, $R^{40b}$, $R^{40c}$, $R^{40d}$, and $R^{40e}$ is independently selected from hydrogen, —F, —Cl, —NO$_2$, —CN, —OH, —SH, —NH$_2$, methyl, —CH$_2$F, —CHF$_2$, —CF$_3$, —CH$_2$Cl, —CHCl$_2$, —CCl$_3$, and —OCH$_3$.

In a further aspect, each of $R^{40a}$, $R^{40b}$, $R^{40c}$, $R^{40d}$, and $R^{40e}$ is independently selected from hydrogen, C1-C4 alkyl, C1-C4 haloalkyl, and C1-C4 alkoxy. In a further aspect, each of $R^{40a}$, $R^{40b}$, $R^{40c}$, $R^{40d}$, and $R^{40e}$ is independently selected from hydrogen, methyl, ethyl, propyl, —CH$_2$F, —CHF$_2$, —CF$_3$, —CH$_2$CH$_2$F, —CH$_2$Cl, —CHCl$_2$, —CCl$_3$, —CH$_2$CH$_2$Cl, —OCH$_3$, and —OCH$_2$CH$_3$. In a still further aspect, each of $R^{40a}$, $R^{40b}$, $R^{40c}$, $R^{40d}$, and $R^{40e}$ is independently selected from hydrogen, methyl, ethyl, —CH$_2$F, —CHF$_2$, —CF$_3$, —CH$_2$Cl, —CHCl$_2$, —CCl$_3$, and —OCH$_3$. In yet a further aspect, each of $R^{40a}$, $R^{40b}$, $R^{40c}$, $R^{40d}$, and $R^{40e}$ is independently selected from hydrogen, methyl, —CH$_2$F, —CHF$_2$, —CF$_3$, —CH$_2$Cl, —CHCl$_2$, —CCl$_3$, and —OCH$_3$.

In a further aspect, each of $R^{40a}$, $R^{40b}$, $R^{40c}$, $R^{40d}$, and $R^{40e}$ is independently selected from hydrogen, C1-C4 alkyl, and C1-C4 alkoxy. In a further aspect, each of $R^{40a}$, $R^{40b}$, $R^{40c}$, $R^{40d}$, and $R^{40e}$ is independently selected from hydrogen, methyl, ethyl, propyl, —OCH$_3$, and —OCH$_2$CH$_3$. In a still further aspect, each of $R^{40a}$, $R^{40b}$, $R^{40c}$, $R^{40d}$, and $R^{40e}$ is independently selected from hydrogen, methyl, ethyl, and —OCH$_3$. In yet a further aspect, each of $R^{40a}$, $R^{40b}$, $R^{40c}$, $R^{40d}$, and $R^{40e}$ is independently selected from hydrogen, methyl, and —OCH$_3$.

In a further aspect, each of $R^{40a}$, $R^{40b}$, $R^{40c}$, $R^{40d}$, and $R^{40e}$ is independently selected from hydrogen and C1-C4 haloalkyl. In a further aspect, each of $R^{40a}$, $R^{40b}$, $R^{40c}$, $R^{40d}$, and $R^{40e}$ is independently selected from hydrogen, —CH$_2$F, —CHF$_2$, —CF$_3$, —CH$_2$CH$_2$F, —CH$_2$Cl, —CHCl$_2$, —CCl$_3$, and —CH$_2$CH$_2$Cl. In a still further aspect, each of $R^{40a}$, $R^{40b}$, $R^{40c}$, $R^{40d}$, and $R^{40e}$ is independently selected from hydrogen, —CH$_2$F, —CHF$_2$, —CF$_3$, —CH$_2$Cl, —CHCl$_2$, and —CCl$_3$. In yet a further aspect, each of $R^{40a}$, $R^{40b}$, $R^{40c}$, $R^{40d}$, and $R^{40e}$ is independently selected from hydrogen, —CHF$_2$, —CF$_3$, —CHCl$_2$, and —CCl$_3$. In an even further aspect, each of $R^{40a}$, $R^{40b}$, $R^{40c}$, $R^{40d}$, and $R^{40e}$ is independently selected from hydrogen, —CF$_3$, and —CCl$_3$. In a still further aspect, each of $R^{40a}$, $R^{40b}$, $R^{40c}$, $R^{40d}$, and $R^{40e}$ is independently selected from hydrogen and —CF$_3$. In yet a further aspect, each of $R^{40a}$, $R^{40b}$, $R^{40c}$, $R^{40d}$, and $R^{40e}$ is independently selected from hydrogen and —CCl$_3$.

In a further aspect, each of $R^{40a}$, $R^{40b}$, $R^{40c}$, $R^{40d}$, and $R^{40e}$ is independently selected from hydrogen, —OCH$_3$, —OCH$_2$CH$_3$, —OCH$_2$CH$_2$CH$_3$, and —OCH(CH$_3$)$_2$. In a still further aspect, each of $R^{40a}$, $R^{40b}$, $R^{40c}$, $R^{40d}$, and $R^{40e}$ is independently selected from hydrogen, —OCH$_3$, and —OCH$_2$CH$_3$. In yet a further aspect, each of $R^{40a}$, $R^{40b}$, $R^{40c}$, $R^{40d}$, and $R^{40e}$ is independently selected from hydrogen and —OCH$_2$CH$_2$CH$_3$. In an even further aspect, each of $R^{40a}$, $R^{40b}$, $R^{40c}$, $R^{40d}$, and $R^{40e}$ is independently selected from hydrogen and —OCH(CH$_3$)$_2$. In a still further aspect, each of $R^{40a}$, $R^{40b}$, $R^{40c}$, $R^{40d}$, and $R^{40e}$ is independently selected from hydrogen and —OCH$_2$CH$_3$. In yet a further aspect, each of $R^{40a}$, $R^{40b}$, $R^{40c}$, $R^{40d}$, and $R^{40e}$ is independently selected from hydrogen and —OCH$_3$.

In a further aspect, each of $R^{40a}$, $R^{40b}$, $R^{40c}$, $R^{40d}$, and $R^{40e}$ is independently selected from hydrogen, methyl, ethyl, n-propyl, i-propyl, n-butyl, i-butyl, s-butyl, and t-butyl. In a still further aspect, each of $R^{40a}$, $R^{40b}$, $R^{40c}$, $R^{40d}$, and $R^{40e}$ is independently selected from hydrogen, methyl, ethyl, n-propyl, and i-propyl. In yet a further aspect, each of $R^{40a}$, $R^{40b}$, $R^{40c}$, $R^{40d}$, and $R^{40e}$ is independently selected from hydrogen, methyl, and ethyl. In an even further aspect, each of $R^{40a}$, $R^{40b}$, $R^{40c}$, $R^{40d}$, and $R^{40e}$ is independently selected from hydrogen and ethyl. In a still further aspect, each of $R^{40a}$, $R^{40b}$, $R^{40c}$, $R^{40d}$, and $R^{40e}$ is independently selected from hydrogen and methyl.

In a further aspect, each of $R^{40a}$, $R^{40b}$, $R^{40c}$, $R^{40d}$, and $R^{40e}$ is independently selected from hydrogen, C1-C4 haloalkyl, C1-C4 alkoxy, and C6-C10 aryl.

In a further aspect, each of $R^{40a}$, $R^{40b}$, $R^{40c}$, $R^{40d}$, and $R^{40e}$ is independently selected from hydrogen, —CF$_3$, —OCH$_3$, and phenyl.

In a further aspect, each of $R^{40a}$, $R^{40b}$, $R^{40c}$, $R^{40d}$, and $R^{40e}$ is hydrogen.

v. $R^{41a}$, $R^{41b}$, $R^{41c}$, $R^{41d}$, and $R^{41e}$ Groups

In one aspect, each of $R^{41a}$, $R^{41b}$, $R^{41c}$, $R^{41d}$, and $R^{41e}$ is independently selected from hydrogen, halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO$_2$R$^{33}$, —CO$_2$R$^{33}$, —(C1-C4 alkyl)CO$_2$R$^{33}$, —(C2-C4 alkenyl)CO$_2$R$^{33}$, —(C=O)(C1-C4 alkyl), —(S=O)(C1-C4 alkyl), —SO$_2$(C1-C4 alkyl), —(C=O)NR$^{34a}$R$^{34b}$, —SO$_2$NR$^{34a}$R$^{34b}$, —O(C=O)NR$^{34a}$R$^{34b}$, —NHSO$_2$NR$^{34a}$R$^{34b}$, —NH(C=O)NR$^{34a}$R$^{34b}$, and —N=NR$^{35}$ In a further aspect, each of $R^{41a}$, $R^{41b}$, $R^{41c}$, $R^{41d}$, and $R^{41e}$ is independently selected from hydrogen, —O(C2-C4 alkenyl), —OCO$_2$R$^{30}$, —(C1-C4 alkyl)CO$_2$R$^{30}$, —(C2-C4 alkenyl)CO$_2$R$^{30}$, and —N=NR$^{32}$.

In a further aspect, each of $R^{41a}$, $R^{41b}$, $R^{41c}$, $R^{41d}$, and $R^{41e}$ is independently selected from hydrogen, —F, —Cl, —NO$_2$, —CN, —OH, —SH, —NH$_2$, methyl, ethyl, propyl, ethenyl, propenyl, ethynyl, propynyl, —CH$_2$F, —CHF$_2$, —CF$_3$, —CH$_2$CH$_2$F, —CH$_2$Cl, —CHCl$_2$, —CCl$_3$, —CH$_2$CH$_2$Cl, —CH$_2$CN, —CH$_2$CH$_2$CN, —CH$_2$OH, —CH$_2$CH$_2$OH, —OCH$_2$F, —OCHF$_2$, —OCF$_3$, —OCH$_3$, —OCH$_2$CH$_3$, —SCH$_3$, —SCH$_2$CH$_3$, —CH$_2$OCH$_3$, —CH$_2$CH$_2$OCH$_2$CH$_3$, —CH$_2$NH$_2$, —CH$_2$CH$_2$NH$_2$, —NHCH$_3$, —NHCH$_2$CH$_3$, —N(CH$_3$)$_2$, —NH(CH$_2$CH$_3$)$_2$, cyclopropyl, cyclobutyl, cyclopentyl, phenyl, —(C=O)CH$_3$, —(C=O)CH$_2$CH$_3$, —(S=O)CH$_3$, —(S=O)CH$_2$CH$_3$, —SO$_2$CH$_3$, —SO$_2$CH$_2$CH$_3$, —CO$_2$CH$_3$, —CO$_2$CH$_2$CH$_3$, —(C=O)NH$_2$, —(C=O)NHCH$_3$, —(C=O)N(CH$_3$)$_2$, —SO$_2$NH$_2$, —SO$_2$NHCH$_3$, —SO$_2$N(CH$_3$)$_2$, —O(C=O)NH$_2$, —O(C=O)NHCH$_3$, —O(C=O)N(CH$_3$)$_2$, —NHSO$_2$NH$_2$, —NHSO$_2$NHCH$_3$, —NHSO$_2$N(CH$_3$)$_2$, —NH(C=O)NH$_2$, —NH(C=O)NHCH$_3$, and —NH(C=O)N(CH$_3$)$_2$. In a still further aspect, each of $R^{41a}$, $R^{41b}$, $R^{41c}$, $R^{41d}$, and $R^{41e}$ is independently selected from hydrogen, —F, —Cl, —NO$_2$, —CN, —OH, —SH, —NH$_2$, methyl, ethyl, ethenyl, ethynyl, —CH$_2$F, —CHF$_2$, —CF$_3$, —CH$_2$Cl, —CHCl$_2$, —CCl$_3$, —CH$_2$CN, —CH$_2$OH, —OCH$_2$F, —OCHF$_2$, —OCF$_3$, —OCH$_3$, —SCH$_3$, —CH$_2$OCH$_3$, —CH$_2$NH$_2$, —NHCH$_3$, —N(CH$_3$)$_2$, cyclopropyl, cyclobutyl, phenyl, —(C=O)CH$_3$, —(S=O)CH$_3$, —SO$_2$CH$_3$, —CO$_2$CH$_3$, —(C=O)NH$_2$, —(C=O)NHCH$_3$, —(C=O)N(CH$_3$)$_2$, —SO$_2$NH$_2$, —SO$_2$NHCH$_3$, —SO$_2$N(CH$_3$)$_2$, —O(C=O)NH$_2$, —O(C=O)NHCH$_3$, —O(C=O)N(CH$_3$)$_2$, —NHSO$_2$NH$_2$, —NHSO$_2$NHCH$_3$, —NHSO$_2$N(CH$_3$)$_2$, —NH(C=O)NH$_2$, —NH(C=O)NHCH$_3$, and —NH(C=O)N(CH$_3$)$_2$. In yet a further aspect, each of $R^{41a}$, $R^{41b}$, $R^{41c}$, $R^{41d}$, and $R^{41e}$ is independently selected from hydrogen, —F, —Cl, —NO$_2$, —CN, —OH, —SH, —NH$_2$, methyl, —CH$_2$F, —CHF$_2$, —CF$_3$, —CH$_2$Cl, —CHCl$_2$, —CCl$_3$, —CH$_2$CN, —CH$_2$OH, —OCH$_2$F, —OCHF$_2$, —OCF$_3$, —OCH$_3$, —SCH$_3$, —CH$_2$OCH$_3$, —CH$_2$NH$_2$, —NHCH$_3$, —N(CH$_3$)$_2$, cyclopropyl, phenyl, —(C=O)CH$_3$, —(S=O)CH$_3$, —SO$_2$CH$_3$, —CO$_2$CH$_3$, —(C=O)NH$_2$, —(C=O)NHCH$_3$, —(C=O)N(CH$_3$)$_2$, —SO$_2$NH$_2$, —SO$_2$NHCH$_3$, —SO$_2$N(CH$_3$)$_2$, —O(C=O)NH$_2$, —O(C=O)NHCH$_3$, —O(C=O)N(CH$_3$)$_2$, —NHSO$_2$NH$_2$, —NHSO$_2$NHCH$_3$, —NHSO$_2$N(CH$_3$)$_2$, —NH(C=O)NH$_2$, —NH(C=O)NHCH$_3$, and —NH(C=O)N(CH$_3$)$_2$.

In a further aspect, each of $R^{41a}$, $R^{41b}$, $R^{41c}$, $R^{41d}$, and $R^{41e}$ is independently selected from hydrogen and C6-C10 aryl. In a still further aspect, each of $R^{41a}$, $R^{41b}$, $R^{41c}$, $R^{41d}$, and $R^{41e}$ is independently selected from hydrogen and phenyl.

In a further aspect, each of $R^{41a}$, $R^{41b}$, $R^{41c}$, $R^{41d}$, and $R^{41e}$ is independently selected from hydrogen, halogen, —NO$_2$, —CN, —OH, —SH, —NH$_2$, C1-C4 alkyl, C1-C4 haloalkyl, C1-C4 alkoxy, C1-C4 thioalkyl, C1-C4 alkyl(C1-C4 alkoxy), C1-C4 alkylamino, and (C1-C4)(C1-C4) dialkylamino. In a further aspect, each of $R^{41a}$, $R^{41b}$, $R^{41c}$, $R^{41d}$, and $R^{41e}$ is independently selected from hydrogen, —F, —Cl, —NO$_2$, —CN, —OH, —SH, —NH$_2$, methyl, ethyl, propyl, —CH$_2$F, —CHF$_2$, —CF$_3$, —CH$_2$CH$_2$F, —CH$_2$Cl, —CHCl$_2$, —CCl$_3$, —CH$_2$CH$_2$Cl, —OCH$_3$, —OCH$_2$CH$_3$, —SCH$_3$, —SCH$_2$CH$_3$, —CH$_2$OCH$_3$, —CH$_2$CH$_2$OCH$_2$CH$_3$, —NHCH$_3$, —NHCH$_2$CH$_3$, —N(CH$_3$)$_2$, and —NH(CH$_2$CH$_3$)$_2$. In a still further aspect, each of $R^{41a}$, $R^{41b}$, $R^{41c}$, $R^{41d}$, and $R^{41e}$ is independently selected from hydrogen, —F, —Cl, —NO$_2$, —CN, —OH, —SH, —NH$_2$, methyl, ethyl, —CH$_2$F, —CHF$_2$, —CF$_3$, —CH$_2$Cl, —CHCl$_2$, —CCl$_3$, —OCH$_3$, —SCH$_3$, —CH$_2$OCH$_3$, —NHCH$_3$, and —N(CH$_3$)$_2$. In yet a further aspect, each of $R^{41a}$, $R^{41b}$, $R^{41c}$, $R^{41d}$ and $R^{41e}$ is independently selected from hydrogen, —F, —Cl, —NO$_2$, —CN, —OH, —SH, —NH$_2$, methyl, —CH$_2$F, —CHF$_2$, —CF$_3$, —CH$_2$Cl, —CHCl$_2$, —CCl$_3$, —OCH$_3$, —SCH$_3$, —CH$_2$OCH$_3$, —NHCH$_3$, and —N(CH$_3$)$_2$.

In a further aspect, each of $R^{41a}$, $R^{41b}$, $R^{41c}$, $R^{41d}$, and $R^{41e}$ is independently selected from hydrogen, halogen, —NO$_2$, —CN, —OH, —SH, —NH$_2$, C1-C4 alkyl, C1-C4 haloalkyl, and C1-C4 alkoxy. In a further aspect, each of $R^{41a}$, $R^{41b}$, $R^{41c}$, $R^{41d}$, and $R^{41e}$ is independently selected from hydrogen, —F, —Cl, —NO$_2$, —CN, —OH, —SH, —NH$_2$, methyl, ethyl, propyl, —CH$_2$F, —CHF$_2$, —CF$_3$, —CH$_2$CH$_2$F, —CH$_2$Cl, —CHCl$_2$, —CCl$_3$, —CH$_2$CH$_2$Cl, —OCH$_3$, and —OCH$_2$CH$_3$. In a still further aspect, each of $R^{41a}$, $R^{41b}$, $R^{41c}$, $R^{41d}$, and $R^{41e}$ is independently selected from hydrogen, —F, —Cl, —NO$_2$, —CN, —OH, —SH, —NH$_2$, methyl, ethyl, —CH$_2$F, —CHF$_2$, —CF$_3$, —CH$_2$Cl, —CHCl$_2$, —CCl$_3$, and —OCH$_3$. In yet a further aspect, each of $R^{41a}$, $R^{41b}$, $R^{41c}$, $R^{41d}$, and $R^{41e}$ is independently selected from hydrogen, —F, —Cl, —NO$_2$, —CN, —OH, —SH, —NH$_2$, methyl, —CH$_2$F, —CHF$_2$, —CF$_3$, —CH$_2$Cl, —CHCl$_2$, —CCl$_3$, and —OCH$_3$.

In a further aspect, each of $R^{41a}$, $R^{41b}$, $R^{41c}$, $R^{41d}$, and $R^{41e}$ is independently selected from hydrogen, C1-C4 alkyl, C1-C4 haloalkyl, and C1-C4 alkoxy. In a further aspect, each of $R^{41a}$, $R^{41b}$, $R^{41c}$, $R^{41d}$, and $R^{41e}$ is independently selected from hydrogen, methyl, ethyl, propyl, —CH$_2$F, —CHF$_2$, —CF$_3$, —CH$_2$CH$_2$F, —CH$_2$Cl, —CHCl$_2$, —CCl$_3$, —CH$_2$CH$_2$Cl, —OCH$_3$, and —OCH$_2$CH$_3$. In a still further aspect, each of $R^{41a}$, $R^{41b}$, $R^{41c}$, $R^{41d}$ and $R^{41e}$ is independently selected from hydrogen, methyl, ethyl, —CH$_2$F, —CHF$_2$, —CF$_3$, —CH$_2$Cl, —CHCl$_2$, —CCl$_3$, and —OCH$_3$. In yet a further aspect, each of $R^{41a}$, $R^{41b}$, $R^{41c}$, $R^{41d}$, and $R^{41e}$ is independently selected from hydrogen, methyl, —CH$_2$F, —CHF$_2$, —CF$_3$, —CH$_2$Cl, —CHCl$_2$, —CCl$_3$, and —OCH$_3$.

In a further aspect, each of $R^{41a}$, $R^{41b}$, $R^{41c}$, $R^{41d}$, and $R^{41e}$ is independently selected from hydrogen, C1-C4 alkyl, and C1-C4 alkoxy. In a further aspect, each of $R^{41a}$, $R^{41b}$, $R^{41c}$, $R^{41d}$, and $R^{41e}$ is independently selected from hydrogen, methyl, ethyl, propyl, —OCH$_3$, and —OCH$_2$CH$_3$. In a still further aspect, each of $R^{41a}$, $R^{41b}$, $R^{41c}$, $R^{41d}$, and $R^{41e}$ is independently selected from hydrogen, methyl, ethyl, and —OCH$_3$. In yet a further aspect, each of $R^{41a}$, $R^{41b}$, $R^{41c}$, $R^{41d}$, and $R^{41e}$ is independently selected from hydrogen, methyl, and —OCH$_3$.

In a further aspect, each of $R^{41a}$, $R^{41b}$, $R^{41c}$, $R^{41d}$, and $R^{41e}$ is independently selected from hydrogen and C1-C4 haloalkyl. In a further aspect, each of $R^{41a}$, $R^{41b}$, $R^{41c}$, $R^{41d}$, and $R^{41e}$ is independently selected from hydrogen, —CH$_2$F, —CHF$_2$, —CF$_3$, —CH$_2$CH$_2$F, —CH$_2$Cl, —CHCl$_2$, —CCl$_3$, and —CH$_2$CH$_2$Cl. In a still further aspect, each of $R^{41a}$, $R^{41b}$, $R^{41c}$, $R^{41d}$, and $R^{41e}$ is independently selected from hydrogen, —CH$_2$F, —CHF$_2$, —CF$_3$, —CH$_2$Cl, —CHCl$_2$, and —CCl$_3$. In yet a further aspect, each of $R^{41a}$, $R^{41b}$, $R^{41c}$, $R^{41d}$, and $R^{41e}$ is independently selected from hydrogen, —CHF$_2$, —CF$_3$, —CHCl$_2$, and —CCl$_3$. In an even further aspect, each of $R^{41a}$, $R^{41b}$, $R^{41c}$, $R^{41d}$, and $R^{41e}$ is independently selected from hydrogen, —CF$_3$, and —CCl$_3$. In a still further aspect, each of $R^{41a}$, $R^{41b}$, $R^{41c}$, $R^{41d}$, and $R^{41e}$ is independently selected from hydrogen and —CF$_3$. In yet a further aspect, each of $R^{41a}$, $R^{41b}$, $R^{41c}$, $R^{41d}$, and $R^{41e}$ is independently selected from hydrogen and —CCl$_3$.

In a further aspect, each of $R^{41a}$, $R^{41b}$, $R^{41c}$, $R^{41d}$, and $R^{41e}$ is independently selected from hydrogen, —OCH$_3$, —OCH$_2$CH$_3$, —OCH$_2$CH$_2$CH$_3$, and —OCH(CH$_3$)$_2$. In a still further aspect, each of $R^{41a}$, $R^{41b}$, $R^{41c}$, $R^{41d}$, and $R^{41e}$ is independently selected from hydrogen, —OCH$_3$, and —OCH$_2$CH$_3$. In yet a further aspect, each of $R^{41a}$, $R^{41b}$, $R^{41c}$, $R^{41d}$, and $R^{41e}$ is independently selected from hydrogen and —OCH$_2$CH$_3$. In an even further aspect, each of $R^{41a}$, $R^{41b}$, $R^{41c}$, $R^{41d}$, and $R^{41e}$ is independently selected from hydrogen and —OCH(CH$_3$)$_2$. In a still further aspect, each of $R^{41a}$, $R^{41b}$, $R^{41c}$, $R^{41d}$, and $R^{41e}$ is independently selected from hydrogen and —OCH$_2$CH$_3$. In yet a further aspect, each of $R^{41a}$, $R^{41b}$, $R^{41c}$, $R^{41d}$, and $R^{41e}$ is independently selected from hydrogen and —OCH$_3$.

In a further aspect, each of $R^{41a}$, $R^{41b}$, $R^{41c}$, $R^{41d}$, and $R^{41e}$ is independently selected from hydrogen, methyl, ethyl, n-propyl, i-propyl, n-butyl, i-butyl, s-butyl, and t-butyl. In a still further aspect, each of $R^{41a}$, $R^{41b}$, $R^{41c}$, $R^{41d}$, and $R^{41e}$ is independently selected from hydrogen, methyl, ethyl, n-propyl, and i-propyl. In yet a further aspect, each of $R^{41a}$, $R^{41b}$, $R^{41c}$, $R^{41d}$, and $R^{41e}$ is independently selected from hydrogen, methyl, and ethyl. In an even further aspect, each of $R^{41a}$, $R^{41b}$, $R^{41c}$, $R^{41d}$, and $R^{41e}$ is independently selected from hydrogen and ethyl. In a still further aspect, each of $R^{41a}$, $R^{41b}$, $R^{41c}$, $R^{41d}$, and $R^{41e}$ is independently selected from hydrogen and methyl.

In a further aspect, each of $R^{41a}$, $R^{41b}$, $R^{41c}$, $R^{41d}$, and $R^{41e}$ is independently selected from hydrogen, C1-C4 haloalkyl, C1-C4 alkoxy, and C6-C10 aryl.

In a further aspect, each of $R^{41a}$, $R^{41b}$, $R^{41c}$, $R^{41d}$, and $R^{41e}$ is independently selected from hydrogen, —CF$_3$, —OCH$_3$, and phenyl.

In a further aspect, each of $R^{41a}$, $R^{41b}$, $R^{41c}$, $R^{41d}$, and $R^{41e}$ is hydrogen.

w. Ar$^1$ Groups

In one aspect, Ar$^1$, when present, is selected from aryl and heteroaryl and is substituted with 0, 1, 2, or 3 groups independently selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO$_2$R$^{30}$, —CO$_2$R$^{30}$, —(C1-C4 alkyl)CO$_2$R$^{30}$, —(C2-C4 alkenyl)CO$_2$R$^{30}$, —(C=O)(C1-C4 alkyl), —(S=O)(C1-C4 alkyl), —SO$_2$(C1-C4 alkyl), —(C=O)NR$^{31a}$R$^{31b}$, —SO$_2$NR$^{31a}$R$^{31b}$, —O(C=O)NR$^{31a}$R$^{31b}$, —NHSO$_2$NR$^{31a}$R$^{31b}$, —NH(C=O)NR$^{31a}$R$^{31b}$, and —N=NR$^{32}$. In a further aspect, Ar$^1$, when present, is selected from aryl and heteroaryl and is substituted with 0, 1, or 2 groups independently selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO$_2$R$^{30}$, —CO$_2$R$^{30}$, —(C1-C4 alkyl)CO$_2$R$^{30}$, —(C2-C4 alkenyl)CO$_2$R$^{30}$, —(C=O)(C1-C4 alkyl), —(S=O)(C1-C4 alkyl), —SO$_2$(C1-C4 alkyl), —(C=O)NR$^{31a}$R$^{31b}$, SO$_2$NR$^{31a}$R$^{31b}$, —O(C=O) NR$^{31a}$R$^{31b}$, —NHSO$_2$NR$^{31a}$R$^{31b}$, —NH(C=O)NR$^{31a}$R$^{31b}$, and —N=NR$^{32}$. In a still further aspect, Ar$^1$, when present, is selected from aryl and heteroaryl and is substituted with 0 or 1 group selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO$_2$R$^{30}$, —CO$_2$R$^{30}$, —(C1-C4 alkyl)CO$_2$R$^{30}$, —(C2-C4 alkenyl)CO$_2$R$^{30}$, —(C=O)(C1-C4 alkyl), —(S=O)(C1-C4 alkyl), —SO$_2$ (C1-C4 alkyl), —(C=O)NR$^{31a}$R$^{31b}$, —SO$_2$NR$^{31a}$R$^{31b}$, —O(C=O)NR$^{31a}$R$^{31b}$, —NHSO$_2$NR$^{31a}$R$^{31b}$, —NH(C=O)NR$^{31a}$R$^{31b}$, and —N=NR$^{32}$. In yet a further aspect, Ar$^1$, when present, is selected from aryl and heteroaryl and is monosubstituted with a group selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO$_2$R$^{30}$, —CO$_2$R$^{30}$, —(C1-C4 alkyl)CO$_2$R$^{30}$, —(C2-

C4 alkenyl)CO$_2$R$^{30}$, —(C=O)(C1-C4 alkyl), —(S=O)(C1-C4 alkyl), —SO$_2$(C1-C4 alkyl), —(C=O)NR$^{31a}$R$^{31b}$, —SO$_2$NR$^{31a}$R$^{31b}$, —O(C=O)NR$^{31a}$R$^{31b}$, —NHSO$_2$NR$^{31a}$R$^{31b}$, —NH(C=O)NR$^{31a}$R$^{31b}$, and —N=NR$^{32}$. In an even further aspect, Ar$^1$, when present, is selected from aryl and heteroaryl and is unsubstituted.

In a further aspect, Ar$^1$, when present, is aryl substituted with 0, 1, 2, or 3 groups independently selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO$_2$R$^{30}$, —CO$_2$R$^{30}$, —(C1-C4 alkyl)CO$_2$R$^{30}$, —(C2-C4 alkenyl)CO$_2$R$^{30}$, —(C=O)(C1-C4 alkyl), —(S=O)(C1-C4 alkyl), —SO$_2$(C1-C4 alkyl), —(C=O)NR$^{31a}$R$^{31b}$SO$_2$NR$^{31a}$R$^{31b}$, —O(C=O)NR$^{31a}$R$^{31b}$, —NHSO$_2$NR$^{31a}$R$^{31b}$, —NH(C=O)NR$^{31a}$R$^{31b}$, and —N=NR$^{32}$. In a still further aspect, Ar$^1$, when present, is aryl substituted with 0, 1, or 2 groups independently selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO$_2$R$^{30}$, —CO$_2$R$^{30}$, —(C1-C4 alkyl)CO$_2$R$^{30}$, —(C2-C4 alkenyl)CO$_2$R$^{30}$, —(C=O)(C1-C4 alkyl), —(S=O)(C1-C4 alkyl), —SO$_2$(C1-C4 alkyl), —(C=O)NR$^{31a}$R$^{31b}$ SO$_2$NR$^{31a}$R$^{31b}$, —O(C=O)NR$^{31a}$R$^{31b}$, —NHSO$_2$NR$^{31a}$R$^{31b}$, —NH(C=O)NR$^{31a}$R$^{31b}$, and —N=NR$^{32}$. In yet a further aspect, Ar$^1$, when present, is aryl substituted with 0 or 1 group selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO$_2$R$^{30}$, —CO$_2$R$^{30}$, —(C1-C4 alkyl)CO$_2$R$^{30}$, —(C2-C4 alkenyl)CO$_2$R$^{30}$, —(C=O)(C1-C4 alkyl), —(S=O)(C1-C4 alkyl), —SO$_2$(C1-C4 alkyl), —(C=O)NR$^{31a}$R$^{31b}$, —SO$_2$NR$^{31a}$R$^{31b}$, —O(C=O)NR$^{31a}$R$^{31b}$, —NHSO$_2$NR$^{31a}$R$^{31b}$, —NH(C=O)NR$^{31a}$R$^{31b}$, and —N=NR$^{32}$. In an even further aspect, Ar$^1$, when present, is aryl monosubstituted with a group selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO$_2$R$^{30}$, —CO$_2$R$^{30}$, —(C1-C4 alkyl)CO$_2$R$^{30}$, —(C2-C4 alkenyl)CO$_2$R$^{30}$, —(C=O)(C1-C4 alkyl), —(S=O)(C1-C4 alkyl), —SO$_2$(C1-C4 alkyl), —(C=O)NR$^{31a}$R$^{31b}$, —SO$_2$NR$^{31a}$R$^{31b}$, —O(C=O)NR$^{31a}$R$^{31b}$, —NHSO$_2$NR$^{31a}$R$^{31b}$, —NH(C=O)NR$^{31a}$R$^{31b}$, and —N=NR$^{32}$. In a still further aspect, Ar$^1$, when present, is unsubstituted aryl.

In a further aspect, Ar$^1$, when present, is phenyl substituted with 0, 1, 2, or 3 groups independently selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 phenyl, —O(C2-C4 alkenyl), —OCO$_2$R$^{30}$, —CO$_2$R$^{30}$, —(C1-C4 alkyl)CO$_2$R$^{30}$, —(C2-C4 alkenyl)CO$_2$R$^{30}$, —(C=O)(C1-C4 alkyl), —(S=O)(C1-C4 alkyl), —SO$_2$(C1-C4 alkyl), —(C=O)NR$^{31a}$R$^{31b}$, —SO$_2$NR$^{31a}$R$^{31b}$, —O(C=O)NR$^{31a}$R$^{31b}$, —NHSO$_2$NR$^{31a}$R$^{31b}$, —NH(C=O)NR$^{31a}$R$^{31b}$, and —N=NR$^{32}$. In a still further aspect, Ar$^1$, when present, is phenyl substituted with 0, 1, or 2 groups independently selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl (C1-C4 alkoxy), C1-C4 aminoalkyl, C1-C4 alkylamino, (C1-C4)(C1-C4) dialkylamino, C3-C7 cycloalkyl, C6-C10 phenyl, —O(C2-C4 alkenyl), —OCO$_2$R$^{30}$, —CO$_2$R$^{30}$, —(C1-C4 alkyl)CO$_2$R$^{30}$, —(C2-C4 alkenyl)CO$_2$R$^{30}$, —(C=O)(C1-C4 alkyl), —(S=O)(C1-C4 alkyl), —SO$_2$(C1-C4 alkyl), —(C=O)NR$^{31a}$R$^{31b}$, —SO$_2$NR$^{31a}$R$^{31b}$, —O(C=O)NR$^{31a}$R$^{31b}$, —NHSO$_2$NR$^{31a}$R$^{31b}$, —NH(C=O)NR$^{31a}$R$^{31b}$, and —N=NR$^{32}$. In yet a further aspect, Ar$^1$, when present, is phenyl substituted with 0 or 1 group selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl (C1-C4 alkoxy), C1-C4 aminoalkyl, C1-C4 alkylamino, (C1-C4)(C1-C4) dialkylamino, C3-C7 cycloalkyl, C6-C10 phenyl, —O(C2-C4 alkenyl), —OCO$_2$R$^{30}$, —CO$_2$R$^{30}$, —(C1-C4 alkyl)CO$_2$R$^{30}$, —(C2-C4 alkenyl)CO$_2$R$^{30}$, —(C=O)(C1-C4 alkyl), —(S=O)(C1-C4 alkyl), —SO$_2$ (C1-C4 alkyl), —(C=O)NR$^{31a}$R$^{31b}$, —SO$_2$NR$^{31a}$R$^{31b}$, —O(C=O)NR$^{31a}$R$^{31b}$, —NHSO$_2$NR$^{31a}$R$^{31b}$, —NH(C=O)NR$^{31a}$R$^{31b}$, and —N=NR$^{32}$. In an even further aspect, Ar$^1$, when present, is phenyl monosubstituted with a group selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl (C1-C4 alkoxy), C1-C4 aminoalkyl, C1-C4 alkylamino, (C1-C4)(C1-C4) dialkylamino, C3-C7 cycloalkyl, C6-C10 phenyl, —O(C2-C4 alkenyl), —OCO$_2$R$^{30}$, —CO$_2$R$^{30}$, —(C1-C4 alkyl)CO$_2$R$^{30}$, —(C2-C4 alkenyl)CO$_2$R$^{30}$, —(C=O)(C1-C4 alkyl), —(S=O)(C1-C4 alkyl), —SO$_2$ (C1-C4 alkyl), —(C=O)NR$^{31a}$R$^{31b}$, —SO$_2$NR$^{31a}$R$^{31b}$, —O(C=O)NR$^{31a}$R$^{31b}$, —NHSO$_2$NR$^{31a}$R$^{31b}$, —NH(C=O)NR$^{31a}$R$^{31b}$, and —N=NR$^{32}$. In a still further aspect, Ar$^1$, when present, is unsubstituted phenyl.

In a further aspect, Ar$^1$, when present, is naphthyl substituted with 0, 1, 2, or 3 groups independently selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 naphthyl, —O(C2-C4 alkenyl), —OCO$_2$R$^{30}$, —CO$_2$R$^{30}$, —(C1-C4 alkyl)CO$_2$R$^{30}$, —(C2-C4 alkenyl)CO$_2$R$^{30}$, —(C=O)(C1-C4 alkyl), —(S=O)(C1-C4 alkyl), —SO$_2$(C1-C4 alkyl), —(C=O)NR$^{31a}$R$^{31b}$, —SO$_2$NR$^{31a}$R$^{31b}$, —O(C=O)NR$^{31a}$R$^{31b}$, —NHSO$_2$NR$^{31a}$R$^{31b}$, —NH(C=O)NR$^{31a}$R$^{31b}$, and —N=NR$^{32}$. In a still further aspect, Ar$^1$, when present, is naphthyl substituted with 0, 1, or 2 groups independently selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl (C1-C4 alkoxy), C1-C4 aminoalkyl, C1-C4 alkylamino, (C1-C4)(C1-C4) dialkylamino, C3-C7 cycloalkyl, C6-C10 naphthyl, —O(C2-C4 alkenyl), —OCO$_2$R$^{30}$, —CO$_2$R$^{30}$, —(C1-C4 alkyl)CO$_2$R$^{30}$, —(C2-C4 alkenyl)CO$_2$R$^{30}$, —(C=O)(C1-C4 alkyl), —(S=O)(C1-C4 alkyl), —SO$_2$(C1-C4 alkyl), —(C=O)NR$^{31a}$R$^{31b}$, —SO$_2$NR$^{31a}$R$^{31b}$, —O(C=O)NR$^{31a}$R$^{31b}$, —NHSO$_2$NR$^{31a}$R$^{31b}$, —NH(C=O)NR$^{31a}$R$^{31b}$, and —N=NR$^{32}$. In yet a further aspect, Ar$^1$, when present, is naphthyl substituted with 0 or 1 group selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 naphthyl, —O(C2-C4 alkenyl), —OCO$_2$R$^{30}$, —CO$_2$R$^{30}$, —(C1-C4 alkyl)CO$_2$R$^{30}$, —(C2-C4 alkenyl)CO$_2$R$^{30}$, —(C=O)(C1-C4 alkyl), —(S=O)(C1-C4 alkyl), —SO$_2$(C1-C4 alkyl), —(C=O)NR$^{31a}$R$^{31b}$, —SO$_2$NR$^{31a}$R$^{31b}$, —O(C=O)NR$^{31a}$R$^{31b}$, —NHSO$_2$NR$^{31a}$R$^{31b}$, —NH(C=O)NR$^{31a}$R$^{31b}$, and —N=NR$^{32}$. In an even further aspect, Ar$^1$, when present, is naphthyl monosubstituted with a group selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 naphthyl, —O(C2-C4 alkenyl), —OCO$_2$R$^{30}$, —CO$_2$R$^{30}$, —(C1-C4 alkyl)CO$_2$R$^{30}$, —(C2-C4 alkenyl)CO$_2$R$^{30}$, —(C=O)(C1-C4 alkyl), —(S=O)(C1-C4 alkyl), —SO$_2$(C1-C4 alkyl), —(C=O)NR$^{31a}$R$^{31b}$, —SO$_2$NR$^{31a}$R$^{31b}$, —O(C=O)NR$^{31a}$R$^{31b}$, —NHSO$_2$NR$^{31a}$R$^{31b}$, —NH(C=O)NR$^{31a}$R$^{31b}$, and —N=NR$^{32}$. In a still further aspect, Ar$^1$, when present, is unsubstituted naphthyl.

In a further aspect, Ar$^1$, when present, is 1-naphthyl substituted with 0, 1, 2, or 3 groups independently selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 1-naphthyl, —O(C2-C4 alkenyl), —OCO$_2$R$^{30}$, —CO$_2$R$^{30}$, —(C1-C4 alkyl)CO$_2$R$^{30}$, —(C2-C4 alkenyl)CO$_2$R$^{30}$, —(C=O)(C1-C4 alkyl), —(S=O)(C1-C4 alkyl), —SO$_2$(C1-C4 alkyl), —(C=O)NR$^{31a}$R$^{31b}$, —SO$_2$NR$^{31a}$R$^{31b}$, —O(C=O)NR$^{31a}$R$^{31b}$, —NHSO$_2$NR$^{31a}$R$^{31b}$, —NH(C=O)NR$^{31a}$R$^{31b}$, and —N=NR$^{32}$. In a still further aspect, Ar$^1$, when present, is 1-naphthyl substituted with 0, 1, or 2 groups independently selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 1-naphthyl, —O(C2-C4 alkenyl), —OCO$_2$R$^{30}$, —CO$_2$R$^{30}$, —(C1-C4 alkyl)CO$_2$R$^{30}$, —(C2-C4 alkenyl)CO$_2$R$^{30}$, —(C=O)(C1-C4 alkyl), —(S=O)(C1-C4 alkyl), —SO$_2$(C1-C4 alkyl), —(C=O)NR$^{31a}$R$^{31b}$, —SO$_2$NR$^{31a}$R$^{31b}$, —O(C=O)NR$^{31a}$R$^{31b}$, —NHSO$_2$NR$^{31a}$R$^{31b}$, —NH(C=O)NR$^{31a}$R$^{31b}$, and —N=NR$^{32}$. In yet a further aspect, Ar$^1$, when present, is 1-naphthyl substituted with 0 or 1 group selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl (C1-C4 alkoxy), C1-C4 aminoalkyl, C1-C4 alkylamino, (C1-C4)(C1-C4) dialkylamino, C3-C7 cycloalkyl, C6-C10 1-naphthyl, —O(C2-C4 alkenyl), —OCO$_2$R$^{30}$, —CO$_2$R$^{30}$, —(C1-C4 alkyl)CO$_2$R$^{30}$, —(C2-C4 alkenyl)CO$_2$R$^{30}$, —(C=O)(C1-C4 alkyl), —(S=O)(C1-C4 alkyl), —SO$_2$(C1-C4 alkyl), —(C=O)NR$^{31a}$R$^{31b}$, —SO$_2$NR$^{31a}$R$^{31b}$, —O(C=O)NR$^{31a}$R$^{31b}$, —NHSO$_2$NR$^{31a}$R$^{31b}$, —NH(C=O)NR$^{31a}$R$^{31b}$, and —N=NR$^{32}$. In an even further aspect, Ar$^1$, when present, is 1-naphthyl monosubstituted with a group selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 1-naphthyl, —O(C2-C4 alkenyl), —OCO$_2$R$^{30}$, —CO$_2$R$^{30}$, —(C1-C4 alkyl)CO$_2$R$^{30}$, —(C2-C4 alkenyl) CO$_2$R$^{30}$, —(C=O)(C1-C4 alkyl), —(S=O)(C1-C4 alkyl), —SO$_2$(C1-C4 alkyl), —(C=O)NR$^{31a}$R$^{31b}$, —SO$_2$NR$^{31a}$R$^{31b}$, —O(C=O)NR$^{31a}$R$^{31b}$, —NHSO$_2$NR$^{31a}$R$^{31b}$, —NH(C=O)NR$^{31a}$R$^{31b}$, and —N=NR$^{32}$. In a still further aspect, Ar$^1$, when present, is unsubstituted 1-naphthyl.

In a further aspect, Ar$^1$, when present, is 2-naphthyl substituted with 0, 1, 2, or 3 groups independently selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 2-naphthyl, —O(C2-C4 alkenyl), —OCO$_2$R$^{30}$, —CO$_2$R$^{30}$, —(C1-C4 alkyl)CO$_2$R$^{30}$, —(C2-C4 alkenyl)CO$_2$R$^{30}$, —(C=O)(C1-C4 alkyl), —(S=O)(C1-C4 alkyl), —SO$_2$(C1-C4 alkyl), —(C=O)NR$^{31a}$R$^{31b}$, —SO$_2$NR$^{31a}$R$^{31b}$, —O(C=O)NR$^{31a}$R$^{31b}$, —NHSO$_2$NR$^{31a}$R$^{31b}$, —NH(C=O)NR$^{31a}$R$^{31b}$, and —N=NR$^{32}$. In a still further aspect, Ar$^1$, when present, is 2-naphthyl substituted with 0, 1, or 2 groups independently selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl (C1-C4 alkoxy), C1-C4 aminoalkyl, C1-C4 alkylamino, (C1-C4)(C1-C4) dialkylamino, C3-C7 cycloalkyl, C6-C10 2-naphthyl, —O(C2-C4 alkenyl), —OCO$_2$R$^{30}$, —CO$_2$R$^{30}$, —(C1-C4 alkyl)CO$_2$R$^{30}$, —(C2-C4 alkenyl)CO$_2$R$^{30}$, —(C=O)(C1-C4 alkyl), —(S=O)(C1-C4 alkyl), —SO$_2$(C1-C4 alkyl), —(C=O)NR$^{31a}$R$^{31b}$, —SO$_2$NR$^{31a}$R$^{31b}$, —O(C=O)NR$^{31a}$R$^{31b}$, —NHSO$_2$NR$^{31a}$R$^{31b}$, —NH(C=O)NR$^{31a}$R$^{31b}$, and —N=NR$^{32}$. In yet a further aspect, Ar$^1$, when present, is 2-naphthyl substituted with 0 or 1 group selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl (C1-C4 alkoxy), C1-C4 aminoalkyl, C1-C4 alkylamino, (C1-C4)(C1-C4) dialkylamino, C3-C7 cycloalkyl, C6-C10 2-naphthyl, —O(C2-C4 alkenyl), —OCO$_2$R$^{30}$, —CO$_2$R$^{30}$, —(C1-C4 alkyl)CO$_2$R$^{30}$, —(C2-C4 alkenyl)CO$_2$R$^{30}$, —(C=O)(C1-C4 alkyl), —(S=O)(C1-C4 alkyl), —SO$_2$(C1-C4 alkyl), —(C=O)NR$^{31a}$R$^{31b}$, —SO$_2$NR$^{31a}$R$^{31b}$, —O(C=O)NR$^{31a}$R$^{31b}$, —NHSO$_2$NR$^{31a}$R$^{31b}$, —NH(C=O)NR$^{31a}$R$^{31b}$, and —N=NR$^{32}$. In an even further aspect, Ar$^1$, when present, is 2-naphthyl monosubstituted with a group selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 2-naphthyl, —O(C2-C4 alkenyl), —OCO$_2$R$^{30}$, —CO$_2$R$^{30}$, —(C1-C4 alkyl)CO$_2$R$^{30}$, —(C2-C4 alkenyl)CO$_2$R$^{30}$, —(C=O)(C1-C4 alkyl), —(S=O)(C1-C4 alkyl), —SO$_2$(C1-C4 alkyl), —(C=O)NR$^{31a}$R$^{31b}$, —SO$_2$NR$^{31a}$R$^{31b}$, —O(C=O)NR$^{31a}$R$^{31b}$, —NHSO$_2$NR$^{31a}$R$^{31b}$, —NH(C=O)NR$^{31a}$R$^{31b}$, and —N=NR$^{32}$. In a still further aspect, Ar$^1$, when present, is unsubstituted 2-naphthyl.

In a further aspect, Ar$^1$, when present, is benzo[d][1,3]dioxolyl substituted with 0, 1, 2, or 3 groups independently selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 benzo[d][1,3]dioxolyl, —O(C2-C4 alkenyl), —OCO$_2$R$^{30}$, —CO$_2$R$^{30}$, —(C1-C4 alkyl)CO$_2$R$^{30}$, —(C2-C4 alkenyl)CO$_2$R$^{30}$, —(C=O)(C1-C4 alkyl), —(S=O)(C1-C4 alkyl), —SO$_2$(C1-C4 alkyl), —(C=O)NR$^{31a}$R$^{31b}$, —SO$_2$NR$^{31a}$R$^{31b}$, —O(C=O)NR$^{31a}$R$^{31b}$, —NHSO$_2$NR$^{31a}$R$^{31b}$, —NH(C=O)NR$^{31a}$R$^{31b}$, and —N=NR$^{32}$. In a still further aspect, Ar$^1$, when present, is benzo[d][1,3]dioxolyl substituted with 0, 1, or 2 groups independently selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 benzo[d][1,3]dioxolyl, —O(C2-C4 alkenyl), —OCO$_2$R$^{30}$, —CO$_2$R$^{30}$, —(C1-C4 alkyl)CO$_2$R$^{30}$, —(C2-C4 alkenyl)CO$_2$R$^{30}$, —(C=O)(C1-C4 alkyl), —(S=O)(C1-C4 alkyl), —SO$_2$(C1-C4 alkyl), —(C=O)NR$^{31a}$R$^{31b}$ SO$_2$NR$^{31a}$R$^{31b}$, —O(C=O)NR$^{31a}$R$^{31b}$, —NHSO$_2$NR$^{31a}$R$^{31b}$, —NH(C=O)NR$^{31a}$R$^{31b}$, and —N=NR$^{32}$. In yet a further aspect, Ar$^1$, when present, is benzo[d][1,3]dioxolyl substituted with 0 or 1 group selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 benzo[d][1,3]dioxolyl, —O(C2-C4 alkenyl), —OCO$_2$R$^{30}$, —CO$_2$R$^{30}$, —(C1-C4 alkyl)CO$_2$R$^{30}$, —(C2-C4 alkenyl)CO$_2$R$^{30}$, —(C=O)(C1-C4 alkyl), —(S=O)(C1-C4 alkyl), —SO$_2$(C1-C4 alkyl), —(C=O)NR$^{31a}$R$^{31b}$, —SO$_2$NR$^{31a}$R$^{31b}$, —O(C=O)NR$^{31a}$R$^{31b}$, —NHSO$_2$NR$^{31a}$R$^{31b}$, —NH(C=O)NR$^{31a}$R$^{31b}$, and —N=NR$^{32}$. In an even further aspect, Ar$^1$, when present, is benzo[d][1,3]dioxolyl monosubstituted with a group selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 benzo[d][1,3]dioxolyl, —O(C2-C4 alkenyl), —OCO$_2$R$^{30}$, —CO$_2$R$^{30}$, —(C1-C4 alkyl)CO$_2$R$^{30}$, —(C2-C4 alkenyl)CO$_2$R$^{30}$, —(C=O)(C1-C4 alkyl), —(S=O)(C1-C4 alkyl), —SO$_2$(C1-C4 alkyl), —(C=O)NR$^{31a}$R$^{31b}$, —SO$_2$NR$^{31a}$R$^{31b}$, —O(C=O)NR$^{31a}$R$^{31b}$, —NHSO$_2$NR$^{31a}$R$^{31b}$, —NH(C=O)NR$^{31a}$R$^{31b}$, and —N=NR$^{32}$. In a still further aspect, Ar$^1$, when present, is unsubstituted benzo[d][1,3]dioxolyl.

In a further aspect, Ar$^1$, when present, is heteroaryl substituted with 0, 1, 2, or 3 groups independently selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO$_2$R$^{30}$, —CO$_2$R$^{30}$, —(C1-C4 alkyl)CO$_2$R$^{30}$, —(C2-C4 alkenyl)CO$_2$R$^{30}$, —(C=O)(C1-C4 alkyl), —(S=O)(C1-C4 alkyl), —SO$_2$(C1-C4 alkyl), —(C=O)NR$^{31a}$R$^{31b}$, —SO$_2$NR$^{31a}$R$^{31b}$, —O(C=O)NR$^{31a}$R$^{31b}$, —NHSO$_2$NR$^{31a}$R$^{31b}$, —NH(C=O)NR$^{31a}$R$^{31b}$, and —N=NR$^{32}$. In a still further aspect, Ar$^1$, when present, is heteroaryl substituted with 0, 1, or 2 groups independently selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl (C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO$_2$R$^{30}$, —CO$_2$R$^{30}$, —(C1-C4 alkyl)CO$_2$R$^{30}$, —(C2-C4 alkenyl)CO$_2$R$^{30}$, —(C=O)(C1-C4 alkyl), —(S=O)(C1-C4 alkyl), —SO$_2$(C1-C4 alkyl), —(C=O)NR$^{31a}$R$^{31b}$, —SO$_2$NR$^{31a}$R$^{31b}$, —O(C=O)NR$^{31a}$R$^{31b}$, —NHSO$_2$NR$^{31a}$R$^{31b}$, —NH(C=O)NR$^{31a}$R$^{31b}$, and —N=NR$^{32}$. In yet a further aspect, Ar$^1$, when present, is heteroaryl substituted with 0 or 1 group selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO$_2$R$^{30}$, —CO$_2$R$^{30}$, —(C1-C4 alkyl)CO$_2$R$^{30}$, —(C2-C4 alkenyl)CO$_2$R$^{30}$, —(C=O)(C1-C4 alkyl), —(S=O)(C1-C4 alkyl), —SO$_2$(C1-C4 alkyl), —(C=O) NR$^{31a}$R$^{31b}$, —SO$_2$NR$^{31a}$R$^{31b}$, —O(C=O)NR$^{31a}$R$^{31b}$, —NHSO$_2$NR$^{31a}$R$^{31b}$, —NH(C=O)NR$^{31a}$R$^{31b}$, and —N=NR$^{32}$. In an even further aspect, Ar$^1$, when present, is heteroaryl monosubstituted with a group selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO$_2$R$^{30}$, —CO$_2$R$^{30}$, —(C1-C4 alkyl)CO$_2$R$^{30}$, —(C2-C4 alkenyl)CO$_2$R$^{30}$, —(C=O)(C1-C4 alkyl), —(S=O)(C1-C4 alkyl), —SO$_2$(C1-C4 alkyl), —(C=O) NR$^{31a}$R$^{31b}$, —SO$_2$NR$^{31a}$R$^{31b}$, —O(C=O)NR$^{31a}$R$^{31b}$, —NHSO$_2$NR$^{31a}$R$^{31b}$, —NH(C=O)NR$^{31a}$R$^{31b}$, and —N=NR$^{32}$. In a still further aspect, Ar$^1$, when present, is unsubstituted heteroaryl.

In a further aspect, Ar$^1$, when present, is pyridinyl substituted with 0, 1, 2, or 3 groups independently selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO$_2$R$^{30}$, —CO$_2$R$^{30}$, —(C1-C4 alkyl)CO$_2$R$^{30}$, —(C2-C4 alkenyl)CO$_2$R$^{30}$, —(C=O)(C1-C4 alkyl), —(S=O)(C1-C4 alkyl), —SO$_2$(C1-C4 alkyl), —(C=O)

$NR^{31a}R^{31b}$, $-SO_2NR^{31a}R^{31b}$, $-O(C=O)NR^{31a}R^{31b}$, $-NHSO_2NR^{31a}R^{31b}$, $-NH(C=O)NR^{31a}R^{31b}$, and $-N=NR^{32}$. In a still further aspect, $Ar^1$, when present, is pyridinyl substituted with 0, 1, or 2 groups independently selected from halogen, $-NO_2$, $-CN$, $-OH$, $-SH$, $-NH_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, $-O(C2-C4$ alkenyl), $-OCO_2R^{30}$, $-CO_2R^{30}$, $-(C1-C4$ alkyl)$CO_2R^{30}$, $-(C2-C4$ alkenyl)$CO_2R^{30}$, $-(C=O)$ (C1-C4 alkyl), $-(S=O)(C1-C4$ alkyl), $-SO_2(C1-C4$ alkyl), $-(C=O)NR^{31a}R^{31b}$, $SO_2NR^{31a}R^{31b}$, $-O(C=O)NR^{31a}R^{31b}$, $-NHSO_2NR^{31a}R^{31b}$, $-NH(C=O)NR^{31a}R^{31b}$, and $-N=NR^{32}$. In yet a further aspect, $Ar^1$, when present, is pyridinyl substituted with 0 or 1 group selected from halogen, $-NO_2$, $-CN$, $-OH$, $-SH$, $-NH_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, $-O(C2-C4$ alkenyl), $-OCO_2R^{30}$, $-CO_2R^{30}$, $-(C1-C4$ alkyl)$CO_2R^{30}$, $-(C2-C4$ alkenyl)$CO_2R^{30}$, $-(C=O)(C1-C4$ alkyl), $-(S=O)(C1-C4$ alkyl), $-SO_2(C1-C4$ alkyl), $-(C=O)NR^{31a}R^{31b}$, $-SO_2NR^{31a}R^{31b}$, $-O(C=O)NR^{31a}R^{31b}$, $-NHSO_2NR^{31a}R^{31b}$, $-NH(C=O)NR^{31a}R^{31b}$, and $-N=NR^{32}$. In an even further aspect, $Ar^1$, when present, is pyridinyl monosubstituted with a group selected from halogen, $-NO_2$, $-CN$, $-OH$, $-SH$, $-NH_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, $-O(C2-C4$ alkenyl), $-OCO_2R^{30}$, $-CO_2R^{30}$, $-(C1-C4$ alkyl)$CO_2R^{30}$, $-(C2-C4$ alkenyl)$CO_2R^{30}$, $-(C=O)(C1-C4$ alkyl), $-(S=O)(C1-C4$ alkyl), $-SO_2(C1-C4$ alkyl), $-(C=O)NR^{31a}R^{31b}$, $-SO_2NR^{31a}R^{31b}$, $-O(C=O)NR^{31a}R^{31b}$, $-NHSO_2NR^{31a}R^{31b}$, $-NH(C=O)NR^{31a}R^{31b}$, and $-N=NR^{32}$. In a still further aspect, $Ar^1$, when present, is unsubstituted pyridinyl.

In a further aspect, $Ar^1$, when present, is quinolinyl substituted with 0, 1, 2, or 3 groups independently selected from halogen, $-NO_2$, $-CN$, $-OH$, $-SH$, $-NH_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4) (C1-C4) dialkylamino, C3-C7 cycloalkyl, C6-C10 aryl, $-O(C2-C4$ alkenyl), $-OCO_2R^{30}$, $-CO_2R^{30}$, $-(C1-C4$ alkyl)$CO_2R^{30}$, $-(C2-C4$ alkenyl)$CO_2R^{30}$, $-(C=O)(C1-C4$ alkyl), $-(S=O)(C1-C4$ alkyl), $-SO_2(C1-C4$ alkyl), $-(C=O)NR^{31a}R^{31b}$, $-SO_2NR^{31a}R^{31b}$, $-O(C=O)NR^{31a}R^{31b}$, $-NHSO_2NR^{31a}R^{31b}$, $-NH(C=O)NR^{31a}R^{31b}$, and $-N=NR^{32}$. In a still further aspect, $Ar^1$, when present, is quinolinyl substituted with 0, 1, or 2 groups independently selected from halogen, $-NO_2$, $-CN$, $-OH$, $-SH$, $-NH_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl (C1-C4 alkoxy), C1-C4 aminoalkyl, C1-C4 alkylamino, (C1-C4)(C1-C4) dialkylamino, C3-C7 cycloalkyl, C6-C10 aryl, $-O(C2-C4$ alkenyl), $-OCO_2R^{30}$, $-CO_2R^{30}$, $-(C1-C4$ alkyl)$CO_2R^{30}$, $-(C2-C4$ alkenyl)$CO_2R^{30}$, $-(C=O)$ (C1-C4 alkyl), $-(S=O)(C1-C4$ alkyl), $-SO_2(C1-C4$ alkyl), $-(C=O)NR^{31a}R^{31b}$, $SO_2NR^{31a}R^{31b}$, $-O(C=O)NR^{31a}R^{31b}$, $-NHSO_2NR^{31a}R^{31b}$, $-NH(C=O)NR^{31a}R^{31b}$, and $-N=NR^{32}$. In yet a further aspect, $Ar^1$, when present, is quinolinyl substituted with 0 or 1 group selected from halogen, $-NO_2$, $-CN$, $-OH$, $-SH$, $-NH_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, $-O(C2-C4$ alkenyl), $-OCO_2R^{30}$, $-CO_2R^{30}$, $-(C1-C4$ alkyl)$CO_2R^{30}$, $-(C2-C4$ alkenyl)$CO_2R^{30}$, $-(C=O)(C1-C4$ alkyl), $-(S=O)(C1-C4$ alkyl), $-SO_2(C1-C4$ alkyl), $-(C=O)NR^{31a}R^{31b}$, $-SO_2NR^{31a}R^{31b}$, $-O(C=O)NR^{31a}R^{31b}$, $-NHSO_2NR^{31a}R^{31b}$, $-NH(C=O)NR^{31a}R^{31b}$, and $-N=NR^{32}$. In an even further aspect, $Ar^1$, when present, is quinolinyl monosubstituted with a group selected from halogen, $-NO_2$, $-CN$, $-OH$, $-SH$, $-NH_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, $-O(C2-C4$ alkenyl), $-OCO_2R^{30}$, $-CO_2R^{30}$, $-(C1-C4$ alkyl)$CO_2R^{30}$, $-(C2-C4$ alkenyl)$CO_2R^{30}$, $-(C=O)(C1-C4$ alkyl), $-(S=O)(C1-C4$ alkyl), $-SO_2(C1-C4$ alkyl), $-(C=O)NR^{31a}R^{31b}$, $-SO_2NR^{31a}R^{31b}$, $-O(C=O)NR^{31a}R^{31b}$, $-NHSO_2NR^{31a}R^{31b}$, $-NH(C=O)NR^{31a}R^{31b}$, and $-N=NR^{32}$. In a still further aspect, $Ar^1$, when present, is unsubstituted quinolinyl.

In a further aspect, $Ar^1$, when present, is furanyl substituted with 0, 1, 2, or 3 groups independently selected from halogen, $-NO_2$, $-CN$, $-OH$, $-SH$, $-NH_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, $-O(C2-C4$ alkenyl), $-OCO_2R^{30}$, $-CO_2R^{30}$, $-(C1-C4$ alkyl)$CO_2R^{30}$, $-(C2-C4$ alkenyl)$CO_2R^{30}$, $-(C=O)(C1-C4$ alkyl), $-(S=O)(C1-C4$ alkyl), $-SO_2(C1-C4$ alkyl), $-(C=O)NR^{31a}R^{31b}$, $-SO_2NR^{31a}R^{31b}$, $-O(C=O)NR^{31a}R^{31b}$, $-NHSO_2NR^{31a}R^{31b}$, $-NH(C=O)NR^{31a}R^{31b}$, and $-N=NR^{32}$. In a still further aspect, $Ar^1$, when present, is furanyl substituted with 0, 1, or 2 groups independently selected from halogen, $-NO_2$, $-CN$, $-OH$, $-SH$, $-NH_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl (C1-C4 alkoxy), C1-C4 aminoalkyl, C1-C4 alkylamino, (C1-C4)(C1-C4) dialkylamino, C3-C7 cycloalkyl, C6-C10 aryl, $-O(C2-C4$ alkenyl), $-OCO_2R^{30}$, $-CO_2R^{30}$, $-(C1-C4$ alkyl)$CO_2R^{30}$, $-(C2-C4$ alkenyl)$CO_2R^{30}$, $-(C=O)$ (C1-C4 alkyl), $-(S=O)(C1-C4$ alkyl), $-SO_2(C1-C4$ alkyl), $-(C=O)NR^{31a}R^{31b}$, $SO_2NR^{31a}R^{31b}$, $-O(C=O)NR^{31a}R^{31b}$, $-NHSO_2NR^{31a}R^{31b}$, $-NH(C=O)NR^{31a}R^{31b}$, and $-N=NR^{32}$. In yet a further aspect, $Ar^1$, when present, is furanyl substituted with 0 or 1 group selected from halogen, $-NO_2$, $-CN$, $-OH$, $-SH$, $-NH_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, $-O(C2-C4$ alkenyl), $-OCO_2R^{30}$, $-CO_2R^{30}$, $-(C1-C4$ alkyl)$CO_2R^{30}$, $-(C2-C4$ alkenyl)$CO_2R^{30}$, $-(C=O)(C1-C4$ alkyl), $-(S=O)(C1-C4$ alkyl), $-SO_2(C1-C4$ alkyl), $-(C=O)$ $NR^{31a}R^{31b}$, $-SO_2NR^{31a}R^{31b}$, $-O(C=O)NR^{31a}R^{31b}$, $-NHSO_2NR^{31a}R^{31b}$, $-NH(C=O)NR^{31a}R^{31b}$, and $-N=NR^{32}$. In an even further aspect, $Ar^1$, when present, is furanyl monosubstituted with a group selected from halogen, $-NO_2$, $-CN$, $-OH$, $-SH$, $-NH_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, $-O(C2-C4$ alkenyl), $-OCO_2R^{30}$, $-CO_2R^{30}$, $-(C1-C4$ alkyl)$CO_2R^{30}$, $-(C2-C4$ alkenyl)$CO_2R^{30}$, $-(C=O)(C1-C4$ alkyl), $-(S=O)(C1-C4$ alkyl), $-SO_2(C1-C4$ alkyl), $-(C=O)NR^{31a}R^{31b}$, $-SO_2NR^{31a}R^{31b}$, $-O(C=O)NR^{31a}R^{31b}$, $-NHSO_2NR^{31a}R^{31b}$, $-NH(C=O)NR^{31a}R^{31b}$, and $-N=NR^{32}$. In a still further aspect, $Ar^1$, when present, is unsubstituted furanyl.

In a further aspect, $Ar^1$ is aryl substituted with 0, 1, 2, or 3 groups independently selected from C1-C4 haloalkyl, C1-C4 alkoxy, and C6-C10 aryl. In a still further aspect, $Ar^1$ is aryl substituted with 0, 1, or 2 groups independently selected from C1-C4 haloalkyl, C1-C4 alkoxy, and C6-C10 aryl. In yet a further aspect, $Ar^1$ is aryl substituted with 0 or 1 group selected from C1-C4 haloalkyl, C1-C4 alkoxy, and C6-C10 aryl. In an even further aspect, $Ar^1$ is aryl monosubstituted with a group selected from C1-C4 haloalkyl, C1-C4 alkoxy, and C6-C10 aryl.

In a further aspect, $Ar^1$ is aryl substituted with 0, 1, 2, or 3 groups independently selected from $-CF_3$, $-OCH_3$, and phenyl. In a still further aspect, $Ar^1$ is aryl substituted with 0, 1, or 2 groups independently selected from $-CF_3$, $-OCH_3$, and phenyl. In yet a further aspect, $Ar^1$ is aryl substituted with 0 or 1 group selected from $-CF_3$, $-OCH_3$, and phenyl. In an even further aspect, $Ar^1$ is aryl monosubstituted with a group selected from $-CF_3$, $-OCH_3$, and phenyl.

x. $Ar^2$ Groups

In one aspect, $Ar^2$, when present, is selected from aryl and heteroaryl and is substituted with 0, 1, 2, or 3 groups independently selected from halogen, $-NO_2$, $-CN$, $-OH$, $-SH$, $-NH_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, $-O(C2-C4$ alkenyl), $-OCO_2R^{33}$, $-CO_2R^{33}$, $-(C1-C4$ alkyl)$CO_2R^{33}$, $-(C2-C4$ alkenyl)$CO_2R^{33}$, $-(C=O)(C1-C4$ alkyl), $-(S=O)(C1-C4$ alkyl), $-SO_2(C1-C4$ alkyl), $-(C=O)NR^{34a}R^{34b}$, $-SO_2NR^{34a}R^{34b}$, $-O(C=O)NR^{34a}R^{34b}$, $-NHSO_2NR^{34a}R^{34b}$, $-NH(C=O)NR^{34a}R^{34b}$, and $-N=NR^{35}$. In a further aspect, $Ar^2$, when present, is selected from aryl and heteroaryl and is substituted with 0, 1, or 2 groups independently selected from halogen, $-NO_2$, $-CN$, $-OH$, $-SH$, $-NH_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, $-O(C2-C4$ alkenyl), $-OCO_2R^{33}$, $-CO_2R^{33}$, $-(C1-C4$ alkyl)$CO_2R^{33}$, $-(C2-C4$ alkenyl)$CO_2R^{33}$, $-(C=O)(C1-C4$ alkyl), $-(S=O)(C1-C4$ alkyl), $-SO_2(C1-C4$ alkyl), $-(C=O)NR^{34a}R^{34b}$, $-SO_2NR^{34a}R^{34b}$, $-O(C=O)NR^{34a}R^{34b}$, $-NHSO_2NR^{34a}R^{34b}$, $-NH(C=O)NR^{34a}R^{34b}$, and $-N=NR^{35}$. In a still further aspect, $Ar^2$, when present, is selected from aryl and heteroaryl and is substituted with 0 or 1 group selected from halogen, $-NO_2$, $-CN$, $-OH$, $-SH$, $-NH_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, $-O(C2-C4$ alkenyl), $-OCO_2R^{33}$, $-CO_2R^{33}$, $-(C1-C4$ alkyl)$CO_2R^{33}$, $-(C2-C4$ alkenyl)$CO_2R^{33}$, $-(C=O)(C1-C4$ alkyl), $-(S=O)(C1-C4$ alkyl), $-SO_2(C1-C4$ alkyl), $-(C=O)NR^{34a}R^{34b}$, $-SO_2NR^{34a}R^{34b}$, $-O(C=O)NR^{34a}R^{34b}$, $-NHSO_2NR^{34a}R^{34b}$, $-NH(C=O)NR^{34a}R^{34b}$, and $-N=NR^{35}$. In an even further aspect, $Ar^2$, when present, is selected from aryl and heteroaryl and is unsubstituted.

In a further aspect, $Ar^2$, when present, is aryl substituted with 0, 1, 2, or 3 groups independently selected from halogen, $-NO_2$, $-CN$, $-OH$, $-SH$, $-NH_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, $-O(C2-C4$ alkenyl), $-OCO_2R^{33}$, $-CO_2R^{33}$, $-(C1-C4$ alkyl)$CO_2R^{33}$, $-(C2-C4$ alkenyl)$CO_2R^{33}$, $-(C=O)(C1-C4$ alkyl), $-(S=O)(C1-C4$ alkyl), $-SO_2(C1-C4$ alkyl), $-(C=O)NR^{34a}R^{34b}$, $-SO_2NR^{34a}R^{34b}$, $-O(C=O)NR^{34a}R^{34b}$, $-NHSO_2NR^{34a}R^{34b}$, $-NH(C=O)NR^{34a}R^{34b}$, and $-N=NR^{35}$. In a still further aspect, $Ar^2$, when present, is aryl substituted with 0, 1, or 2 groups independently selected from halogen, $-NO_2$, $-CN$, $-OH$, $-SH$, $-NH_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4) (C1-C4) dialkylamino, C3-C7 cycloalkyl, C6-C10 aryl, $-O(C2-C4$ alkenyl-$OCO_2R^{33}$, $-CO_2R^{33}$, $-(C1-C4$ alkyl)$CO_2R^{33}$, $-(C2-C4$ alkenyl)$CO_2R^{33}$, $-(C=O)(C1-C4$ alkyl), $-(S=O)(C1-C4$ alkyl), $-SO_2(C1-C4$ alkyl), $-(C=O)NR^{34a}R^{34b}$, $-SO_2NR^{34a}R^{34b}$, $-O(C=O)NR^{34a}R^{34b}$, $-NHSO_2NR^{34a}R^{34b}$, $-NH(C=O)NR^{34a}R^{34b}$, and $-N=NR^{35}$. In yet a further aspect, $Ar^2$, when present, is aryl substituted with 0 or 1 group selected from halogen, $-NO_2$, $-CN$, $-OH$, $-SH$, $-NH_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, $-O(C2-C4$ alkenyl), $-OCO_2R^{33}$, $-CO_2R^{33}$, $-(C1-C4$ alkyl)$CO_2R^{33}$, $-(C2-C4$ alkenyl)$CO_2R^{33}$, $-(C=O)(C1-C4$ alkyl), $-(S=O)(C1-C4$ alkyl), $-SO_2(C1-C4$ alkyl), $-(C=O)NR^{34a}R^{34b}$, $-SO_2NR^{34a}R^{34b}$, $-O(C=O)NR^{34a}R^{34b}$, $-NHSO_2NR^{34a}R^{34b}$, $-NH(C=O)NR^{34a}R^{34b}$, and $-N=NR^{35}$. In an even further aspect, $Ar^2$, when present, is aryl monosubstituted with a group selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO$_2$R$^{33}$, —CO$_2$R$^{33}$, —(C1-C4 alkyl)CO$_2$R$^{33}$, —(C2-C4 alkenyl)CO$_2$R$^{33}$, —(C=O)(C1-C4 alkyl), —(S=O)(C1-C4 alkyl), —SO$_2$(C1-C4 alkyl), —(C=O)NR$^{34a}$R$^{34b}$, —SO$_2$NR$^{34a}$R$^{34b}$, —O(C=O)NR$^{34a}$R$^{34b}$, —NHSO$_2$NR$^{34a}$R$^{34b}$, —NH(C=O)NR$^{34a}$R$^{34b}$, and —N=NR$^{35}$. In a still further aspect, Ar$^2$, when present, is unsubstituted aryl.

In a further aspect, Ar$^2$, when present, is phenyl substituted with 0, 1, 2, or 3 groups independently selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 phenyl, —O(C2-C4 alkenyl), —OCO$_2$R$^{33}$, —CO$_2$R$^{33}$, —(C1-C4 alkyl)CO$_2$R$^{33}$, —(C2-C4 alkenyl)CO$_2$R$^{33}$, —(C=O)(C1-C4 alkyl), —(S=O)(C1-C4 alkyl), —SO$_2$(C1-C4 alkyl), —(C=O)NR$^{34a}$R$^{34b}$, —SO$_2$NR$^{34a}$R$^{34b}$, —O(C=O)NR$^{34a}$R$^{34b}$, —NHSO$_2$NR$^{34a}$R$^{34b}$, —NH(C=O)NR$^{34a}$R$^{34b}$, and —N=NR$^{35}$. In a still further aspect, Ar$^2$, when present, is phenyl substituted with 0, 1, or 2 groups independently selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl (C1-C4 alkoxy), C1-C4 aminoalkyl, C1-C4 alkylamino, (C1-C4)(C1-C4) dialkylamino, C3-C7 cycloalkyl, C6-C10 phenyl, —O(C2-C4 alkenyl), —OCO$_2$R$^{33}$, —CO$_2$R$^{33}$, —(C1-C4 alkyl)CO$_2$R$^{33}$, —(C2-C4 alkenyl)CO$_2$R$^{33}$, —(C=O)(C1-C4 alkyl), —(S=O)(C1-C4 alkyl), —SO$_2$(C1-C4 alkyl), —(C=O)NR$^{34a}$R$^{34b}$, —SO$_2$NR$^{34a}$R$^{34b}$, —O(C=O)NR$^{34a}$R$^{34b34}$, —NHSO$_2$NR$^{34a}$R$^{34b}$, —NH(C=O)NR$^{34a}$R$^{34b}$, and —N=NR$^{35}$. In yet a further aspect, Ar$^2$, when present, is phenyl substituted with 0 or 1 group selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl (C1-C4 alkoxy), C1-C4 aminoalkyl, C1-C4 alkylamino, (C1-C4)(C1-C4) dialkylamino, C3-C7 cycloalkyl, C6-C10 phenyl, —O(C2-C4 alkenyl), —OC$_2$R$^{33}$, —CO$_2$R$^{33}$, —(C1-C4 alkyl)CO$_2$R$^{33}$, —(C2-C4 alkenyl)CO$_2$R$^{33}$, —(C=O)(C1-C4 alkyl), —(S=O)(C1-C4 alkyl), —SO$_2$(C1-C4 alkyl), —(C=O)NR$^{34a}$R$^{34b}$, —SO$_2$NR$^{34a}$R$^{34b}$, —O(C=O)NR$^{34a}$R$^{34b}$, —NHSO$_2$NR$^{34a}$R$^{34b}$, —NH(C=O)NR$^{34a}$R$^{34b}$, and —N=NR$^{35}$. In an even further aspect, Ar$^2$, when present, is phenyl monosubstituted with a group selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4) (C1-C4) dialkylamino, C3-C7 cycloalkyl, C6-C10 phenyl, —O(C2-C4 alkenyl), —OCO$_2$R$^{33}$, —CO$_2$R$^{33}$, —(C1-C4 alkyl)CO$_2$R$^{33}$, —(C2-C4 alkenyl)CO$_2$R$^{33}$, —(C=O)(C1-C4 alkyl), —(S=O)(C1-C4 alkyl), —SO$_2$(C1-C4 alkyl), —(C=O)NR$^{34a}$R$^{34b}$, —SO$_2$NR$^{34a}$R$^{34b}$, —O(C=O)NR$^{34a}$R$^{34b}$, —NHSO$_2$NR$^{34a}$R$^{34b}$, —NH(C=O)NR$^{34a}$R$^{34b}$, and —N=NR$^{35}$. In a still further aspect, Ar$^2$, when present, is unsubstituted phenyl.

In a further aspect, Ar$^2$, when present, is naphthyl substituted with 0, 1, 2, or 3 groups independently selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 naphthyl, —O(C2-C4 alkenyl), —OCO$_2$R$^{33}$, —CO$_2$R$^{33}$, —(C1-C4 alkyl)CO$_2$R$^{33}$, —(C2-C4 alkenyl)CO$_2$R$^{33}$, —(C=O)(C1-C4 alkyl), —(S=O)(C1-C4 alkyl), —SO$_2$(C1-C4 alkyl), —(C=O)NR$^{34a}$R$^{34b}$, —SO$_2$NR$^{34a}$R$^{34b}$, —O(C=O)NR$^{34a}$R$^{34b}$, —NHSO$_2$NR$^{34a}$R$^{34b}$, —NH(C=O)NR$^{34a}$R$^{34b}$, and —N=NR$^{35}$. In a still further aspect, Ar$^2$, when present, is naphthyl substituted with 0, 1, or 2 groups independently selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl (C1-C4 alkoxy), C1-C4 aminoalkyl, C1-C4 alkylamino, (C1-C4)(C1-C4) dialkylamino, C3-C7 cycloalkyl, C6-C10 naphthyl, —O(C2-C4 alkenyl), —OCO$_2$R$^{33}$, —CO$_2$R$^{33}$, —(C1-C4 alkyl)CO$_2$R$^{33}$, —(C2-C4 alkenyl)CO$_2$R$^{33}$, —(C=O)(C1-C4 alkyl), —(S=O)(C1-C4 alkyl), —SO$_2$ (C1-C4 alkyl), —(C=O)NR$^{34a}$R$^{34b}$, —SO$_2$NR$^{34a}$R$^{34b}$, —O(C=O)NR$^{34a}$R$^{34b34}$, —NHSO$_2$NR$^{34a}$R$^{34b}$, —NH(C=O)NR$^{34a}$R$^{34b}$, and —N=NR$^{35}$. In yet a further aspect, Ar$^2$, when present, is naphthyl substituted with 0 or 1 group selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl (C1-C4 alkoxy), C1-C4 aminoalkyl, C1-C4 alkylamino, (C1-C4)(C1-C4) dialkylamino, C3-C7 cycloalkyl, C6-C10 naphthyl, —O(C2-C4 alkenyl), —OCO$_2$R$^{33}$, —CO$_2$R$^{33}$, —(C1-C4 alkyl)CO$_2$R$^{33}$, —(C2-C4 alkenyl)CO$_2$R$^{33}$, —(C=O)(C1-C4 alkyl), —(S=O)(C1-C4 alkyl), —SO$_2$ (C1-C4 alkyl), —(C=O)NR$^{34a}$R$^{34b}$, —SO$_2$NR$^{34a}$R$^{34b}$, —O(C=O)NR$^{34a}$R$^{34b}$, —NHSO$_2$NR$^{34a}$R$^{34b}$, —NH(C=O)NR$^{34a}$R$^{34b}$, and —N=NR$^{35}$. In an even further aspect, Ar$^2$, when present, is naphthyl monosubstituted with a group selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl (C1-C4 alkoxy), C1-C4 aminoalkyl, C1-C4 alkylamino, (C1-C4)(C1-C4) dialkylamino, C3-C7 cycloalkyl, C6-C10 naphthyl, —O(C2-C4 alkenyl), —OCO$_2$R$^{33}$, —CO$_2$R$^{33}$, —(C1-C4 alkyl)CO$_2$R$^{33}$, —(C2-C4 alkenyl)CO$_2$R$^{33}$, —(C=O)(C1-C4 alkyl), —(S=O)(C1-C4 alkyl), —SO$_2$ (C1-C4 alkyl), —(C=O)NR$^{34a}$R$^{34b}$, —SO$_2$NR$^{34a}$R$^{34b}$, —O(C=O)NR$^{34a}$R$^{34b}$, —NHSO$_2$NR$^{34a}$R$^{34b}$, —NH(C=O)NR$^{34a}$R$^{34b}$, and —N=NR$^{35}$. In a still further aspect, Ar$^2$, when present, is unsubstituted naphthyl.

In a further aspect, Ar$^2$, when present, is 1-naphthyl substituted with 0, 1, 2, or 3 groups independently selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4) (C1-C4) dialkylamino, C3-C7 cycloalkyl, C6-C10 1-naphthyl, —O(C2-C4 alkenyl), —OCO$_2$R$^{33}$, —CO$_2$R$^{33}$, —(C1-C4 alkyl)CO$_2$R$^{33}$, —(C2-C4 alkenyl)CO$_2$R$^{33}$, —(C=O) (C1-C4 alkyl), —(S=O)(C1-C4 alkyl), —SO$_2$(C1-C4 alkyl), —(C=O)NR$^{34a}$R$^{34b}$, —SO$_2$NR$^{34a}$R$^{34b}$, —O(C=O) NR$^{34a}$R$^{34b}$, —NHSO$_2$NR$^{34a}$R$^{34b}$, —NH(C=O)NR$^{34a}$R$^{34b}$, and —N=NR³⁵. In a still further aspect, Ar², when present, is 1-naphthyl substituted with 0, 1, or 2 groups independently selected from halogen, —NO₂, —CN, —OH, —SH, —NH₂, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 1-naphthyl, —O(C2-C4 alkenyl), —OCO₂R³³, —CO₂R³³, —(C1-C4 alkyl)CO₂R³³, —(C2-C4 alkenyl)CO₂R³³, —(C=O)(C1-C4 alkyl), —(S=O)(C1-C4 alkyl), —SO₂(C1-C4 alkyl), —(C=O)NR³⁴ᵃR³⁴ᵇ, —SO₂NR³⁴ᵃR³⁴ᵇ, —O(C=O)NR³⁴ᵃR³⁴ᵇ³⁴, —NHSO₂NR³⁴ᵃR³⁴ᵇ, —NH(C=O)NR³⁴ᵃR³⁴ᵇ, and —N=NR³⁵. In yet a further aspect, Ar², when present, is 1-naphthyl substituted with 0 or 1 group selected from halogen, —NO₂, —CN, —OH, —SH, —NH₂, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 1-naphthyl, —O(C2-C4 alkenyl), —OCO₂R³³, —(C1-C4 alkyl)CO₂R³³, —(C2-C4 alkenyl)CO₂R³³, —(C=O)(C1-C4 alkyl), —(S=O)(C1-C4 alkyl), —SO₂(C1-C4 alkyl), —(C=O)NR³⁴ᵃR³⁴ᵇ, —SO₂NR³⁴ᵃR³⁴ᵇ, —O(C=O)NR³⁴ᵃR³⁴ᵇ, —NHSO₂NR³⁴ᵃR³⁴ᵇ, —NH(C=O)NR³⁴ᵃR³⁴ᵇ, and —N=NR³⁵. In an even further aspect, Ar², when present, is 1-naphthyl monosubstituted with a group selected from halogen, —NO₂, —CN, —OH, —SH, —NH₂, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 1-naphthyl, —O(C2-C4 alkenyl), —OCO₂R³³, —CO₂R³³, —(C1-C4 alkyl)CO₂R³³, —(C2-C4 alkenyl)CO₂R³³, —(C=O)(C1-C4 alkyl), —(S=O)(C1-C4 alkyl), —SO₂(C1-C4 alkyl), —(C=O)NR³⁴ᵃR³⁴ᵇ, —SO₂NR³⁴ᵃR³⁴ᵇ, —O(C=O)NR³⁴ᵃR³⁴ᵇ, —NHSO₂NR³⁴ᵃR³⁴ᵇ, —NH(C=O)NR³⁴ᵃR³⁴ᵇ, and —N=NR³⁵. In a still further aspect, Ar², when present, is unsubstituted 1-naphthyl.

In a further aspect, Ar², when present, is 2-naphthyl substituted with 0, 1, 2, or 3 groups independently selected from halogen, —NO₂, —CN, —OH, —SH, —NH₂, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 2-naphthyl, —O(C2-C4 alkenyl), —OCO₂R³³, —CO₂R³³, —(C1-C4 alkyl)CO₂R³³, —(C2-C4 alkenyl)CO₂R³³, —(C=O)(C1-C4 alkyl), —(S=O)(C1-C4 alkyl), —SO₂(C1-C4 alkyl), —(C=O)NR³⁴ᵃR³⁴ᵇ, —SO₂NR³⁴ᵃR³⁴ᵇ, —O(C=O)NR³⁴ᵃR³⁴ᵇ, —NHSO₂NR³⁴ᵃR³⁴ᵇ, —NH(C=O)NR³⁴ᵃR³⁴ᵇ, and —N=NR³⁵. In a still further aspect, Ar², when present, is 2-naphthyl substituted with 0, 1, or 2 groups independently selected from halogen, —NO₂, —CN, —OH, —SH, —NH₂, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 2-naphthyl, —O(C2-C4 alkenyl), —OCO₂R³³, —CO₂R³³, —(C1-C4 alkyl)CO₂R³³, —(C2-C4 alkenyl)CO₂R³³, —(C=O)(C1-C4 alkyl), —(S=O)(C1-C4 alkyl), —SO₂(C1-C4 alkyl), —(C=O)NR³⁴ᵃR³⁴ᵇ, —SO₂NR³⁴ᵃR³⁴ᵇ, —O(C=O)NR³⁴ᵃR³⁴ᵇ, —NHSO₂NR³⁴ᵃR³⁴ᵇ, —NH(C=O)NR³⁴ᵃR³⁴ᵇ, and —N=NR³⁵. In yet a further aspect, Ar², when present, is 2-naphthyl substituted with 0 or 1 group selected from halogen, —NO₂, —CN, —OH, —SH, —NH₂, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 2-naphthyl, —O(C2-C4 alkenyl), —OCO₂R³³, —CO₂R³³, —(C1-C4 alkyl)CO₂R³³, —(C2-C4 alkenyl)CO₂R³³, —(C=O)(C1-C4 alkyl), —(S=O)(C1-C4 alkyl), —SO₂(C1-C4 alkyl), —(C=O)NR³⁴ᵃR³⁴ᵇ, —SO₂NR³⁴ᵃR³⁴ᵇ, —O(C=O)NR³⁴ᵃR³⁴ᵇ, —NHSO₂NR³⁴ᵃR³⁴ᵇ, —NH(C=O)NR³⁴ᵃR³⁴ᵇ, and —N=NR³⁵. In an even further aspect, Ar², when present, is 2-naphthyl monosubstituted with a group selected from halogen, —NO₂, —CN, —OH, —SH, —NH₂, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 2-naphthyl, —O(C2-C4 alkenyl), —OCO₂R³³, —CO₂R³³, —(C1-C4 alkyl)CO₂R³³, —(C2-C4 alkenyl)CO₂R³³, —(C=O)(C1-C4 alkyl), —(S=O)(C1-C4 alkyl), —SO₂(C1-C4 alkyl), —(C=O)NR³⁴ᵃR³⁴ᵇ, —SO₂NR³⁴ᵃR³⁴ᵇ, —O(C=O)NR³⁴ᵃR³⁴ᵇ, —NHSO₂NR³⁴ᵃR³⁴ᵇ, —NH(C=O)NR³⁴ᵃR³⁴ᵇ, and —N=NR³⁵. In a still further aspect, Ar², when present, is unsubstituted 2-naphthyl.

In a further aspect, Ar², when present, is benzo[d][1,3]dioxolyl substituted with 0, 1, 2, or 3 groups independently selected from halogen, —NO₂, —CN, —OH, —SH, —NH₂, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 benzo[d][1,3]dioxolyl, —O(C2-C4 alkenyl), —OCO₂R³³, —CO₂R³³, —(C1-C4 alkyl)CO₂R³³, —(C2-C4 alkenyl)CO₂R³³, —(C=O)(C1-C4 alkyl), —(S=O)(C1-C4 alkyl), —SO₂(C1-C4 alkyl), —(C=O)NR³⁴ᵃR³⁴ᵇ, —SO₂NR³⁴ᵃR³⁴ᵇ, —O(C=O)NR³⁴ᵃR³⁴ᵇ, —NHSO₂NR³⁴ᵃR³⁴ᵇ, —NH(C=O)NR³⁴ᵃR³⁴ᵇ, and —N=NR³⁵. In a still further aspect, Ar², when present, is benzo[d][1,3]dioxolyl substituted with 0, 1, or 2 groups independently selected from halogen, —NO₂, —CN, —OH, —SH, —NH₂, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 benzo[d][1,3]dioxolyl, —O(C2-C4 alkenyl), —OCO₂R³³, —CO₂R³³, —(C1-C4 alkyl)CO₂R³³, —(C2-C4 alkenyl)CO₂R³³, —(C=O)(C1-C4 alkyl), —(S=O)(C1-C4 alkyl), —SO₂(C1-C4 alkyl), —(C=O)NR³⁴ᵃR³⁴ᵇ, —SO₂NR³⁴ᵃR³⁴ᵇ, —O(C=O)NR³⁴ᵃR³⁴ᵇ, —NHSO₂NR³⁴ᵃR³⁴ᵇ, —NH(C=O)NR³⁴ᵃR³⁴ᵇ, and —N=NR³⁵. In yet a further aspect, Ar², when present, is benzo[d][1,3]dioxolyl substituted with 0 or 1 group selected from halogen, —NO₂, —CN, —OH, —SH, —NH₂, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 benzo[d][1,3]dioxolyl, —O(C2-C4 alkenyl), —OCO₂R³³, —CO$_2$R$^{33}$, —(C1-C4 alkyl)CO$_2$R$^{33}$, —(C2-C4 alkenyl)CO$_2$R$^{33}$, —(C═O)(C1-C4 alkyl), —(S═O)(C1-C4 alkyl), —SO$_2$(C1-C4 alkyl), —(C═O)NR$^{34a}$R$^{34b}$, —SO$_2$NR$^{34a}$R$^{34b}$, —O(C═O)NR$^{34a}$R$^{34b}$, —NHSO$_2$NR$^{34a}$R$^{34b}$, —NH(C═O)NR$^{34a}$R$^{34b}$, and —N═NR$^{35}$. In an even further aspect, Ar$^2$, when present, is benzo[d][1,3]dioxolyl monosubstituted with a group selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 benzo[d][1,3]dioxolyl, —O(C2-C4 alkenyl), —OCO$_2$R$^{33}$, —CO$_2$R$^{33}$, —(C1-C4 alkyl)CO$_2$R$^{33}$, —(C2-C4 alkenyl)CO$_2$R$^{33}$, —(C═O)(C1-C4 alkyl), —(S═O)(C1-C4 alkyl), —SO$_2$(C1-C4 alkyl), —(C═O)NR$^{34a}$R$^{34b}$, —SO$_2$NR$^{34a}$R$^{34b}$, —O(C═O)NR$^{34a}$R$^{34b}$, —NHSO$_2$NR$^{34a}$R$^{34b}$, —NH(C═O)NR$^{34a}$R$^{34b}$, and —N═NR$^{35}$. In a still further aspect, Ar$^2$, when present, is unsubstituted benzo[d][1,3]dioxolyl.

In a further aspect, Ar$^2$, when present, is heteroaryl substituted with 0, 1, 2, or 3 groups independently selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO$_2$R$^{33}$, —CO$_2$R$^{33}$, —(C1-C4 alkyl)CO$_2$R$^{33}$, —(C2-C4 alkenyl)CO$_2$R$^{33}$, —(C═O)(C1-C4 alkyl), —(S═O)(C1-C4 alkyl), —SO$_2$(C1-C4 alkyl), —(C═O)NR$^{34a}$R$^{34b}$, —SO$_2$NR$^{34a}$R$^{34b}$, —O(C═O)NR$^{34a}$R$^{34b}$, —NHSO$_2$NR$^{34a}$R$^{34b}$, —NH(C═O)NR$^{34a}$R$^{34b}$, and —N═NR$^{35}$. In a still further aspect, Ar$^2$, when present, is heteroaryl substituted with 0, 1, or 2 groups independently selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl (C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO$_2$R$^{33}$, —CO$_2$R$^{33}$, —(C1-C4 alkyl)CO$_2$R$^{33}$, —(C2-C4 alkenyl)CO$_2$R$^{33}$, —(C═O)(C1-C4 alkyl), —(S═O)(C1-C4 alkyl), —SO$_2$(C1-C4 alkyl), —(C═O)NR$^{34a}$R$^{34b}$, —SO$_2$NR$^{34a}$R$^{34b}$, —O(C═O)NR$^{34a}$R$^{34b}$, —NHSO$_2$NR$^{34a}$R$^{34b}$, —NH(C═O)NR$^{34a}$R$^{34b}$, and —N═NR$^{35}$. In yet a further aspect, Ar$^2$, when present, is heteroaryl substituted with 0 or 1 group selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO$_2$R$^{33}$, —CO$_2$R$^{33}$, —(C1-C4 alkyl)CO$_2$R$^{33}$, —(C2-C4 alkenyl)CO$_2$R$^{33}$, —(C═O)(C1-C4 alkyl), —(S═O)(C1-C4 alkyl), —SO$_2$(C1-C4 alkyl), —(C═O)NR$^{34a}$R$^{34b}$, —SO$_2$NR$^{34a}$R$^{34b}$, —O(C═O)NR$^{34a}$R$^{34b}$, —NHSO$_2$NR$^{34a}$R$^{34b}$, —NH(C═O)NR$^{34a}$R$^{34b}$, and —N═NR$^{35}$. In an even further aspect, Ar$^2$, when present, is heteroaryl monosubstituted with a group selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO$_2$R$^{33}$, —CO$_2$R$^{33}$, —(C1-C4 alkyl)CO$_2$R$^{33}$, —(C2-C4 alkenyl)CO$_2$R$^{33}$, —(C═O)(C1-C4 alkyl), —(S═O)(C1-C4 alkyl), —SO$_2$(C1-C4 alkyl), —(C═O)NR$^{34a}$R$^{34b}$, —SO$_2$NR$^{34a}$R$^{34b}$, —O(C═O)NR$^{34a}$R$^{34b}$, —NHSO$_2$NR$^{34a}$R$^{34b}$, —NH(C═O)NR$^{34a}$R$^{34b}$, and —N═NR$^{35}$. In a still further aspect, Ar$^2$, when present, is unsubstituted heteroaryl.

In a further aspect, Ar$^2$, when present, is pyridinyl substituted with 0, 1, 2, or 3 groups independently selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO$_2$R$^{33}$, —CO$_2$R$^{33}$, —(C1-C4 alkyl)CO$_2$R$^{33}$, —(C2-C4 alkenyl)CO$_2$R$^{33}$, —(C═O)(C1-C4 alkyl), —(S═O)(C1-C4 alkyl), —SO$_2$(C1-C4 alkyl), —(C═O)NR$^{34a}$R$^{34b}$, —SO$_2$NR$^{34a}$R$^{34b}$, —O(C═O)NR$^{34a}$R$^{34b}$, —NHSO$_2$NR$^{34a}$R$^{34b}$, —NH(C═O)NR$^{34a}$R$^{34b}$, and —N═NR$^{35}$. In a still further aspect, Ar$^2$, when present, is pyridinyl substituted with 0, 1, or 2 groups independently selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl (C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO$_2$R$^{33}$, —CO$_2$R$^{33}$, —(C1-C4 alkyl)CO$_2$R$^{33}$, —(C2-C4 alkenyl)CO$_2$R$^{33}$, —(C═O)(C1-C4 alkyl), —(S═O)(C1-C4 alkyl), —SO$_2$(C1-C4 alkyl), —(C═O)NR$^{34a}$R$^{34b}$, —SO$_2$NR$^{34a}$R$^{34b}$, —O(C═O)NR$^{34a}$R$^{34b}$, —NHSO$_2$NR$^{34a}$R$^{34b}$, —NH(C═O)NR$^{34a}$R$^{34b}$, and —N═NR$^{35}$. In yet a further aspect, Ar$^2$, when present, is pyridinyl substituted with 0 or 1 group selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO$_2$R$^{33}$, —CO$_2$R$^{33}$, —(C1-C4 alkyl)CO$_2$R$^{33}$, —(C2-C4 alkenyl)CO$_2$R$^{33}$, —(C═O)(C1-C4 alkyl), —(S═O)(C1-C4 alkyl), —SO$_2$(C1-C4 alkyl), —(C═O)NR$^{34a}$R$^{34b}$, —SO$_2$NR$^{34a}$R$^{34b}$, —O(C═O)NR$^{34a}$R$^{34b}$, —NHSO$_2$NR$^{34a}$R$^{34b}$, —NH(C═O)NR$^{34a}$R$^{34b}$, and —N═NR$^{35}$. In an even further aspect, Ar$^2$, when present, is pyridinyl monosubstituted with a group selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO$_2$R$^{33}$, —CO$_2$R$^{33}$, —(C1-C4 alkyl)CO$_2$R$^{33}$, —(C2-C4 alkenyl)CO$_2$R$^{33}$, —(C═O)(C1-C4 alkyl), —(S═O)(C1-C4 alkyl), —SO$_2$(C1-C4 alkyl), —(C═O)NR$^{34a}$R$^{34b}$, —SO$_2$NR$^{34a}$R$^{34b}$, —O(C═O)NR$^{34a}$R$^{34b}$, —NHSO$_2$NR$^{34a}$R$^{34b}$, —NH(C═O)NR$^{34a}$R$^{34b}$, and —N═NR$^{35}$. In a still further aspect, Ar$^2$, when present, is unsubstituted pyridinyl.

In a further aspect, Ar$^2$, when present, is quinolinyl substituted with 0, 1, 2, or 3 groups independently selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO$_2$R$^{33}$, —CO$_2$R$^{33}$, —(C1-C4 alkyl)CO$_2$R$^{33}$, —(C2-C4 alkenyl)CO$_2$R$^{33}$, —(C=O)(C1-C4 alkyl), —(S=O)(C1-C4 alkyl), —SO$_2$(C1-C4 alkyl), —(C=O)NR$^{34a}$R$^{34b}$, —SO$_2$NR$^{34a}$R$^{34b}$, —O(C=O)NR$^{34a}$R$^{34b}$, —NHSO$_2$NR$^{34a}$R$^{34b}$, —NH(C=O)NR$^{34a}$R$^{34b}$, and —N=NR$^{35}$. In a still further aspect, Ar$^2$, when present, is quinolinyl substituted with 0, 1, or 2 groups independently selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO$_2$R$^{33}$, —CO$_2$R$^{33}$, —(C1-C4 alkyl)CO$_2$R$^{33}$, —(C2-C4 alkenyl)CO$_2$R$^{33}$, —(C=O)(C1-C4 alkyl), —(S=O)(C1-C4 alkyl), —SO$_2$(C1-C4 alkyl), —(C=O)NR$^{34a}$R$^{34b}$, —SO$_2$NR$^{34a}$R$^{34b}$, —O(C=O)NR$^{34a}$R$^{34b}$, —NHSO$_2$NR$^{34a}$R$^{34b}$, —NH(C=O)NR$^{34a}$R$^{34b}$, and —N=NR$^{35}$. In yet a further aspect, Ar$^2$, when present, is quinolinyl substituted with 0 or 1 group selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO$_2$R$^{33}$, —CO$_2$R$^{33}$, —(C1-C4 alkyl)CO$_2$R$^{33}$, —(C2-C4 alkenyl)CO$_2$R$^{33}$, —(C=O)(C1-C4 alkyl), —(S=O)(C1-C4 alkyl), —SO$_2$(C1-C4 alkyl), —(C=O)NR$^{34a}$R$^{34b}$, —SO$_2$NR$^{34a}$R$^{34b}$, —O(C=O)NR$^{34a}$R$^{34b}$, —NHSO$_2$NR$^{34a}$R$^{34b}$, —NH(C=O)NR$^{34a}$R$^{34b}$, and —N=NR$^{35}$. In an even further aspect, Ar$^2$, when present, is quinolinyl monosubstituted with a group selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO$_2$R$^{33}$, —CO$_2$R$^{33}$, —(C1-C4 alkyl)CO$_2$R$^{33}$, —(C2-C4 alkenyl)CO$_2$R$^{33}$, —(C=O)(C1-C4 alkyl), —(S=O)(C1-C4 alkyl), —SO$_2$(C1-C4 alkyl), —(C=O)NR$^{34a}$R$^{34b}$, —SO$_2$NR$^{34a}$R$^{34b}$, —O(C=O)NR$^{34a}$R$^{34b}$, —NHSO$_2$NR$^{34a}$R$^{34b}$, —NH(C=O)NR$^{34a}$R$^{34b}$, and —N=NR$^{35}$. In a still further aspect, Ar$^2$, when present, is unsubstituted quinolinyl.

In a further aspect, Ar$^2$, when present, is furanyl substituted with 0, 1, 2, or 3 groups independently selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO$_2$R$^{33}$, —CO$_2$R$^{33}$, —(C1-C4 alkyl)CO$_2$R$^{33}$, —(C2-C4 alkenyl)CO$_2$R$^{33}$, —(C=O)(C1-C4 alkyl), —(S=O)(C1-C4 alkyl), —SO$_2$(C1-C4 alkyl), —(C=O)NR$^{34a}$R$^{34b}$, —SO$_2$NR$^{34a}$R$^{34b}$, —O(C=O)NR$^{34a}$R$^{34b}$, —NHSO$_2$NR$^{34a}$R$^{34b}$, —NH(C=O)NR$^{34a}$R$^{34b}$, and —N=NR$^{35}$. In a still further aspect, Ar$^2$, when present, is furanyl substituted with 0, 1, or 2 groups independently selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO$_2$R$^{33}$, —CO$_2$R$^{33}$, —(C1-C4 alkyl)CO$_2$R$^{33}$, —(C2-C4 alkenyl)CO$_2$R$^{33}$, —(C=O)(C1-C4 alkyl), —(S=O)(C1-C4 alkyl), —SO$_2$(C1-C4 alkyl), —(C=O)NR$^{34a}$R$^{34b}$, —SO$_2$NR$^{34a}$R$^{34b}$, —O(C=O)NR$^{34a}$R$^{34b}$, —NHSO$_2$NR$^{34a}$R$^{34b}$, —NH(C=O)NR$^{34a}$R$^{34b}$, and —N=NR$^{35}$. In yet a further aspect, Ar$^2$, when present, is furanyl substituted with 0 or 1 group selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO$_2$R$^{33}$, —CO$_2$R$^{33}$, —(C1-C4 alkyl)CO$_2$R$^{33}$, —(C2-C4 alkenyl)CO$_2$R$^{33}$, —(C=O)(C1-C4 alkyl), —(S=O)(C1-C4 alkyl), —SO$_2$(C1-C4 alkyl), —(C=O)NR$^{34a}$R$^{34b}$, —SO$_2$NR$^{34a}$R$^{34b}$, —O(C=O)NR$^{34a}$R$^{34b}$, —NHSO$_2$NR$^{34a}$R$^{34b}$, —NH(C=O)NR$^{34a}$R$^{34b}$, and —N=NR$^{35}$. In an even further aspect, Ar$^2$, when present, is furanyl monosubstituted with a group selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO$_2$R$^{33}$, —CO$_2$R$^{33}$, —(C1-C4 alkyl)CO$_2$R$^{33}$, —(C2-C4 alkenyl)CO$_2$R$^{33}$, —(C=O)(C1-C4 alkyl), —(S=O)(C1-C4 alkyl), —SO$_2$(C1-C4 alkyl), —(C=O)NR$^{34a}$R$^{34b}$, —SO$_2$NR$^{34a}$R$^{34b}$, —O(C=O)NR$^{34a}$R$^{34b}$, —NHSO$_2$NR$^{34a}$R$^{34b}$, —NH(C=O)NR$^{34a}$R$^{34b}$, and —N=NR$^{35}$. In a still further aspect, Ar$^2$, when present, is unsubstituted furanyl.

In a further aspect, Ar$^2$ is aryl substituted with 0, 1, 2, or 3 groups independently selected from C1-C4 haloalkyl, C1-C4 alkoxy, and C6-C10 aryl. In a still further aspect, Ar$^2$ is aryl substituted with 0, 1, or 2 groups independently selected from C1-C4 haloalkyl, C1-C4 alkoxy, and C6-C10 aryl. In yet a further aspect, Ar$^2$ is aryl substituted with 0 or 1 group selected from C1-C4 haloalkyl, C1-C4 alkoxy, and C6-C10 aryl. In an even further aspect, Ar$^2$ is aryl monosubstituted with a group selected from C1-C4 haloalkyl, C1-C4 alkoxy, and C6-C10 aryl.

In a further aspect, Ar$^2$ is aryl substituted with 0, 1, 2, or 3 groups independently selected from —CF$_3$, —OCH$_3$, and phenyl. In a still further aspect, Ar$^2$ is aryl substituted with 0, 1, or 2 groups independently selected from —CF$_3$, —OCH$_3$, and phenyl. In yet a further aspect, Ar$^2$ is aryl substituted with 0 or 1 group selected from —CF$_3$, —OCH$_3$, and phenyl. In an even further aspect, Ar$^2$ is aryl monosubstituted with a group selected from —CF$_3$, —OCH$_3$, and phenyl.

In a further aspect, Ar$^2$ is C6-aryl substituted with 0, 1, 2, or 3 groups independently selected from C1-C4 haloalkyl, C1-C4 alkoxy, and C6-C10 aryl. In a still further aspect, Ar$^2$ is C6-aryl substituted with 0, 1, or 2 groups independently selected from C1-C4 haloalkyl, C1-C4 alkoxy, and C6-C10 aryl. In yet a further aspect, Ar$^2$ is C6-aryl substituted with 0 or 1 group selected from C1-C4 haloalkyl, C1-C4 alkoxy, and C6-C10 aryl. In an even further aspect, Ar$^2$ is C6-aryl monosubstituted with a group selected from C1-C4 haloalkyl, C1-C4 alkoxy, and C6-C10 aryl.

In a further aspect, Ar$^2$ is C6-aryl substituted with 0, 1, 2, or 3 groups independently selected from —CF$_3$, —OCH$_3$, and phenyl. In a still further aspect, Ar$^2$ is C6-aryl substituted with 0, 1, or 2 groups independently selected from —CF$_3$, —OCH$_3$, and phenyl. In yet a further aspect, Ar$^2$ is C6-aryl substituted with 0 or 1 group selected from —CF$_3$, —OCH$_3$, and phenyl. In an even further aspect, Ar$^2$ is C6-aryl monosubstituted with a group selected from —CF$_3$, —OCH$_3$, and phenyl.

In a further aspect, Ar$^2$ is C6-aryl substituted with 0, 1, 2, or 3 groups independently selected from —CF$_3$, and phenyl. In a still further aspect, Ar$^2$ is C6-aryl substituted with 0, 1, or 2 groups independently selected from —CF$_3$, and phenyl. In yet a further aspect, Ar$^2$ is C6-aryl substituted with 0 or 1 group selected from —CF$_3$, and phenyl. In an even further aspect, Ar$^2$ is C6-aryl monosubstituted with a group selected from —CF$_3$, and phenyl.

y. Ar$^3$ Groups

In one aspect, Ar$^3$ is selected from aryl and heteroaryl and is substituted with 0, 1, 2, or 3 groups independently selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO$_2$R$^{36}$, —CO$_2$R$^{36}$, —(C1-C4 alkyl)CO$_2$R$^{36}$, —(C2-C4 alkenyl)CO$_2$R$^{36}$, —(C=O)(C1-C4 alkyl), —(S=O)(C1-C4 alkyl), —SO$_2$(C1-C4 alkyl), —(C=O)NR$^{37a}$R$^{37b}$, —SO$_2$NR$^{37a}$R$^{37b}$, —O(C=O)NR$^{37a}$R$^{37b}$, —NHSO$_2$NR$^{37a}$R$^{37b}$, —NH(C=O)NR$^{37a}$R$^{37b}$, and —N=NR$^{38}$. In a further aspect, Ar$^3$ is selected from aryl and heteroaryl and is substituted with 0, 1, or 2 groups independently selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO$_2$R$^{36}$, —CO$_2$R$^{36}$, —(C1-C4 alkyl)CO$_2$R$^{36}$, —(C2-C4 alkenyl)CO$_2$R$^{36}$, —(C=O)(C1-C4 alkyl), —(S=O)(C1-C4 alkyl), —SO$_2$(C1-C4 alkyl), —(C=O)NR$^{37a}$R$^{37b}$, —SO$_2$NR$^{37a}$R$^{37b}$, —O(C=O)NR$^{37a}$R$^{37b}$, —NHSO$_2$NR$^{37a}$R$^{37b}$, —NH(C=O)NR$^{37a}$R$^{37b}$, and —N=NR$^{38}$. In a still further aspect, Ar$^3$ is selected from aryl and heteroaryl and is substituted with 0 or 1 group selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO$_2$R$^{36}$, —CO$_2$R$^{36}$, —(C1-C4 alkyl)CO$_2$R$^{36}$, —(C2-C4 alkenyl)CO$_2$R$^{36}$, —(C=O)(C1-C4 alkyl), —(S=O)(C1-C4 alkyl), —SO$_2$(C1-C4 alkyl), —(C=O)NR$^{37a}$R$^{37b}$, —SO$_2$NR$^{37a}$R$^{37b}$, —O(C=O)NR$^{37a}$R$^{37b}$, —NHSO$_2$NR$^{37a}$R$^{37b}$, —NH(C=O)NR$^{37a}$R$^{37b}$, and —N=NR$^{38}$. In yet a further aspect, Ar$^3$ is selected from aryl and heteroaryl and is monosubstituted with a group selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO$_2$R$^{36}$, —CO$_2$R$^{36}$, —(C1-C4 alkyl)CO$_2$R$^{36}$, —(C2-C4 alkenyl)CO$_2$R$^{36}$, —(C=O)(C1-C4 alkyl), —(S=O)(C1-C4 alkyl), —SO$_2$(C1-C4 alkyl), —(C=O)NR$^{37a}$R$^{37b}$, —SO$_2$NR$^{37a}$R$^{37b}$, —O(C=O)NR$^{37a}$R$^{37b}$, —NHSO$_2$NR$^{37a}$R$^{37b}$, —NH(C=O)NR$^{37a}$R$^{37b}$, and —N=NR$^{38}$. In an even further aspect, Ar$^3$ is selected from aryl and heteroaryl and is unsubstituted.

In a further aspect, Ar$^3$ is aryl substituted with 0, 1, 2, or 3 groups independently selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO$_2$R$^{36}$, —CO$_2$R$^{36}$, —(C1-C4 alkyl)CO$_2$R$^{36}$, —(C2-C4 alkenyl)CO$_2$R$^{36}$, —(C=O)(C1-C4 alkyl), —(S=O)(C1-C4 alkyl), —SO$_2$(C1-C4 alkyl), —(C=O)NR$^{37a}$R$^{37b}$, —SO$_2$NR$^{37a}$R$^{37b}$, —O(C=O)NR$^{37a}$R$^{37b}$, —NHSO$_2$NR$^{37a}$R$^{37b}$, —NH(C=O)NR$^{37a}$R$^{37b}$, and —N=NR$^{38}$. In a still further aspect, Ar$^3$ is aryl substituted with 0, 1, or 2 groups independently selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OC$_2$R$^{36}$, —CO$_2$R$^{36}$, —(C1-C4 alkyl)CO$_2$R$^{36}$, —(C2-C4 alkenyl)CO$_2$R$^{36}$, —(C=O)(C1-C4 alkyl), —(S=O)(C1-C4 alkyl), —SO$_2$(C1-C4 alkyl), —(C=O)NR$^{37a}$R$^{37b}$, —SO$_2$NR$^{37a}$R$^{37b}$, —O(C=O)NR$^{37a}$R$^{37b}$, —NHSO$_2$NR$^{37a}$R$^{37b}$, —NH(C=O)NR$^{37a}$R$^{37b}$, and —N=NR$^{38}$. In yet a further aspect, Ar$^3$ is aryl substituted with 0 or 1 group selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OC$_2$R$^{36}$, —CO$_2$R$^{36}$, —(C1-C4 alkyl)CO$_2$R$^{36}$, —(C2-C4 alkenyl)CO$_2$R$^{36}$, —(C=O)(C1-C4 alkyl), —(S=O)(C1-C4 alkyl), —SO$_2$(C1-C4 alkyl), —(C=O)NR$^{37a}$R$^{37b}$, —SO$_2$NR$^{37a}$R$^{37b}$, —O(C=O)NR$^{37a}$R$^{37b}$, —NHSO$_2$NR$^{37a}$R$^{37b}$, —NH(C=O)NR$^{37a}$R$^{37b}$, and —N=NR$^{38}$. In an even further aspect, Ar$^3$ is aryl monosubstituted with a group selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO$_2$R$^{36}$, —CO$_2$R$^{36}$, —(C1-C4 alkyl)CO$_2$R$^{36}$, —(C2-C4 alkenyl)CO$_2$R$^{36}$, —(C=O)(C1-C4 alkyl), —(S=O)(C1-C4 alkyl), —SO$_2$(C1-C4 alkyl), —(C=O)NR$^{37a}$R$^{37b}$, —SO$_2$NR$^{37a}$R$^{37b}$, —O(C=O)NR$^{37a}$R$^{37b}$, —NHSO$_2$NR$^{37a}$R$^{37b}$, —NH(C=O)NR$^{37a}$R$^{37b}$, and —N=NR$^{38}$. In a still further aspect, Ar$^3$ is unsubstituted aryl.

In a further aspect, Ar$^3$ is phenyl substituted with 0, 1, 2, or 3 groups independently selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 phenyl, —O(C2-C4 alkenyl), —OCO$_2$R$^{36}$, —CO$_2$R$^{36}$, —(C1-C4 alkyl)CO$_2$R$^{36}$, —(C2-

C4 alkenyl)$CO_2R^{36}$, —(C=O)(C1-C4 alkyl), —(S=O)(C1-C4 alkyl), —$SO_2$(C1-C4 alkyl), —(C=O)$NR^{37a}R^{37b}$, —$SO_2NR^{37a}R^{37b}$, —O(C=O)$NR^{37a}R^{37b}$, —$NHSO_2NR^{37a}R^{37b}$, —NH(C=O)$NR^{37a}R^{37b}$, and —N=$NR^{38}$. In a still further aspect, $Ar^3$ is phenyl substituted with 0, 1, or 2 groups independently selected from halogen, —$NO_2$, —CN, —OH, —SH, —$NH_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 phenyl, —O(C2-C4 alkenyl), —$OCO_2R^{36}$, —$CO_2R^{36}$, —(C1-C4 alkyl)$CO_2R^{36}$, —(C2-C4 alkenyl)$CO_2R^{36}$, —(C=O)(C1-C4 alkyl), —(S=O)(C1-C4 alkyl), —$SO_2$(C1-C4 alkyl), —(C=O)$NR^{37a}R^{37b}$, —$SO_2NR^{37a}R^{37b}$, —O(C=O)$NR^{37a}R^{37b}$, —$NHSO_2NR^{37a}R^{37b}$, —NH(C=O)$NR^{37a}R^{37b}$, and —N=$NR^{38}$. In yet a further aspect, $Ar^3$ is phenyl substituted with 0 or 1 group selected from halogen, —$NO_2$, —CN, —OH, —SH, —$NH_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 phenyl, —O(C2-C4 alkenyl), —$OC_2R^{36}$, —$CO_2R^{36}$, —(C1-C4 alkyl)$CO_2R^{36}$, —(C2-C4 alkenyl)$CO_2R^{36}$, —(C=O)(C1-C4 alkyl), —(S=O)(C1-C4 alkyl), —$SO_2$(C1-C4 alkyl), —(C=O)$NR^{37a}R^{37b}$, —$SO_2NR^{37a}R^{37b}$, —O(C=O)$NR^{37a}R^{37b}$, —$NHSO_2NR^{37a}R^{37b}$, —NH(C=O)$NR^{37a}R^{37b}$, and —N=$NR^{38}$. In an even further aspect, $Ar^3$ is phenyl monosubstituted with a group selected from halogen, —$NO_2$, —CN, —OH, —SH, —$NH_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 phenyl, —O(C2-C4 alkenyl), —$OCO_2R^{36}$, —$CO_2R^{36}$, —(C1-C4 alkyl)$CO_2R^{36}$, —(C2-C4 alkenyl)$CO_2R^{36}$, —(C=O)(C1-C4 alkyl), —(S=O)(C1-C4 alkyl), —$SO_2$(C1-C4 alkyl), —(C=O)$NR^{37a}R^{37b}$, —$SO_2NR^{37a}R^{37b}$, —O(C=O)$NR^{37a}R^{37b}$, —$NHSO_2NR^{37a}R^{37b}$, —NH(C=O)$NR^{37a}R^{37b}$, and —N=$NR^{38}$. In a still further aspect, $Ar^3$ is unsubstituted phenyl.

In a further aspect, $Ar^3$ is naphthyl substituted with 0, 1, 2, or 3 groups independently selected from halogen, —$NO_2$, —CN, —OH, —SH, —$NH_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 naphthyl, —O(C2-C4 alkenyl), —$OCO_2R^{36}$, —$CO_2R^{36}$, —(C1-C4 alkyl)$CO_2R^{36}$, —(C2-C4 alkenyl)$CO_2R^{36}$, —(C=O)(C1-C4 alkyl), —(S=O)(C1-C4 alkyl), —$SO_2$(C1-C4 alkyl), —(C=O)$NR^{37a}R^{37b}$, —$SO_2NR^{37a}R^{37b}$, —O(C=O)$NR^{37a}R^{37b}$, —$NHSO_2NR^{37a}R^{37b}$, —NH(C=O)$NR^{37a}R^{37b}$, and —N=$NR^{38}$. In a still further aspect, $Ar^3$ is naphthyl substituted with 0, 1, or 2 groups independently selected from halogen, —$NO_2$, —CN, —OH, —SH, —$NH_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 naphthyl, —O(C2-C4 alkenyl), —$OC_2R^{36}$, —$CO_2R^{36}$, —(C1-C4 alkyl)$CO_2R^{36}$, —(C2-C4 alkenyl)$CO_2R^{36}$, —(C=O)(C1-C4 alkyl), —(S=O)(C1-C4 alkyl), —$SO_2$(C1-C4 alkyl), —(C=O)$NR^{37a}R^{37b}$, —$SO_2NR^{37a}R^{37b}$, —O(C=O)$NR^{37a}R^{37b}$, —$NHSO_2NR^{37a}R^{37b}$, —NH(C=O)$NR^{37a}R^{37b}$, and —N=$NR^{38}$. In yet a further aspect, $Ar^3$ is naphthyl substituted with 0 or 1 group selected from halogen, —$NO_2$, —CN, —OH, —SH, —$NH_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 naphthyl, —O(C2-C4 alkenyl), —$OC_2R^{36}$, —$CO_2R^{36}$, —(C1-C4 alkyl)$CO_2R^{36}$, —(C2-C4 alkenyl)$CO_2R^{36}$, —(C=O)(C1-C4 alkyl), —(S=O)(C1-C4 alkyl), —$SO_2$(C1-C4 alkyl), —(C=O)$NR^{37a}R^{37b}$, —$SO_2NR^{37a}R^{37b}$, —O(C=O)$NR^{37a}R^{37b}$, —$NHSO_2NR^{37a}R^{37b}$, —NH(C=O)$NR^{37a}R^{37b}$, and —N=$NR^{38}$. In an even further aspect, $Ar^3$ is naphthyl monosubstituted with a group selected from halogen, —$NO_2$, —CN, —OH, —SH, —$NH_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 naphthyl, —O(C2-C4 alkenyl), —$OCO_2R^{36}$, —$CO_2R^{36}$, —(C1-C4 alkyl)$CO_2R^{36}$, —(C2-C4 alkenyl)$CO_2R^{36}$, —(C=O)(C1-C4 alkyl), —(S=O)(C1-C4 alkyl), —$SO_2$(C1-C4 alkyl), —(C=O)$NR^{37a}R^{37b}$, —$SO_2NR^{37a}R^{37b}$, —O(C=O)$NR^{37a}R^{37b}$, —$NHSO_2NR^{37a}R^{37b}$, —NH(C=O)$NR^{37a}R^{37b}$, and —N=$NR^{38}$. In a still further aspect, $Ar^3$ is unsubstituted naphthyl.

In a further aspect, $Ar^3$ is 1-naphthyl substituted with 0, 1, 2, or 3 groups independently selected from halogen, —$NO_2$, —CN, —OH, —SH, —$NH_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 1-naphthyl, —O(C2-C4 alkenyl), —$OCO_2R^{36}$, —$CO_2R^{36}$, —(C1-C4 alkyl)$CO_2R^{36}$, —(C2-C4 alkenyl)$CO_2R^{36}$, —(C=O)(C1-C4 alkyl), —(S=O)(C1-C4 alkyl), —$SO_2$(C1-C4 alkyl), —(C=O)$NR^{37a}R^{37b}$, —$SO_2NR^{37a}R^{37b}$, —O(C=O)$NR^{37a}R^{37b}$, —$NHSO_2NR^{37a}R^{37b}$, —NH(C=O)$NR^{37a}R^{37b}$, and —N=$NR^{38}$. In a still further aspect, $Ar^3$ is 1-naphthyl substituted with 0, 1, or 2 groups independently selected from halogen, —$NO_2$, —CN, —OH, —SH, —$NH_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 1-naphthyl, —O(C2-C4 alkenyl), —$OC_2R^{36}$, —$CO_2R^{36}$, —(C1-C4 alkyl)$CO_2R^{36}$, —(C2-C4 alkenyl)$CO_2R^{36}$, —(C=O)(C1-C4 alkyl), —(S=O)(C1-C4 alkyl), —$SO_2$(C1-C4 alkyl), —(C=O)$NR^{37a}R^{37b}$, —$SO_2NR^{37a}R^{37b}$, —O(C=O)$NR^{37a}R^{37b}$, —$NHSO_2NR^{37a}R^{37b}$, —NH(C=O)$NR^{37a}R^{37b}$, and —N=$NR^{38}$. In yet a further aspect, $Ar^3$ is 1-naphthyl substituted with 0 or 1 group selected from halogen, —$NO_2$, —CN, —OH, —SH, —$NH_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 1-naphthyl, —O(C2-C4 alkenyl), —$OC_2R^{36}$, —$CO_2R^{36}$, —(C1-C4 alkyl)$CO_2R^{36}$, —(C2-C4 alkenyl)CO$_2$R$^{36}$, —(C=O)(C1-C4 alkyl), —(S=O)(C1-C4 alkyl), —SO$_2$(C1-C4 alkyl), —(C=O)NR$^{37a}$R$^{37b}$, —SO$_2$NR$^{37a}$R$^{37b}$, —O(C=O)NR$^{37a}$R$^{37b}$, —NHSO$_2$NR$^{37a}$R$^{37b}$, —NH(C=O)NR$^{37a}$R$^{37b}$, and —N=NR$^{38}$. In an even further aspect, Ar$^3$ is 1-naphthyl monosubstituted with a group selected from halogen, —NO$_2$, —CN, —OH, —SH, —NH$_2$, C1-C4 alkyl, C2-C4 alkenyl, C2-C4 alkynyl, C1-C4 haloalkyl, C1—C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 1-naphthyl, —O(C2-C4 alkenyl), —OCO$_2$R$^{36}$, —CO$_2$R$^{36}$, —(C1-C4 alkyl)CO$_2$R$^{36}$, —(C2-C4 alkenyl)CO$_2$R$^{36}$, —(C=O)(C1-C4 alkyl), —(S=O)(C1-C4 alkyl), —SO$_2$(C1-C4 alkyl), —(C=O)NR$^{37a}$R$^{37b}$, —SO$_2$NR$^{37a}$R$^{37b}$, —O(C=O)NR$^{37a}$R$^{37b}$, —NHSO$_2$NR$^{37a}$R$^{37b}$, —NH(C=O)NR$^{37a}$R$^{37b}$, and —N=NR$^{38}$. In a still further aspect, Ar$^3$ is unsubstituted 1-naphthyl.

In a further aspect, Ar$^3$ is 2-naphthyl substituted with 0, 1, 2, or 3 groups independently selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 2-naphthyl, —O(C2-C4 alkenyl), —OCO$_2$R$^{36}$, —CO$_2$R$^{36}$, —(C1-C4 alkyl)CO$_2$R$^{36}$, —(C2-C4 alkenyl)CO$_2$R$^{36}$, —(C=O)(C1-C4 alkyl), —(S=O)(C1-C4 alkyl), —SO$_2$(C1-C4 alkyl), —(C=O)NR$^{37a}$R$^{37b}$, —SO$_2$NR$^{37a}$R$^{37b}$, —O(C=O)NR$^{37a}$R$^{37b}$, —NHSO$_2$NR$^{37a}$R$^{37b}$, —NH(C=O)NR$^{37a}$R$^{37b}$, and —N=NR$^{38}$. In a still further aspect, Ar$^3$ is 2-naphthyl substituted with 0, 1, or 2 groups independently selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 2-naphthyl, —O(C2-C4 alkenyl), —OC$_2$R$^{36}$, —CO$_2$R$^{36}$, —(C1-C4 alkyl)CO$_2$R$^{36}$, —(C2-C4 alkenyl)CO$_2$R$^{36}$, —(C=O)(C1-C4 alkyl), —(S=O)(C1-C4 alkyl), —SO$_2$(C1-C4 alkyl), —(C=O)NR$^{37a}$R$^{37b}$, —SO$_2$NR$^{37a}$R$^{37b}$, —O(C=O)NR$^{37a}$R$^{37b}$, —NHSO$_2$NR$^{37a}$R$^{37b}$, —NH(C=O)NR$^{37a}$R$^{37b}$, and —N=NR$^{38}$. In yet a further aspect, Ar$^3$ is 2-naphthyl substituted with 0 or 1 group selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 2-naphthyl, —O(C2-C4 alkenyl), —OCO$_2$R$^{36}$, CO$_2$R$^{36}$, —(C1-C4 alkyl)CO$_2$R$^{36}$, —(C2-C4 alkenyl)CO$_2$R$^{36}$, —(C=O)(C1-C4 alkyl), —(S=O)(C1-C4 alkyl), —SO$_2$(C1-C4 alkyl), —(C=O)NR$^{37a}$R$^{37b}$, —SO$_2$NR$^{37a}$R$^{37b}$, —O(C=O)NR$^{37a}$R$^{37b}$, —NHSO$_2$NR$^{37a}$R$^{37b}$, —NH(C=O)NR$^{37a}$R$^{37b}$, and —N=NR$^{38}$. In an even further aspect, Ar$^3$ is 2-naphthyl monosubstituted with a group selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 2-naphthyl, —O(C2-C4 alkenyl), —OCO$_2$R$^{36}$, —CO$_2$R$^{36}$, —(C1-C4 alkyl)CO$_2$R$^{36}$, —(C2-C4 alkenyl)CO$_2$R$^{36}$, —(C=O)(C1-C4 alkyl), —(S=O)(C1-C4 alkyl), —SO$_2$(C1-C4 alkyl), —(C=O)NR$^{37a}$R$^{37b}$, —SO$_2$NR$^{37a}$R$^{37b}$, —O(C=O)NR$^{37a}$R$^{37b}$, —NHSO$_2$NR$^{37a}$R$^{37b}$, —NH(C=O)NR$^{37a}$R$^{37b}$, and —N=NR$^{38}$. In a still further aspect, Ar$^3$ is unsubstituted 2-naphthyl.

In a further aspect, Ar$^3$ is benzo[d][1,3]dioxolyl substituted with 0, 1, 2, or 3 groups independently selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 benzo[d][1,3]dioxolyl, —O(C2-C4 alkenyl), —OCO$_2$R$^{36}$, —CO$_2$R$^{36}$, —(C1-C4 alkyl)CO$_2$R$^{36}$, —(C2-C4 alkenyl)CO$_2$R$^{36}$, —(C=O)(C1-C4 alkyl), —(S=O)(C1-C4 alkyl), —SO$_2$(C1-C4 alkyl), —(C=O)NR$^{37a}$R$^{37b}$, —SO$_2$NR$^{37a}$R$^{37b}$, —O(C=O)NR$^{37a}$R$^{37b}$, —NHSO$_2$NR$^{37a}$R$^{37b}$, —NH(C=O)NR$^{37a}$R$^{37b}$, and —N=NR$^{38}$. In a still further aspect, Ar$^3$ is benzo[d][1,3]dioxolyl substituted with 0, 1, or 2 groups independently selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 benzo[d][1,3]dioxolyl, —O(C2-C4 alkenyl), —OCO$_2$R$^{36}$, —CO$_2$R$^{36}$, —(C1-C4 alkyl)CO$_2$R$^{36}$, —(C2-C4 alkenyl)CO$_2$R$^{36}$, —(C=O)(C1-C4 alkyl), —(S=O)(C1-C4 alkyl), —SO$_2$(C1-C4 alkyl), —(C=O)NR$^{37a}$R$^{37b}$, —SO$_2$NR$^{37a}$R$^{37b}$, —O(C=O)NR$^{37a}$R$^{37b}$, —NHSO$_2$NR$^{37a}$R$^{37b}$, —NH(C=O)NR$^{37a}$R$^{37b}$, and —N=NR$^{38}$. In yet a further aspect, Ar$^3$ is benzo[d][1,3]dioxolyl substituted with 0 or 1 group selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 benzo[d][1,3]dioxolyl, —O(C2-C4 alkenyl), —OCO$_2$R$^{36}$, —CO$_2$R$^{36}$, —(C1-C4 alkyl) CO$_2$R$^{36}$, —(C2-C4 alkenyl)CO$_2$R$^{36}$, —(C=O)(C1-C4 alkyl), —(S=O)(C1-C4 alkyl), —SO$_2$(C1-C4 alkyl), —(C=O)NR$^{37a}$R$^{37b}$, —SO$_2$NR$^{37a}$R$^{37b}$, —O(C=O) NR$^{37a}$R$^{37b}$, —NHSO$_2$NR$^{37a}$R$^{37b}$, —NH(C=O)NR$^{37a}$R$^{37b}$, and —N=NR$^{38}$. In an even further aspect, Ar$^3$ is benzo[d][1,3]dioxolyl monosubstituted with a group selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 benzo[d][1,3]dioxolyl, —O(C2-C4 alkenyl), —OCO$_2$R$^{36}$, —CO$_2$R$^{36}$, —(C1-C4 alkyl)CO$_2$R$^{36}$, —(C2-C4 alkenyl)CO$_2$R$^{36}$, —(C=O)(C1-C4 alkyl), —(S=O)(C1-C4 alkyl), —SO$_2$ (C1-C4 alkyl), —(C=O)NR$^{37a}$R$^{37b}$, —SO$_2$NR$^{37a}$R$^{37b}$, —O(C=O)NR$^{37a}$R$^{37b}$, —NHSO$_2$NR$^{37a}$R$^{37b}$, —NH(C=O)NR$^{37a}$R$^{37b}$, and —N=NR$^{38}$. In a still further aspect, Ar$^3$ is unsubstituted benzo[d][1,3]dioxolyl.

In a further aspect, Ar$^3$ is heteroaryl substituted with 0, 1, 2, or 3 groups independently selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO$_2$R$^{36}$, —CO$_2$R$^{36}$, —(C1-C4 alkyl)CO$_2$R$^{36}$, —(C2-C4 alkenyl) CO$_2$R$^{36}$, —(C=O)(C1-C4 alkyl), —(S=O)(C1-C4 alkyl), —SO$_2$(C1-C4 alkyl), —(C=O)NR$^{37a}$R$^{37b}$, —SO$_2$NR$^{37a}$R$^{37b}$, —O(C=O)NR$^{37a}$R$^{37b}$, —NHSO$_2$NR$^{37a}$R$^{37b}$, —NH(C=O)NR$^{37a}$R$^{37b}$, and —N=NR$^{38}$. In a still further aspect, Ar$^3$ is heteroaryl substituted with 0, 1, or 2 groups independently selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OC$_2$R$^{36}$, —CO$_2$R$^{36}$, —(C1-C4 alkyl)CO$_2$R$^{36}$, —(C2-C4 alkenyl)CO$_2$R$^{36}$, —(C=O)(C1-C4 alkyl), —(S=O)(C1-C4 alkyl), —SO$_2$(C1-C4 alkyl), —(C=O)NR$^{37a}$R$^{37b}$, —SO$_2$NR$^{37a}$R$^{37b}$, —O(C=O)NR$^{37a}$R$^{37b}$, —NHSO$_2$NR$^{37a}$R$^{37b}$, —NH(C=O)NR$^{37a}$R$^{37b}$, and —N=NR$^{38}$. In yet a further aspect, Ar$^3$ is heteroaryl substituted with 0 or 1 group selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OC$_2$R$^{36}$, —CO$_2$R$^{36}$, —(C1-C4 alkyl)CO$_2$R$^{36}$, —(C2-C4 alkenyl) CO$_2$R$^{36}$, —(C=O)(C1-C4 alkyl), —(S=O)(C1-C4 alkyl), —SO$_2$(C1-C4 alkyl), —(C=O)NR$^{37a}$R$^{37b}$, —SO$_2$NR$^{37a}$R$^{37b}$, —O(C=O)NR$^{37a}$R$^{37b}$, —NHSO$_2$NR$^{37a}$R$^{37b}$, —NH(C=O)NR$^{37a}$R$^{37b}$, and —N=NR$^{38}$. In an even further aspect, Ar$^3$ is heteroaryl monosubstituted with a group selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO$_2$R$^{36}$, —CO$_2$R$^{36}$, —(C1-C4 alkyl)CO$_2$R$^{36}$, —(C2-C4 alkenyl)CO$_2$R$^{36}$, —(C=O)(C1-C4 alkyl), —(S=O) (C1-C4 alkyl), —SO$_2$(C1-C4 alkyl), —(C=O)NR$^{37a}$R$^{37b}$, —SO$_2$NR$^{37a}$R$^{37b}$, —O(C=O)NR$^{37a}$R$^{37b}$, —NHSO$_2$NR$^{37a}$R$^{37b}$, —NH(C=O)NR$^{37a}$R$^{37b}$, and —N=NR$^{38}$. In a still further aspect, Ar$^3$ is unsubstituted heteroaryl.

In a further aspect, Ar$^3$ is pyridinyl substituted with 0, 1, 2, or 3 groups independently selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO$_2$R$^{36}$, —CO$_2$R$^{36}$, —(C1-C4 alkyl)CO$_2$R$^{36}$, —(C2-C4 alkenyl) CO$_2$R$^{36}$, —(C=O)(C1-C4 alkyl), —(S=O)(C1-C4 alkyl), —SO$_2$(C1-C4 alkyl), —(C=O)NR$^{37a}$R$^{37b}$, —SO$_2$NR$^{37a}$R$^{37b}$, —O(C=O)NR$^{37a}$R$^{37b}$, —NHSO$_2$NR$^{37a}$R$^{37b}$, —NH(C=O)NR$^{37a}$R$^{37b}$, and —N=NR$^{38}$. In a still further aspect, Ar$^3$ is pyridinyl substituted with 0, 1, or 2 groups independently selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OC$_2$R$^{36}$, —CO$_2$R$^{36}$, —(C1-C4 alkyl)CO$_2$R$^{36}$, —(C2-C4 alkenyl) CO$_2$R$^{36}$, —(C=O)(C1-C4 alkyl), —(S=O)(C1-C4 alkyl), —SO$_2$(C1-C4 alkyl), —(C=O)NR$^{37a}$R$^{37b}$, —SO$_2$NR$^{37a}$R$^{37b}$, —O(C=O)NR$^{37a}$R$^{37b}$, —NHSO$_2$NR$^{37a}$R$^{37b}$, —NH(C=O)NR$^{37a}$R$^{37b}$, and —N=NR$^{38}$. In yet a further aspect, Ar$^3$ is pyridinyl substituted with 0 or 1 group selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OC$_2$R$^{36}$, —CO$_2$R$^{36}$, —(C1-C4 alkyl)CO$_2$R$^{36}$, —(C2-C4 alkenyl) CO$_2$R$^{36}$, —(C=O)(C1-C4 alkyl), —(S=O)(C1-C4 alkyl), —SO$_2$(C1-C4 alkyl), —(C=O)NR$^{37a}$R$^{37b}$, —SO$_2$NR$^{37a}$R$^{37b}$, —O(C=O)NR$^{37a}$R$^{37b}$, —NHSO$_2$NR$^{37a}$R$^{37b}$, —NH(C=O)NR$^{37a}$R$^{37b}$, and —N=NR$^{38}$. In an even further aspect, Ar$^3$ is pyridinyl monosubstituted with a group selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OC$_2$R$^{36}$, —CO$_2$R$^{36}$, —(C1-C4 alkyl)CO$_2$R$^{36}$, —(C2-C4 alkenyl)CO$_2$R$^{36}$, —(C=O)(C1-C4 alkyl), —(S=O)(C1-C4 alkyl), —SO$_2$(C1-C4 alkyl), —(C=O)NR$^{37a}$R$^{37b}$, —SO$_2$NR$^{37a}$R$^{37b}$, —O(C=O)NR$^{37a}$R$^{37b}$, —NHSO$_2$NR$^{37a}$R$^{37b}$, —NH(C=O)NR$^{37a}$R$^{37b}$, and —N=NR$^{38}$. In a still further aspect, Ar$^3$ is unsubstituted pyridinyl.

In a further aspect, Ar$^3$ is quinolinyl substituted with 0, 1, 2, or 3 groups independently selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO$_2$R$^{36}$, —CO$_2$R$^{36}$, —(C1-C4 alkyl)CO$_2$R$^{36}$, —(C2-C4 alkenyl) CO$_2$R$^{36}$, —(C=O)(C1-C4 alkyl), —(S=O)(C1-C4 alkyl), —SO$_2$(C1-C4 alkyl), —(C=O)NR$^{37a}$R$^{37b}$, —SO$_2$NR$^{37a}$R$^{37b}$, —O(C=O)NR$^{37a}$R$^{37b}$, —NHSO$_2$NR$^{37a}$R$^{37b}$, —NH(C=O)NR$^{37a}$R$^{37b}$, and —N=NR$^{38}$. In a still further aspect, Ar$^3$ is quinolinyl substituted with 0, 1, or 2 groups independently selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO$_2$R$^{36}$, —CO$_2$R$^{36}$, —(C1-C4 alkyl)CO$_2$R$^{36}$, —(C2-C4 alkenyl)CO$_2$R$^{36}$, —(C=O)(C1-C4 alkyl), —(S=O)(C1-C4 alkyl), —SO$_2$(C1-C4 alkyl), —(C=O)NR$^{37a}$R$^{37b}$, —SO$_2$NR$^{37a}$R$^{37b}$, —O(C=O) NR$^{37a}$R$^{37b}$, —NHSO$_2$NR$^{37a}$R$^{37b}$, —NH(C=O)NR$^{37a}$R$^{37b}$, and —N=NR$^{38}$. In yet a further aspect, Ar$^3$ is quinolinyl substituted with 0 or 1 group selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO$_2$R$^{36}$, —CO$_2$R$^{36}$, —(C1-C4 alkyl)CO$_2$R$^{36}$, —(C2-C4 alkenyl)CO$_2$R$^{36}$, —(C=O)(C1-C4 alkyl), —(S=O)(C1-C4 alkyl), —SO$_2$(C1-C4 alkyl), —(C=O)NR$^{37a}$R$^{37b}$, —SO$_2$NR$^{37a}$R$^{37b}$, —O(C=O)NR$^{37a}$R$^{37b}$, —NHSO$_2$NR$^{37a}$R$^{37b}$, —NH(C=O)NR$^{37a}$R$^{37b}$, and —N=NR$^{38}$. In an even further aspect, Ar$^3$ is quinolinyl monosubstituted with a group selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OC$_2$R$^{36}$, —CO$_2$R$^{36}$, —(C1-C4 alkyl)CO$_2$R$^{36}$, —(C2-C4 alkenyl)CO$_2$R$^{36}$, —(C=O)(C1-C4 alkyl), —(S=O)(C1-C4 alkyl), —SO$_2$(C1-C4 alkyl), —(C=O)NR$^{37a}$R$^{37b}$, —SO$_2$NR$^{37a}$R$^{37b}$, —O(C=O)NR$^{37a}$R$^{37b}$, —NHSO$_2$NR$^{37a}$R$^{37b}$, —NH(C=O)NR$^{37a}$R$^{37b}$, and —N=NR$^{38}$. In a still further aspect, Ar$^3$ is unsubstituted quinolinyl.

In a further aspect, Ar$^3$ is furanyl substituted with 0, 1, 2, or 3 groups independently selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO$_2$R$^{36}$, —CO$_2$R$^{36}$, —(C1-C4 alkyl)CO$_2$R$^{36}$, —(C2-C4 alkenyl)CO$_2$R$^{36}$, —(C=O)(C1-C4 alkyl), —(S=O)(C1-C4 alkyl), —SO$_2$(C1-C4 alkyl), —(C=O)NR$^{37a}$R$^{37b}$, —SO$_2$NR$^{37a}$R$^{37b}$, —O(C=O)NR$^{37a}$R$^{37b}$, —NHSO$_2$NR$^{37a}$R$^{37b}$, —NH(C=O)NR$^{37a}$R$^{37b}$, and —N=NR$^{38}$. In a still further aspect, Ar$^3$ is furanyl substituted with 0, 1, or 2 groups independently selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO$_2$R$^{36}$, —CO$_2$R$^{36}$, —(C1-C4 alkyl)CO$_2$R$^{36}$, —(C2-C4 alkenyl)CO$_2$R$^{36}$, —(C=O)(C1-C4 alkyl), —(S=O)(C1-C4 alkyl), —SO$_2$(C1-C4 alkyl), —(C=O)NR$^{37a}$R$^{37b}$, —SO$_2$NR$^{37a}$R$^{37b}$, —O(C=O)NR$^{37a}$R$^{37b}$, —NHSO$_2$NR$^{37a}$R$^{37b}$, —NH(C=O)NR$^{37a}$R$^{37b}$, and —N=NR$^{38}$. In yet a further aspect, Ar$^3$ is furanyl substituted with 0 or 1 group selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO$_2$R$^{36}$, —CO$_2$R$^{36}$, —(C1-C4 alkyl)CO$_2$R$^{36}$, —(C2-C4 alkenyl)CO$_2$R$^{36}$, —(C=O)(C1-C4 alkyl), —(S=O)(C1-C4 alkyl), —SO$_2$(C1-C4 alkyl), —(C=O)NR$^{37a}$R$^{37b}$, —SO$_2$NR$^{37a}$R$^{37b}$, —O(C=O)NR$^{37a}$R$^{37b}$, —NHSO$_2$NR$^{37a}$R$^{37b}$, —NH(C=O)NR$^{37a}$R$^{37b}$, and —N=NR$^{38}$. In an even further aspect, Ar$^3$ is furanyl monosubstituted with a group selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO$_2$R$^{36}$, —CO$_2$R$^{36}$, —(C1-C4 alkyl)CO$_2$R$^{36}$, —(C2-C4 alkenyl)CO$_2$R$^{36}$, —(C=O)(C1-C4 alkyl), —(S=O)(C1-C4 alkyl), —SO$_2$(C1-C4 alkyl), —(C=O)NR$^{37a}$R$^{37b}$, —SO$_2$NR$^{37a}$R$^{37b}$, —O(C=O)NR$^{37a}$R$^{37b}$, —NHSO$_2$NR$^{37a}$R$^{37b}$, —NH(C=O)NR$^{37a}$R$^{37b}$, and —N=NR$^{38}$. In a still further aspect, Ar$^3$ is unsubstituted furanyl.

2. Compound Examples

In one aspect, a compound is selected from:

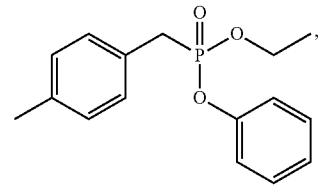

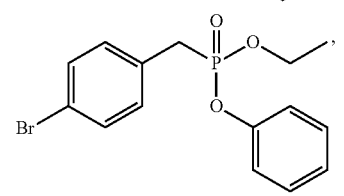

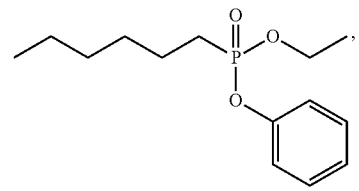

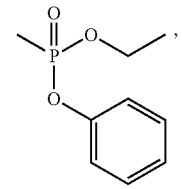

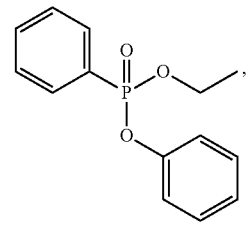

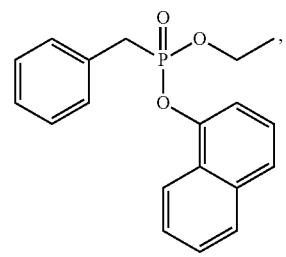

97
-continued
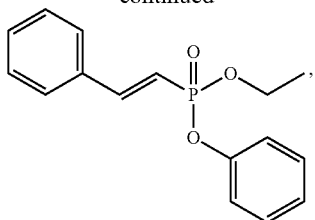
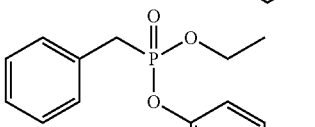
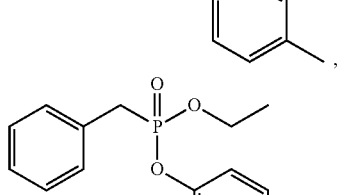
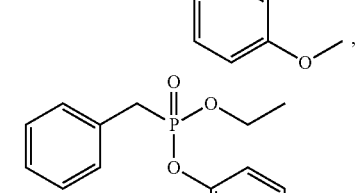
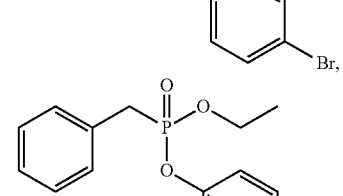
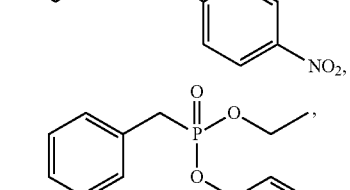
98
-continued
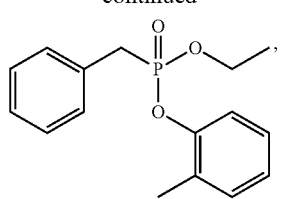
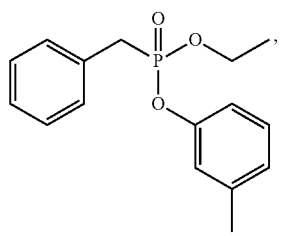
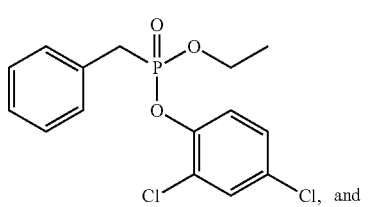
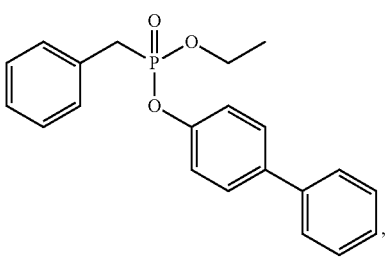
or a salt thereof.
In one aspect, the compound is selected from:
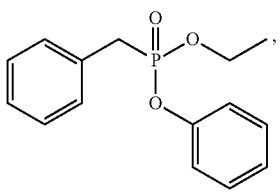
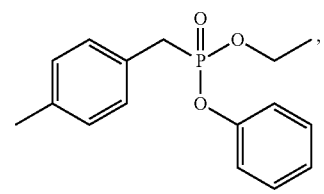
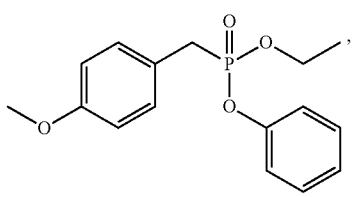
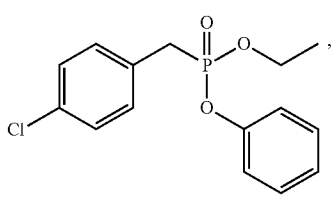
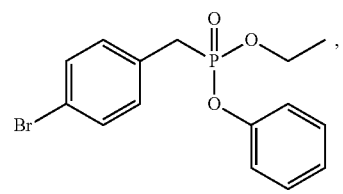
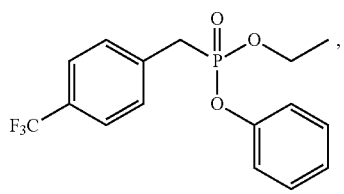

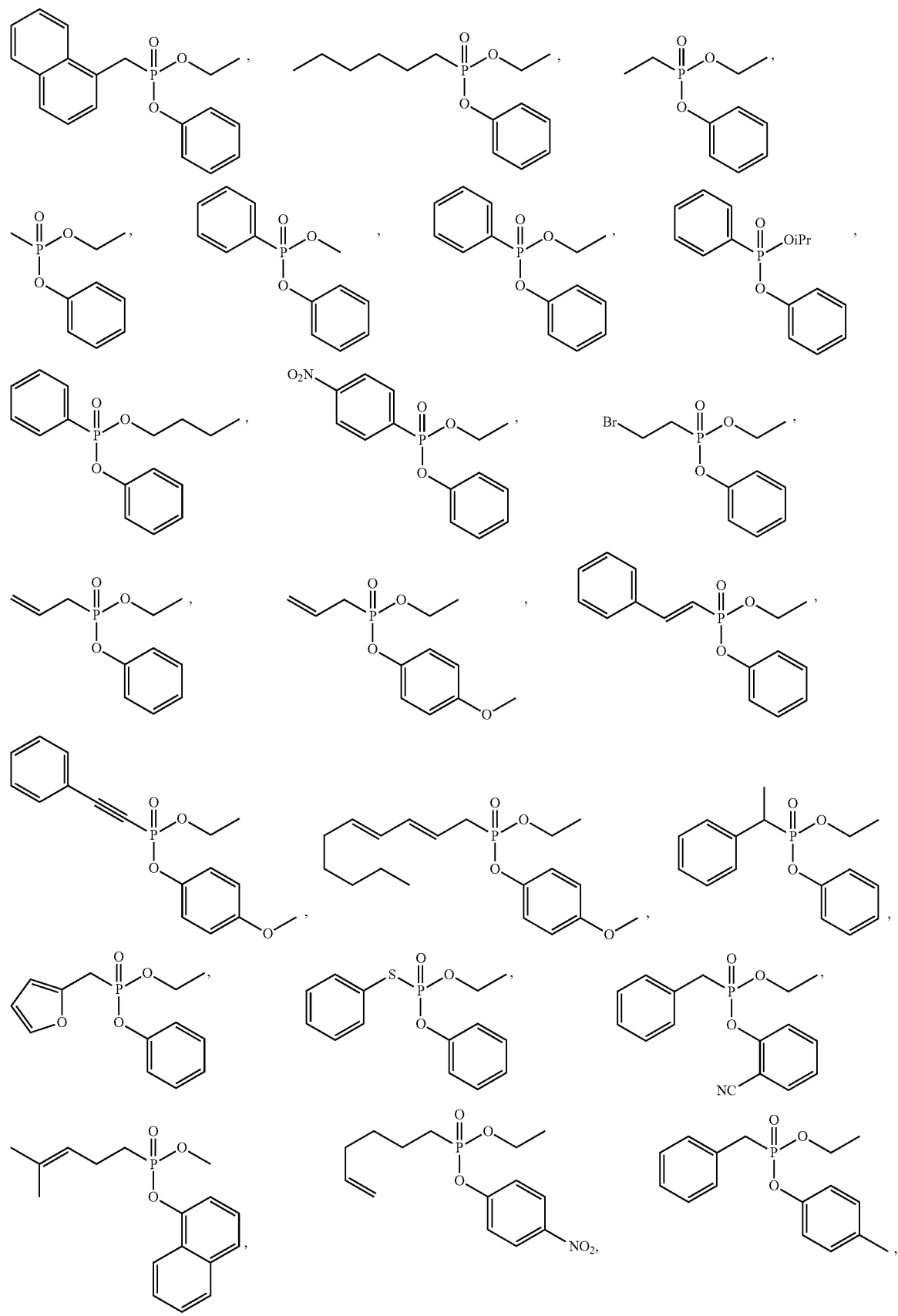

101
-continued
102
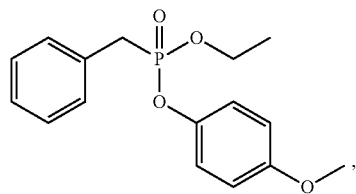
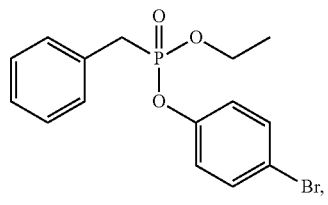
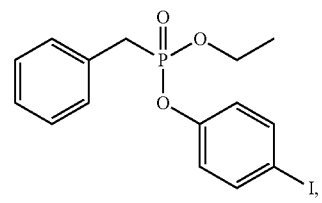
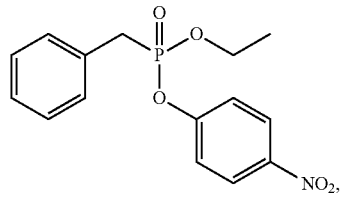
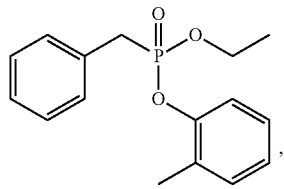
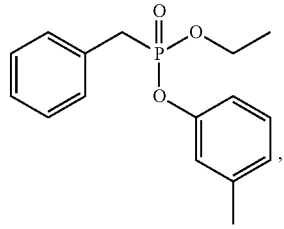
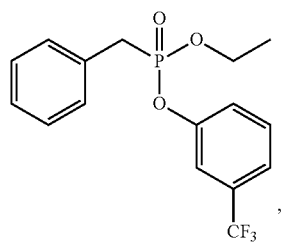
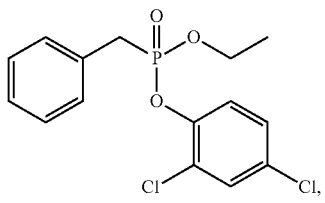
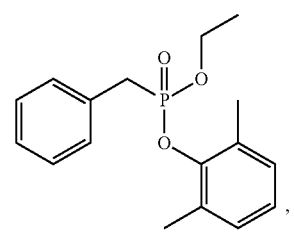
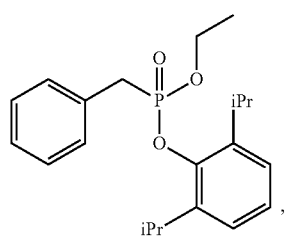
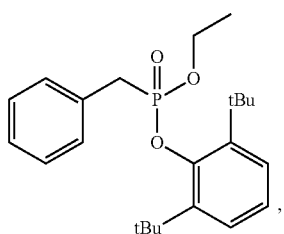
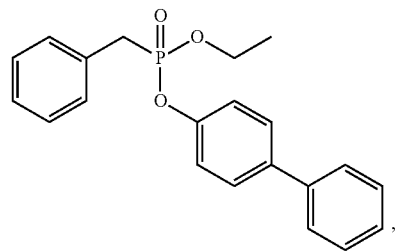
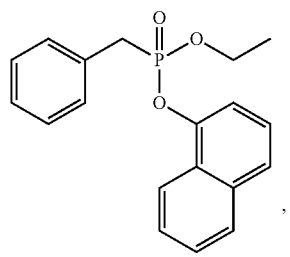
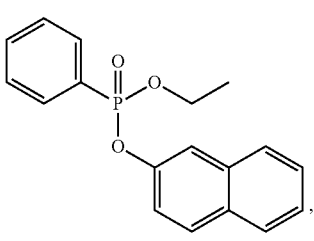
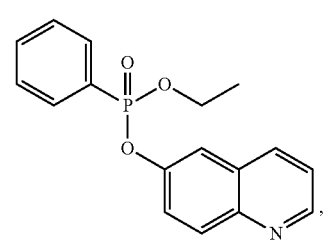
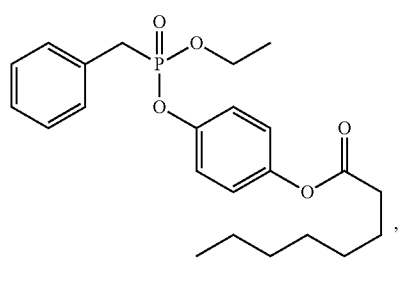
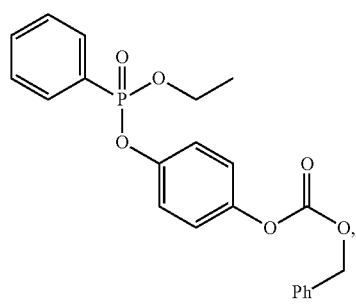

-continued
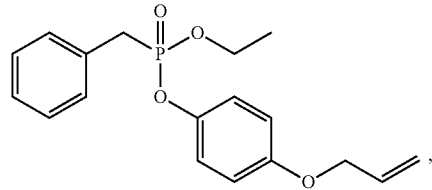
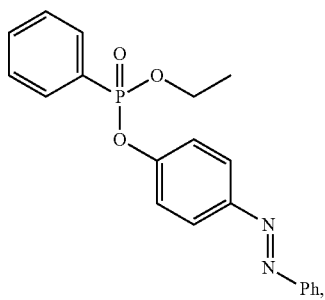
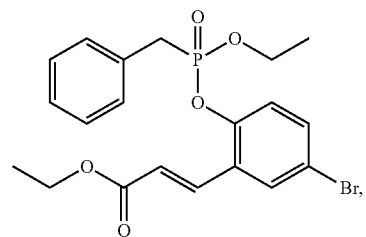
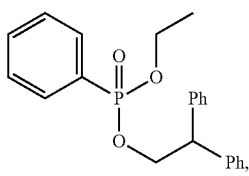
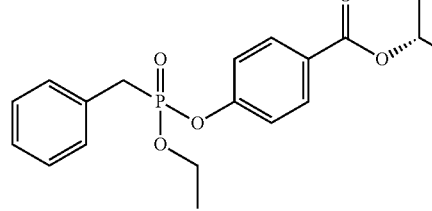
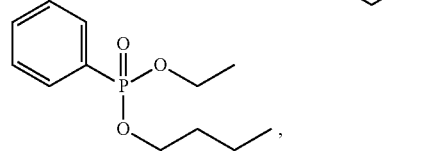
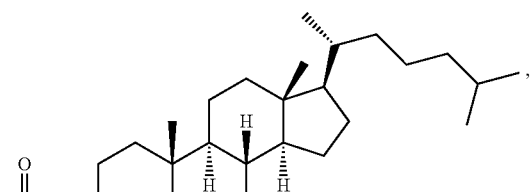
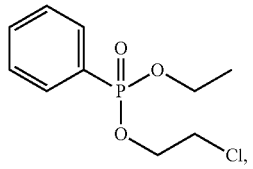
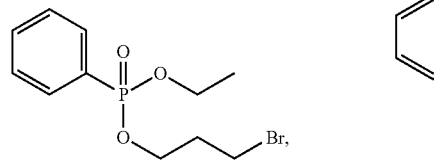
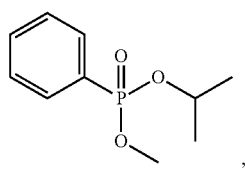
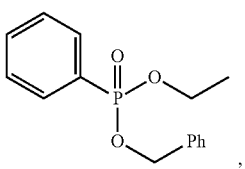
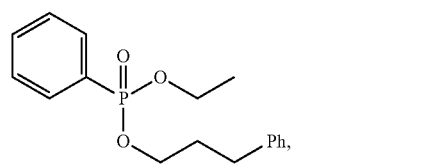
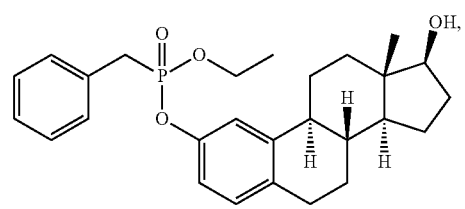

-continued
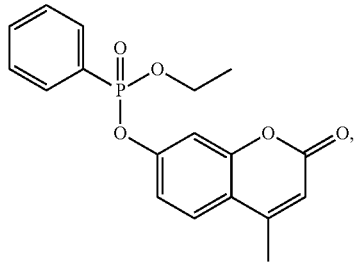
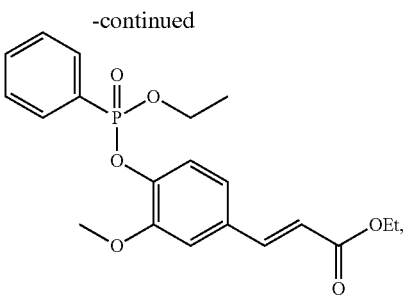
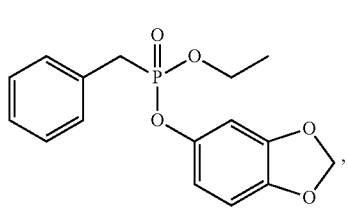
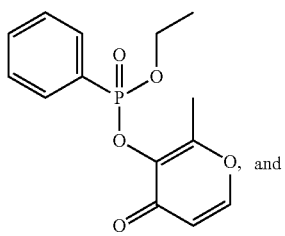
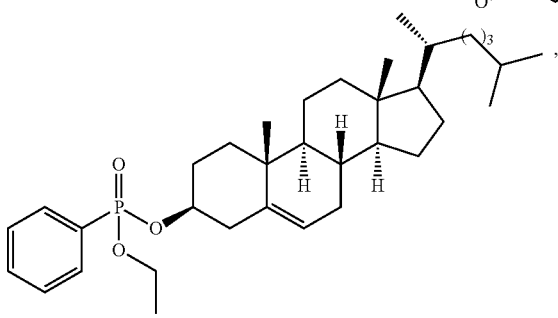
or a salt thereof.
In one aspect, the compound is selected from:
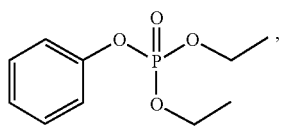 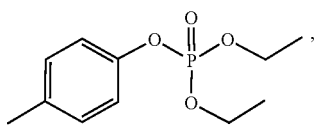 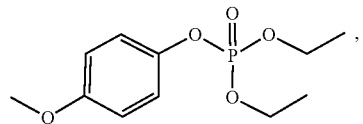
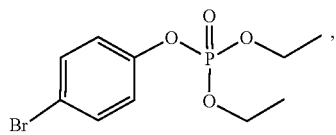 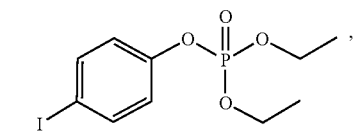 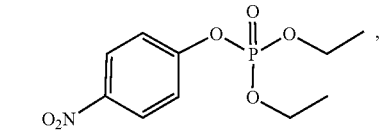
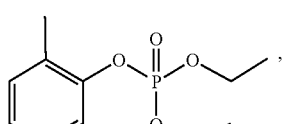 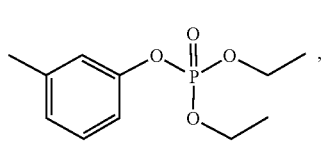 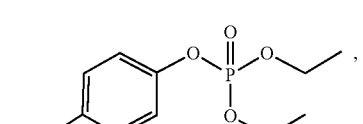
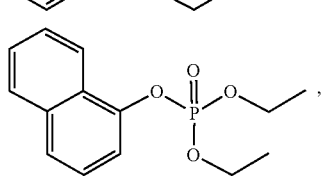 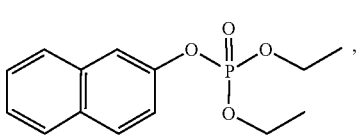 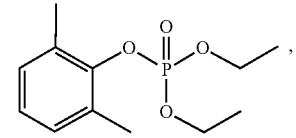

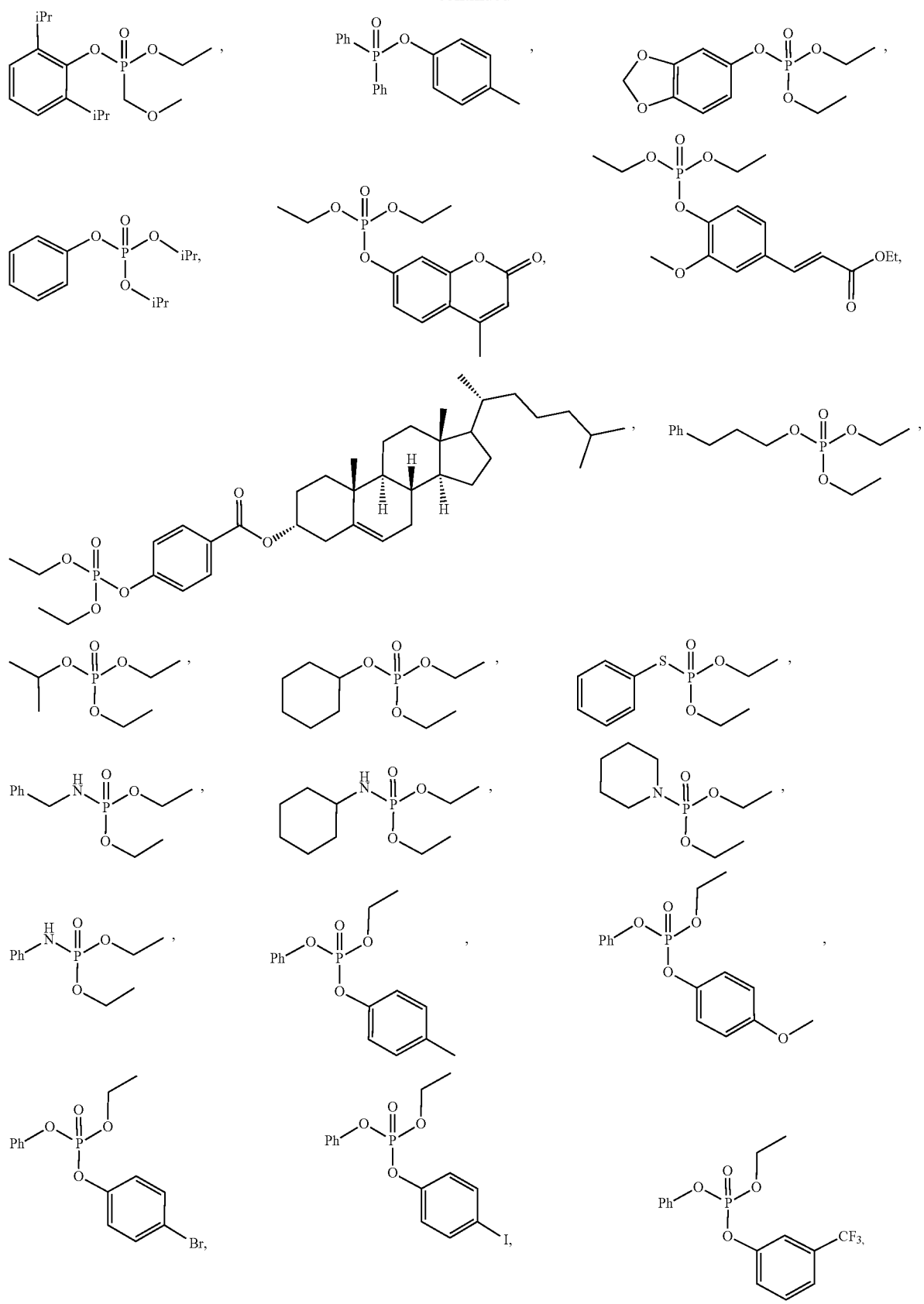

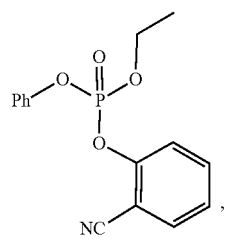
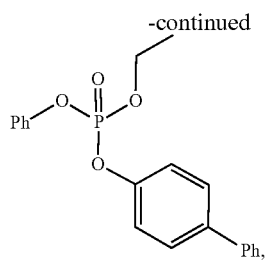
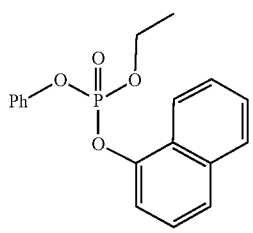
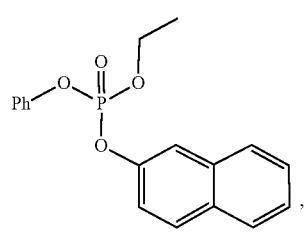
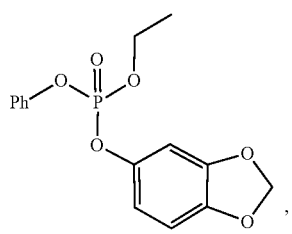
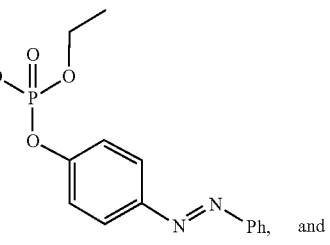, and
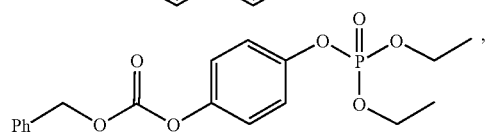
or a salt thereof.
In one aspect, the compound is selected from:
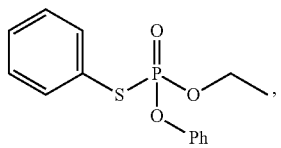
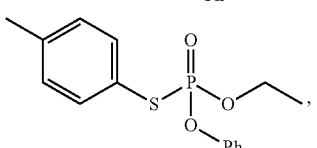
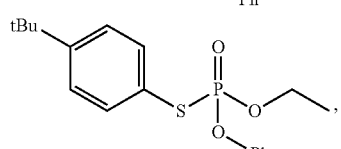
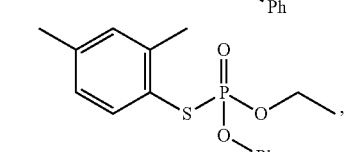
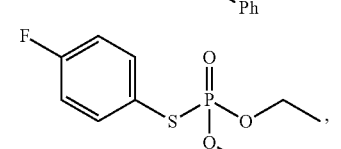
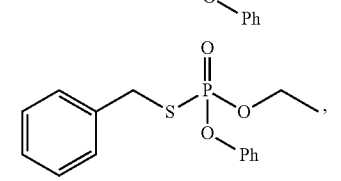
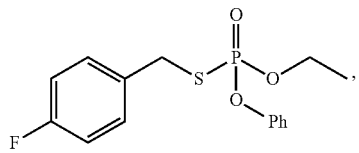
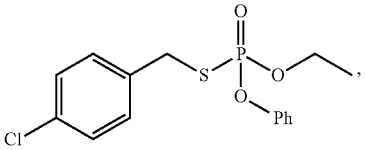
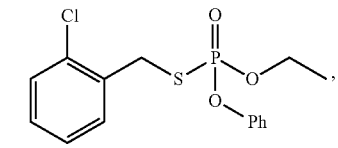
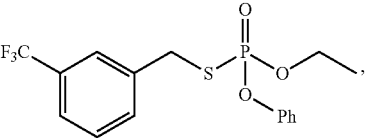
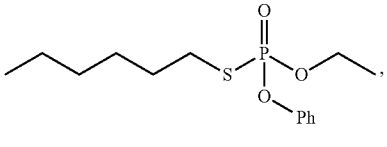
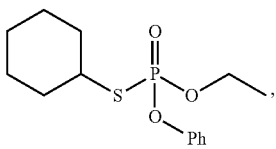

-continued

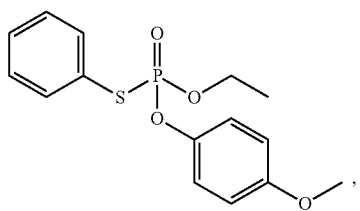

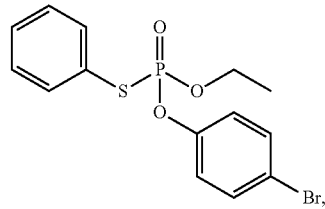

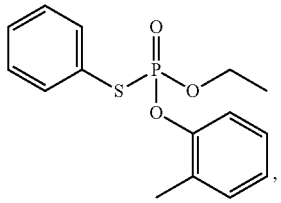

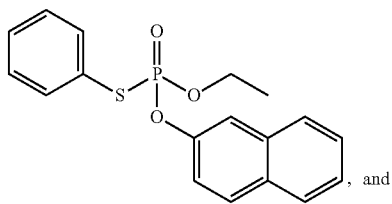

or a salt thereof.

In a further aspect, the compound is:

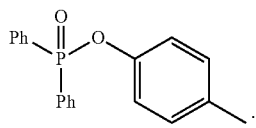 [SMILES: Cc1ccc(OP(=O)(c2ccccc2)c2ccccc2)cc1]

3. Prophetic Examples

The following compound examples are prophetic, and can be prepared using the synthesis methods described herein above and other general methods as needed as would be known to one skilled in the art. Thus, in one aspect, a compound can be:

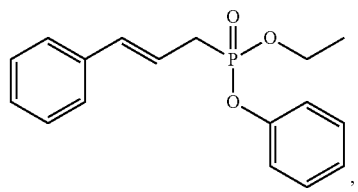 [SMILES: CCOP(=O)(C/C=C/c1ccccc1)Oc1ccccc1]

or a salt thereof.

C. Methods of Making the Disclosed Compounds

In one aspect, disclosed are methods of making a disclosed compound.

Thus, in one aspect, disclosed are methods of making a compound having a structure represented by a formula:

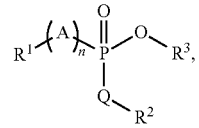

wherein n is 0 or 1; wherein A is selected from O, S, $NR^{20}$, and $CHR^{21}$; wherein $R^{20}$, when present, is selected from hydrogen and methyl; wherein $R^{21}$, when present, is selected from hydrogen and methyl; wherein Q is selected from O, S, and $NR^{22}$; wherein $R^{22}$, when present, is selected from hydrogen and C1-C8 alkyl; wherein $R^1$ is selected from C1-C8 alkyl, C2-C10 alkenyl, C1-C8 haloalkyl, C3-C6 cycloalkyl, —(C1-C4 alkyl)$Ar^1$, —(C2-C4 alkenyl)$Ar^1$, —(C2-C4 alkynyl)$Ar^1$, $Ar^1$, and a structure represented by a formula selected from:

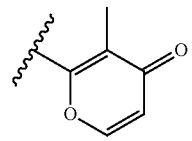

and

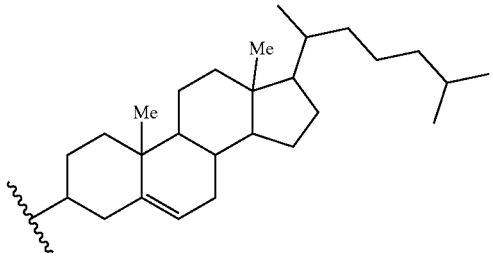

and wherein the C3-C6 cycloalkyl, when present, is substituted with 0 or 1 C1-C4 alkyl group; wherein $Ar^1$, when present, is selected from aryl and heteroaryl and is substituted with 0, 1, 2, or 3 groups independently selected from halogen, —$NO_2$, —CN, —OH, —SH, —$NH_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —$OCO_2R^{30}$, —$CO_2R^{30}$, —(C1-C4 alkyl)$CO_2R^{30}$, —(C2-C4 alkenyl)$CO_2R^{30}$, —(C=O)(C1-C4 alkyl), —(S=O)(C1-C4 alkyl), —$SO_2$(C1-C4 alkyl), —(C=O)

NR$^{31a}$R$^{31b}$, SO$_2$NR$^{31a}$R$^{31b}$, —O(C=O)NR$^{31a}$R$^{31b}$, —NHSO$_2$NR$^{31a}$R$^{31b}$, —NH(C=O)NR$^{31a}$R$^{31b}$, and —N=NR$^{32}$; wherein R$^{30}$, when present, is selected from hydrogen, C1-C8 alkyl, —(C1-C4 alkyl)phenyl, phenyl, and a structure represented by a formula:

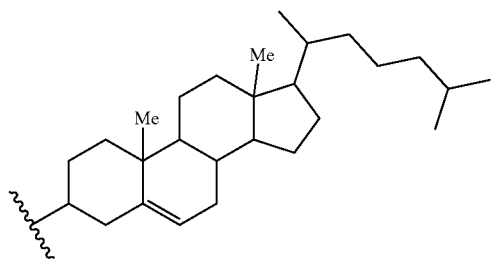

;

wherein each of R$^{31a}$ and R$^{31b}$, when present, is independently selected from hydrogen, C1-C8 alkyl, —(C1-C4 alkyl)phenyl, and phenyl; wherein R$^{32}$, when present, is selected from hydrogen, C1-C4 alkyl, and phenyl; or wherein each of R$^{1}$ and R$^{20}$, when present, are optionally covalently bonded together and, together with the intermediate carbon atoms, comprise a 3- to 6-membered heterocycloalkyl; wherein R$^{2}$ is selected from hydrogen, C1-C8 alkyl substituted with 0-1 phenyl groups, C2-C10 alkenyl, C1-C8 haloalkyl, C3-C6 cycloalkyl, —(C1-C4 alkyl)Ar$^{2}$, —(C2-C4 alkenyl)Ar$^{2}$, —(C2-C4 alkynyl)Ar$^{2}$, Ar$^{2}$, and a structure represented by a formula selected from:

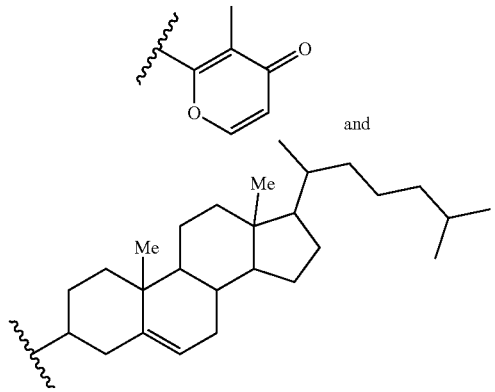

and wherein the C3-C6 cycloalkyl, when present, is substituted with 0 or 1 C1-C4 alkyl groups; wherein Ar$^{2}$, when present, is selected from aryl and heteroaryl and is substituted with 0, 1, 2, or 3 groups independently selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO$_2$R$^{33}$, —CO$_2$R$^{33}$, —(C1-C4 alkyl)CO$_2$R$^{33}$, —(C2-C4 alkenyl)CO$_2$R$^{33}$, —(C=O)(C1-C4 alkyl), —(S=O)(C1-C4 alkyl), —SO$_2$(C1-C4 alkyl), —(C=O)NR$^{34a}$R$^{34b}$, —SO$_2$NR$^{34a}$R$^{34b}$, —O(C=O)NR$^{34a}$R$^{34b}$, —NHSO$_2$NR$^{34a}$R$^{34b}$, —NH(C=O)NR$^{34a}$R$^{34b}$, and —N=NR$^{35}$; wherein R$^{33}$ when present, is selected from hydrogen, C1-C8 alkyl, —(C1-C4 alkyl)phenyl, phenyl, and a structure represented by a formula:

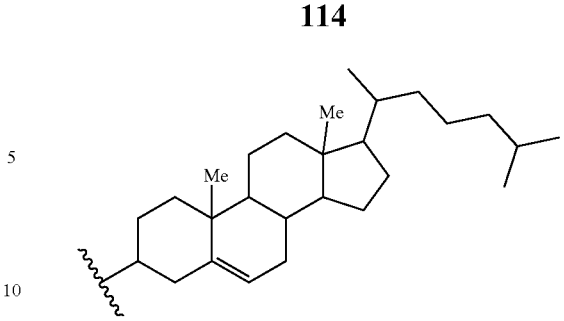

wherein each of R$^{34a}$ and R$^{34b}$, when present, is independently selected from hydrogen, C1-C8 alkyl, —(C1-C4 alkyl)phenyl, and phenyl; wherein R$^{35}$, when present, is selected from hydrogen, C1-C4 alkyl, and phenyl; and wherein R$^{3}$ is C1-C4 alkyl, or a salt thereof, the method comprising the step of reacting a phosphonate derivative having a structure represented by a formula:

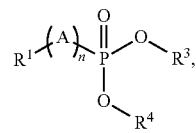

wherein R$^{4}$ is C1-C4 alkyl, provided that R$^{2}$ and R$^{4}$ are different, or a salt thereof, with a nucleophile having a structure represented by a formula:

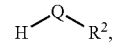

in the presence of an activating agent and a base.

In a further aspect, the compound has a structure represented by a formula:

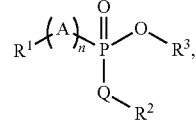

wherein n is 0 or 1; wherein A is selected from O, S, and CHR$^{21}$; wherein R$^{21}$, when present, is selected from hydrogen and methyl; wherein Q is selected from O, S, and NR$^{22}$; wherein R$^{22}$, when present, is selected from hydrogen and C1-C8 alkyl; wherein R$^{1}$ is selected from —(C1-C4 alkyl)Ar$^{1}$ and Ar$^{1}$; wherein Ar$^{1}$, when present, is selected from aryl and heteroaryl and is substituted with 0, 1, 2, or 3 groups independently selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO$_2$R$^{30}$, —CO$_2$R$^{30}$, —(C1-C4 alkyl)CO$_2$R$^{30}$, —(C2-C4 alkenyl)CO$_2$R$^{30}$, —(C=O)(C1-C4 alkyl), —(S=O)(C1-C4 alkyl), —SO$_2$(C1-C4 alkyl), —(C=O)NR$^{31a}$R$^{31b}$, —SO$_2$NR$^{31a}$R$^{31b}$, —O(C=O)NR$^{31a}$R$^{31b}$, —NHSO$_2$NR$^{31a}$R$^{31b}$, —NH(C=O)NR$^{31a}$R$^{31b}$, and —N=NR$^{32}$; wherein R$^{30}$, when present, is selected from hydrogen, C1-C8 alkyl, —(C1-C4 alkyl)phenyl, phenyl, and a structure represented by a formula:

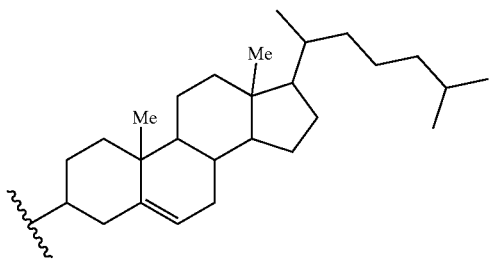

;

wherein each of $R^{31a}$ and $R^{31b}$, when present, is independently selected from hydrogen, C1-C8 alkyl, —(C1-C4 alkyl)phenyl, and phenyl; wherein $R^{32}$, when present, is selected from hydrogen, C1-C4 alkyl, and phenyl; wherein $R^2$ is selected from —(C1-C4 alkyl)Ar$^2$ and Ar$^2$; wherein Ar$^2$, when present, is selected from aryl and heteroaryl and is substituted with 0, 1, 2, or 3 groups independently selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OC$_2$R$^{33}$, —CO$_2$R$^{33}$, —(C1-C4 alkyl)CO$_2$R$^{33}$, —(C2-C4 alkenyl)CO$_2$R$^{33}$, —(C=O)(C1-C4 alkyl), —(S=O)(C1-C4 alkyl), —SO$_2$(C1-C4 alkyl), —(C=O)NR$^{34a}$R$^{34b}$, —SO$_2$NR$^{34a}$R$^{34b}$, —O(C=O)NR$^{34a}$R$^{34b}$, —NHSO$_2$NR$^{34a}$R$^{34b}$, —NH(C=O)NR$^{34a}$R$^{34b}$, and —N=NR$^{35}$; wherein R$^{33}$, when present, is selected from hydrogen, C1-C8 alkyl, —(C1-C4 alkyl)phenyl, phenyl, and a structure represented by a formula:

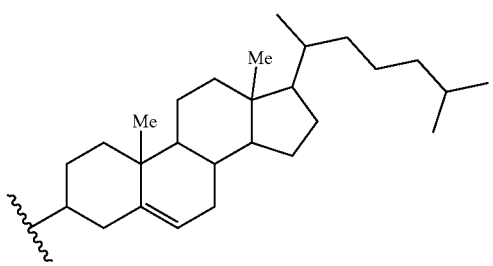

;

wherein each of $R^{34a}$ and $R^{34b}$, when present, is independently selected from hydrogen, C1-C8 alkyl, —(C1-C4 alkyl)phenyl, and phenyl; wherein $R^{35}$, when present, is selected from hydrogen, C1-C4 alkyl, and phenyl; and wherein $R^3$ is C1-C4 alkyl.

In one aspect, disclosed are methods of making a compound having a structure represented by a formula:

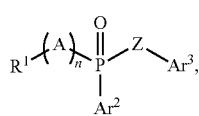

wherein n is 0 or 1; wherein A is selected from O, S, NR$^{20}$, and CHR$^{21}$; wherein R$^{20}$, when present, is selected from hydrogen and methyl; wherein R$^{21}$, when present, is selected from hydrogen and methyl; wherein Z is selected from O, S, and NR$^{23}$; wherein R$^{23}$, when present, is selected from hydrogen and methyl; wherein R$^1$ is selected from C1-C8 alkyl, C2-C10 alkenyl, C1-C8 haloalkyl, C3-C6 cycloalkyl, —(C1-C4 alkyl)Ar$^1$, —(C2-C4 alkenyl)Ar$^1$, —(C2-C4 alkynyl)Ar$^1$, Ar$^1$, and a structure represented by a formula selected from:

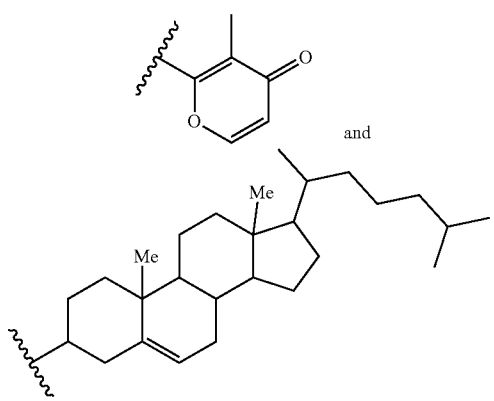

and

, and wherein the C3-C6 cycloalkyl, when present, is substituted with 0 or 1 C1-C4 alkyl group; wherein Ar$^1$, when present, is selected from aryl and heteroaryl and is substituted with 0, 1, 2, or 3 groups independently selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO$_2$R$^{30}$, —CO$_2$R$^{30}$, —(C1-C4 alkyl)CO$_2$R$^{30}$, —(C2-C4 alkenyl)CO$_2$R$^{33}$, —(C=O)(C1-C4 alkyl), —(S=O)(C1-C4 alkyl), —SO$_2$(C1-C4 alkyl), —(C=O)NR$^{31a}$R$^{31b}$, —SO$_2$NR$^{31a}$R$^{31b}$, —O(C=O)NR$^{31a}$R$^{31b}$, —NHSO$_2$NR$^{31a}$R$^{31b}$, —NH(C=O)NR$^{31a}$R$^{31b}$, and —N=NR$^{32}$; wherein R$^{30}$, when present, is selected from hydrogen, C1-C8 alkyl, —(C1-C4 alkyl)phenyl, phenyl, and a structure represented by a formula:

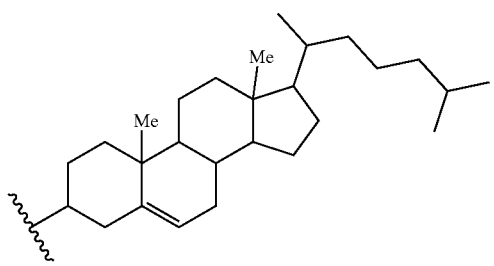

;

wherein each of $R^{31a}$ and $R^{31b}$, when present, is independently selected from hydrogen, C1-C8 alkyl, —(C1-C4 alkyl)phenyl, and phenyl; wherein $R^{32}$, when present, is selected from hydrogen, C1-C4 alkyl, and phenyl; or wherein each of $R^1$ and $R^{20}$, when present, are optionally covalently bonded together and, together with the intermediate carbon atoms, comprise a 3- to 6-membered heterocycloalkyl; wherein Ar$^2$ is selected from aryl and heteroaryl and is substituted with 0, 1, 2, or 3 groups independently selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl (C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO$_2$R$^{33}$, —CO$_2$R$^{33}$, —(C1-C4 alkyl)CO$_2$R$^{33}$, —(C2-C4 alkenyl)CO$_2$R$^{33}$, —(C=O)(C1-C4 alkyl), —(S=O)(C1-C4 alkyl), —SO$_2$(C1-C4 alkyl), —(C=O)NR$^{34a}$R$^{34b}$, —SO$_2$NR$^{34a}$R$^{34b}$, —O(C=O)NR$^{34a}$R$^{34b}$, —NHSO$_2$NR$^{34a}$R$^{34b}$, —NH(C=O)NR$^{34a}$R$^{34b}$, and —N=NR$^{35}$; wherein R$^{33}$, when present, is selected from hydrogen, C1-C8 alkyl, —(C1-C4 alkyl)phenyl, phenyl, and a structure represented by a formula:

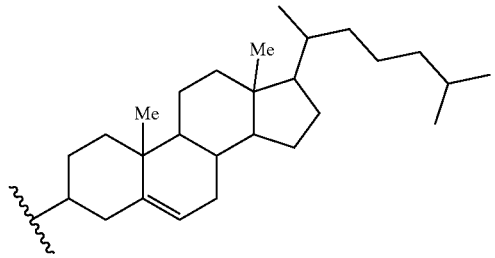

wherein each of R$^{34a}$ and R$^{34b}$, when present, is independently selected from hydrogen, C1-C8 alkyl, —(C1-C4 alkyl)phenyl, and phenyl; wherein R$^{35}$, when present, is selected from hydrogen, C1-C4 alkyl, and phenyl; wherein Ar$^4$ is selected from aryl and heteroaryl and is substituted with 0, 1, 2, or 3 groups independently selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OC$_2$R$^{36}$, —CO$_2$R$^{36}$, —(C1-C4 alkyl)CO$_2$R$^{36}$, —(C2-C4 alkenyl)CO$_2$R$^{36}$, —(C=O)(C1-C4 alkyl), —(S=O)(C1-C4 alkyl), —SO$_2$(C1-C4 alkyl), —(C=O)NR$^{37a}$R$^{37b}$, —SO$_2$NR$^{37a}$R$^{37b}$, —O(C=O)NR$^{37a}$R$^{37b}$, —NHSO$_2$NR$^{37a}$R$^{37b}$, —NH(C=O)NR$^{37a}$R$^{37b}$, and —N=NR$^{38}$; wherein R$^{36}$, when present, is selected from hydrogen, C1-C8 alkyl, —(C1-C4 alkyl)phenyl, phenyl, and a structure represented by a formula:

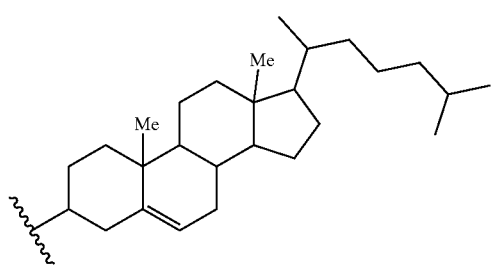

wherein each of R$^{37a}$ and R$^{37b}$, when present, is independently selected from hydrogen, C1-C8 alkyl, —(C1-C4 alkyl)phenyl, and phenyl; wherein R$^{38}$, when present, is selected from hydrogen, C1-C4 alkyl, and phenyl, or a salt thereof, the method comprising the step of reacting a phosphinate derivative having a structure represented by a formula:

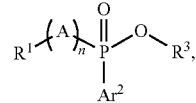

wherein R$^3$ is C1-C4 alkyl, or a salt thereof, with a nucleophile having a structure represented by a formula:

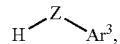

in the presence of an activating agent and a base.

In a further aspect, the compound has a structure represented by a formula:

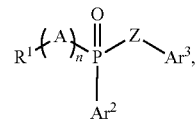

wherein n is 0 or 1; wherein A is selected from O, S, and CHR$^{21}$; wherein R$^{21}$, when present, is selected from hydrogen and methyl; wherein Z is selected from O, S, and NR$^{23}$; wherein R$^{23}$, when present, is selected from hydrogen and methyl; wherein R$^1$ is selected from —(C1-C4 alkyl)Ar$^1$ and Ar$^1$; wherein Ar$^2$, when present, is selected from aryl and heteroaryl and is substituted with 0, 1, 2, or 3 groups independently selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO$_2$R$^{30}$, —CO$_2$R$^{30}$, —(C1-C4 alkyl)CO$_2$R$^{30}$, —(C2-C4 alkenyl)CO$_2$R$^{33}$, —(C=O)(C1-C4 alkyl), —(S=O)(C1-C4 alkyl), —SO$_2$(C1-C4 alkyl), —(C=O)NR$^{31a}$R$^{31b}$, —SO$_2$NR$^{31a}$R$^{31b}$, —O(C=O)NR$^{31a}$R$^{31b}$, —NHSO$_2$NR$^{31a}$R$^{31b}$, —NH(C=O)NR$^{31a}$R$^{31b}$, and —N=NR$^{32}$; wherein R$^{30}$, when present, is selected from hydrogen, C1-C8 alkyl, —(C1-C4 alkyl)phenyl, phenyl, and a structure represented by a formula:

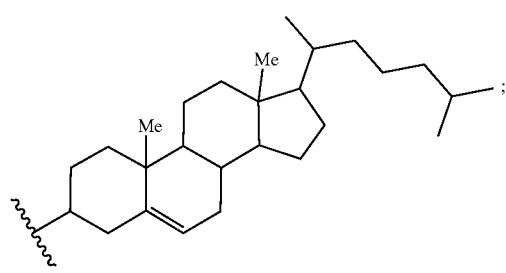 [SMILES: *C1CCC2(C)C(=CCC3C2CCC2(C)C(C(C)CCCC(C)C)CCC32)C1]

wherein each of R$^{31a}$ and R$^{31b}$, when present, is independently selected from hydrogen, C1-C8 alkyl, —(C1-C4 alkyl)phenyl, and phenyl; wherein R$^{32}$, when present, is selected from hydrogen, C1-C4 alkyl, and phenyl; wherein Ar$^2$, when present, is selected from aryl and heteroaryl and is substituted with 0, 1, 2, or 3 groups independently selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4) (C1-C4) dialkylamino, C3-C7 cycloalkyl, C6-C10 aryl, —O(C2-C4 alkenyl), —OCO$_2$R$^{33}$, —CO$_2$R$^{33}$, —(C1-C4 alkyl)CO$_2$R$^{33}$, —(C2-C4 alkenyl)CO$_2$R$^{33}$, —(C=O)(C1-C4 alkyl), —(S=O)(C1-C4 alkyl), —SO$_2$(C1-C4 alkyl), —(C=O)NR$^{34a}$R$^{34b}$, —SO$_2$NR$^{34a}$R$^{34b}$, —O(C=O)NR$^{34a}$R$^{34b}$, —NHSO$_2$NR$^{34a}$R$^{34b}$, —NH(C=O)NR$^{34a}$R$^{34b}$, and —N=NR$^{35}$; wherein R$^{33}$, when present, is selected from hydrogen, C1-C8 alkyl, —(C1-C4 alkyl)phenyl, phenyl, and a structure represented by a formula:

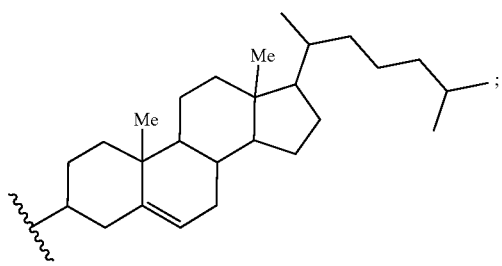 [SMILES: *C1CCC2(C)C(=CCC3C2CCC2(C)C(C(C)CCCC(C)C)CCC32)C1]

wherein each of R$^{34a}$ and R$^{34b}$, when present, is independently selected from hydrogen, C1-C8 alkyl, —(C1-C4 alkyl)phenyl, and phenyl; wherein R$^{35}$, when present, is selected from hydrogen, C1-C4 alkyl, and phenyl; and wherein Ar$^3$ is selected from aryl and heteroaryl and is substituted with 0, 1, 2, or 3 groups independently selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4) (C1-C4) dialkylamino, C3-C7 cycloalkyl, C6-C10 aryl, —O(C2-C4 alkenyl), —OCO$_2$R$^{36}$, —CO$_2$R$^{36}$, —(C1-C4 alkyl)CO$_2$R$^{36}$, —(C2-C4 alkenyl)CO$_2$R$^{36}$, —(C=O)(C1-C4 alkyl), —(S=O)(C1-C4 alkyl), —SO$_2$(C1-C4 alkyl), —(C=O)NR$^{37a}$R$^{37b}$, —SO$_2$NR$^{37a}$R$^{37b}$, —O(C=O)NR$^{37a}$R$^{37b}$, —NHSO$_2$NR$^{37a}$R$^{37b}$, —NH(C=O)NR$^{37a}$R$^{37b}$, and —N=NR$^{38}$; wherein R$^{36}$, when present, is selected from hydrogen, C1-C8 alkyl, —(C1-C4 alkyl)phenyl, phenyl, and a structure represented by a formula:

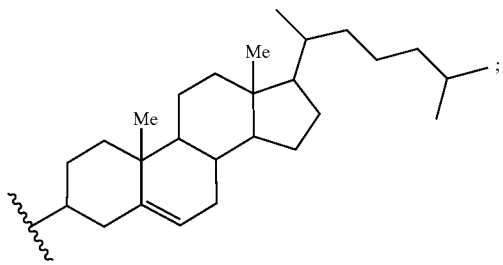 [SMILES: *C1CCC2(C)C(=CCC3C2CCC2(C)C(C(C)CCCC(C)C)CCC32)C1]

wherein each of R$^{37a}$ and R$^{37b}$, when present, is independently selected from hydrogen, C1-C8 alkyl, —(C1-C4 alkyl)phenyl, and phenyl; wherein R$^{38}$, when present, is selected from hydrogen, C1-C4 alkyl, and phenyl.

In a further aspect, the phosphonate derivative, the nucleophile, the activating agent, and the base are simultaneously reacted. In a still further aspect, the phosphonate derivative, the nucleophile, the activating agent, and the base are sequentially reacted.

In a further aspect, the phosphinate derivative, the nucleophile, the activating agent, and the base are simultaneously reacted. In a still further aspect, the phosphinate derivative, the nucleophile, the activating agent, and the base are sequentially reacted.

In a further aspect, the phosphonate derivative, the activating agent, and the base react to form a reaction product, and wherein the reaction product reacts with the nucleophile.

In a further aspect, the phosphinate derivative, the activating agent, and the base react to form a reaction product, and wherein the reaction product reacts with the nucleophile.

As used herein, the term "activating agent" means an agent capable of replacing a ligand on a phosphine atom with a desired leaving group. Examples of activating agents include, but are not limited to, triflic anhydride, mesyl chloride, tosyl chloride, oxalyl chloride, thionyl chloride, acetic anhydride, benzoic anhydride, and trifluoroacetic anhydride. In a further aspect, the activating agent is triflic anhydride.

Examples of bases that can be used in the disclosed methods include, but are not limited to, piperidine, pyridine, pyrimidine, trimethylamine, imidazole, quinoline, indole, pyrazole, morpholine, N-methylmorpholine, pyrrole, thiazole, 2-iodopyridine, 2-fluoropyridine, 2-chloropyridine, 2-MeO-pyridine, and 4-iodopyridine. In a further aspect, the base is pyridine.

The compounds of this invention can be prepared by employing reactions as shown in the following schemes, in addition to other standard manipulations that are known in the literature, exemplified in the experimental sections or clear to one skilled in the art. For clarity, examples having a single substituent are shown where multiple substituents are allowed under the definitions disclosed herein.

1. Route I

In one aspect, disclosed organophosphorous compounds can be prepared as shown below.

SCHEME IA.

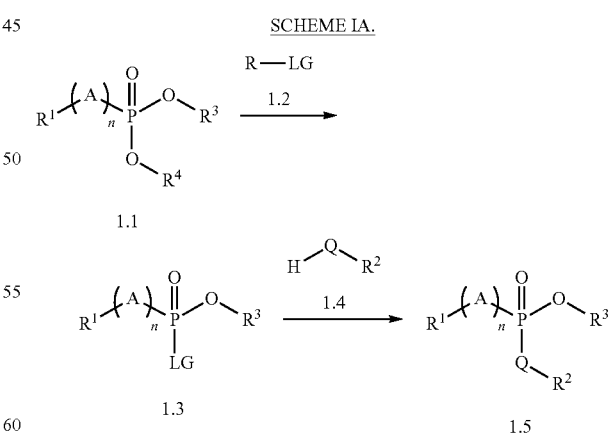

Compounds are represented in generic form, wherein R is the activating agent (minus the leaving group), wherein LG is a leaving group, and with other substituents as noted in compound descriptions elsewhere herein. A more specific example is set forth below.

SCHEME IB.

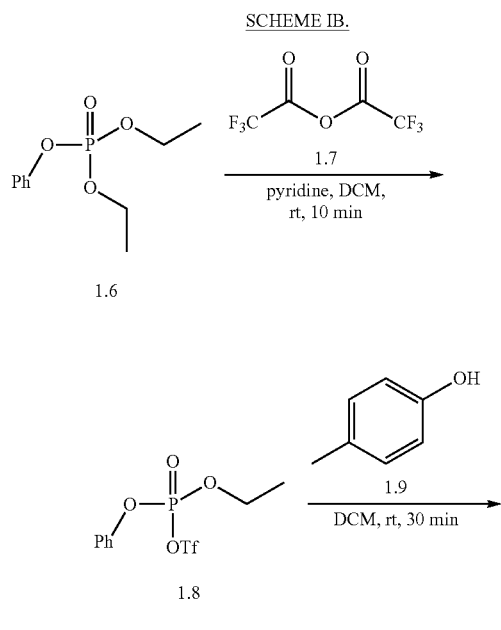

SCHEME IIA.

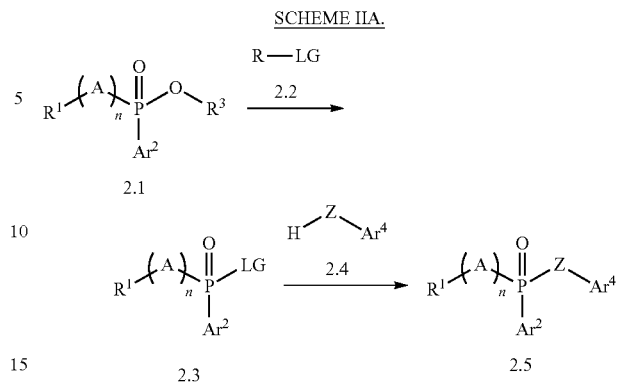

Compounds are represented in generic form, wherein R is the activating agent (minus the leaving group), wherein LG is a leaving group, and with other substituents as noted in compound descriptions elsewhere herein. A more specific example is set forth below.

SCHEME IIB.

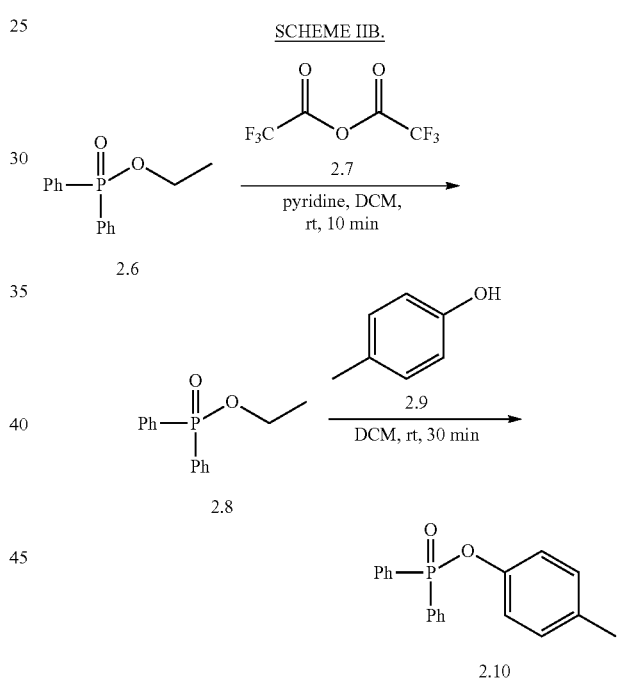

In one aspect, the synthesis of an organophosphorous compound can begin with a phosphonate derivative. Phosphonate derivatives are commercially available or readily prepared by one skilled in the art. Thus, compounds of type 1.10 and similar compounds can be prepared according to reaction Scheme ib above. Compounds of type 1.8 can be prepared by activation of an appropriate phosphonate derivative, e.g., 1.6 as shown above. The activation is carried out in the presence of an appropriate activating agent, e.g., triflic anhydride, and an appropriate base, e.g., pyridine, in an appropriate solvent, e.g., dichloromethane, for an appropriate period of time, e.g., 10 minutes. Compounds of type 1.10 can be prepared by a nucleophilic substitution reaction between an organophosphorous compound having a leaving group, e.g., 1.8, and an appropriate nucleophile, e.g., 1.9 as shown above. Appropriate nucleophiles are commercially available or readily prepared by one skilled in the art. The nucleophilic substitution reaction is carried out in an appropriate solvent, e.g., dichloromethane, for an appropriate period of time, e.g., 30 min. As can be appreciated by one skilled in the art, the above reaction provides an example of a generalized approach wherein compounds similar in structure to the specific reactants above (compounds similar to compounds of type 1.1, 1.2, 1.3, and 1.4), can be substituted in the reaction to provide substituted organophosphorous compounds similar to Formula 1.4.

2. Route II

In one aspect, disclosed organophosphorous compounds can be prepared as shown below.

In one aspect, the synthesis of an organophosphorous compound can begin with a phosphinate derivative. Phosphinate derivatives are commercially available or readily prepared by one skilled in the art. Thus, compounds of type 2.10 and similar compounds can be prepared according to reaction Scheme iib above. Compounds of type 2.8 can be prepared by activation of an appropriate phosphinate derivative, e.g., 2.6 as shown above. The activation is carried out in the presence of an appropriate activating agent, e.g., triflic anhydride, and an appropriate base, e.g., pyridine, in an appropriate solvent, e.g., dichloromethane, for an appropriate period of time, e.g., 10 minutes. Compounds of type 2.10 can be prepared by a nucleophilic substitution reaction between an organophosphorous compound having a leaving group, e.g., 2.8, and an appropriate nucleophile, e.g., 2.9 as shown above. Appropriate nucleophiles are commercially available or readily prepared by one skilled in the art. The nucleophilic substitution reaction is carried out in an appropriate solvent, e.g., dichloromethane, for an appropriate period of time, e.g., 30 min. As can be appreciated by one skilled in the art, the above reaction provides an example of a generalized approach wherein compounds similar in structure to the specific reactants above (compounds similar to compounds of type 2.1, 2.2, 2.3, and 2.4), can be substituted in the reaction to provide substituted organophosphorous compounds similar to Formula 2.4.

D. EXAMPLES

Figure 3:
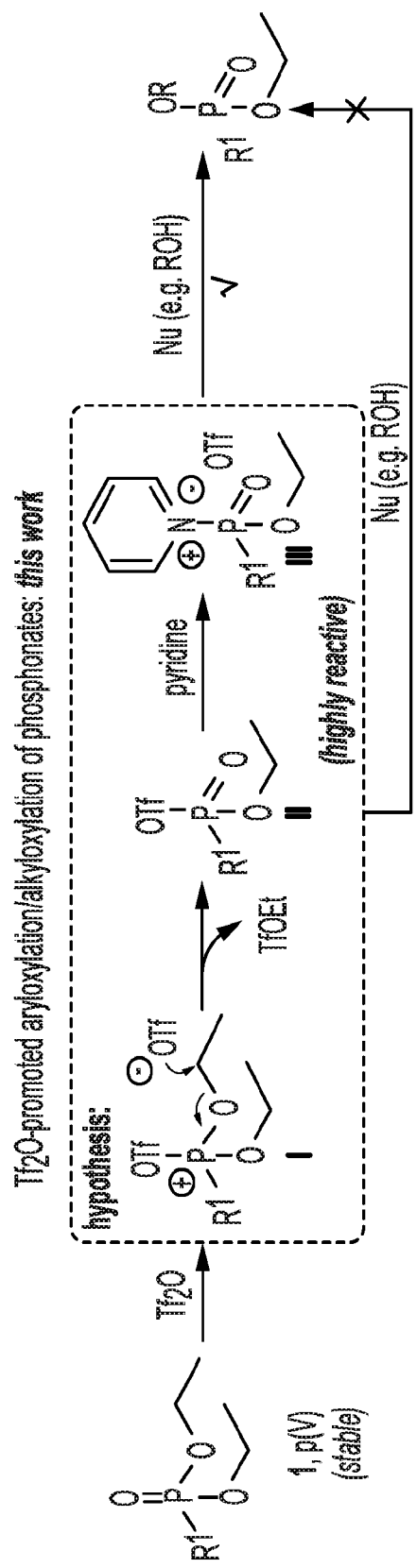
FIG. 3 shows Tf$_2$O-promoted aryloxylation/alkyloxylation of phosphonates as further disclosed herein.

It was hypothesized that the terminal oxygen P(V)=O of dialkylphosphonates 1 could be activated by $Tf_2O$ to afford a phosphonium intermediate I (FIG. 3; Kenny et al. (2015) *Chem. Commun.* 51: 16561; Imamoto et al. (2001) *Org. Lett.* 3: 87), which is then converted to TfO-substituted phosphonate intermediate II via nucleophilic substitution reaction (Rajendran et al. (2015) *J. Am. Chem. Soc.* 137: 9375). Finally, it was envisioned that the phosphonate intermediate II in presence of pyridine could be transformed to a highly reactive pyridinium phosphonate intermediate III (Sigurdsson and Stromberg (2002) *J. Chem. Am. Soc. Perkin Trans.* 2, 1682; Li et al. (2015) *Tetrahedron Lett.* 56: 4694; Ladame et al. (2001) *Phosphorus Sulfur Silicon Relat. Elem.* 174: 37). With this idea in mind, the development of new electrophilic P-species using the chemically inert dialkylphosphonates was explored or a facile synthesis of mixed phosphonates. Herein, a metal-free, chloride reagent-free, and $Tf_2O$-mediated activation of phosphonates for the synthesis of mixed phosphonates via direct aryloxylation/alkyloxylation strategies is described.

The following examples are put forth so as to provide those of ordinary skill in the art with a complete disclosure and description of how the compounds, and/or methods disclosed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

The Examples are provided herein to illustrate the invention, and should not be construed as limiting the invention in any way. Examples are provided herein to illustrate the invention and should not be construed as limiting the invention in any way.

1. Chemistry Experimental a. General Experimental

All reactions were carried out under air atmosphere in oven-dried glassware with magnetic stirring bar. Dry solvents (THF, toluene, and DCM) were obtained by solvent purification system under argon. All commercially available reagents were used as received without further purification. The tubes used for the reaction were showed in Figure S1. Purification of reaction products was carried out by flash column chromatography using silica gel 60 (230-400 mesh). Analytical thin layer chromatography was performed on 0.25 mm aluminum-backed silica gel 60-F plates. Visualization was accompanied with UV light and $KMnO_4$ solution. Concentration under reduced pressure refers to the removal of volatiles using a rotary evaporator attached to a dry diaphragm pump (10-15 mm Hg) followed by pumping to a constant weight with an oil pump (<300 mTorr). Infrared (IR) spectra were recorded on an IR spectrometer with KBr wafers or a film on KBr plate. High-resolution mass spectra (HRMS) were recorded on LCMS-IT-TOF mass spectrometer using ESI (electrospray ionization) or APCI (Atmospheric Pressure Chemical Ionization). $^1$H NMR spectra were recorded in $CDCl_3$ on 400 MHz NMR spectrometer. The $^1$H chemical shifts are referenced to residual solvent signals at δ 7.26 ($CHCl_3$) or δ 0.00 (TMS). $^1$H NMR coupling constants (J) are reported in Hertz (Hz) and multiplicities are indicated as follows: s (singlet), bs (broad singlet), d (doublet), t (triplet), q (quartet), m (multiplet), dd (doublet of doublets), dt (doublet of triplets), td (triplet of doublets), tt (triplet of triplets). $^{13}$C NMR spectra were proton decoupled and recorded in $CDCl_3$ on 100.5 MHz NMR spectrometer. The $^{13}$C chemical shifts are referenced to solvent signals at δ 77.16 ($CDCl_3$). $^{31}$P NMR spectra were proton decoupled and recorded in $CDCl_3$ on 162 MHz NMR spectrometer. $^{31}$P chemical shifts are reported relative to 85% $H_3PO_4$ (0.00 ppm) as an external standard.

b. General Procedure for the Synthesis of Mixed Phosphonates

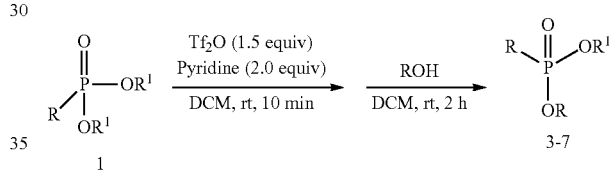

Ethyl phenyl benzylphosphonate (3a as example): To a solution of diethyl benzylphosphonate 1a (45.4 mg, 0.2 mmol), $Tf_2O$ (50.5 µL, 0.3 mmol) in DCM (1.0 mL) was added pyridine (32 µL, 0.4 mmol). After the mixture was stirred for 10 min, phenol (46.5 mg, 0.5 mmol) was added to vial under air condition. After being stirred for another 30 min at room temperature, the resulting solution was directly concentrated to give the crude material which was then purified by column chromatography on silica gel (PE/EA=3:1) to afford ethyl phenyl benzylphosphonate (3a).

i. Ethyl phenyl benzylphosphonate (3A)

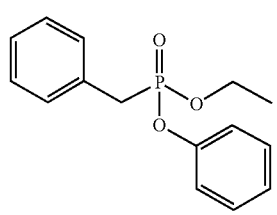

50.8 mg, 92%; as a colorless oil; $R_f$ 0.20 ($v_{Hexane}/v_{EA}$=2:1); IR v (KBr, $cm^{-1}$) 3032, 2981, 2908, 2593, 1489, 1261, 1207, 1037, 925; $^1$H NMR (400 MHz, $CDCl_3$) δ 7.35-7.23 (m, 7H), 7.16-7.08 (m, 3H), 4.11-4.04 (m, 2H), 3.31 (dd, J=21.6, 2.8 Hz, 2H), 1.20 (t, J=6.8 Hz, 3H); $^{13}$C NMR (100.5

MHz, CDCl$_3$) δ 150.6 (d, J=8.9 Hz), 130.9 (d, J=8.9 Hz), 129.9 (d, J=7.4 Hz), 129.6, 128.6 (d, J=3.0 Hz), 127.1 (d, J=3.7 Hz), 124.8 (d, J=1.5 Hz), 120.5 (d, J=4.5 Hz), 63.0 (d, J=6.7 Hz), 33.8 (d, J=138.4 Hz), 16.2 (d, J=5.9 Hz); $^{31}$P NMR (162 MHz, CDCl$_3$): δ 23.8 ppm.

ii. Ethyl phenyl 4-methylbenzylphosphonate (3B)

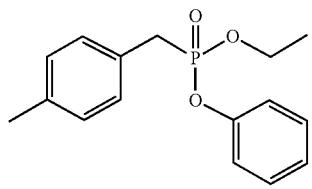

3b 52.8 mg, 91%; as a colorless oil; R$_f$ 0.20 (ν$_{Hexane}$/ν$_{EA}$=2:1); IR ν (KBr, cm$^{-1}$) 2981, 2924, 1593, 1489, 1261, 1207, 1037, 925; $^1$H NMR (400 MHz, CDCl$_3$) δ 7.29 (t, J=8.0 Hz, 2H), 7.27 (dd, J=7.6, 1.6 Hz, 2H), 7.16-7.08 (m, 5H), 4.14-4.00 (m, 2H), 3.28 (d, J=21.6 Hz, 2H), 2.33 (s, 3H), 1.20 (t, J=7.2 Hz, 3H); $^{13}$C NMR (100.5 MHz, CDCl$_3$) δ 150.6 (d, J=8.9 Hz), 136.7 (d, J=3.7 Hz), 129.9 (d, J=7.4 Hz), 129.7 (d, J=6.7 Hz), 129.6, 129.3 (d, J=3.0 Hz), 127.7 (d, J=9.7 Hz), 124.7, 120.5 (d, J=3.7 Hz), 63.0 (d, J=6.7 Hz), 33.3 (d, J=138.4 Hz), 21.0, 16.2 (d, J=6.0 Hz); $^{31}$P NMR (162 MHz, CDCl$_3$): δ 24.16 ppm.

iii. Ethyl phenyl 4-methoxybenzylphosphonate (3C)

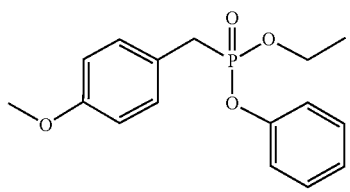

3c 57.5 mg, 94%; as a colorless oil; R$_f$ 0.20 (ν$_{Hexane}$/ν$_{EA}$=2:1); IR ν (KBr, cm$^{-1}$) 3039, 2981, 2908, 1593, 1489, 1249, 1207, 1037, 925; $^1$H NMR (400 MHz, CDCl$_3$) δ 7.32-7.21 (m, 4H), 7.15-7.09 (m, 3H), 6.87-6.83 (m, 2H), 4.14-4.00 (m, 2H), 3.25 (d, J=21.2, 2.8 Hz, 2H), 1.20 (dt, J=6.8, 0.8 Hz, 3H); $^{13}$C NMR (100.5 MHz, CDCl$_3$) δ 158.7 (d, J=3.8 Hz), 150.6 (d, J=9.0 Hz), 130.9 (d, J=6.7 Hz), 129.6, 124.7 (d, J=1.5 Hz), 122.7 (d, J=8.9 Hz), 120.5 (d, J=3.7 Hz), 114.1 (d, J=3.0 Hz), 63.0 (d, J=7.4 Hz), 55.2, 32.7 (d, J=138.4 Hz), 16.3 (d, J=5.3 Hz); $^{31}$P NMR (162 MHz, CDCl$_3$): δ 24.23 ppm.

iv. Ethyl phenyl 4-chlorobenzylphosphonate (3D)

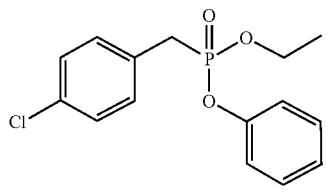

3d 54.6 mg, 88%; as a colorless oil; R$_f$ 0.20 (ν$_{Hexane}$/ν$_{EA}$=2:1); IR ν (KBr, cm$^{-1}$) 3062, 2981, 2908, 1593, 1489, 1261, 1207, 1037, 925; $^1$H NMR (400 MHz, CDCl$_3$) δ 7.33-7.23 (m, 6H), 7.17-7.14 (m, 1H), 7.13-7.09 (m, 2H), 4.17-4.01 (m, 2H), 3.28 (dd, J=22.0, 2.4 Hz, 2H), 1.21 (t, J=7.2 Hz, 3H); $^{13}$C NMR (100.5 MHz, CDCl$_3$) δ 150.4 (d, J=8.9 Hz), 133.1 (d, J=4.4 Hz), 131.2 (d, J=6.7 Hz), 129.7, 129.5 (d, J=8.9 Hz), 128.7 (d, J=3.0 Hz), 124.9, 120.4 (d, J=4.4 Hz), 63.2 (d, J=6.7 Hz), 33.1 (d, J=138.4 Hz), 16.2 (d, J=5.2 Hz); $^{31}$P NMR (162 MHz, CDCl$_3$): δ 23.00 ppm.

v. Ethyl phenyl 4-bromobenzylphosphonate (3E)

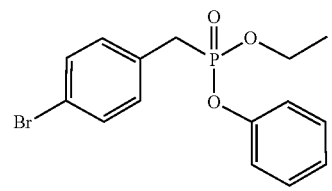

3e 63.7 mg, 90%; as a colorless oil; R$_f$ 0.20 (ν$_{Hexane}$/ν$_{EA}$=2:1); $^1$H NMR (400 MHz, CDCl$_3$) δ 7.44 (dd, J=8.4, 0.8 Hz, 2H), 7.36-7.27 (m, 2H), 7.19 (dd, J=8.4, 2.4 Hz, 2H), 7.17-7.14 (m, 1H), 7.13-7.08 (m, 2H), 4.13-4.01 (m, 2H), 3.26 (dd, J=22.0, 2.0 Hz, 2H), 1.21 (t, J=7.2 Hz, 3H); $^{13}$C NMR (100.5 MHz, CDCl$_3$) δ 150.4 (d, J=8.9 Hz), 131.7 (d, J=3.0 Hz), 131.5 (d, J=6.7 Hz), 130.1 (d, J=9.7 Hz), 129.7, 124.9 (d, J=1.5 Hz), 121.2 (d, J=4.5 Hz), 120.4 (d, J=4.4 Hz), 63.2 (d, J=6.7 Hz), 33.2 (d, J=139.2 Hz), 16.2 (d, J=5.9 Hz); $^{31}$P NMR (162 MHz, CDCl$_3$): δ 22.80 ppm. Spectroscopy data of this compound matches with the data reported in the corresponding reference (Fafianas-Mastral and Feringa (2014) *J. Am. Chem. Soc.* 136: 9894).

vi. Ethyl phenyl 4-(trifluoromethyl)benzylphosphonate (3F)

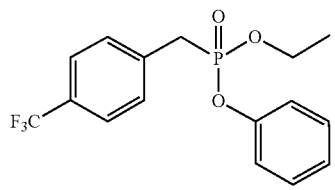

3f 58.5 mg, 86%; as a colorless oil; R$_f$ 0.20 (ν$_{Hexane}$/ν$_{EA}$=2:1); IR ν (KBr, cm$^{-1}$) 3066, 2985, 2912, 1593, 1489, 1327, 1261, 1165, 1126, 1037, 929; $^1$H NMR (400 MHz, CDCl$_3$) δ 7.58 (d, J=8.4 Hz, 2H), 7.44 (dd, J=8.4, 2.0 Hz, 2H), 7.33-7.27 (m, 2H), 7.18-7.08 (m, 3H), 4.18-4.04 (m, 2H), 3.37 (d, J=22.4 Hz, 2H), 1.22 (t, J=7.2 Hz, 3H); $^{13}$C NMR (100.5 MHz, CDCl$_3$) δ 150.4 (d, J=8.9 Hz), 135.3 (dd, J=10.4, 1.5 Hz), 130.2 (d, J=6.7 Hz), 129.7, 129.4 (dd, J=32.0, 3.7 Hz), 125.5 (q, J=2.7 Hz), 125.0, 124.1 (dd, J=284.3, 1.5 Hz), 120.3 (d, J=4.5 Hz), 63.3 (d, J=7.4 Hz), 33.7 (d, J=138.4 Hz), 16.2 (d, J=5.2 Hz); $^{31}$P NMR (162 MHz, CDCl$_3$): δ 22.41 ppm.

vii. Ethyl phenyl (naphthalen-1-ylmethyl)phosphonate (3G)

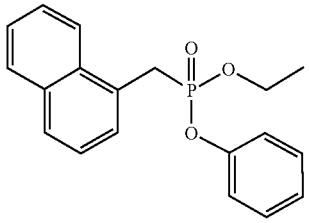

58.6 mg, 90%; as a colorless oil; $R_f$ 0.20 ($v_{Hexane}/v_{EA}$=2:1); IR ν (KBr, cm$^{-1}$) 3043, 2981, 2927, 1593, 1489, 1261, 1207, 1037, 925; $^1$H NMR (400 MHz, CDCl$_3$) δ 8.11 (d, J=8.4 Hz, 1H), 7.85 (d, J=8.0 Hz, 1H), 7.78 (dd, J=8.4, 2.4 Hz, 1H), 7.57-7.40 (m, 4H), 7.26 (t, J=7.6 Hz, 1H), 7.14-7.06 (m, 3H), 4.02-3.93 (m, 2H), 3.58 (d, J=21.6 Hz, 2H), 1.06 (t, J=6.8 Hz, 3H); $^{13}$C NMR (100.5 MHz, CDCl$_3$) δ 150.6 (d, J=8.9 Hz), 133.9 (d, J=3.0 Hz), 132.0 (d, J=5.3 Hz), 129.6, 128.7 (d, J=6.7 Hz), 128.6, 128.0 (d, J=3.8 Hz), 127.4 (d, J=9.6 Hz), 126.2 (d, J=1.5 Hz), 125.8, 125.4 (d, J=3.7 Hz), 124.7, 124.3 (d, J=1.5 Hz), 63.2 (d, J=7.5 Hz), 30.8 (d, J=139.2 Hz), 16.1 (d, J=6.0 Hz); $^{31}$P NMR (162 MHz, CDCl$_3$): δ 23.48 ppm.

viii. Ethyl phenyl hexylphosphonate (3H)

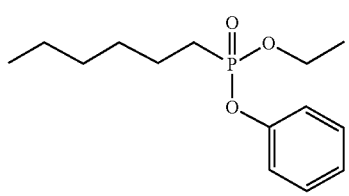

48.1 mg, 89%; as a colorless oil; $R_1$-0.40 ($v_{Hexane}/v_{EA}$=2:1); IR ν (KBr, cm$^{-1}$) 3066, 2951, 2931, 1593, 1489, 1257, 1211, 1041, 921; $^1$H NMR (400 MHz, CDCl$_3$) δ 7.33 (t, J=8.4 Hz, 2H), 7.20 (d, J=8.4 Hz, 2H), 7.15 (t, J=7.2 Hz, 1H), 4.27-4.07 (m, 2H), 1.93-1.83 (m, 2H), 1.74-1.62 (m, 2H), 1.45-1.35 (m, 2H), 1.34-1.24 (m, 7H), 0.88 (t, J=6.8 Hz, 3H); $^{13}$C NMR (100.5 MHz, CDCl$_3$) δ 150.7 (d, J=8.2 Hz), 129.6, 124.7, 120.5 (d, J=4.5 Hz), 62.2 (d, J=7.5 Hz), 31.2 (d, J=1.5 Hz), 30.1 (d, J=17.2 Hz), 25.7 (d, J=139.9 Hz), 22.3, 22.2 (d, J=6.0 Hz), 16.3 (d, J=5.9 Hz), 14.0; $^{31}$P NMR (162 MHz, CDCl$_3$): δ 30.29 ppm.

ix. Ethyl phenyl ethylphosphonate (3I)

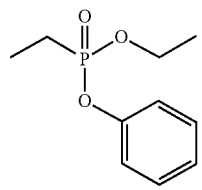

38.5 mg, 90%; as a colorless oil; $R_f$ 0.20 ($v_{Hexane}/v_{EA}$=2:1); IR ν (KBr, cm$^{-1}$) 3066, 2981, 2943, 1593, 1489, 1257, 1207, 1045, 921; $^1$H NMR (400 MHz, CDCl$_3$) δ 7.33 (t, J=8.4 Hz, 2H), 7.21 (d, J=8.4 Hz, 2H), 7.15 (t, J=7.6 Hz, 1H), 4.28-4.08 (m, 2H), 1.96-1.84 (m, 2H), 1.33-1.19 (m, 6H); $^{13}$C NMR (100.5 MHz, CDCl$_3$) δ 150.6 (d, J=8.9 Hz), 129.7, 124.7, 120.4 (d, J=3.7 Hz), 62.3 (d, J=6.7 Hz), 18.9 (d, J=142.2 Hz), 16.3 (d, J=5.9 Hz), 6.5 (d, J=6.7 Hz); $^{31}$P NMR (162 MHz, CDCl$_3$): δ 31.30 ppm.

x. Ethyl Phenyl Methylphosphonate (3J)

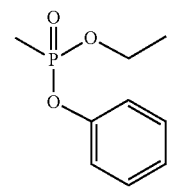

35.8 mg, 85%; as a colorless oil; $R_f$ 0.10 ($v_{Hexane}/v_{EA}$=2:1); IR ν (KBr, cm$^{-1}$) 3066, 2985, 2927, 1593, 1489, 1315, 1246, 1207, 1041, 933; $^1$H NMR (400 MHz, CDCl$_3$) δ 7.34 (t, J=8.4 Hz, 2H), 7.23-7.14 (m, 3H), 4.29-4.09 (m, 2H), 1.63 (d, J=17.6 Hz, 2H), 1.32 (t, J=7.2 Hz, 6H); $^{13}$C NMR (100.5 MHz, CDCl$_3$) δ 150.5 (d, J=8.1 Hz), 129.7, 124.9, 120.5 (d, J=4.5 Hz), 62.4 (d, J=6.7 Hz), 16.3 (d, J=6.0 Hz), 11.4 (d, J=144.3 Hz); $^{31}$P NMR (162 MHz, CDCl$_3$): δ 28.18 ppm. Spectroscopy data of the this compound matches with the data reported in the corresponding reference (Fañanás-Mastral and Feringa (2014) *J. Am. Chem. Soc.* 136: 9894).

xi. Methyl Phenyl Phenylphosphonate (3K)

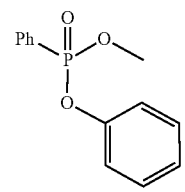

40.3 mg, 81%; as a colorless oil; $R_f$ 0.15 ($v_{Hexane}/v_{EA}$=2:1); IR ν (KBr, cm$^{-1}$) 3062, 2951, 2854, 1593, 1489, 1261, 1207, 1130, 1041, 929; $^1$H NMR (400 MHz, CDCl$_3$) δ 7.92-7.84 (m, 2H), 7.61-7.55 (m, 1H), 7.51-7.44 (m, 2H), 7.31-7.26 (m, 2H), 7.19-7.10 (m, 3H), 3.87 (dd, J=11.2, 1.2 Hz, 3H); $^{13}$C NMR (100.5 MHz, CDCl$_3$) δ 150.5 (d, J=7.4 Hz), 132.9 (d, J=3.7 Hz), 132.0 (d, J=9.6 Hz), 129.6, 128.6 (d, J=14.9 Hz), 126.9 (d, J=190.6 Hz), 124.9, 120.5 (d, J=4.5 Hz), 53.1 (d, J=5.9 Hz); $^{31}$P NMR (162 MHz, CDCl$_3$): δ 17.45 ppm.

xii. Ethyl phenyl phenylphosphonate (3L)

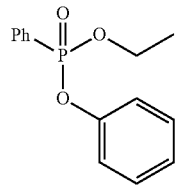

47.7 mg, 91%; as a colorless oil; $R_f$ 0.20 ($v_{Hexane}/v_{EA}$=2:1); $^1$H NMR (400 MHz, CDCl$_3$) δ 7.92-7.84 (m, 2H), 7.59-7.54 (m, 1H), 7.50-7.44 (m, 2H), 7.30-7.24 (m, 2H), 7.18-7.09 (m, 3H), 4.32-4.18 (m, 2H), 1.35 (dt, J=7.2, 0.4 Hz, 3H); $^{13}$C NMR (100.5 MHz, CDCl$_3$) δ 150.6 (d, J=7.4 Hz), 132.7 (d, J=3.0 Hz), 132.0 (d, J=9.7 Hz), 129.6, 128.5 (d, J=15.6 Hz), 127.7 (d, J=189.8 Hz), 124.8, 120.5 (d, J=3.7 Hz), 62.8 (d, J=6.0 Hz), 16.3 (d, J=6.7 Hz); $^{31}$P NMR (162 MHz, CDCl$_3$): δ 16.05 ppm. Spectroscopy data of the this compound matches with the data reported in the corresponding reference (Fafianas-Mastral and Feringa (2014) *J. Am. Chem. Soc.* 136: 9894).

xiii. Isopropyl phenyl phenylphosphonate (3M)

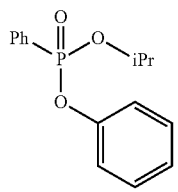

51.3 mg, 93%; as a colorless oil; $R_f$ 0.40 ($v_{Hexane}/v_{EA}$=2:1); IR ν (KBr, cm$^{-1}$) 3062, 2981, 2931, 1593, 1489, 1257, 1207, 1134, 991, 925; $^1$H NMR (400 MHz, CDCl$_3$) δ 7.91-7.84 (m, 2H), 7.58-7.52 (m, 1H), 7.49-7.43 (m, 2H), 7.30-7.24 (m, 2H), 7.18-7.13 (m, 2H), 7.11 (dt, J=7.2, 0.8 Hz, 1H), 4.94-4.82 (m, 1H), 1.37 (d, J=6.0 Hz, 3H), 1.32 (d, J=6.0 Hz, 3H); $^{13}$C NMR (100.5 MHz, CDCl$_3$) δ 150.6 (d, J=7.4 Hz), 132.5 (d, J=3.0 Hz), 131.9 (d, J=10.4 Hz), 129.5, 128.5 (d, J=190.5 Hz), 128.4 (d, J=15.6 Hz), 124.7 (d, J=1.5 Hz), 120.6 (d, J=4.5 Hz), 72.0 (d, J=6.0 Hz), 23.9 (d, J=4.4 Hz), 23.8 (d, J=3.0 Hz); $^{31}$P NMR (162 MHz, CDCl$_3$): δ 14.96 ppm.

xiv. Butyl phenyl phenylphosphonate (3N)

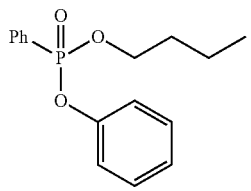

51.7 mg, 85%; as a colorless oil; $R_f$ 0.30 ($v_{Hexane}/v_{EA}$=2:1); IR ν (KBr, cm$^{-1}$) 3062, 2985, 2873, 1593, 1489, 1261, 1207, 1130, 1022, 929; $^1$H NMR (400 MHz, CDCl$_3$) δ 7.91-7.84 (m, 2H), 7.59-7.54 (m, 1H), 7.50-7.44 (m, 2H), 7.30-7.24 (m, 2H), 7.18-7.09 (m, 3H), 4.24-4.11 (m, 2H), 1.74-1.64 (m, 2H), 1.45-1.34 (m, 2H), 0.90 (t, J=7.2 Hz, 3H); $^{13}$C NMR (100.5 MHz, CDCl$_3$) δ 150.6 (d, J=7.5 Hz), 132.7 (d, J=2.9 Hz), 132.0 (d, J=9.7 Hz), 129.6, 128.5 (d, J=15.6 Hz), 127.7 (d, J=189.8 Hz), 124.7, 120.5 (d, J=4.5 Hz), 66.5 (d, J=5.9 Hz), 32.3 (d, J=6.7 Hz), 18.7, 13.5; $^{31}$P NMR (162 MHz, CDCl$_3$): δ 16.04 ppm.

xv. Ethyl phenyl (4-nitrophenyl)phosphonate (3O)

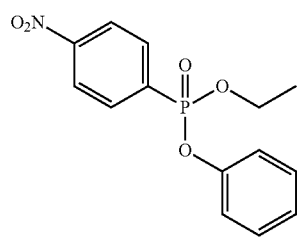

17.0 mg, 28%; as a colorless oil; $R_f$ 0.30 ($v_{Hexane}/v_{EA}$=2:1); IR ν (KBr, cm$^{-1}$) 3066, 2985, 2931, 1593, 1527, 1489, 1350, 1265, 1203, 1126, 1033, 929; $^1$H NMR (400 MHz, CDCl$_3$) δ 7.92-7.84 (m, 2H), 7.59-7.54 (m, 1H), 7.50-7.44 (m, 2H), 7.30-7.24 (m, 2H), 7.18-7.09 (m, 3H), 4.32-4.18 (m, 2H), 1.35 (dt, J=7.2, 0.4 Hz, 3H); $^{13}$C NMR (100.5 MHz, CDCl$_3$) δ 150.5, 150.0 (d, J=7.4 Hz), 134.8 (d, J=189.0 Hz), 133.2 (d, J=10.4 Hz), 129.8, 125.3 (d, J=1.5 Hz), 123.4 (d, J=15.6 Hz), 120.4 (d, J=4.5 Hz), 63.7 (d, J=6.0 Hz), 16.3 (d, J=6.0 Hz); $^{31}$P NMR (162 MHz, CDCl$_3$): δ 12.14 ppm.

xvi. Ethyl phenyl (2-bromoethyl)phosphonate (3P)

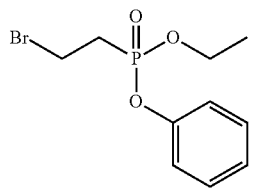

53.0 mg, 91%; as a colorless oil; $^1$H NMR (400 MHz, CDCl$_3$) δ 7.38-7.32 (m, 2H), 7.22-7.16 (m, 3H), 4.30-4.10 (m, 2H), 3.65-3.57 (m, 2H), 2.60-2.50 (m, 2H), 1.30 (t, J=6.8 Hz, 3H); $^{13}$C NMR (100.5 MHz, CDCl$_3$) δ 150.1 (d, J=8.2 Hz), 129.9, 125.2, 120.4 (d, J=4.5 Hz), 63.0 (d, J=6.7 Hz), 30.7 (d, J=134.7 Hz), 23.3, 16.3 (d, J=6.0 Hz); $^{31}$P NMR (162 MHz, CDCl$_3$): δ 23.00 ppm. Spectroscopy data of the this compound matches with the data reported in the corresponding reference (Fafianas-Mastral and Feringa (2014) *J. Am. Chem. Soc.* 136: 9894).

xvii. Ethyl phenyl allylphosphonate (3Q)

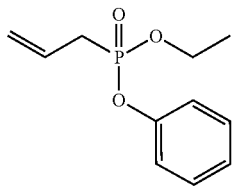

3q 41.1 mg, 91%; as a colorless oil; $R_f$ 0.17 ($v_{Hexane}/v_{EA}$=2: 1); IR ν (KBr, cm$^{-1}$) 3070, 2981, 2904, 1593, 1489, 1265, 1207, 1037, 925; $^1$H NMR (400 MHz, CDCl$_3$) δ 7.36-7.30 (m, 2H), 7.23-7.17 (m, 3H), 5.92-5.79 (m, 1H), 5.30-5.22 (m, 2H), 4.28-4.11 (m, 2H), 2.82-2.73 (m, 2H), 1.30 (t, J=6.8 Hz, 3H); $^{13}$C NMR (100.5 MHz, CDCl$_3$) δ 150.5 (d, J=8.2 Hz), 129.7, 126.8 (d, J=11.1 Hz), 124.9 (d, J=1.5 Hz), 120.6 (d, J=6.7 Hz), 120.5 (d, J=3.7 Hz), 62.8 (d, J=7.4 Hz), 31.7 (d, J=139.2 Hz), 16.3 (d, J=6.0 Hz); $^{31}$P NMR (162 MHz, CDCl$_3$): δ 24.54 ppm.

xviii. Ethyl (4-methoxyphenyl) allylphosphonate (3R)

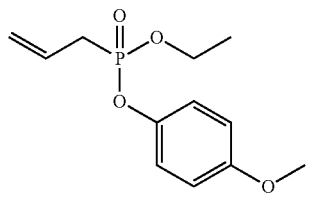

3r 47.6 mg, 93%; as a colorless oil; $R_f$ 0.15 ($v_{Hexane}/v_{EA}$=2: 1); IR ν (KBr, cm$^{-1}$) 3082, 2981, 2908, 1504, 1253, 1203, 1033, 933; $^1$H NMR (400 MHz, CDCl$_3$) δ 7.15-7.10 (m, 2H), 6.86-6.81 (m, 2H), 5.91-5.78 (m, 1H), 5.29-5.22 (m, 2H), 4.26-4.10 (m, 2H), 3.78 (s, 3H), 2.79-2.70 (m, 2H), 1.30 (t, J=6.8 Hz, 3H); $^{13}$C NMR (100.5 MHz, CDCl$_3$) δ 156.6, 144.0 (d, J=8.2 Hz), 126.9 (d, J=11.9 Hz), 121.4 (d, J=4.5 Hz), 120.5 (d, J=14.9 Hz), 114.6, 62.8 (d, J=7.4 Hz), 55.6, 31.5 (d, J=139.1 Hz), 16.3 (d, J=6.0 Hz); $^{31}$P NMR (162 MHz, CDCl$_3$): δ 24.89 ppm.

xix. (E)-Ethyl phenyl styrylphosphonate (3S)

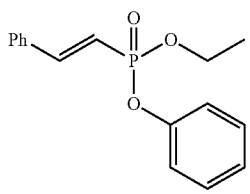

3s 50.7 mg, 88%; as a colorless oil; $R_f$ 0.20 ($v_{Hexane}/v_{EA}$=2: 1); IR ν (KBr, cm$^{-1}$) 2981, 2931, 1616, 1593, 1489, 1261, 1207, 1037, 929; $^1$H NMR (400 MHz, CDCl$_3$) δ 7.59 (dd, J=23.2, 17.6 Hz, 1H), 7.52-7.48 (m, 2H), 7.41-7.36 (m, 3H), 7.34-7.29 (m, 2H), 7.25-7.21 (m, 2H), 7.17-7.12 (m, 1H), 6.36 (dd, J=18.4, 17.6 Hz, 1H), 4.32-4.18 (m, 2H), 1.37 (dt, J=7.6, 0.8 Hz, 3H); $^{13}$C NMR (100.5 MHz, CDCl$_3$) δ 150.5 (d, J=7.4 Hz), 149.9 (d, J=6.7 Hz), 134.6 (d, J=23.9 Hz), 130.5, 129.7, 128.9, 127.8, 124.8 (d, J=1.5 Hz), 120.5 (d, J=4.5 Hz), 113.1 (d, J=193.5 Hz), 62.6 (d, J=6.0 Hz), 16.3 (d, J=5.9 Hz); $^{31}$P NMR (162 MHz, CDCl$_3$): δ 16.94 ppm.

xx. Ethyl (4-methoxyphenyl) (phenylethynyl)phosphonate (3T)

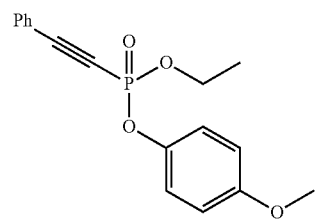

3t 60.0 mg, 95%; as a colorless oil; $R_f$ 0.20 ($v_{Hexane}/v_{EA}$=2: 1); IR ν (KBr, cm$^{-1}$) 3062, 2985, 2904, 2187, 1504, 1273, 1199, 1033, 941; $^1$H NMR (400 MHz, CDCl$_3$) δ 7.53-7.49 (m, 2H), 7.45 (tt, J=7.6, 2.4 Hz, 1H), 7.39-7.33 (m, 2H), 7.24-7.19 (m, 2H), 6.89-6.84 (m, 2H), 4.38-4.29 (m, 2H), 1.44 (dt, J=7.2, 0.4 Hz, 3H); $^{13}$C NMR (100.5 MHz, CDCl$_3$) δ 157.0 (d, J=1.5 Hz), 143.5 (d, J=6.7 Hz), 132.6 (d, J=3.0 Hz), 130.9, 128.6, 121.6 (d, J=4.5 Hz), 119.2 (d, J=6.0 Hz), 114.7 (d, J=1.5 Hz), 100.4 (d, J=53.6 Hz), 77.8 (d, J=307.4 Hz), 64.0 (d, J=5.2 Hz), 55.6, 16.1 (d, J=6.7 Hz); $^{31}$P NMR (162 MHz, CDCl$_3$): δ−8.74 ppm.

xxi. Ethyl (4-methoxyphenyl) (2E, 4E)-undeca-2,4-dien-1-ylphosphonate (3U)

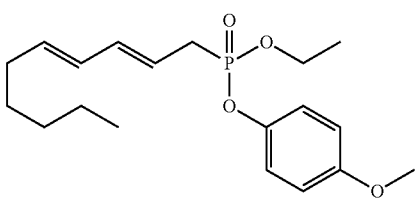

3u 43.3 mg, 64%; as a colorless oil; $R_f$ 0.25 ($v_{Hexane}/v_{EA}$=2: 1); IR ν (KBr, cm$^{-1}$) 2954, 2927, 2858, 1504, 1249, 1199, 1037, 933; $^1$H NMR (400 MHz, CDCl$_3$) δ 7.11 (dd, J=9.2, 1.2 Hz, 2H), 6.86-6.80 (m, 2H), 6.19-6.11 (m, 1H), 6.07-5.98 (m, 1H), 5.70-5.61 (m, 1H), 5.58-5.47 (m, 1H), 4.26-4.08 (m, 2H), 3.78 (s, 3H), 2.74 (dd, J=22.4, 7.6 Hz, 2H), 2.07 (dd, J=14.4, 7.2 Hz, 2H), 1.42-1.21 (m, 9H), 0.89 (t, J=6.8 Hz, 3H); $^{13}$C NMR (100.5 MHz, CDCl$_3$) δ 156.6, 144.0 (d, J=8.9 Hz), 135.9 (d, J=4.9 Hz), 135.2 (d, J=4.4 Hz), 129.3 (d, J=4.4 Hz), 121.4 (d, J=3.8 Hz), 118.4 (d, J=12.7 Hz), 114.6, 62.8 (d, J=7.4 Hz), 55.6, 32.5, 31.4, 30.4 (d, J=139.9 Hz), 28.8 (d, J=1.5 Hz), 22.5, 16.3 (d, J=5.2 Hz), 14.0; $^{31}$P NMR (162 MHz, CDCl$_3$): δ 25.13 ppm.

xxii. Ethyl phenyl (1-phenylethyl)phosphonate (3V)

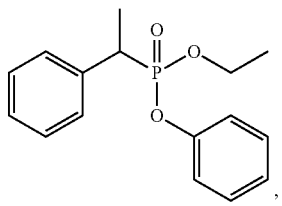

dr = 1.6:1

44.1 mg, 76% with dr=1.6:1; as a colorless oil; $R_f$ 0.20 ($v_{Hexane}/v_{EA}$=2:1); IR v (KBr, cm$^{-1}$) 3028, 2978, 2935, 1593, 1489, 1257, 1207, 1026, 925; $^1$H NMR (400 MHz, CDCl$_3$, * denotes minor rotamer peaks) δ 7.41-7.36 (m, 2H), 7.36-7.21 (m, 5H), 7.15-7.06 (m, 2H), 7.02-7.08 (m, 1H), 4.19-4.00* (m, 2H), 3.99-3.83 (m, 2H), 3.43-3.36* (m, 1H), 3.36-3.30 (m, 1H), 1.71* (dd, J=7.2, 2.0 Hz, 2H), 1.66 (dd, J=7.2, 2.0 Hz, 2H), 1.23* (t, J=7.2 Hz, 3H), 1.07 (t, J=7.2 Hz, 3H); $^{13}$C NMR (100.5 MHz, CDCl$_3$) δ 150.9 (d, J=3.7 Hz), 150.8 (d, J=3.7 Hz), 137.5 (d, J=7.4 Hz), 137.3 (d, J=7.5 Hz), 129.6, 129.5, 128.8 (d, J=3.7 Hz), 128.7 (d, J=3.7 Hz), 128.52, 128.50, 127.3 (d, J=3.7 Hz), 127.2 (d, J=3.7 Hz), 127.7, 124.7, 120.5 (d, J=4.5 Hz), 120.4 (d, J=3.7 Hz), 63.4 (d, J=7.4 Hz), 63.0 (d, J=7.4 Hz), 38.7 (d, J=137.7 Hz), 38.5 (d, J=137.7 Hz), 16.3 (d, J=5.9 Hz), 16.1 (d, J=5.2 Hz), 15.7 (d, J=4.4 Hz), 15.6 (d, J=6.0 Hz); $^{31}$P NMR (162 MHz, CDCl$_3$): δ 27.30, 27.00 ppm.

xxiii. Ethyl phenyl (furan-2-ylmethyl)phosphonate (3W)

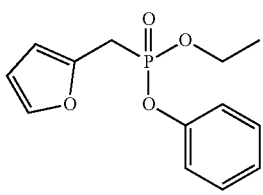

44.2 mg, 83%; as a colorless oil; $R_f$ 0.20 ($v_{Hexane}/v_{EA}$=2:1); IR v (KBr, cm$^{-1}$) 2981, 2908, 1720, 1593, 149, 1265, 1207, 1037, 933; $^1$H NMR (400 MHz, CDCl$_3$) δ 7.35-7.36 (m, 1H), 7.34-7.28 (m, 2H), 7.18-7.13 (m, 3H), 6.36-6.33 (m, 1H), 6.30-6.27 (m, 1H), 4.24-4.09 (m, 2H), 3.40 (d, J=20.8 Hz), 1.27 (dt, J=7.2, 0.8 Hz, 3H); $^{13}$C NMR (100.5 MHz, CDCl$_3$) δ 150.4, 144.9 (d, J=9.6 Hz), 142.1 (d, J=3.0 Hz), 129.7, 125.0 (d, J=1.5 Hz), 120.5 (d, J=4.4 Hz), 110.8 (d, J=3.0 Hz), 108.6 (d, J=7.4 Hz), 63.3 (d, J=6.7 Hz), 26.7 (d, J=144.3 Hz), 16.2 (d, J=5.9 Hz); $^{31}$P NMR (162 MHz, CDCl$_3$): δ 20.49 ppm.

xxiv. O-Ethyl O,S-diphenyl phosphorothioate (3X)

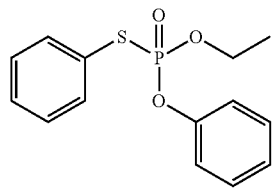

47.6 mg, 81%; as a colorless oil; $R_f$ 0.30 ($v_{Hexane}/v_{EA}$=2:1); IR v (KBr, cm$^{-1}$) 3062, 2985, 2904, 1589, 1489, 1265, 1199, 1022, 929; $^1$H NMR (400 MHz, CDCl$_3$) δ 7.55-7.50 (m, 2H), 7.40-7.29 (m, 5H), 7.17 (t, J=8.0 Hz, 3H), 4.37-4.22 (m, 2H), 1.34 (t, J=7.2 Hz, 3H); $^{13}$C NMR (100.5 MHz, CDCl$_3$) δ 150.4 (d, J=7.4 Hz), 134.9 (d, J=5.2 Hz), 129.6, 129.4 (d, J=3.0 Hz), 129.3 (d, J=3.7 Hz), 125.7 (d, J=6.7 Hz), 125.3 (d, J=1.5 Hz), 120.4 (d, J=5.2 Hz), 64.8 (d, J=6.0 Hz), 16.0 (d, J=7.5 Hz); $^{31}$P NMR (162 MHz, CDCl$_3$): δ 19.53 ppm.

xxv. Ethyl p-tolyl benzylphosphonate (4A)

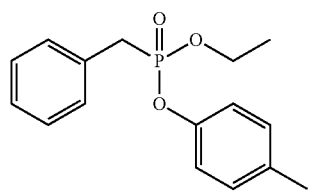

54.0 mg, 88%; as a colorless oil; $R_f$ 0.20 ($v_{Hexane}/v_{EA}$=2:1); IR v (KBr, cm$^{-1}$) 3032, 2981, 108, 145, 1261, 1207, 1037, 925; $^1$H NMR (400 MHz, CDCl$_3$) δ 7.35-7.23 (m, 5H), 7.10-7.06 (m, 2H), 7.00-6.96 (m, 2H), 4.13-3.99 (m, 2H), 3.30 (dd, J=21.6, 3.2 Hz, 2H), 2.30 (s, 3H), 1.19 (dt, J=6.8, 0.8 Hz, 3H); $^{13}$C NMR (100.5 MHz, CDCl$_3$) δ 148.3 (d, J=8.9 Hz), 134.3 (d, J=1.5 Hz), 131.0 (d, J=8.9 Hz), 130.1 (d, J=1.4 Hz), 129.9 (d, J=6.7 Hz), 128.6 (d, J=2.9 Hz), 127.0 (d, J=3.7 Hz), 120.2 (d, J=4.5 Hz), 63.0 (d, J=7.5 Hz), 33.7 (d, J=138.4 Hz), 20.7, 16.0 (d, J=5.9 Hz); $^{31}$P NMR (162 MHz, CDCl$_3$): δ 23.89 ppm.

xxvi. Ethyl (4-methoxyphenyl) benzylphosphonate (4B)

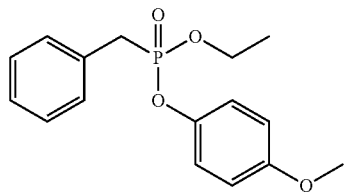

55.0 mg, 90%; as a colorless oil; $R_f$ 0.20 ($v_{Hexane}/v_{EA}$=2:1); IR v (KBr, cm$^{-1}$) 2981, 2908, 1504, 1442, 1257, 1203, 1037, 933; $^1$H NMR (400 MHz, CDCl$_3$) δ 7.32 (d, J=4.4 Hz, 4H), 7.30-7.24 (m, 1H), 7.04-6.99 (m, 2H), 6.80 (d, J=8.8 Hz, 2H), 4.13-3.98 (m, 2H), 3.77 (s, 3H), 3.29 (dd, J=21.6, 2.8 Hz, 2H), 2.30 (s, 3H), 1.19 (dt, J=7.2, 0.8 Hz, 3H); $^{13}$C NMR (100.5 MHz, CDCl$_3$) δ 156.5, 144.0 (d, J=8.9 Hz), 131.0 (d, J=9.7 Hz), 129.9 (d, J=6.7 Hz), 128.6 (d, J=3.0 Hz), 127.0 (d, J=3.7 Hz), 121.3 (d, J=3.7 Hz), 114.6, 63.0 (d, J=6.7 Hz), 55.6, 33.6 (d, J=138.4 Hz), 16.2 (d, J=5.9 Hz); $^{31}$P NMR (162 MHz, CDCl$_3$): δ 24.17 ppm;

xxvii. 4-bromophenyl ethyl benzylphosphonate (4C)

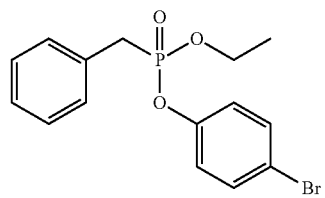

63.5 mg, 89%; as a colorless oil; R$_f$ 0.20 (ν$_{Hexane}$/ν$_{EA}$=2:1); IR ν (KBr, cm$^{-1}$) 3062, 2981, 2908, 1485, 1261, 1215, 1037, 921; $^1$H NMR (400 MHz, CDCl$_3$) δ 7.41-7.36 (m, 2H), 7.34-7.24 (m, 5H), 6.99-6.94 (m, 2H), 4.15-4.00 (m, 2H), 3.31 (dd, J=21.6, 1.6 Hz, 2H), 1.21 (dt, J=7.2, 0.4 Hz, 3H); $^{13}$C NMR (100.5 MHz, CDCl$_3$) δ 149.7 (d, J=8.2 Hz), 132.6, 130.6 (d, J=9.7 Hz), 129.9 (d, J=6.7 Hz), 128.6 (d, J=3.0 Hz), 127.2 (d, J=3.8 Hz), 122.2 (d, J=4.4 Hz), 117.7, 63.2 (d, J=7.5 Hz), 33.8 (d, J=137.7 Hz), 16.2 (d, J=6.0 Hz); $^{31}$P NMR (162 MHz, CDCl$_3$): δ 24.16 ppm.

xxviii. Ethyl (4-iodophenyl) benzylphosphonate (4D)

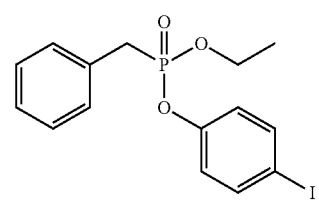

68.2 mg, 85%; as a colorless oil; R$_f$ 0.20 (ν$_{Hexane}$/ν$_{EA}$=2:1); IR ν (KBr, cm$^{-1}$) 3059, 2981, 2908, 1481, 1261, 1215, 1037, 921; $^1$H NMR (400 MHz, CDCl$_3$) δ 7.60-7.55 (m, 2H), 7.34-7.24 (m, 5H), 6.87-6.82 (m, 2H), 4.15-4.00 (m, 2H), 3.31 (dd, J=21.6, 1.6 Hz, 2H), 1.21 (dt, J=7.2, 0.4 Hz, 3H); $^{13}$C NMR (100.5 MHz, CDCl$_3$) δ 150.5 (d, J=8.9 Hz), 138.6, 130.6 (d, J=9.7 Hz), 129.9 (d, J=6.7 Hz), 128.6 (d, J=3.0 Hz), 127.2 (d, J=4.8 Hz), 122.6 (d, J=3.7 Hz), 88.4 (d, J=1.5 Hz), 63.2 (d, J=6.7 Hz), 33.8 (d, J=137.6 Hz), 16.2 (d, J=5.2 Hz); $^{31}$P NMR (162 MHz, CDCl$_3$): δ 24.10 ppm.

xxix. Ethyl (4-nitrophenyl) benzylphosphonate (4E)

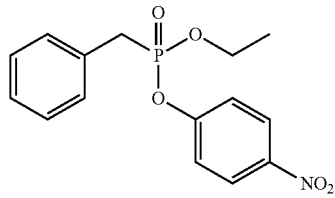

59.3 mg, 92%; as a colorless oil; R$_f$ 0.15 (ν$_{Hexane}$/ν$_{EA}$=2:1); IR ν (KBr, cm$^{-1}$) 3082, 2985, 2912, 1612, 1589, 1519, 1492, 1346, 1265, 1226, 1033, 918; $^1$H NMR (400 MHz, CDCl$_3$) δ 8.19-8.13 (m, 2H), 7.36-7.25 (m, 5H), 7.23-7.17 (m, 2H), 4.21-4.07 (m, 2H), 3.42-3.32 (m, 2H), 1.29-1.23 (m, 3H); $^{13}$C NMR (100.5 MHz, CDCl$_3$) δ 155.7 (d, J=8.2 Hz), 144.4, 130.0 (d, J=9.7 Hz), 129.9 (d, J=6.7 Hz), 128.8 (d, J=3.7 Hz), 127.4 (d, J=3.7 Hz), 125.5, 120.8 (d, J=4.5 Hz), 63.5 (d, J=7.4 Hz), 34.0 (d, J=138.4 Hz), 16.2 (d, J=5.9 Hz); $^{31}$P NMR (162 MHz, CDCl$_3$): δ 24.57 ppm.

xxx. Ethyl o-tolyl benzylphosphonate (4F)

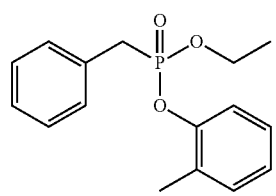

52.1 mg, 90%; as a colorless oil; R$_f$ 0.15 (ν$_{Hexane}$/ν$_{EA}$=3:1); IR ν (KBr, cm$^{-1}$) 3032, 2981, 2912, 1585, 1492, 1454, 1261, 1226, 1180, 1037, 929; $^1$H NMR (400 MHz, CDCl$_3$) δ 7.34-7.24 (m, 5H), 7.22 (d, J=8.0 Hz, 1H), 7.16-7.08 (m, 2H), 7.03 (t, J=7.6 Hz, 1H), 4.13-3.97 (m, 2H), 3.34 (dd, J=21.2, 0.8 Hz, 2H), 2.12 (s, 3H), 1.17 (t, J=6.8 Hz, 3H); $^{13}$C NMR (100.5 MHz, CDCl$_3$) δ 149.0 (d, J=9.6 Hz), 131.3, 131.1 (d, J=9.7 Hz), 129.9 (d, J=6.7 Hz), 129.5 (d, J=5.9 Hz), 128.5 (d, J=3.0 Hz), 127.0 (d, J=3.7 Hz), 126.9 (d, J=1.5 Hz), 124.7, 120.2 (d, J=3.0 Hz), 63.2 (d, J=6.7 Hz), 33.9 (d, J=139.2 Hz), 16.2 (d, J=6.7 Hz); $^{31}$P NMR (162 MHz, CDCl$_3$): δ 23.74 ppm.

xxxi. Ethyl m-tolyl benzylphosphonate (4G)

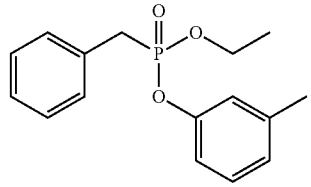

53.9 mg, 93%; as a colorless oil; R$_f$ 0.15 (ν$_{Hexane}$/ν$_{EA}$=3:1); IR ν (KBr, cm$^{-1}$) 2032, 2981, 2912, 1608, 1585, 1489, 1261, 1149, 1037, 952; $^1$H NMR (400 MHz, CDCl$_3$) δ

7.35-7.24 (m, 5H), 7.16 (t, J=8.8 Hz, 1H), 6.96-6.87 (m, 3H), 4.15-4.00 (m, 2H), 3.31 (dd, J=21.6, 1.6 Hz, 2H), 2.30 (s, 3H), 1.20 (dt, J=7.2, 1.2 Hz, 3H); $^{13}$C NMR (100.5 MHz, CDCl$_3$) δ 150.5 (d, J=8.2 Hz), 139.8, 131.0 (d, J=9.6 Hz), 129.9 (d, J=6.7 Hz), 129.3, 128.5 (d, J=2.9 Hz), 127.0 (d, J=3.7 Hz), 125.6, 121.1 (d, J=4.5 Hz), 117.3 (d, J=4.4 Hz), 63.0 (d, J=6.7 Hz), 33.7 (d, J=138.5 Hz), 21.3, 16.2 (d, J=6.0 Hz); $^{31}$P NMR (162 MHz, CDCl$_3$): δ 23.71 ppm.

xxxii. Ethyl (3-(trifluoromethyl)phenyl) benzylphosphonate (4H)

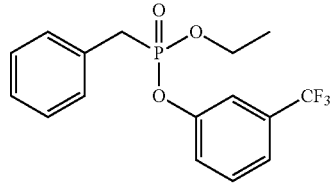

4h 59.9 mg, 83%; as a colorless oil; R$_f$ 0.15 (ν$_{Hexane}$/ν$_{EA}$=3:1); IR ν (KBr, cm$^{-1}$) 3059, 2985, 2866, 1593, 1492, 1450, 1327, 1261, 1168, 1130, 1037, 948; $^1$H NMR (400 MHz, CDCl$_3$) δ 7.44-7.37 (m, 2H), 7.39-7.26 (m, 7H), 4.16-4.05 (m, 2H), 3.35 (d, J=21.6 Hz, 2H), 1.23 (dt, J=7.2, 1.2 Hz, 3H); $^{13}$C NMR (100.5 MHz, CDCl$_3$) δ 150.7 (d, J=8.9 Hz), 132.0 (d, J=32.7 Hz), 130.4 (d, J=9.7 Hz), 130.2, 129.9 (d, J=6.7 Hz), 128.7 (d, J=3.7 Hz), 127.3 (d, J=3.7 Hz), 123.9 (d, J=3.0 Hz), 123.3 (d, J=271.6 Hz), 121.5 (d, J=3.0 Hz), 117.7 (m), 63.3 (d, J=7.5 Hz), 33.9 (d, J=137.7 Hz), 16.2 (d, J=5.9 Hz); $^{31}$P NMR (162 MHz, CDCl$_3$): δ 26.98 ppm.

xxxiii. 2,4-Dichlorophenyl ethyl benzylphosphonate (4I)

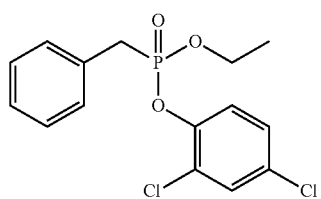

4i 52.9 mg, 77%; as a colorless oil; R$_f$ 0.15 (ν$_{Hexane}$/ν$_{EA}$=3:1); IR ν (KBr, cm$^{-1}$) 3032, 2962, 2927, 1477, 1269, 1234, 1099, 1033, 921; $^1$H NMR (400 MHz, CDCl$_3$) δ 7.39-7.37 (m, 1H), 7.36-7.25 (m, 5H), 7.15-7.09 (m, 2H), 4.19-4.05 (m, 2H), 3.38 (d, J=22.0 Hz, 2H), 1.22 (t, J=7.2 Hz, 3H); $^{13}$C NMR (100.5 MHz, CDCl$_3$) δ 145.6 (d, J=8.2 Hz), 130.3 (d, J=5.2 Hz), 130.2 (d, J=3.0 Hz), 130.1, 129.9 (d, J=6.7 Hz), 128.7 (d, J=3.8 Hz), 127.8, 127.3 (d, J=3.7 Hz), 126.4 (d, J=5.9 Hz), 122.7 (d, J=2.3 Hz), 63.5 (d, J=7.5 Hz), 34.0 (d, J=138.4 Hz), 16.2 (d, J=6.0 Hz); $^{31}$P NMR (162 MHz, CDCl$_3$): δ 24.98 ppm.

xxxiv. 2,6-Dimethylphenyl ethyl benzylphosphonate (4J)

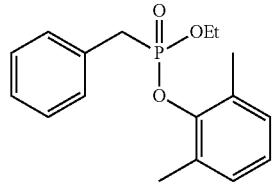

4j 52.9 mg, 87%; as a colorless oil; R$_f$ 0.35 (ν$_{Hexane}$/ν$_{EA}$=2:1); IR ν (KBr, cm$^{-1}$) 3032, 2978, 2924, 1473, 1261, 1172, 1037, 929; $^1$H NMR (400 MHz, CDCl$_3$) δ 7.40-7.25 (m, 5H), 7.00-6.91 (m, 3H), 3.99-3.84 (m, 2H), 3.37 (dd, J=21.6, 5.2 Hz, 2H), 2.25 (s, 6H), 1.05 (dt, J=6.8, 0.4 Hz, 3H); $^{13}$C NMR (100.5 MHz, CDCl$_3$) δ 147.7 (d, J=11.2 Hz), 131.4 (d, J=9.7 Hz), 130.5 (d, J=3.0 Hz), 130.0 (d, J=6.7 Hz), 128.9 (d, J=2.2 Hz), 128.5 (d, J=3.0 Hz), 127.0 (d, J=4.5 Hz), 124.8 (d, J=1.5 Hz), 63.4 (d, J=6.7 Hz), 34.3 (d, J=140.7 Hz), 17.3, 16.1 (d, J=6.0 Hz); $^{31}$P NMR (162 MHz, CDCl$_3$): δ 23.55 ppm.

xxxv. 2,6-Diisopropylphenyl ethyl benzylphosphonate (4K)

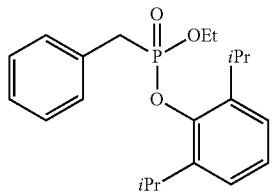

4k 40.3 mg, 56%; as a colorless oil; R$_f$ 0.30 (ν$_{Hexane}$/ν$_{EA}$=2:1); IR ν (KBr, cm$^{-1}$) 3028, 2966, 2927, 1442, 1261, 1165, 1037, 929; $^1$H NMR (400 MHz, CDCl$_3$) δ 7.40-7.25 (m, 5H), 7.14-7.06 (m, 3H), 3.97-3.81 (m, 2H), 3.46-3.30 (m, 4H), 1.15 (dd, J=8.8, 6.8 Hz, 12H), 1.03 (dt, J=6.8, 0.4 Hz, 3H); $^{13}$C NMR (100.5 MHz, CDCl$_3$) δ 145.0, 140.8 (d, J=3.0 Hz), 131.4 (d, J=9.7 Hz), 130.0 (d, J=6.7 Hz), 128.5 (d, J=3.0 Hz), 127.0 (d, J=3.7 Hz), 125.5 (d, J=2.2 Hz), 124.1 (d, J=1.5 Hz), 63.6 (d, J=6.7 Hz), 34.4 (d, J=140.7 Hz), 26.9, 23.5 (d, J=26.8 Hz), 16.1 (d, J=5.2 Hz); $^{31}$P NMR (162 MHz, CDCl$_3$): δ 22.50 ppm.

xxxvi. [1,1'-biphenyl]-4-yl ethyl benzylphosphonate (4M)

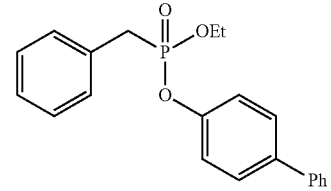

4m 64.0 mg, 91%; as a colorless oil; $R_f$ 0.30 ($\nu_{Hexane}/\nu_{EA}$=2:1); IR $\nu$ (KBr, cm$^{-1}$) 3059, 3032, 2981, 1604, 1516, 1485, 1261, 1215, 1168, 1037, 925; $^1$H NMR (400 MHz, CDCl$_3$) δ 7.56-7.48 (m, 4H), 7.45-7.40 (m, 2H), 7.38-7.25 (m, 6H), 7.19-7.14 (m, 2H), 4.19-4.04 (m, 2H), 3.36 (dd, J=21.6, 1.6 Hz, 2H), 1.24 (dt, J=7.2, 1.2 Hz, 3H); $^{13}$C NMR (100.5 MHz, CDCl$_3$) δ 150.1 (d, J=8.2 Hz), 140.3, 137.9 (d, J=1.5 Hz), 130.9 (d, J=9.6 Hz), 129.9 (d, J=6.7 Hz), 128.8, 128.6 (d, J=3.7 Hz), 128.3, 127.2, 127.1 (d, J=3.7 Hz), 127.0, 120.7 (d, J=3.8 Hz), 63.1 (d, J=6.7 Hz), 33.8 (d, J=137.7 Hz), 16.3 (d, J=5.9 Hz); $^{31}$P NMR (162 MHz, CDCl$_3$): δ 24.06 ppm.

xxxvii. Ethyl naphthalen-1-yl Benzylphosphonate (4N)

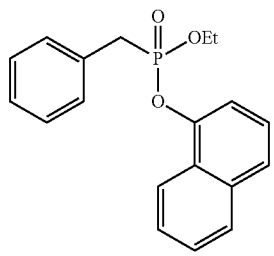

45.4 mg, 70%; as a colorless oil; $R_f$ 0.30 ($\nu_{Hexane}/\nu_{EA}$=2:1); IR $\nu$ (KBr, cm$^{-1}$) 3059, 2981, 2908, 1597, 1537, 1462, 1392, 1261, 1230, 1083, 1033, 921; $^1$H NMR (400 MHz, CDCl$_3$) δ 7.89 (dd, J=8.4, 1.2 Hz, 1H), 7.81 (dd, J=7.6, 1.2 Hz, 1H), 7.73 (d, J=8.0 Hz, 1H), 7.51-7.22 (m, 9H), 4.02-3.59 (m, 2H), 3.42 (d, J=21.6 Hz, 2H), 1.14 (t, J=7.2 Hz, 3H); $^{13}$C NMR (100.5 MHz, CDCl$_3$) δ 146.5 (d, J=9.7 Hz), 134.7, 131.0 (d, J=9.0 Hz), 130.0 (d, J=6.7 Hz), 128.6 (d, J=3.0 Hz), 127.7, 127.1 (d, J=3.7 Hz), 126.6 (d, J=5.2 Hz), 126.5, 126.1, 125.5, 124.7 (d, J=1.5 Hz), 121.8, 115.5 (d, J=3.8 Hz), 63.3 (d, J=6.7 Hz), 33.9 (d, J=138.4 Hz), 16.2 (d, J=6.0 Hz); $^{31}$P NMR (162 MHz, CDCl$_3$): δ 24.15 ppm.

xxxviii. Ethyl naphthalen-2-yl phenylphosphonate (4O)

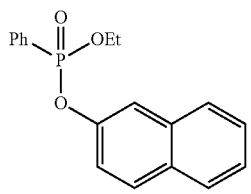

54.3 mg, 87%; as a colorless oil; $R_f$ 0.25 ($\nu_{Hexane}/\nu_{EA}$=2:1); IR $\nu$ (KBr, cm$^{-1}$) 3059, 2981, 1631, 1597, 1508, 1465, 1257, 1211, 1161, 1130, 1037, 968; $^1$H NMR (400 MHz, CDCl$_3$) δ 7.95-7.88 (m, 2H), 7.75 (dd, J=15.2, 7.2 Hz, 3H), 7.64 (s, 1H), 7.58-7.53 (m, 1H), 7.49-7.37 (m, 4H), 7.33-7.29 (m, 1H), 4.35-4.21 (m, 2H), 1.36 (t, J=7.2 Hz, 3H); $^{13}$C NMR (100.5 MHz, CDCl$_3$) δ 148.2 (d, J=7.5 Hz), 133.9, 132.8 (d, J=3.0 Hz), 132.0 (d, J=10.5 Hz), 130.8, 129.7, 128.6, 128.5, 127.6 (d, J=14.9 Hz), 127.5 (d, J=189.7 Hz), 126.6, 125.3, 120.6 (d, J=4.4 Hz), 117.0 (d, J=5.2 Hz), 63.0 (d, J=5.9 Hz), 16.3 (d, J=6.0 Hz); $^{31}$P NMR (162 MHz, CDCl$_3$): δ 16.24 ppm.

xxxix. Ethyl quinolin-6-yl phenylphosphonate (4P)

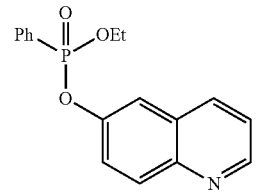

45.0 mg, 72%; as a colorless oil; $R_f$ 0.20 ($\nu_{DCM}/\nu_{MeOH}$=98:2); IR $\nu$ (KBr, cm$^{-1}$) 3059, 2981, 1624, 1597, 1500, 1261, 1215, 1130, 1037, 968; $^1$H NMR (400 MHz, CDCl$_3$) δ 8.85 (dd, J=4.0, 1.6 Hz, 1H), 8.08 (d, J=8.4 Hz, 1H), 8.03 (d, J=9.2 Hz, 1H), 7.96-7.89 (m, 2H), 7.67 (t, J=2.0 Hz, 1H), 7.63-7.56 (m, 1H), 7.59-7.46 (m, 3H), 7.38 (dd, J=8.4, 4.4 Hz, 1H), 4.38-4.23 (m, 2H), 1.38 (t, J=7.2 Hz, 3H); $^{13}$C NMR (100.5 MHz, CDCl$_3$) δ 149.8, 148.3 (d, J=6.7 Hz), 145.7, 135.7, 133.0 (d, J=3.0 Hz), 132.0 (d, J=9.6 Hz), 131.3, 128.7, 128.6 (d, J=15.7 Hz), 127.2 (d, J=189.8 Hz), 124.1 (d, J=14.1 Hz), 121.6, 116.7 (d, J=4.5 Hz), 63.1 (d, J=6.0 Hz), 16.3 (d, J=6.0 Hz); $^{31}$P NMR (162 MHz, CDCl$_3$): δ 16.52 ppm.

xl. 4-((Benzyl(ethoxy)phosphoryl)oxy)phenyl octanoate (4Q)

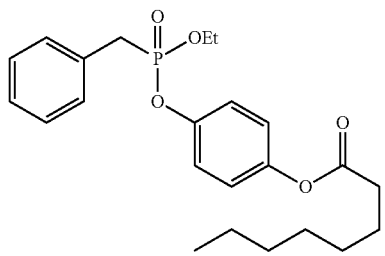

61.7 mg, 74%; as a colorless oil; $R_f$ 0.25 ($\nu_{Hexane}/\nu_{EA}$=2:1); IR $\nu$ (KBr, cm$^{-1}$) 3062, 2972, 2858, 1759, 1500, 1454, 1265, 1184, 1141, 1037, 925; $^1$H NMR (400 MHz, CDCl$_3$) δ 7.34-7.24 (m, 5H), 7.09 (d, J=8.8 Hz, 2H), 6.99 (d, J=8.4 Hz, 2H), 4.07 (br, 2H), 3.32 (d, J=21.2 Hz, 2H), 2.53 (t, J=7.6 Hz, 2H), 1.78-1.69 (m, 2H), 1.44-1.24 (m, 8H), 1.20 (t, J=6.4 Hz, 3H), 0.89 (t, J=6.8 Hz, 3H); $^{13}$C NMR (100.5 MHz, CDCl$_3$) δ 172.2, 147.9 (d, J=7.4 Hz), 148.3, 147.4, 130.8 (d, J=8.2 Hz), 129.9 (d, J=5.2 Hz), 128.7, 127.1, 122.6, 121.3, 63.2 (d, J=5.9 Hz), 34.3, 34.0 (d, J=137.6 Hz), 31.6, 29.0, 28.9, 24.9, 22.6, 16.3, 14.1; $^{31}$P NMR (162 MHz, CDCl$_3$): δ 24.15 ppm.

xli. Benzyl (4-((ethoxy(phenyl)phosphoryl)oxy)phenyl) carbonate (4R)

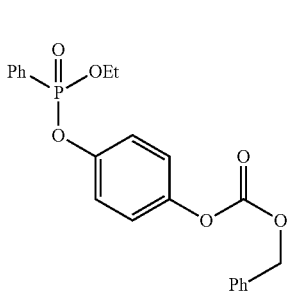

70.7 mg, 86%; as a colorless oil; $R_f$ 0.20 ($v_{Hexane}/v_{EA}$=2:1); IR ν (KBr, cm$^{-1}$) 3062, 2985, 2927, 1759, 1500, 1438, 1381, 1269, 1199, 1130, 925; $^1$H NMR (400 MHz, CDCl$_3$) δ 7.88 (d, J=7.2 Hz, 1H), 7.84 (d, J=7.6 Hz, 2H), 7.57 (t, J=7.2 Hz, 1H), 7.50-7.44 (m, 2H), 7.43-7.35 (m, 5H), 7.17 (d, J=8.8 Hz, 2H), 7.09 (d, J=9.2 Hz, 2H), 5.23 (s, 2H), 4.32-4.18 (m, 2H), 1.35 (t, J=7.2 Hz, 3H); $^{13}$C NMR (100.5 MHz, CDCl$_3$) δ 153.5, 148.1 (d, J=7.5 Hz), 147.7, 134.6, 132.9 (d, J=3.0 Hz), 132.0 (d, J=9.7 Hz), 128.8, 128.7, 128.6, 128.5, 127.4 (d, J=189.8 Hz), 122.1, 121.4 (d, J=4.4 Hz), 63.0 (d, J=6.0 Hz), 16.3 (d, J=6.0 Hz); $^{31}$P NMR (162 MHz, CDCl$_3$): δ 16.30 ppm.

xlii. 4-(Allyloxy)phenyl ethyl benzylphosphonate (4S)

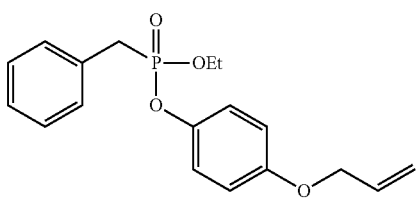

58.4 mg, 88%; as a colorless oil; $R_f$ 0.15 ($v_{Hexane}/v_{EA}$=2:1); IR ν (KBr, cm$^{-1}$) 3032, 2981, 2918, 1504, 1454, 1261, 1199, 1037, 933; $^1$H NMR (400 MHz, CDCl$_3$) δ 7.35-7.23 (m, 5H), 7.03-6.97 (m, 2H), 6.85-6.79 (m, 2H), 6.08-5.97 (m, 1H), 5.42-5.36 (m, 1H), 5.30-5.25 (m, 1H), 4.48 (td, J=5.6, 1.2 Hz, 2H), 4.13-4.00 (m, 2H), 3.23 (dd, J=21.6, 2.8 Hz, 2H), 1.19 (t, J=7.2 Hz, 3H); $^{13}$C NMR (100.5 MHz, CDCl$_3$) δ 155.6, 144.1 (d, J=8.9 Hz), 133.1, 131.0 (d, J=9.7 Hz), 129.9 (d, J=6.7 Hz), 128.6 (d, J=3.7 Hz), 127.0 (d, J=3.7 Hz), 121.3 (d, J=4.5 Hz), 117.7, 115.5, 69.2, 63.0 (d, J=7.5 Hz), 33.6 (d, J=137.6 Hz), 16.2 (d, J=6.0 Hz); $^{31}$P NMR (162 MHz, CDCl$_3$): δ 24.16 ppm.

xliii. (E)-ethyl (4-(phenyldiazenyl)phenyl)phenylphosphonate (4T)

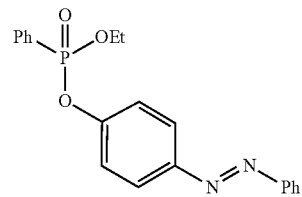

68.8 mg, 94%; as an orange oil; $R_f$ 0.25 ($v_{Hexane}/v_{EA}$=2:1); IR ν (KBr, cm$^{-1}$) 3059, 2981, 2904, 1593, 1492, 1261, 1226, 1207, 1130, 1037, 918; $^1$H NMR (400 MHz, CDCl$_3$) δ 7.94-7.85 (m, 6H), 7.61-7.56 (m, 1H), 7.54-7.48 (m, 5H), 7.38-7.29 (m, 2H), 4.37-4.28 (m, 2H), 1.38 (dt, J=6.8, 0.8 Hz, 3H); $^{13}$C NMR (100.5 MHz, CDCl$_3$) δ 152.7 (d, J=7.5 Hz), 152.5, 149.5, 133.0 (d, J=3.0 Hz), 132.0 (d, J=9.7 Hz), 131.0, 129.1, 128.6 (d, J=5.6 Hz), 127.3 (d, J=189.8 Hz), 124.4, 122.8, 121.1 (d, J=4.5 Hz), 63.1 (d, J=5.9 Hz), 16.3 (d, J=6.6 Hz); $^{31}$P NMR (162 MHz, CDCl$_3$): δ 16.21 ppm.

xliv. (E)-ethyl 3-(2-((benzyl(ethoxy)phosphoryl)oxy)-5-bromophenyl)acrylate (4U)

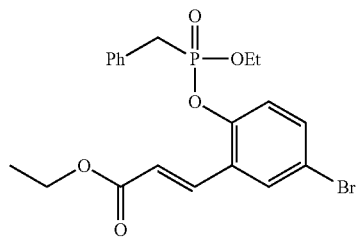

73.6 mg, 82%; as a colorless oil; $R_f$ 0.30 ($v_{Hexane}/v_{EA}$=2:1); IR ν (KBr, cm$^{-1}$) 3062, 2981, 2931, 1712, 1635, 1477, 1215, 1273, 1222, 1180, 1033, 929; $^1$H NMR (400 MHz, CDCl$_3$) δ 7.80 (d, J=16.0 Hz, 1H), 7.67 (d, J=0.5 Hz, 1H), 7.37 (dd, J=8.8, 2.8 Hz, 1H), 7.34-7.25 (m, 5H), 7.14 (dd, J=8.8, 1.2 Hz, 1H), 6.40 (d, J=16.4 Hz, 1H), 4.28 (q, J=7.2 Hz, 1H), 4.15-4.02 (m, 2H), 3.37 (d, J=22.0 Hz, 2H), 1.34 (t, J=7.2 Hz, 3H), 1.21 (dt, J=7.2, 0.4 Hz, 3H); $^{13}$C NMR (100.5 MHz, CDCl$_3$) δ 166.3, 148.3 (d, J=9.6 Hz), 136.9, 133.8, 130.2, 130.1 (d, J=9.7 Hz), 129.9 (d, J=9.4 Hz), 128.7 (d, J=3.0 Hz), 127.3 (d, J=3.7 Hz), 122.8 (d, J=2.9 Hz), 121.1, 117.9, 63.5 (d, J=6.7 Hz), 60.7, 34.0 (d, J=138.4 Hz), 16.2 (d, J=5.2 Hz), 14.3; $^{31}$P NMR (162 MHz, CDCl$_3$): δ 24.71 ppm.

xlv. (3R, 8S, 9S, 10R, 13R, 14S, 17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl 4-((benzyl(ethoxy)phosphoryl)oxy)benzoate (4V)

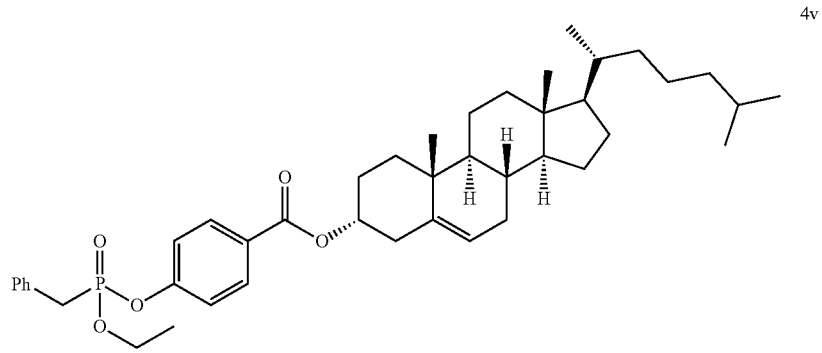

4v 115.9 mg, 84%; as a colorless oil; IR ν (KBr, cm$^{-1}$) 3062, 2939, 286, 1712, 1604, 1504, 1458, 1273, 1219, 1161, 1118, 1037, 921; $^1$H NMR (400 MHz, CDCl$_3$) δ 7.93 (d, J=8.4 Hz, 2H), 7.35-7.26 (m, 5H), 7.14 (dd, J=8.8, 0.8 Hz, 2H), 5.33-5.29 (m, 1H), 5.22 (t, J=2.4 Hz, 1H), 4.28-4.03 (m, 2H), 3.34 (dd, J=21.6, 1.6 Hz, 2H), 2.57 (td, J=15.6, 2.4 Hz, 1H), 2.33 (td, J=15.2, 2.4 Hz, 1H), 2.07-1.78 (m, 5H), 1.75-1.68 (m, 1H), 1.63-1.00 (m, 23H), 1.22 (t, J=7.2 Hz, 3H), 0.93 (d, J=6.4 Hz, 3H), 0.86 (d, J=6.8 Hz, 3H), 0.85 (d, J=6.8 Hz, 3H), 0.70 (s, 3H); $^{13}$C NMR (100.5 MHz, CDCl$_3$) δ 165.1, 154.2 (d, J=9.0 Hz), 138.8, 131.4, 130.5 (d, J=8.9 Hz), 129.9 (d, J=6.7 Hz), 128.7 (d, J=3.0 Hz), 127.7 (d, J=8.5 Hz), 127.2 (d, J=3.7 Hz), 122.4, 120.1 (d, J=4.4 Hz), 71.3, 63.3 (d, J=7.5 Hz), 56.7, 56.2, 50.3, 42.3, 39.7, 39.5, 37.1, 36.6, 36.2, 35.8, 34.0, 33.9 (d, J=138.4 Hz), 31.9, 31.8, 28.2, 28.0, 26.3, 24.3, 23.8, 22.8, 22.5, 20.8, 18.9, 18.7, 16.2 (d, J=6.0 Hz), 11.9; $^{31}$P NMR (162 MHz, CDCl$_3$): δ 24.02 ppm;

xlvi. Butyl ethyl phenylphosphonate (5A)

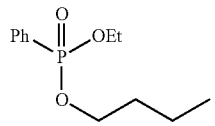

5a 41.1 mg, 81%; as a colorless oil; R$_f$ 0.50 (ν$_{DCM}$/ν$_{EA}$=95:5); $^1$H NMR (400 MHz, CDCl$_3$) δ 7.86-7.78 (m, 2H), 7.59-7.53 (m, 1H), 7.51-7.44 (m, 2H), 4.22-3.96 (m, 4H), 1.71-1.62 (m, 2H), 1.46-1.26 (m, 5H), 0.91 (dt, J=7.2, 2.0 Hz, 3H); $^{13}$C NMR (100.5 MHz, CDCl$_3$) δ 132.3 (d, J=3.0 Hz), 131.7 (d, J=10.4 Hz), 128.4 (d, J=14.9 Hz), 128.3 (d, J=186.8 Hz), 65.8 (d, J=5.2 Hz), 62.1 (d, J=5.9 Hz), 32.4 (d, J=6.0 Hz), 18.7, 16.3 (d, J=6.7 Hz), 13.5; $^{31}$P NMR (162 MHz, CDCl$_3$): δ 19.41 ppm; Spectroscopy data of the this compound matches with the data reported in the corresponding reference (Ilia et al. (2015) *Heteroatom Chemistry* 26: 29).

xlvii. Ethyl (4-methylcyclohexyl) phenylphosphonate (5B)

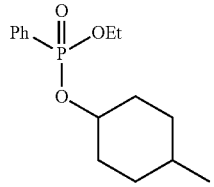

5b 41.0 mg, 73%; as a colorless oil; R$_f$ 0.25 (ν$_{Hexane}$/ν$_{EA}$=2:1); IR ν (KBr, cm$^{-1}$) 2931, 2866, 1454, 1438, 1249, 1130, 1049, 1010, 964; $^1$H NMR (400 MHz, CDCl$_3$) δ 7.85-7.78 (m, 2H), 7.56-7.51 (m, 1H), 7.48-7.42 (m, 2H), 4.38-4.27 (m, 1H), 4.17-3.99 (m, 2H), 2.18-2.11 (m, 1H), 1.95-1.87 (m, 1H), 1.76-1.62 (m, 2H), 1.58-1.28 (m, 6H), 0.86 (d, J=6.4 Hz, 3H); $^{13}$C NMR (100.5 MHz, CDCl$_3$) δ 132.1 (d, J=2.9 Hz), 131.7 (d, J=9.7 Hz), 129.3 (d, J=186.8 Hz), 128.3 (d, J=14.8 Hz), 61.8 (d, J=5.2 Hz), 33.9 (d, J=3.7 Hz), 33.6 (d, J=4.4 Hz), 33.0 (d, J=5.2 Hz), 31.4, 21.7, 16.3 (d, J=6.7 Hz), 13.5; $^{31}$P NMR (162 MHz, CDCl$_3$): δ 18.33 ppm.

xlviii. 2-Chloroethyl ethyl phenylphosphonate (5C)

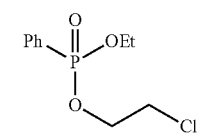

5c 35.8 mg, 72%; as a colorless oil; R$_f$ 0.11 (ν$_{Hexane}$/ν$_{EA}$=2:1); IR ν (KBr, cm$^{-1}$) 2985, 2908, 1643, 1438, 1238, 1134, 1022, 964; $^1$H NMR (400 MHz, CDCl$_3$) δ 7.88-7.79 (m, 2H), 7.61-7.55 (m, 1H), 7.52-7.45 (m, 2H), 4.39-4.08 (m, 4H), 3.75-3.64 (m, 2H), 1.35 (t, J=7.2 Hz, 3H); $^{13}$C NMR (100.5 MHz, CDCl$_3$) δ 132.7 (d, J=3.0 Hz), 131.8 (d, J=9.7

Hz), 128.5 (d, J=14.9 Hz), 127.5 (d, J=188.3 Hz), 65.2 (d, J=5.2 Hz), 62.5 (d, J=5.2 Hz), 42.7 (d, J=7.4 Hz), 16.3 (d, J=6.7 Hz); $^{31}$P NMR (162 MHz, CDCl$_3$): δ 19.91 ppm.

xlix. 3-Bromopropyl ethyl phenylphosphonate (5D)

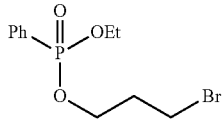

44.2 mg, 72%; as a colorless oil; R$_f$ 0.15 (ν$_{Hexane}$/ν$_{EA}$=1:1); IR ν (KBr, cm$^{-1}$) 2978, 2904, 1643, 1438, 1242, 1130, 1014, 964; $^1$H NMR (400 MHz, CDCl$_3$) δ 7.81 (dd, J=13.2, 7.2 Hz, 2H), 7.58 (t, J=7.2 Hz, 1H), 7.52-7.45 (m, 2H), 4.27-4.05 (m, 4H), 3.53-3.46 (m, 2H), 2.24-2.15 (m, 2H), 1.34 (t, J=6.8 Hz, 3H); $^{13}$C NMR (100.5 MHz, CDCl$_3$) δ 132.6 (d, J=3.0 Hz), 131.8 (d, J=9.7 Hz), 128.5 (d, J=14.9 Hz), 127.8 (d, J=184.6 Hz), 63.5 (d, J=6.0 Hz), 62.3 (d, J=6.0 Hz), 33.3 (d, J=6.7 Hz), 29.1, 16.3 (d, J=6.7 Hz); $^{31}$P NMR (162 MHz, CDCl$_3$): δ 19.74 ppm.

l. Isopropyl methyl phenylphosphonate (5E)

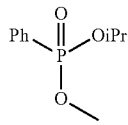

31.5 mg, 74%; as a colorless oil; R$_f$ 0.10 (ν$_{Hexane}$/ν$_{EA}$=1:1); IR ν (KBr, cm$^{-1}$) 3059, 2978, 2951, 1438, 1377, 1253, 1134, 1045, 991; $^1$H NMR (400 MHz, CDCl$_3$) δ 7.86-7.78 (m, 2H), 7.59-7.52 (m, 1H), 7.50-7.43 (m, 2H), 4.81-4.68 (m, 1H), 3.73 (dd, J=11.2, 2.4 Hz, 3H), 1.40 (dd, J=6.4, 1.6 Hz, 2H), 1.27 (dd, J=6.0, 1.6 Hz, 3H); $^{13}$C NMR (100.5 MHz, CDCl$_3$) δ 132.3 (d, J=3.0 Hz), 131.7 (d, J=9.7 Hz), 128.4 (d, J=188.3 Hz), 128.3 (d, J=14.9 Hz), 71.1 (d, J=6.0 Hz), 52.3 (d, J=5.9 Hz), 24.0 (d, J=3.7 Hz), 23.8 (d, J=4.5 Hz); $^{31}$P NMR (162 MHz, CDCl$_3$): δ 19.75 ppm.

li. Benzyl ethyl phenylphosphonate (5F)

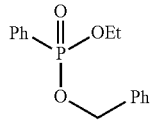

34.8 mg, 63%; as a colorless oil; R$_f$ 0.15 (ν$_{Hexane}$/ν$_{EA}$=2:1); $^1$H NMR (400 MHz, CDCl$_3$) δ 7.85-7.78 (m, 2H), 7.57-7.52 (m, 1H), 7.48-7.42 (m, 2H), 7.37-7.27 (m, 5H), 5.17-5.49 (m, 2H), 4.19-4.04 (m, 2H), 1.30 (dt, J=7.2, 0.4 Hz, 3H); $^{13}$C NMR (100.5 MHz, CDCl$_3$) δ 136.2 (d, J=6.7 Hz), 132.5 (d, J=3.0 Hz), 131.8 (d, J=9.7 Hz), 128.5, 128.4 (d, J=14.9 Hz), 128.3, 128.0 (d, J=188.2 Hz), 127.8, 67.4 (d, J=5.2 Hz), 62.3 (d, J=5.2 Hz), 16.3 (d, J=6.7 Hz); $^{31}$P NMR (162 MHz, CDCl$_3$): δ 19.82 ppm; Spectroscopy data of the this compound matches with the data reported in the corresponding reference (Xu et al. (2014) *Adv. Synth. Catal.* 356: 3331).

lii. Ethyl (3-phenylpropyl) phenylphosphonate (5G)

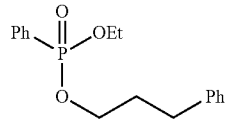

43.1 mg, 71%; as a colorless oil; R$_f$ 0.30 (ν$_{Hexane}$/ν$_{EA}$=1:1); IR ν (KBr, cm$^{-1}$) 3028, 2981, 2958, 1643, 1438, 1246, 1130, 1018, 968; $^1$H NMR (400 MHz, CDCl$_3$) δ 7.86-7.78 (m, 2H), 7.58-7.53 (m, 1H), 7.50-7.44 (m, 2H), 7.26 (t, J=7.6 Hz, 5H), 7.20-7.12 (m, 3H), 4.21-3.98 (m, 4H), 2.70 (t, J=7.6 Hz, 2H), 2.03-1.95 (m, 2H), 1.32 (t, J=7.2 Hz, 3H); $^{13}$C NMR (100.5 MHz, CDCl$_3$) δ 141.0, 132.4 (d, J=3.0 Hz), 131.8 (d, J=9.7 Hz), 128.5, 128.4, 128.3, 128.27 (d, J=187.5 Hz), 126.0, 65.2 (d, J=5.2 Hz), 62.1 (d, J=5.2 Hz), 32.0 (d, J=6.7 Hz), 31.7, 16.3 (d, J=6.7 Hz); $^{31}$P NMR (162 MHz, CDCl$_3$): δ 19.49 ppm.

liii. 2,2-Diphenylethyl ethyl phenylphosphonate (5H)

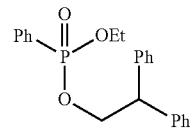

59.3 mg, 81%; as a colorless oil; R$_f$ 0.36 (ν$_{Hexane}$/ν$_{EA}$=1:1); IR ν (KBr, cm$^{-1}$) 3028, 2981, 2900, 1438, 1492, 1249, 1130, 1014, 964; $^1$H NMR (400 MHz, CDCl$_3$) δ 7.68-7.59 (m, 2H), 7.50 (dt, J=7.2, 1.6 Hz, 1H), 7.41-7.34 (m, 2H), 7.31-7.17 (m, 10H), 4.66-4.59 (m, 1H), 4.53-4.45 (m, 1H), 4.37 (t, J=7.2 Hz, 1H), 4.00-3.92 (m, 2H), 1.22 (t, J=6.8 Hz, 3H); $^{13}$C NMR (100.5 MHz, CDCl$_3$) δ 140.7 (d, J=1.5 Hz), 132.2 (d, J=3.0 Hz), 131.7 (d, J=9.7 Hz), 128.5, 128.4, 128.3 (d, J=2.2 Hz), 128.0 (d, J=188.3 Hz), 126.0, 68.0 (d, J=5.9 Hz), 62.1 (d, J=5.2 Hz), 51.4 (d, J=7.4 Hz), 16.2 (d, J=6.7 Hz); $^{31}$P NMR (162 MHz, CDCl$_3$): δ 19.31 ppm.

liv. Ethyl (4-methyl-2-oxo-2H-chromen-7-yl) phenylphosphonate (6A)

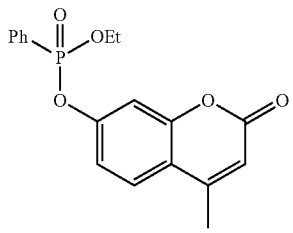

49.5 mg, 72%; as a colorless oil; $R_f$ 0.25 ($v_{DCM}/v_{EA}$=9:1); IR ν (KBr, cm$^{-1}$) 3062, 2985, 1728, 1570, 1489, 1431, 1257, 1161, 1130, 1037, 960; $^1$H NMR (400 MHz, CDCl$_3$) δ 7.93-7.85 (m, 2H), 7.61 (dt, J=7.6, 1.6 Hz, 1H), 7.54-7.47 (m, 2H), 7.40 (t, J=2.4 Hz, 1H), 7.32-7.22 (m, 2H), 6.30 (d, J=0.8 Hz, 1H), 4.35-4.20 (m, 2H), 2.36 (d, J=1.2 Hz, 3H), 1.38 (t, J=7.2 Hz, 3H); $^{13}$C NMR (100.5 MHz, CDCl$_3$) δ 160.4, 151.7, 150.3, 146.5 (d, J=7.5 Hz), 133.1 (d, J=3.8 Hz), 132.0 (d, J=10.4 Hz), 128.7 (d, J=15.6 Hz), 127.0 (d, J=189.8 Hz), 124.3 (d, J=4.5 Hz), 120.6, 118.2, 116.1 (d, J=4.5 Hz), 115.7, 63.2 (d, J=6.0 Hz), 18.6, 16.3 (d, J=5.9 Hz); $^{31}$P NMR (162 MHz, CDCl$_3$): δ 16.96 ppm.

lv. (E)-ethyl 3-(4-((ethoxy(phenyl)phosphoryl)oxy)-3-methoxyphenyl)acrylate (6B)

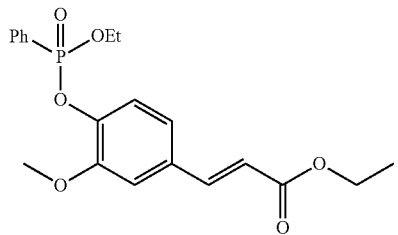

6b 67.8 mg, 87%; as a colorless oil; $R_f$ 0.20 ($v_{Hexane}/v_{EA}$=2:1); IR ν (KBr, cm$^{-1}$) 3059, 2981, 2935, 1708, 1635, 1508, 1261, 1157, 1130, 1033, 914; $^1$H NMR (400 MHz, CDCl$_3$) δ 7.95-7.88 (m, 2H), 7.62-7.54 (m, 2H), 7.51-7.44 (m, 2H), 7.24 (dd, J=8.8, 1.2 Hz, 1H), 7.05-7.01 (m, 2H), 6.33 (d, J=16.4 Hz, 1H), 4.35-4.22 (m, 4H), 3.77 (s, 3H), 1.38 (t, J=6.8 Hz, 3H), 1.33 (dt, J=7.2, 0.4 Hz, 3H); $^{13}$C NMR (100.5 MHz, CDCl$_3$) δ 166.8, 151.0 (d, J=4.5 Hz), 143.8, 141.4 (d, J=7.5 Hz), 132.7 (d, J=3.0 Hz), 132.0, 131.9 (d, J=10.4 Hz), 128.3 (d, J=15.6 Hz), 127.8 (d, J=191.3 Hz), 122.0 (d, J=3.7 Hz), 121.3 (d, J=1.5 Hz), 118.0, 111.4, 62.9 (d, J=5.9 Hz), 60.5, 55.7, 16.3 (d, J=6.7 Hz), 14.3; $^{31}$P NMR (162 MHz, CDCl$_3$): δ 16.62 ppm;

lvi. Ethyl ((8R, 9S, 13S, 14S, 17S)-17-hydroxy-13-methyl-7,8,9,11,12,13,14,15,16,17-decahydro-6H-cyclopenta[A]phenanthren-3-yl) benzylphosphonate (6C)

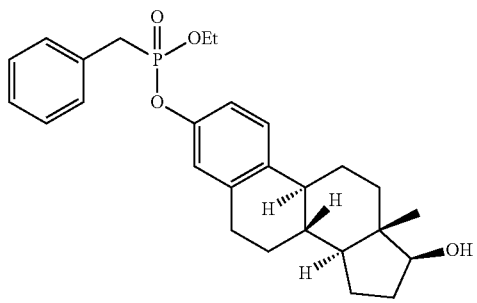

6c 37.1 mg, 41%; as a colorless oil; $R_f$ 0.20 ($v_{Hexane}/v_{EA}$=1:1); IR ν (KBr, cm$^{-1}$) 3421, 2032, 2927, 2866, 1643, 1608, 1492, 1226, 1037, 968; $^1$H NMR (400 MHz, CDCl$_3$) δ 7.35-7.24 (m, 5H), 7.18 (d, J=8.4 Hz, 1H), 6.84 (d, J=8.8 Hz, 2H), 6.78 (s, 1H), 4.15-4.03 (m, 2H), 2.34-1.18 (m, 16H), 0.77 (s, 3H); $^{13}$C NMR (100.5 MHz, CDCl$_3$) δ 148.3 (d, J=8.9 Hz), 138.4, 136.9, 131.1 (d, J=9.6 Hz), 129.9 (d, J=7.4 Hz), 128.5 (d, J=3.0 Hz), 127.0 (d, J=3.0 Hz), 120.4 (d, J=2.9 Hz), 117.5 (d, J=3.7 Hz), 62.9 (d, J=7.4 Hz), 50.0, 44.0, 43.2, 38.5, 36.6, 33.7 (d, J=138.4 Hz), 30.5, 29.5, 27.0, 26.2, 23.1, 16.2 (d, J=5.9 Hz), 11.0; $^{31}$P NMR (162 MHz, CDCl$_3$): δ 23.87 ppm.

lvii. Benzo [D][1,3]dioxol-5-yl ethyl benzylphosphonate (6D)

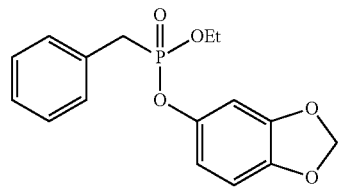

6d 57.6 mg, 90%; as a colorless oil; $R_f$ 0.20 ($v_{Hexane}/v_{EA}$=2:1); IR ν (KBr, cm$^{-1}$) 3062, 2981, 2904, 1631, 1608, 1481, 1246, 1172, 1126, 1033, 956; $^1$H NMR (400 MHz, CDCl$_3$) δ 7.34-7.25 (m, 5H), 6.68 (d, J=8.4 Hz, 1H), 6.60 (dd, J=2.4, 1.2 Hz, 1H), 6.54-6.57 (m, 1H), 5.94 (s, 2H), 4.14-4.00 (m, 2H), 3.29 (dd, J=21.2, 2.4 Hz, 3H), 1.20 (dt, J=7.2, 0.8 Hz, 3H); $^{13}$C NMR (100.5 MHz, CDCl$_3$) δ 148.0, 144.8 (d, J=8.9 Hz), 144.6, 130.9 (d, J=9.7 Hz), 129.9 (d, J=6.7 Hz), 128.6 (d, J=3.0 Hz), 127.1 (d, J=3.7 Hz), 112.8 (d, J=3.7 Hz), 107.9 (d, J=1.5 Hz), 102.9 (d, J=3.7 Hz), 101.6, 63.1 (d, J=6.7 Hz), 33.6 (d, J=138.4 Hz), 16.2 (d, J=5.9 Hz); $^{31}$P NMR (162 MHz, CDCl$_3$): δ 24.28 ppm.

lviii. Ethyl (2-methyl-4-oxo-4H-pyran-3-yl) phenylphosphonate (6E)

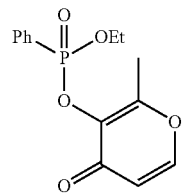

6e 30.0 mg, 51%; as a colorless oil; $R_f$ 0.30 ($v_{Hexane}/v_{EA}$=1:1); IR ν (KBr, cm$^{-1}$) 3078, 2927, 2854, 1654, 1438, 1249, 1180, 1033; $^1$H NMR (400 MHz, CDCl$_3$) δ 8.02-7.95 (m, 2H), 7.61 (d, J=6.0 Hz, 1H), 7.58 (dd, J=7.6, 2.0 Hz, 1H), 7.53-7.46 (m, 2H), 6.36 (d, J=5.6 Hz, 1H), 4.47-4.32 (m, 2H), 2.26 (d, J=1.6 Hz, 3H), 1.38 (t, J=6.8 Hz, 3H); $^{13}$C NMR (100.5 MHz, CDCl$_3$) δ 172.7, 159.0 (d, J=5.2 Hz), 153.7, 139.1 (d, J=8.9 Hz), 132.7 (d, J=3.7 Hz), 131.8 (d, J=9.7 Hz), 128.4 (d, J=15.7 Hz), 128.1 (d, J=194.3 Hz), 116.8, 63.5 (d, J=5.9 Hz), 16.3 (d, J=6.7 Hz), 15.7; $^{31}$P NMR (162 MHz, CDCl$_3$): δ 17.50 ppm.

lix. Ethyl (((S)-4-(prop-1-en-2-yl)cyclohex-1-en-1-yl)methyl) phenylphosphonate (6F)

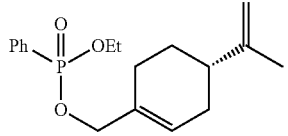

44.8 mg, 70%; as a colorless oil; $R_f$ 0.30 ($v_{Hexane}/v_{EA}$=2:1); IR v (KBr, cm$^{-1}$) 2978, 2927, 2839, 1643, 1438, 1234, 1130, 1022, 983; $^1$H NMR (400 MHz, CDCl$_3$) δ 7.85-7.78 (m, 2H), 7.58-7.52 (m, 1H), 7.49-7.43 (m, 2H), 5.75 (s, 1H), 4.73-4.67 (m, 2H), 4.50-4.35 (m, 2H), 4.21-4.14 (m, 2H), 2.13-1.75 (m, 7H), 1.71 (t, J=0.8 Hz, 3H), 1.33 (dt, J=6.8, 0.4 Hz, 3H); $^{13}$C NMR (100.5 MHz, CDCl$_3$) δ 149.5, 133.0, 132.9 (d, J=5.9 Hz), 132.3 (dd, J=3.0, 1.5 Hz), 131.8 (dd, J=9.7, 2.3 Hz), 128.5 (d, J=187.6 Hz), 128.4 (d, J=14.9 Hz), 126.2 (d, J=10.4 Hz), 69.9 (dd, J=5.2, 3.7 Hz), 62.1 (d, J=4.4 Hz), 40.7 (d, J=5.2 Hz), 30.4, 27.1 (d, J=2.2 Hz), 26.0 (d, J=5.2 Hz), 24.7, 20.7 (d, J=3.7 Hz), 16.3 (d, J=6.7 Hz); $^{31}$P NMR (162 MHz, CDCl$_3$): δ 19.62 ppm.

lx. (3S, 8S, 9S, 10R, 13R, 14S, 17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl ethyl phenylphosphonate (6G)

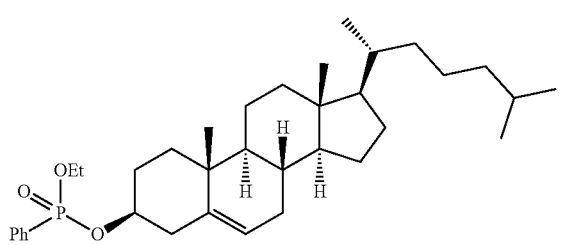

6g, dr = 1.15:1

89.8 mg, 81%; as a white solid; $R_f$ 0.15 ($v_{Hexane}/v_{EA}$=2:1); $^1$H NMR (400 MHz, CDCl$_3$, * denotes minor rotamer peaks) δ 7.86-7.78 (m, 2H), 7.56-7.51 (m, 1H), 7.49-7.42 (m, 2H), 5.38* (d, J=4.8 Hz, 1H), 5.27 (d, J=5.2 Hz, 1H), 4.33-4.21 (m, 1H), 4.18-4.00 (m, 2H), 2.49 (d, J=8.0 Hz, 1H), 2.45-2.36 (m, 1H), 2.30-2.23* (m, 1H), 2.08-0.94 (m, 32H), 0.91 (d, J=6.4 Hz, 3H), 0.86 (d, J=6.8 Hz, 3H), 0.85 (d, J=6.8 Hz, 3H), 0.66 (s, 3H); $^{13}$C NMR (100.5 MHz, CDCl$_3$) δ 139.5, 139.4, 132.2 (d, J=1.5 Hz), 132.1 (d, J=1.5 Hz), 131.7 (d, J=9.6 Hz), 129.2 (d, J=188.3 Hz), 129.1 (d, J=186.8 Hz), 128.4 (d, J=14.9 Hz), 128.3 (d, J=14.9 Hz), 122.8, 1227, 76.8 (d, J=6.0 Hz), 76.7 (d, J=6.0 Hz), 61.9, 61.8, 56.6, 56.1, 49.9, 42.3, 40.3 (d, J=3.7 Hz), 40.1 (d, J=5.2 Hz), 39.7, 39.5, 36.92, 36.89, 36.4, 36.1, 35.7, 31.9, 31.8, 31.79, 31.78, 30.0 (d, J=3.0 Hz), 29.8 (d, J=3.7 Hz), 28.2, 28.0, 24.2, 23.8, 22.8, 22.5, 21.0, 19.2, 18.7, 16.3 (d, J=6.7 Hz), 11.8; $^{31}$P NMR (162 MHz, CDCl$_3$): δ 18.29 ppm; Spectroscopy data of the this compound matches with the data reported in the corresponding reference (Kalek et al. (2008) Org. Lett. 10: 4637).

lxi. 2-Cyanophenyl ethyl benzylphosphonate (7A)

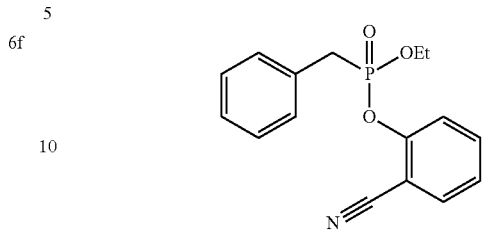

Methyl naphthalen-1-yl (4-methylpent-3-en-1-yl)phosphonate (7b): 54.8 mg, 91%; as a colorless oil; $R_f$ 0.15 ($v_{Hexane}/v_{EA}$=2:1); $^1$H NMR (400 MHz, CDCl$_3$) δ 7.61-7.57 (m, 1H), 7.50-7.44 (m, 1H), 7.39-7.24 (m, 6H), 7.19 (tt, J=7.6, 0.8 Hz, 1H), 4.24-4.11 (m, 2H), 3.44 (d, J=22.0 Hz, 2H), 1.25 (t, J=7.2 Hz, 3H); $^{13}$C NMR (100.5 MHz, CDCl$_3$) δ 152.4 (d, J=8.2 Hz), 134.3, 133.4, 130.0 (d, J=6.7 Hz), 129.9 (d, J=9.6 Hz), 128.7 (d, J=3.0 Hz), 127.3 (d, J=3.7 Hz), 124.8, 121.1 (d, J=2.3 Hz), 115.5, 105.5 (d, J=6.0 Hz), 63.7 (d, J=7.4 Hz), 34.1 (d, J=137.7 Hz), 16.2 (d, J=6.7 Hz); $^{31}$P NMR (162 MHz, CDCl$_3$): δ 25.03 ppm; Spectroscopy data of the this compound matches with the data reported in the corresponding reference (Bera et al. (2016) ACS Catal. 6: 3575).

lxii. Methyl naphthalen-1-yl (4-methylpent-3-en-1-yl)phosphonate (7B)

51.0 mg, 84%; as a colorless oil; $R_f$ 0.15 ($v_{Hexane}/v_{EA}$=2:1); $^1$H NMR (400 MHz, CDCl$_3$) δ 8.17-8.12 (m, 1H), 7.87-7.82 (m, 1H), 7.66 (d, J=8.0 Hz, 1H), 7.56-7.49 (m, 3H), 7.41 (t, J=8.4 Hz, 1H), 5.13 (t, J=7.2 Hz, 2H), 7.80 (dd, J=11.2, 0.8 Hz, 3H), 2.47-2.36 (m, 2H), 2.07-1.98 (m, 2H), 1.66 (s, 3H), 1.58 (s, 3H), 1.33 (t, J=7.6 Hz, 3H); $^{13}$C NMR (100.5 MHz, CDCl$_3$) δ 146.5, 134.8, 133.3 (d, J=8.5 Hz), 127.8, 126.6, 126.5, 126.3, 125.6 (d, J=1.5 Hz), 124.6 (d, J=1.4 Hz), 122.7 (d, J=17.2 Hz), 121.6, 115.3 (d, J=3.0 Hz), 52.9 (d, J=7.4 Hz), 25.8 (d, J=137.7 Hz), 25.6, 21.1 (d, J=4.5 Hz), 17.6; $^{31}$P NMR (162 MHz, CDCl$_3$): δ 31.17 ppm; Spectroscopy data of the this compound matches with the data reported in the corresponding reference (Foust et al. (2017) ACS Med. Chem. Lett. 8: 914).

lxiii. Ethyl (4-nitrophenyl) hex-5-en-1-ylphosphonate (7B)

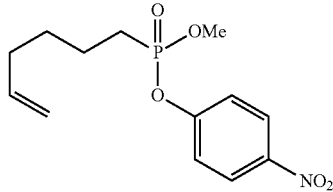

54.5 mg, 87%; as a colorless oil; $R_f$ 0.30 ($v_{Hexane}/v_{EA}$=2:1); IR v (KBr, cm$^{-1}$) 2981, 2935, 2866, 1593, 1523, 1492, 1346, 1226, 1037, 910; $^1$H NMR (400 MHz, CDCl$_3$) δ 8.24 (td, J=9.2, 3.2 Hz, 2H), 7.42-7.36 (m, 2H), 5.84-5.72 (m, 1H), 5.05-4.95 (m, 2H), 4.30-4.10 (m, 2H), 2.13-2.05 (m, 2H), 2.00-1.90 (m, 2H), 1.76-1.67 (m, 2H), 1.57-1.48 (m, 2H), 1.33 (t, J=7.6 Hz, 3H); $^{13}$C NMR (100.5 MHz, CDCl$_3$) δ 155.7 (d, J=8.9 Hz), 144.5, 137.8, 125.6, 120.9 (d, J=4.5 Hz), 115.1, 62.9 (d, J=7.5 Hz), 33.0 (d, J=1.5 Hz), 29.5 (d, J=7.2 Hz), 25.9 (d, J=139.2 Hz), 21.6 (d, J=5.2 Hz), 16.3 (d, J=5.2 Hz); $^{31}$P NMR (162 MHz, CDCl$_3$): δ 30.84 ppm.

lxiv. O-ethyl S-phenyl phenylphosphonothioate (8A)

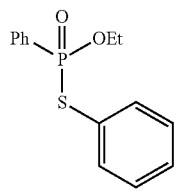

8.1 mg, 14%; as a colorless oil; $R_1$ 0.20 ($v_{Hexane}/v_{EA}$=2:1); IR v (KBr, cm$^{-1}$) 3059, 2981, 2924, 1643, 1438, 1230, 1118, 1022, 956; $^1$H NMR (400 MHz, CDCl$_3$) δ 7.69-7.62 (m, 2H), 7.53-7.47 (m, 1H), 7.40-7.34 (m, 2H), 7.32-7.26 (m, 3H), 7.21 (t, J=7.2 Hz, 2H), 4.43-4.27 (m, 2H), 1.41 (t, J=7.2 Hz, 3H); $^{13}$C NMR (100.5 MHz, CDCl$_3$) δ 135.5 (d, J=4.4 Hz), 132.4 (d, J=3.7 Hz), 131.5 (d, J=149.6 Hz), 131.4 (d, J=10.5 Hz), 129.1 (d, J=2.2 Hz), 128.9 (d, J=3.0 Hz), 128.2 (d, J=14.9 Hz), 126.6 (d, J=5.2 Hz), 62.4 (d, J=7.4 Hz), 16.3 (d, J=6.7 Hz); $^{31}$P NMR (162 MHz, CDCl$_3$): δ 42.26 ppm.

c. General Procedure for the Synthesis of Phosphate Derivatives

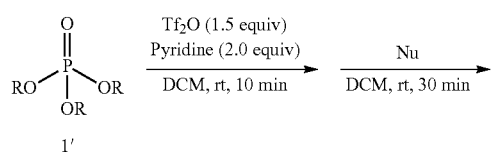

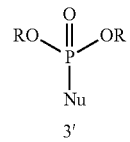

Diethyl phenyl phosphate (3a'): To a solution of triethyl phosphate 1a (36.4 mg, 0.2 mmol), Tf$_2$O (50.5 μL, 0.3 mmol) in DCM (1.0 mL) was added pyridine (32 μL, 0.4 mmol) in a 2-dram vial with a PTFE cap. After stirring for 10 min, phenol (38.1 mg, 0.4 mmol) was added to the reaction mixture. After stirring for another 30 min at room temperature, the resulting mixture was concentrated to give the crude product which was then purified by column chromatography on silica gel (PE/EA=3:1) to afford ethyl phenyl benzylphosphonate (3a').

i. Ethyl phenyl benzylphosphonate (3A')

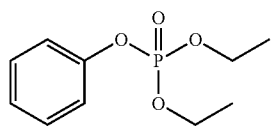

42.3 mg, 92%; as a colorless oil; $R_f$=0.20 ($v_{Hexane}/v_{EA}$=2:1); $^1$H NMR (400 MHz, CDCl$_3$) δ 7.37-7.30 (m, 2H), 7.24-7.20 (m, 2H), 7.19-7.14 (m, 1H), 4.28-4.15 (m, 4H), 1.35 (td, J=7.2, 1.2 Hz, 6H); $^{13}$C NMR (100.5 MHz, CDCl$_3$) δ 150.8, 129.6, 124.9, 119.9 (d, J=4.4 Hz), 64.5 (d, J=5.9 Hz), 16.0 (d, J=6.7 Hz); Spectroscopy data of the compound match with the data reported in the corresponding reference (Panmand et al. (2014) *Tetrahedron Lett.* 55: 5898-5901).

ii. Diethyl p-tolyl phosphate (3B')

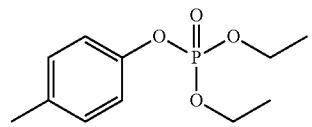

43.9 mg, 90%; as a colorless oil; $R_f$=0.20 ($v_{Hexane}/v_{EA}$=2:1); $^1$H NMR (400 MHz, CDCl$_3$) δ 7.15-7.07 (m, 4H), 4.27-4.14 (m, 4H), 2.32 (s, 3H), 1.38-1.32 (m, 6H); $^{13}$C NMR (100.5 MHz, CDCl$_3$) δ 148.5 (d, J=6.7 Hz), 134.5, 130.1, 119.7 (d, J=4.5 Hz), 64.4 (d, J=5.9 Hz), 20.7, 16.1 (d, J=6.7 Hz); Spectroscopy data of the compound match with the data reported in the corresponding reference (Jeon et al. (2013) *Tetrahedron* 69: 5152-5159).

iii. Diethyl (4-methoxyphenyl) phosphate (3c')

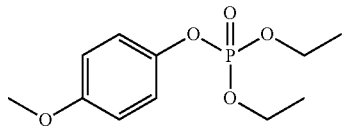

46.3 mg, 89%; as a colorless oil; $R_f$=0.10 ($v_{Hexane}/v_{EA}$=2:1); $^1$H NMR (400 MHz, CDCl$_3$) δ 7.17-7.11 (m, 2H), 6.84 (d, J=8.8 Hz, 2H), 4.27-4.13 (m, 4H), 3.78 (s, 3H), 1.37-1.33 (m, 6H); $^{13}$C NMR (100.5 MHz, CDCl$_3$) δ 156.6 (d, J=1.5 Hz), 144.3, 120.8 (d, J=5.4 Hz), 114.6, 64.5 (d, J=5.9 Hz), 55.6, 16.1 (d, J=6.7 Hz); Spectroscopy data of the compound match with the data reported in the corresponding reference (Jones and Smanmoo (2005) *Org. Lett.* 7: 3271-3274).

iv. 4-Bromophenyl diethyl Phosphate (3D')

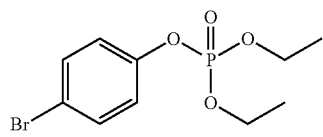

3d'

52.4 mg, 85%; as a colorless oil; $R_f$=0.20 ($v_{Hexane}/v_{EA}$=2:1); $^1$H NMR (400 MHz, CDCl$_3$) δ 7.47-7.42 (m, 2H), 7.14-7.10 (m, 2H), 4.27-4.15 (m, 4H), 1.35 (td, J=6.8, 1.2 Hz, 6H); $^{13}$C NMR (100.5 MHz, CDCl$_3$) δ 149.8 (d, J=6.7 Hz), 132.6, 121.8 (d, J=5.2 Hz), 117.8, 64.7 (d, J=6.0 Hz), 16.0 (d, J=6.7 Hz); Spectroscopy data of the compound match with the data reported in the corresponding reference (Jones and Smanmoo (2005) *Org. Lett.* 7: 3271-3274).

v. Diethyl (4-iodophenyl) phosphate (3E')

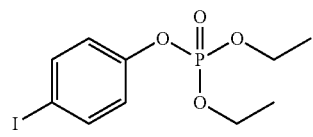

3e'

61.9 mg, 87%; as a colorless oil; $R_f$=0.20 ($v_{Hexane}/v_{EA}$=2:1); $^1$H NMR (400 MHz, CDCl$_3$) δ 7.67-7.62 (m, 2H), 7.03-6.97 (m, 2H), 4.28-4.16 (m, 4H), 1.39-1.32 (m, 6H); $^{13}$C NMR (100.5 MHz, CDCl$_3$) δ 150.7 (d, J=7.4 Hz), 138.7, 122.2 (d, J=5.2 Hz), 88.5, 64.7 (d, J=5.9 Hz), 16.1 (d, J=6.7 Hz); Spectroscopy data of the compound match with the data reported in the corresponding reference (Wang et al. (2014) *Chem. Sci.* 5: 3952-3957).

vi. Diethyl (4-nitrophenyl) phosphate (3F')

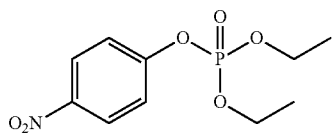

3f'

46.7 mg, 85%; as a colorless oil; $R_f$=0.15 ($v_{Hexane}/v_{EA}$=2:1); $^1$H NMR (400 MHz, CDCl$_3$) δ 8.28-8.22 (m, 2H), 7.43-7.37 (m, 2H), 4.33-4.21 (m, 4H), 1.42-1.36 (m, 6H); $^{13}$C NMR (100.5 MHz, CDCl$_3$) δ 155.5 (d, J=6.7 Hz), 144.6, 125.6, 120.5 (d, J=5.2 Hz), 65.1 (d, J=5.9 Hz), 16.0 (d, J=5.9 Hz); Spectroscopy data of the compound match with the data reported in the corresponding reference (Jones and Smanmoo (2005) *Org. Lett.* 7: 3271-3274).

vii. Diethyl o-tolyl phosphate (3G')

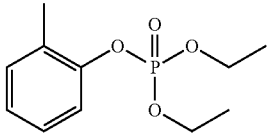

3g'

34.6 mg, 71%; as a colorless oil; $R_f$=0.20 ($v_{Hexane}/v_{EA}$=2:1); $^1$H NMR (400 MHz, CDCl$_3$) δ 7.29 (d, J=8.0 Hz, 1H), 7.21-7.13 (m, 2H), 7.06 (t, J=7.2 Hz, 1H), 4.29-4.15 (m, 4H), 2.32 (s, 3H), 1.38-1.33 (m, 6H); $^{13}$C NMR (100.5 MHz, CDCl$_3$) δ 149.2, 131.3, 129.2 (d, J=6.7 Hz), 126.9, 124.9, 119.7 (d, J=3.0 Hz), 64.5 (d, J=5.9 Hz), 16.3, 16.1 (d, J=6.7 Hz); Spectroscopy data of the compound match with the data reported in the corresponding reference (Jeon et al. (2013) *Tetrahedron* 69: 5152-5159).

viii. Diethyl m-tolyl phosphate (3H')

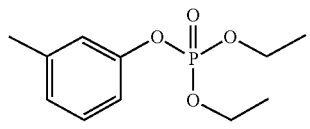

3h'

44.4 mg, 91%; as a colorless oil; $R_f$=0.20 ($v_{Hexane}/v_{EA}$=2:1); $^1$H NMR (400 MHz, CDCl$_3$) δ 7.21 (t, J=7.6 Hz, 1H), 7.06-6.96 (m, 3H), 4.28-4.15 (m, 4H), 2.35 (s, 3H), 1.39-1.33 (m, 6H); $^{13}$C NMR (100.5 MHz, CDCl$_3$) δ 150.7 (d, J=6.6 Hz), 139.9, 129.3, 125.7, 120.5 (d, J=5.2 Hz), 116.8 (d, J=4.4 Hz), 64.5 (d, J=5.9 Hz), 21.3, 16.0 (d, J=6.7 Hz); Spectroscopy data of the compound match with the data reported in the corresponding reference (Jeon et al. (2013) *Tetrahedron* 69: 5152-5159).

ix. [1,1'-biphenyl]-4-yl diethyl phosphate (3I')

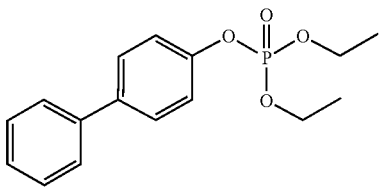

3i'

52.0 mg, 85%; as a colorless oil; $R_f$=0.20 ($v_{Hexane}/v_{EA}$=2:1); IR v (KBr, cm$^{-1}$) 3059, 2985, 2908, 1604, 1516, 1485, 1280, 1222, 1165, 1099, 1033, 960; $^1$H NMR (400 MHz, CDCl$_3$) δ 7.57-7.52 (m, 4H), 7.46-7.40 (m, 2H), 7.37-7.25 (m, 3H), 4.30-4.20 (m, 4H), 1.37 (td, J=7.2, 0.8 Hz, 6H); $^{13}$C NMR (100.5 MHz, CDCl$_3$) δ 150.2 (d, J=6.7 Hz), 140.2, 138.1, 128.8, 128.4, 127.3, 127.0, 120.2 (q, J=5.2 Hz), 64.6 (d, J=5.9 Hz), 16.1 (d, J=6.7 Hz); $^{31}$P NMR (162 MHz, CDCl$_3$): δ −5.63 ppm; HRMS (ESI): m/z calcd. for C$_{16}$H$_{19}$O$_4$P ([M+H]$^+$): 307.1094; Found: 307.1092.

x. Diethyl naphthalen-1-yl phosphate (3J')

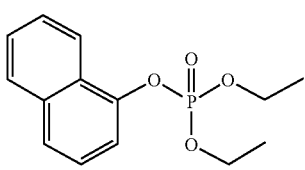

46.4 mg, 82%; as a colorless oil; R$_f$=0.25 (v$_{Hexane}$/v$_{EA}$=2:1); IR ν (KBr, cm$^{-1}$) 3059, 2985, 2908, 1597, 1508, 1462, 1392, 1280, 1234, 1037, 964; $^1$H NMR (400 MHz, CDCl$_3$) δ 8.20-8.16 (m, 1H), 7.87-7.82 (m, 1H), 7.66 (d, J=8.0 Hz, 1H), 7.57-7.48 (m, 3H), 7.41 (dt, J=8.0, 1.2 Hz), 4.33-4.18 (m, 4H), 1.38-1.31 (m, 6H); $^{13}$C NMR (100.5 MHz, CDCl$_3$) δ 146.6 (d, J=7.4 Hz), 134.7, 127.7, 126.6, 126.4 (d, J=6.7 Hz), 126.3, 125.5 (d, J=1.5 Hz), 124.8 (q, J=8.5 Hz), 121.6, 114.8 (d, J=3.0 Hz), 64.7 (d, J=5.9 Hz), 16.1 (d, J=6.7 Hz); $^{31}$P NMR (162 MHz, CDCl$_3$): δ −5.44 ppm; HRMS (ESI): m/z calcd. for C$_{14}$H$_{17}$O$_4$P ([M+H]$^+$): 281.0937; Found: 281.0927.

xi. Diethyl naphthalen-2-yl phosphate (3K')

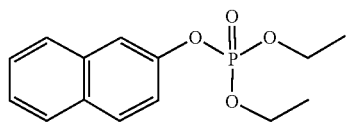

43.6 mg, 78%; as a colorless oil; R$_f$=0.25 (v$_{Hexane}$/v$_{EA}$=2:1); $^1$H NMR (400 MHz, CDCl$_3$) δ 7.81 (t, J=9.2 Hz, 3H), 7.69 (d, J=1.2 Hz, 1H), 7.51-7.41 (m, 2H), 7.39-7.34 (m, 1H), 4.32-4.18 (m, 4H), 1.39-1.33 (m, 6H); $^{13}$C NMR (100.5 MHz, CDCl$_3$) δ 148.3 (d, J=7.5 Hz), 133.9, 130.9, 129.8, 127.7, 127.5, 126.7, 125.4, 120.0 (d, J=5.2 Hz), 116.3 (d, J=4.5 Hz), 64.7 (d, J=6.0 Hz), 16.1 (d, J=6.7 Hz); Spectroscopy data of the compound match with the data reported in the corresponding reference (Panmand et al. (2014) Tetrahedron Lett. 55: 5898-5901).

xii. 2,6-Dimethylphenyl diethyl phosphate (3L')

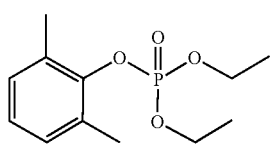

41.3 mg, 80%; as a colorless oil; R$_f$=0.20 (v$_{Hexane}$/v$_{EA}$=2:1); $^1$H NMR (400 MHz, CDCl$_3$) δ 7.04-6.94 (m, 3H), 4.27-4.13 (m, 4H), 2.37 (s, 6H), 1.37-1.31 (m, 6H); $^{13}$C NMR (100.5 MHz, CDCl$_3$) δ 148.1 (d, J=8.1 Hz), 130.3 (d, J=3.8 Hz), 128.9 (d, J=1.5 Hz), 125.0 (d, J=2.2 Hz), 64.4 (d, J=5.9 Hz), 17.1, 16.1 (d, J=6.7 Hz); Spectroscopy data of the compound match with the data reported in the corresponding reference (You et al. (2013) Org. Lett. 15: 1610-1613).

xiii. 2,6-Diisopropylphenyl diethyl phosphate (3M')

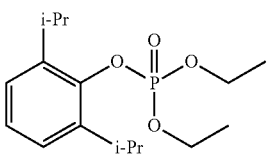

33.4 mg, 53%; as a colorless oil; R$_f$=0.50 (v$_{Hexane}$/v$_{EA}$=2:1); $^1$H NMR (400 MHz, CDCl$_3$) δ 7.15-7.10 (m, 3H), 4.27-4.11 (m, 4H), 3.56-3.45 (m, 2H), 1.36-1.30 (m, 6H), 1.22 (dd, J=6.8, 1.2 Hz, 12H); $^{13}$C NMR (100.5 MHz, CDCl$_3$) δ 145.5, 140.6 (d, J=2.9 Hz), 125.6 (d, J=2.3 Hz), 124.1 (d, J=1.4 Hz), 64.3 (d, J=5.9 Hz), 26.8, 23.5, 16.1 (d, J=6.7 Hz); Spectroscopy data of the compound match with the data reported in the corresponding reference (Guzmin and Diaz (1997) Syn. Commun. 27: 3035-3038).

xiv. Diisopropyl phenyl phosphate (3N')

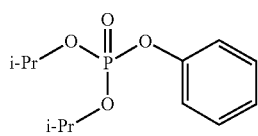

37.7 mg, 73%; as a colorless oil; R$_f$=0.30 (v$_{Hexane}$/v$_{EA}$=2:1); IR ν (KBr, cm$^{-1}$) 2981, 2935, 1593, 1492, 1384, 1276, 1215, 1107, 1010, 941; $^1$H NMR (400 MHz, CDCl$_3$) δ 7.36-7.30 (m, 2H), 7.25-7.20 (m, 2H), 7.18-7.12 (m, 1H), 4.81-4.69 (m, 4H), 1.36 (d, J=6.0 Hz, 3H), 1.31 (d, J=6.0 Hz, 3H); $^{13}$C NMR (100.5 MHz, CDCl$_3$) δ 151.0, 129.5, 124.7, 120.0 (d, J=5.3 Hz), 73.4 (d, J=6.7 Hz), 23.6 (d, J=5.2 Hz), 23.5 (d, J=5.2 Hz); $^{31}$P NMR (162 MHz, CDCl$_3$): δ −7.42 ppm; HRMS (ESI): m/z calcd. for C$_{12}$H$_{19}$O$_4$P ([M+H]$^+$): 259.1094; Found: 259.1091.

xv. Benzyl (4-((diethoxyphosphoryl)Oxy)phenyl) carbonate (3O')

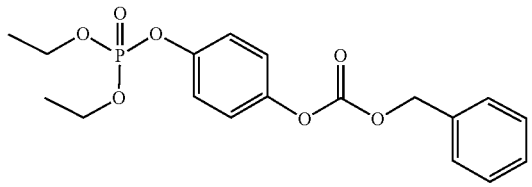

63.8 mg, 84%; as a colorless oil; R$_f$=0.10 (v$_{Hexane}$/v$_{EA}$=2:1); IR ν (KBr, cm$^{-1}$) 3066, 2985, 2912, 1762, 1500, 1265, 1195, 1053, 1029, 960; $^1$H NMR (400 MHz, CDCl$_3$) δ 7.46-7.35 (m, 5H), 7.26-7.20 (m, 2H), 7.18-7.13 (m, 2H), 5.27 (s, 2H), 4.28-4.14 (m, 4H), 1.38-1.32 (m, 6H); $^{13}$C NMR (100.5 MHz, CDCl₃) δ 153.5, 148.3 (d, J=6.7 Hz), 147.8 (d, J=8.5 Hz), 134.6, 128.7 (d, J=11.1 Hz), 128.5, 122.1, 120.8 (d, J=5.2 Hz), 70.4, 64.7 (d, J=6.0 Hz), 16.1, 16.0 (d, J=6.7 Hz); $^{31}$P NMR (162 MHz, CDCl₃): δ −5.77 ppm; HRMS (ESI): m/z calcd. for $C_{18}H_{21}O_7P$ ([M+H]$^+$): 381.1098; Found: 381.1093.

xvi. Diethyl (4-methyl-2-oxo-2H-chromen-7-yl) phosphate (3P')

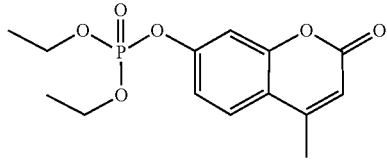

55.5 mg, 89%; as a colorless oil; $R_f$=0.20 ($v_{DCM}/v_{EA}$=5:1); $^1$H NMR (400 MHz, CDCl₃) δ 7.48 (d, J=1.2 Hz, 1H), 7.42-7.38 (m, 1H), 7.31 (d, J=8.8 Hz, 1H), 6.33 (d, J=0.8 Hz, 3H), 4.32-4.18 (m, 4H), 2.44 (d, J=1.2 Hz, 3H), 1.38 (td, J=6.8, 1.2 Hz, 6H); $^{13}$C NMR (100.5 MHz, CDCl₃) δ 160.3, 151.6, 150.4, 146.8 (d, J=6.7 Hz), 123.7 (d, J=4.5 Hz), 120.7, 118.2, 115.8, 115.4 (d, J=5.2 Hz), 64.8 (d, J=5.9 Hz), 18.6, 16.1 (d, J=6.0 Hz); Spectroscopy data of the compound match with the data reported in the corresponding reference (Jeon et al. (2013) *Tetrahedron* 69: 5152-5159).

xvii. Benzo [d][1,3]dioxol-5-yl diethyl phosphate (3Q')

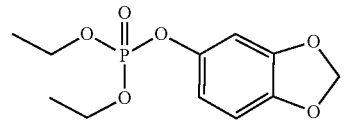

49.8 mg, 91%; as a colorless oil; $R_f$=0.10 ($v_{hexane}/v_{EA}$=2:1); $^1$H NMR (400 MHz, CDCl₃) δ 6.77-6.65 (m, 3H), 5.96 (s, 2H), 4.26-4.16 (m, 4H), 1.40-1.32 (m, 6H); $^{13}$C NMR (100.5 MHz, CDCl₃) δ 148.0, 145.1 (d, J=6.7 Hz), 144.7, 112.3 (d, J=5.2 Hz), 108.0, 102.5 (d, J=4.5 Hz), 101.6, 64.5 (d, J=5.9 Hz), 16.1 (d, J=6.7 Hz); Spectroscopy data of the compound match with the data reported in the corresponding reference (Lazzaroni et al. (2009) *Org. Lett.* 11: 349-352).

xviii. (E)-Ethyl 3-(4-((diethoxyphosphoryl)oxy)-3-methoxyphenyl)acrylate (3R')

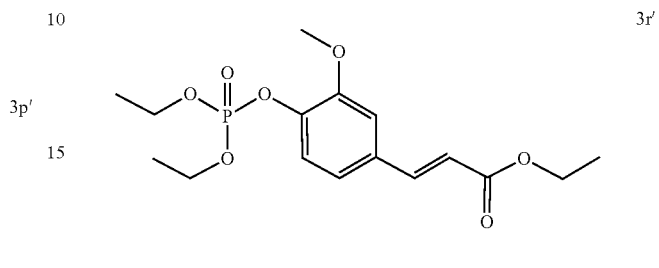

60.1 mg, 84%; as a colorless oil; $R_f$=0.10 ($v_{Hexane}/v_{EA}$=2:1); IR v (KBr, cm$^{-1}$) 2981, 2939, 1708, 1635, 1589, 1512, 1265, 1176, 1161, 1033, 960; $^1$H NMR (400 MHz, CDCl₃) δ 7.62 (d, J=16.0 Hz, 1H), 7.31 (d, J=8.8 Hz, 1H), 7.09 (s, 1H), 7.08 (d, J=6.4 Hz, 1H), 6.37 (d, J=16.0 Hz, 1H), 4.31-4.20 (m, 6H), 3.90 (s, 3H), 1.40-1.22 (m, 9H); $^{13}$C NMR (100.5 MHz, CDCl₃) δ 166.8, 150.9 (d, J=6.0 Hz), 143.7, 141.5 (d, J=6.7 Hz), 132.1 (d, J=1.5 Hz), 121.5 (d, J=3.0 Hz), 121.3, 118.2, 111.4, 64.6 (d, J=6.0 Hz), 60.5, 55.9, 16.0 (d, J=6.7 Hz), 14.3; $^{31}$P NMR (162 MHz, CDCl₃): δ −5.63 ppm; HRMS (ESI): m/z calcd. for $C_{16}H_{23}O_7P$ ([M+H]$^+$): 359.1254; Found: 359.1255.

xix. (3R, 8S, 9R, 10S, 13R, 14R)-8, 9, 10, 13, 14-pentamethyl-17-((R)-6-methylheptan-2-yl)-2, 3, 4, 7, 8, 9, 10, 11, 12, 13, 14, 15, 16, 17-tetradecahydro-1H-cyclopenta[A]phenanthren-3-yl 4-((diethoxyphosphoryl)oxy)benzoate (3S')

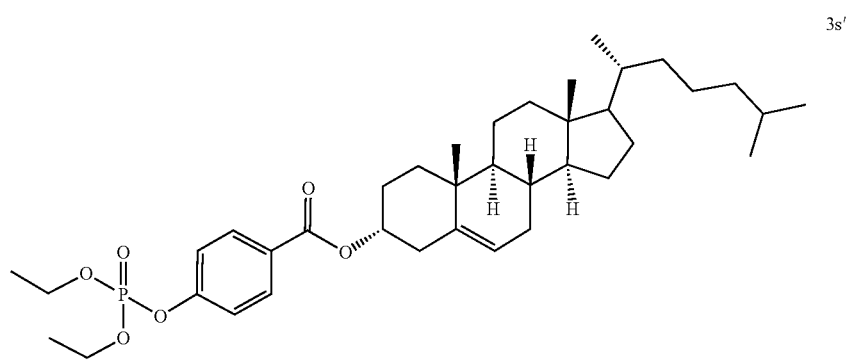

97.6 mg, 76%; as a colorless oil; $R_f$=0.20 ($v_{Hexane}/v_{EA}$=2:1); IR v (KBr, cm$^{-1}$) 2939, 2866, 1716, 1604, 1504, 1465, 1276, 1226, 1056, 1029, 960; $^1$H NMR (400 MHz, CDCl₃) δ 8.00 (dd, J=8.8, 1.2 Hz, 2H), 7.30-7.24 (m, 2H), 5.33-5.29 (m, 1H), 5.23 (s, 1H), 4.30-4.18 (m, 4H), 2.57 (d, J=15.2 Hz, 1H), 2.33 (d, J=15.2 Hz, 1H), 2.07-1.80 (m, 5H), 1.72 (d, J=14.0 Hz, 1H), 1.63-1.01 (m, 29H), 0.93 (d, J=5.6 Hz, 3H), 0.87 (dd, J=6.8, 2.0 Hz, 6H), 0.70 (s, 3H); $^{13}$C NMR (100.5 MHz, CDCl$_3$) δ 165.1, 154.2 (d, J=6.7 Hz), 138.3, 131.4, 127.8, 122.4, 119.7 (d, J=5.2 Hz), 71.3, 64.7 (d, J=6.7 Hz), 56.7, 56.2, 50.3, 42.3, 39.7, 39.5, 37.1, 36.6, 36.2, 35.8, 34.0, 31.9, 31.8, 28.2, 28.0, 26.3, 24.2, 23.8, 22.8, 22.5, 20.8, 18.9, 18.7, 16.0 (d, J=6.7 Hz), 11.8; $^{31}$P NMR (162 MHz, CDCl$_3$): δ −6.21 ppm; HRMS (ESI): m/z calcd. for C$_{38}$H$_{59}$O$_6$P ([M+H]$^+$): 643.4122; Found: 643.4120.

xx. Diethyl (3-phenylpropyl) phosphate (3T′)

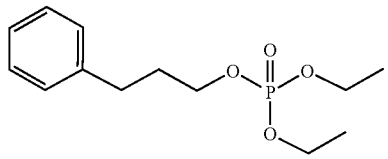

47.3 mg, 87%; as a colorless oil; R$_f$=0.20 (ν$_{Hexane}$/ν$_{EA}$=2:1); IR ν (KBr, cm$^{-1}$) 3028, 2981, 1604, 1496, 1454, 1392, 1273, 1165, 1029, 975; $^1$H NMR (400 MHz, CDCl$_3$) δ 7.32-7.26 (m, 2H), 7.23-7.17 (m, 3H), 4.16-4.02 (m, 6H), 2.73 (t, J=7.6 Hz, 2H), 2.05-1.96 (m, 2H), 1.37-1.32 (m, 6H); $^{13}$C NMR (100.5 MHz, CDCl$_3$) δ 141.0, 128.4, 126.0, 66.7 (d, J=5.9 Hz), 63.7 (d, J=6.0 Hz), 31.9 (d, J=6.7 Hz), 31.6, 16.1 (d, J=6.7 Hz); $^{31}$P NMR (162 MHz, CDCl$_3$): δ −0.28 ppm; HRMS (ESI): m/z calcd. for C$_{13}$H$_{21}$O$_4$P ([M+H]$^+$): 273.1250; Found: 273.1258.

xxi. Diethyl isopropyl phosphate (3U′)

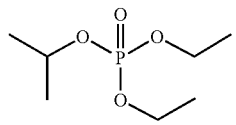

26.1 mg, 65%; as a colorless oil; R$_f$=0.3 (ν$_{EA}$/ν$_{Hexane}$=9:1); $^1$H NMR (400 MHz, CDCl$_3$) δ 4.67-4.62 (1H, m), 4.14-4.06 (4H, m), 1.36-1.32 (12H, m); $^{13}$C NMR (100.5 MHz, CDCl$_3$), δ 72.3 (d, J=6.0 Hz), 63.4 (d, J=6.0 Hz), 23.4 (d, J=5.1 Hz), 16.1 (d, J=6.2 Hz); Spectroscopy data of the compound match with the data reported in the corresponding reference (Jones and Smanmoo (2005) *Org. Lett.* 7: 3271-3274).

xxii. Cyclohexyl diethyl phosphate (3V′)

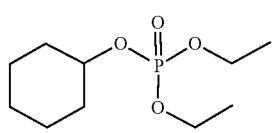

23.1 mg, 49%; as a colorless oil; R$_f$=0.3 (ν$_{EA}$/ν$_{Hexane}$=9:1); $^1$H NMR (400 MHz, CDCl$_3$) δ 4.38-4.35 (1H, m), 4.14-4.06 (4H, m), 1.96-1.93 (2H, m), 1.77-1.74 (2H, m), 1.58-1.50 (3H, m), 1.34 (6H, td, J=7.2 Hz), 1.29-1.23 (3H, m); $^{13}$C NMR (100.5 MHz, CDCl$_3$) δ 77.1 (d, J=7.2 Hz), 63.4 (d, J=6 Hz), 33.3 (d, J=4.5 Hz), 25.0 (d, J=7.5 Hz), 23.4, 16.1 (d, J=6.7 Hz); Spectroscopy data of the compound match with the data reported in the corresponding reference (Jones et al. (2003) *J. Org. Chem.* 68: 5211-5216).

xxiii. Diethyl benzylphosphoramidate (3W′)

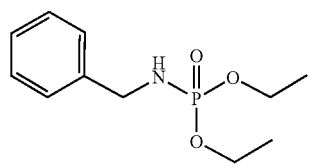

27.2 mg, 56%; as a colorless oil; R$_f$=0.10 (ν$_{DCM}$/ν$_{EA}$=2:1); $^1$H NMR (400 MHz, CDCl$_3$) δ 7.35-7.26 (m, 5H), 4.11-3.94 (m, 6H), 3.40-3.30 (m, 1H), 1.31-1.25 (m, 6H); $^{13}$C NMR (100.5 MHz, CDCl$_3$) δ 139.7 (d, J=6.7 Hz), 128.5, 127.3, 127.2, 62.2 (d, J=5.2 Hz), 45.3, 16.1 (d, J=7.5 Hz); Spectroscopy data of the compound match with the data reported in the corresponding reference (Kadina et al. (2015) *Org. Lett.* 17: 2586-2589).

xxiv. Diethyl cyclohexylphosphoramidate (3X′)

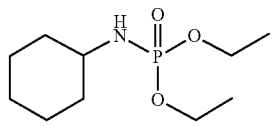

12.3 mg, 25%, as a colorless solid; R$_f$=0.2 (ν$_{DCM}$/ν$_{EA}$=2:1); $^1$H NMR (400 MHz, CDCl$_3$) δ 4.11-4.0 (4H, m), 2.99-2.95 (1H, m), 2.47 (1H, m), 1.94-1.90 (2H, m), 1.72-1.67 (2H, m), 1.59-1.55 (1H, m), 1.33-1.25 (8H, m), 1.18-1.09 (3H, m); $^{13}$C NMR (100.5 MHz, CDCl$_3$) δ 62.1 (d, J=5.2), 50.5, 35.7 (d, J=5.2), 25.4, 24.9, 16.2 (d, J=6.7); Spectroscopy data of the compound match with the data reported in the corresponding reference (Kaboudin et al. (2015) *Tetrahedron Lett.* 56: 6364-6367).

xxv. Diethyl piperidin-1-ylphosphonate (3Y′)

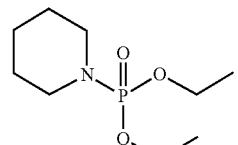

4.2 mg, 10% as a yellow oil; R$_f$=0.2 (ν$_{DCM}$/ν$_{EA}$=2:1); $^1$H NMR (400 MHz, CDCl$_3$) δ 4.06-3.99 (4H, m), 3.12-3.07 (4H, m), 1.58-1.52 (6H, m), 1.31, (6H, td, J=7.2); $^{13}$C NMR (100.5 MHz, CDCl$_3$) δ 61.9 (d, J=6.0 Hz), 45.3 (d, J=2.0

Hz), 26.0 (d, J=5.2 Hz), 24.4, 16.2 (d, J=6.7 Hz); Spectroscopy data of the compound match with the data reported in the corresponding reference (Dhineshkumar and Prabhu (2013) *Org. Lett.* 15: 6062-6065).

xxvi. Diethyl phenylphosphoramidate (3Z')

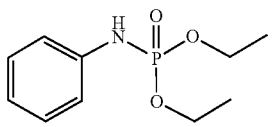

3z'

8.4 mg, 18% as a colorless solid; $R_f$=0.3 ($v_{EA}/v_{Hexane}$=2:1); $^1$H NMR (400 MHz, CDCl$_3$) δ 7.25 (2H, t, J=7.2 Hz), 7.01-6.94 (3H, m), 5.82 (1H, d, J=8.0 Hz), 4.22-4.06 (4H, m), 1.32 (6H, t, J=7.2 Hz); $^{13}$C NMR (100.5 MHz, CDCl$_3$) 139.6, 129.3, 121.6, 117.2 (d, J=8 Hz), 62.7 (d, J=5.2 Hz), 16.1 (d, J=7.0 Hz); Spectroscopy data of the compound match with the data reported in the corresponding reference (Kaboudin et al. (2015) *Tetrahedron Lett.* 56: 6364-6367).

xxvii. O,O-Diethyl S-phenyl phosphorothioate (3AA')

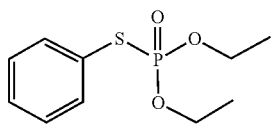

3aa'

16.2 mg, 33%; as a colorless oil; $R_f$=0.20 ($v_{hexane}/v_{EA}$=2:1); $^1$H NMR (400 MHz, CDCl$_3$) δ 7.59-7.54 (m, 2H), 7.37-7.32 (m, 3H), 4.27-4.10 (m, 4H), 1.33-1.27 (m, 6H); $^{13}$C NMR (100.5 MHz, CDCl$_3$) δ 134.5 (d, J=5.3 Hz), 129.3 (d, J=2.2 Hz), 128.9 (d, J=2.9 Hz), 126.6 (d, J=7.5 Hz), 64.0 (d, J=6.0 Hz), 16.0 (d, J=7.4 Hz); Spectroscopy data of the compound match with the data reported in the corresponding reference (Xu et al. (2016) *Org. Lett.* 18: 1266-1269).

d. General Procedure for the Synthesis of Mixed Diaryl Phosphates

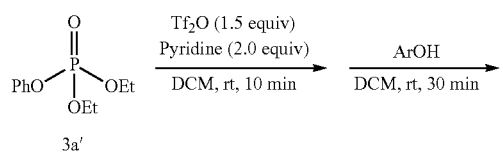

i. Ethyl phenyl p-tolyl phosphate (4A')

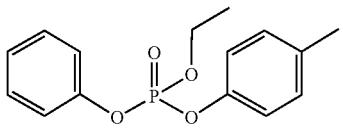

4a'

To a solution of diethyl phenyl phosphate 3a' (46.3 mg, 0.2 mmol), Tf$_2$O (50.5 µL, 0.3 mmol) in DCM (1.0 mL) was added pyridine (32 µL, 0.4 mmol) in a 2-dram vial with a PTFE cap. After stirring for 10 min, p-cresol (43.2 mg, 0.4 mmol) was added to the reaction mixture. After stirring for another 30 min at room temperature, the resulting mixture was concentrated to give the crude product which was then purified by column chromatography on silica gel (PE/EA=5:1) to afford ethyl phenyl benzylphosphonate (3a'): 49.6 mg, 85%; as a colorless oil; $R_f$=0.20 ($v_{Hexane}/v_{EA}$=5:1); $^1$H NMR (400 MHz, CDCl$_3$) δ 7.36-7.30 (m, 2H), 7.25-7.15 (m, 3H), 7.14-7.08 (m, 4H), 4.35-4.27 (m, 2H), 2.32 (s, 3H), 1.36 (td, J=6.8, 1.2 Hz, 3H); $^{13}$C NMR (100.5 MHz, CDCl$_3$) δ 150.6 (d, J=6.7 Hz), 148.4 (d, J=6.7 Hz), 134.9 (d, J=1.5 Hz), 130.2, 129.7, 125.2, 120.0 (d, J=4.5 Hz), 119.7 (d, J=5.2 Hz), 65.4 (d, J=6.7 Hz), 20.7, 16.0 (d, J=6.7 Hz); Spectroscopy data of the compound match with the data reported in the corresponding reference (Dhawan and Redmore (1986) *J. Org. Chem.* 51: 179-183).

ii. Ethyl (4-methoxyphenyl) phenyl phosphate (4B')

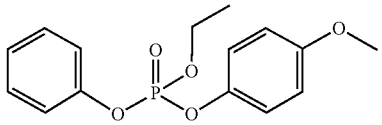

4b'

54.2 mg, 88%; as a colorless oil; $R_f$=0.10 ($v_{Hexane}/v_{EA}$=5:1); IR ν (KBr, cm$^{-1}$) 3066, 2985, 2912, 1593, 1504, 1288, 1188, 1037, 956; $^1$H NMR (400 MHz, CDCl$_3$) δ 7.36-7.30 (m, 2H), 7.24-7.12 (m, 5H), 6.86-6.81 (m, 2H), 4.35-4.27 (m, 2H), 3.78 (s, 3H), 1.39-1.33 (m, 6H); $^{13}$C NMR (100.5 MHz, CDCl$_3$) δ 156.8, 150.6 (d, J=7.4 Hz), 144.1 (d, J=7.5 Hz), 129.7, 125.2, 120.9 (d, J=4.5 Hz), 120.0 (d, J=4.5 Hz), 114.6, 65.4 (d, J=5.9 Hz), 55.6, 16.1 (d, J=6.7 Hz); $^{31}$P NMR (162 MHz, CDCl$_3$): δ –10.78 ppm; HRMS (ESI): m/z calcd. for C$_{15}$H$_{17}$O$_5$P ([M+H]$^+$): 309.0886; Found: 309.0876.

iii. 4-Bromophenyl ethyl phenyl phosphate (4C')

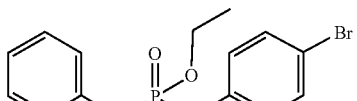

4c'

58.3 mg, 82%; as a colorless oil; $R_f$=0.10 ($v_{Hexane}/v_{EA}$=5:1); IR ν (KBr, cm$^{-1}$) 3066, 2985, 2912, 1589, 1485, 1292, 1195, 1165, 1041, 984; $^1$H NMR (400 MHz, CDCl$_3$) δ

7.47-7.42 (m, 2H), 7.37-7.31 (m, 2H), 7.24-7.17 (m, 3H), 7.14-7.09 (m, 2H), 4.37-4.28 (m, 2H), 1.37 (td, J=7.2, 1.2 Hz, 3H); $^{13}$C NMR (100.5 MHz, CDCl$_3$) δ 150.4 (d, J=7.5 Hz), 149.6 (d, J=6.7 Hz), 132.7, 129.8 (d, J=6.0 Hz), 125.4 (d, J=1.5 Hz), 121.9 (d, J=5.2 Hz), 120.0 (d, J=4.5 Hz), 118.2 (d, J=1.5 Hz), 65.7 (d, J=6.7 Hz), 16.0 (d, J=6.7 Hz); $^{31}$P NMR (162 MHz, CDCl$_3$): δ −11.50 ppm; HRMS (ESI): m/z calcd. for C$_{14}$H$_{14}$O$_4$PBr ([M+H]$^+$): 356.9886; Found: 356.9869.

iv. Ethyl (4-iodophenyl) phenyl phosphate (4D')

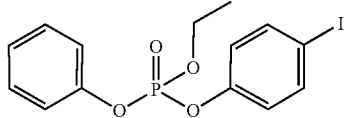

4d'

61.3 mg, 76%; as a colorless oil; R$_f$=0.10 (ν$_{Hexane}$/ν$_{EA}$=5:1); IR ν (KBr, cm$^{-1}$) 3066, 2981, 1589, 1481, 1288, 1226, 1195, 1165, 1041, 952; $^1$H NMR (400 MHz, CDCl$_3$) δ 7.66-7.61 (m, 2H), 7.37-7.31 (m, 2H), 7.24-7.17 (m, 3H), 7.02-6.97 (m, 2H), 4.36-4.28 (m, 2H), 1.37 (td, J=7.2, 1.2 Hz, 3H); $^{13}$C NMR (100.5 MHz, CDCl$_3$) δ 150.5 (d, J=6.7 Hz), 150.4 (d, J=7.5 Hz), 138.8, 129.8, 125.4, 122.3 (d, J=5.2 Hz), 120.0 (d, J=4.5 Hz), 89.0, 65.7 (d, J=6.0 Hz), 16.1 (d, J=6.0 Hz); $^{31}$P NMR (162 MHz, CDCl$_3$): δ −11.54 ppm; HRMS (ESI): m/z calcd. for C$_{14}$H$_{14}$O$_4$PI ([M+Na]$^+$): 426.9567; Found: 426.9569.

v. Ethyl phenyl (3-(trifluoromethyl)Phenyl) phosphate (4E')

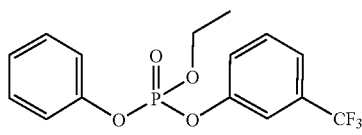

4e'

52.6 mg, 76%; as a colorless oil; R$_f$=0.10 (ν$_{Hexane}$/ν$_{EA}$=5:1); IR ν (KBr, cm$^{-1}$) 3074, 2989, 2912, 1593, 1492, 1450, 1327, 1296, 1195, 1130, 1041, 960; $^1$H NMR (400 MHz, CDCl$_3$) δ 7.50-7.42 (m, 4H), 7.38-7.32 (m, 2H), 7.25-7.18 (m, 3H), 4.40-4.31 (m, 2H), 1.39 (td, J=7.2, 1.2 Hz, 3H); $^{13}$C NMR (100.5 MHz, CDCl$_3$) δ 150.7 (d, J=6.7 Hz), 150.3 (d, J=6.7 Hz), 132.3 (q, J=33.5 Hz), 130.4, 129.9, 125.5, 123.5 (d, J=4.4 Hz), 123.3 (d, J=270.9 Hz), 122.0 (m), 120.0 (d, J=5.2 Hz), 117.4 (m), 65.8 (d, J=5.9 Hz), 16.0 (d, J=5.9 Hz); $^{31}$P NMR (162 MHz, CDCl$_3$): δ −11.59 ppm; HRMS (ESI): m/z calcd. for C$_{15}$H$_{14}$O$_4$F$_3$P ([M+H]$^+$): 347.0655; Found: 347.0640.

vi. 2-Cyanophenyl ethyl phenyl phosphate (4F')

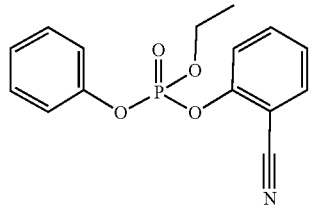

4f'

44.8 mg, 74%; as a colorless oil; R$_f$=0.10 (ν$_{Hexane}$/ν$_{EA}$=3:1); IR ν (KBr, cm$^{-1}$) 3070, 2985, 2912, 2233, 1600, 1489, 1450, 1296, 1203, 1184, 1165, 1037, 952; $^1$H NMR (400 MHz, CDCl$_3$) δ 7.68-7.62 (m, 1H), 7.61-7.53 (m, 2H), 7.39-7.32 (m, 2H), 7.30-7.25 (m, 3H), 7.24-7.18 (m, 1H), 4.49-4.40 (m, 2H), 1.42 (td, J=6.8, 1.2 Hz, 3H); $^{13}$C NMR (100.5 MHz, CDCl$_3$) δ 152.0 (d, J=6.0 Hz), 150.2 (d, J=7.5 Hz), 134.4 (d, J=1.5 Hz), 133.6, 129.9, 125.7, 125.4, 120.6 (d, J=3.0 Hz), 120.0 (d, J=4.5 Hz), 115.0 (d, J=1.5 Hz), 105.6 (d, J=7.4 Hz), 66.5 (d, J=6.7 Hz), 16.0 (d, J=6.7 Hz); $^{31}$P NMR (162 MHz, CDCl$_3$): δ −12.50 ppm; HRMS (ESI): m/z calcd. for C$_{15}$H$_{14}$NO$_4$P ([M+H]$^+$): 304.0733; Found: 304.0724.

vii. [1,1'-Biphenyl]-4-yl ethyl phenyl phosphate (4G')

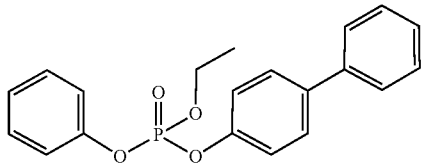

4g'

46.4 mg, 80%; as a colorless oil; R$_f$=0.10 (ν$_{Hexane}$/ν$_{EA}$=5:1); IR ν (KBr, cm$^{-1}$) 3059, 2985, 1593, 1516, 1485, 1292, 1226, 1195, 1165, 1041, 952; $^1$H NMR (400 MHz, CDCl$_3$) δ 7.57-7.52 (m, 4H), 7.45-7.40 (m, 2H), 7.38-7.23 (m, 7H), 7.22-7.16 (m, 1H), 4.39-4.30 (m, 2H), 1.39 (td, J=7.2, 1.2 Hz, 3H); $^{13}$C NMR (100.5 MHz, CDCl$_3$) δ 150.6 (d, J=7.5 Hz), 150.0 (d, J=6.7 Hz), 140.1, 138.4, 129.8, 128.8, 128.4, 127.4, 127.0, 125.3 (d, J=1.5 Hz), 120.3 (d, J=5.2 Hz), 120.1 (d, J=5.2 Hz), 65.6 (d, J=6.0 Hz), 16.1 (d, J=6.7 Hz); $^{31}$P NMR (162 MHz, CDCl$_3$): δ −11.22 ppm; HRMS (ESI): m/z calcd. for C$_{20}$H$_{19}$O$_4$P ([M+H]$^+$): 355.1094; Found: 355.1104.

viii. Ethyl naphthalen-1-yl phenyl phosphate (4H')

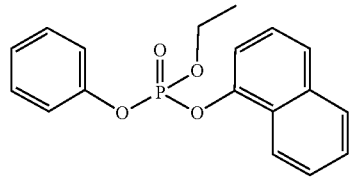

4h'

47.9 mg, 73%; as a colorless oil; R$_f$=0.10 (ν$_{Hexane}$/ν$_{EA}$=5:1); IR ν (KBr, cm$^{-1}$) 3062, 2985, 2908, 1597, 1489, 1392, 1292, 1207, 1087, 1037, 948; $^1$H NMR (400 MHz, CDCl$_3$) δ 8.10-8.05 (m, 1H), 7.86-7.81 (m, 1H), 7.67 (dd, J=8.4, 0.8 Hz, 1H), 7.53-7.48 (m, 3H), 7.40 (t, J=8.0 Hz, 1H), 7.36-7.30 (m, 2H), 7.27-7.22 (m, 2H), 7.21-7.15 (m, 1H), 4.41-4.30 (m, 2H), 1.35 (td, J=7.2, 1.2 Hz, 3H); $^{13}$C NMR (100.5 MHz, CDCl$_3$) δ 150.6 (d, J=7.4 Hz), 146.5 (d, J=7.3 Hz), 134.7, 129.8, 127.7, 126.6, 126.4, 126.3 (d, J=6.7 Hz), 125.4 (d, J=2.2 Hz), 125.3, 125.1 (d, J=1.5 Hz), 121.6, 120.1 (d, J=5.2 Hz), 115.0 (d, J=3.0 Hz), 65.7 (d, J=5.9 Hz), 16.1 (d, J=6.0 Hz); $^{31}$P NMR (162 MHz, CDCl$_3$): δ −11.03 ppm; HRMS (ESI): m/z calcd. for C$_{18}$H$_{17}$O$_4$P ([M+H]$^+$): 329.0937; Found: 329.0942.

ix. Ethyl naphthalen-2-yl phenyl phosphate (4I')

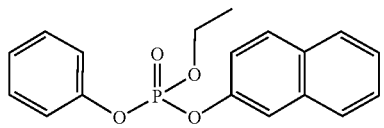

4i'

55.7 mg, 85%; as a colorless oil; $R_f$=0.10 ($v_{Hexane}/v_{EA}$=5:1); IR ν (KBr, cm$^{-1}$) 3059, 2985, 2912, 1631, 1593, 1508, 1489, 1465, 1292, 1041, 972; $^1$H NMR (400 MHz, CDCl$_3$) δ 7.82 (d, J=8.4 Hz, 2H), 7.79 (d, J=8.0 Hz, 1H), 7.70 (s, 1H), 7.51-7.42 (m, 2H), 7.37-7.31 (m, 3H), 7.27-7.23 (m, 2H), 7.21-7.16 (m, 1H), 4.40-4.31 (m, 2H), 1.38 (td, J=7.2, 1.2 Hz, 3H); $^{13}$C NMR (100.5 MHz, CDCl$_3$) δ 150.6 (d, J=7.5 Hz), 148.2 (d, J=7.5 Hz), 133.8, 131.0, 129.9, 129.8, 127.7, 127.6, 126.8, 125.6, 125.3 (d, J=1.5 Hz), 120.1 (d, J=4.5 Hz), 119.9 (d, J=5.2 Hz), 116.6 (d, J=4.5 Hz), 65.6 (d, J=6.7 Hz), 16.1 (d, J=6.7 Hz); $^{31}$P NMR (162 MHz, CDCl$_3$): δ -11.25 ppm; HRMS (ESI): m/z calcd. for C$_{18}$H$_{17}$O$_4$P ([M+H]$^+$): 329.0937; Found: 329.0929.

x. Benzo [d][1,3]dioxol-5-yl ethyl phenyl phosphate (4J')

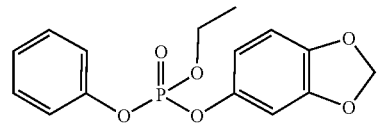

4j'

52.1 mg, 81%; as a colorless oil; $R_f$=0.10 ($v_{Hexane}/v_{EA}$=5:1); IR ν (KBr, cm$^{-1}$) 2985, 2904, 1593, 1485, 1292, 1246, 1126, 1037, 964; $^1$H NMR (400 MHz, CDCl$_3$) δ 7.37-7.31 (m, 2H), 7.24-7.16 (m, 2H), 6.76-6.66 (m, 3H), 5.96 (s, 2H), 4.35-4.27 (m, 2H), 1.37 (td, J=7.2, 1.2 Hz, 3H); $^{13}$C NMR (100.5 MHz, CDCl$_3$) δ 150.6, 148.1, 144.9, 144.8, 129.7, 125.3 (d, J=1.5 Hz), 120.0 (d, J=5.2 Hz), 112.5 (d, J=5.2 Hz), 108.0, 102.5 (d, J=4.5 Hz), 101.7, 65.5 (d, J=6.0 Hz), 16.0 (d, J=6.0 Hz); $^{31}$P NMR (162 MHz, CDCl$_3$): δ -10.88 ppm; HRMS (ESI): m/z calcd. for C$_{15}$H$_{15}$O$_6$P ([M+H]$^+$): 323.0679; Found: 323.0687.

xi. (E)-Ethyl phenyl (4-(phenyldiazenyl)phenyl) phosphate (4K')

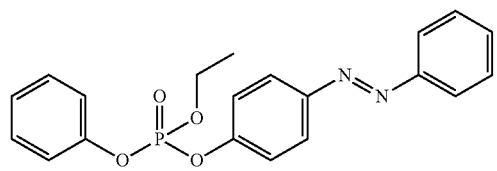

4k'

66.4 mg, 87%; as a colorless oil; $R_f$=0.20 ($v_{Hexane}/v_{EA}$=3:1); IR ν (KBr, cm$^{-1}$) 3066, 2985, 2908, 1593, 1489, 1296, 1230, 1192, 1041, 952; $^1$H NMR (400 MHz, CDCl$_3$) δ 7.96-7.88 (m, 4H), 7.54-7.44 (m, 3H), 7.41-7.32 (m, 4H), 7.27-7.17 (m, 3H), 4.41-4.32 (m, 2H), 1.39 (td, J=7.6, 1.2 Hz, 3H); $^{13}$C NMR (100.5 MHz, CDCl$_3$) δ 152.4 (d, J=2.2 Hz), 150.4 (d, J=7.5 Hz), 149.8 (d, J=1.5 Hz), 131.1, 129.8, 129.1, 125.4 (d, J=1.5 Hz), 124.4, 122.8, 120.6 (d, J=5.2 Hz), 120.1, 120.0, 65.7 (d, J=6.7 Hz), 16.1 (d, J=6.7 Hz); $^{31}$P NMR (162 MHz, CDCl$_3$): δ -11.68 ppm; HRMS (ESI): m/z calcd. for C$_{20}$H$_{19}$N$_2$O$_4$P ([M+H]$^+$): 383.1155; Found: 383.1152.

e. General Procedure for the Synthesis of Aryl Phosphinate

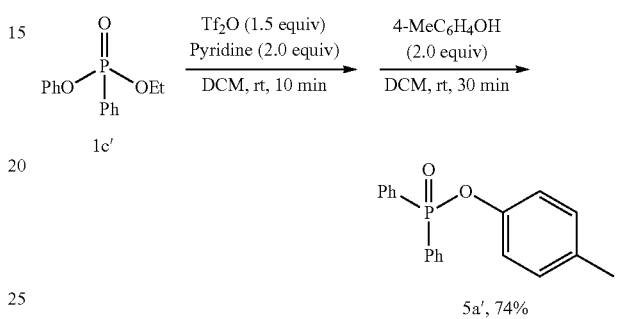

i. p-tolyl diphenylphosphinate (5A')

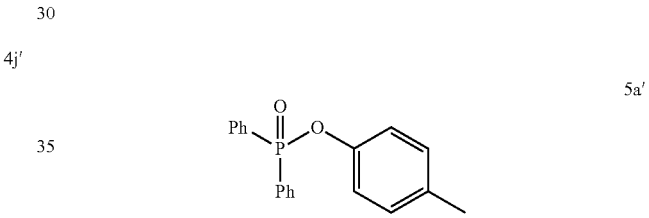

5a'

To a solution of ethyl diphenylphosphinate 1c' (49.3 mg, 0.2 mmol), Tf$_2$O (50.5 μL, 0.3 mmol) in DCM (1.0 mL) was added pyridine (32 μL, 0.4 mmol) in a 2-dram vial with a PTFE cap. After stirring for 10 min, p-cresol (43.6 mg, 0.4 mmol) was added to the reaction mixture. After stirring for another 30 min at room temperature, the resulting mixture was concentrated to give the crude product which was then purified by column chromatography on silica gel (PE/EA=5:1) to afford p-Tolyl diphenylphosphinate (5$^{a'}$): 45.6 mg, 74%; as a colorless oil; $R_f$=0.50 ($v_{Hexane}/v_{EA}$=1:1); $^1$H NMR (400 MHz, CDCl$_3$) δ 7.93-7.84 (m, 4H), 7.56-7.42 (m, 6H), 7.11-6.98 (m, 4H), 2.23 (s, 3H); $^{13}$C NMR (100.5 MHz, CDCl$_3$) δ 148.6 (d, J=7.4 Hz), 134.0, 132.3 (d, J=3.0 Hz), 131.8 (d, J=10.4 Hz), 131.1 (d, J=137.0 Hz), 130.1, 128.6, 128.4, 120.4 (d, J=4.5 Hz), 20.6; Spectroscopy data of the compound match with the data reported in the corresponding reference (Xiong et al. (2015) *ACS Catal.* 5: 537-543).

f. Large-Scale Experiment

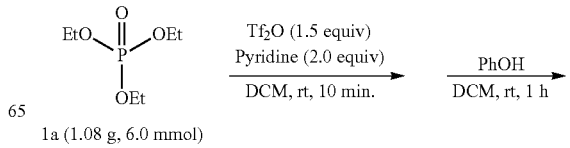

-continued

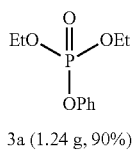

3a (1.24 g, 90%)

To a solution of triethyl phosphate 1a' (1.08 g, 6.0 mmol) in DCM (30 mL) was added Tf₂O (1.50 mL, 9.0 mmol) and pyridine (1.00 mL 12.0 mmol) in a 48 mL glass tube (Figure S1, tube C). The resulting mixture was stirred for 10 min. After stirring for 10 min, phenol (1.14 g, 12.0 mmol) was added to the tube under. After stirring for another 1 h, the resulting solution was concentrated to give the crude product which was purified by column chromatography on silica gel (PE/EA=3:1-2:1) to afford 3a' (1.24 g, 90%).

g. Continuous Flow Chemistry

All tubings, connectors and needles were purchased from VWR international, unless otherwise stated. Syringe pump was purchased from KD Scientific—The Syringe Pump Company. The equipment configurations that were used for the flow reactions are depicted in Figure S2. The tubing reactors and all connecting tubings in all figures use Chemfluor®PTFE Fluoropolymer Tubing (1/16"I.D.×1/8" O.D.).

h. General Procedure for Flow Synthesis Experiment in 2 mmol Scale (3a' as Example)

Syringe A was loaded with a solution of phosphoryl pyridine-1-ium (0.4 M) in DCM and then fitted to a syringe pump. Syringe B was loaded with a solution of phenol 2a' (0.8 M) in DCM and then fitted to a same syringe pump. Following the setup as shown in Figure S2, the solutions of phosphoryl pyridine-1-ium and 2a' were injected in the tubing reactor over 30 min. After reaching steady state for 30 min, the reaction mixtures were collected by argon purging into a flask. The collected solution was evaporated under reduced pressure, and the residue was purified by flash column chromatography on silica gel (eluent: from hexane to hexane:EA=2:1) to give the colorless oil product 3a': 358 mg in 78% yield.

2. Synthesis of Mixed Phosphonates a. Initial Screening of Nucleophiles

To test the hypothesis, Tf₂O, pyridine, and diethyl benzylphosphonate 1a were utilized to screen nucleophiles and the outcomes are shown in Scheme 1 below. When Grignard reagent and morpholine were employed as nucleophiles, a mixture of unidentified compounds were generated. Thiophenol and 2-naphtol substrates, in which only thiophenol triflate and morpholine triflate were isolated in 35% and 37% yields, respectively, also failed to give the corresponding mixed phosphonates. Notably, when phenol was introduced as a nucleophile, mixed phosphonate 3a was furnished in 77% NMR yield, which evidenced a new potential route for mixed phosphonate synthesis. With promising initial results, it was decided to further explore this direct aryloxylation of various dialkyl phosphonates.

SCHEME 1.

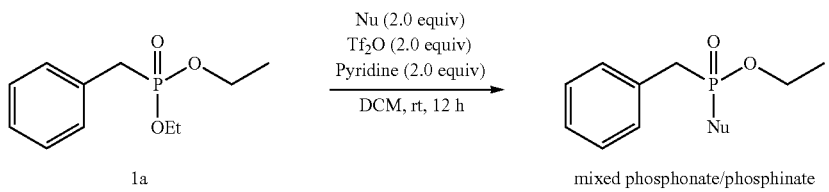

Nu:

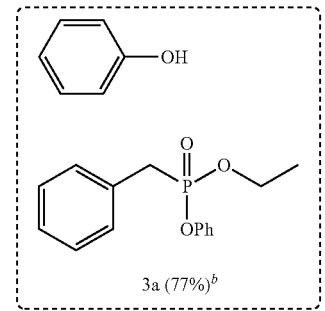

Outcomes:

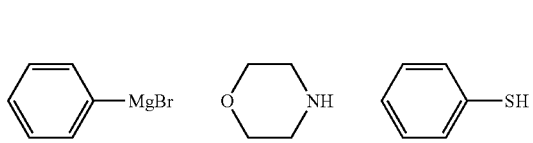

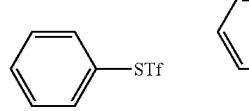

Reaction conditions: 1a (0.2 mmol), Tf₂O (0.4 mmol), Nu (0.4 mmol), pyridine (0.4 mmol) in DCM (1.0 mL) for 12 h. [a]Isolated yields. [b]Yields was determined by ¹H NMR on the crude reaction mixture using 1,3,5-trimethylbenzene as an internal standard.

b. Optimization of Reaction Conditions

Optimization of the reaction conditions was carried out with diethyl benzylphosphonate 1a and phenol 2a. Initially, pre-activation time for the generation of the intermediate III shown in FIG. 3 was studied. It was found that a pre-reaction time of 10 min prior to the addition of 2a to a mixture of 1a and $Tf_2O$/pyridine is required for high yields (Table 1, entry 1). Screening of other bases did not improve the product yield but a phenyl triflate byproduct was formed. In contrast, there was no target product without bases (Table 1, entry 2). Among the screened solvents, DCM is superior to other solvents (Table 1, entries 3-8). Further optimization revealed that the highest yield of 3a (99% yield by NMR) could be achieved with an excess of $Tf_2O$ (1.5 equiv), pyridine (2.0 equiv), and phenol 2a (2.5 equiv) (Table 1, entry 9).

TABLE 1

| entry | base | solvent | X:Y:Z | yield (%)[a] |
|---|---|---|---|---|
| 1 | pyridine | DCM | 2.0:2.0:2.0 | 85 |
| 2 | — | DCM | 2.0:2.0:2.0 | NR |
| 3 | pyridine | CHCl$_3$ | 2.0:2.0:2.0 | 37 |
| 4 | pyridine | DCE | 2.0:2.0:2.0 | 49 |
| 5 | pyridine | Et$_2$O | 2.0:2.0:2.0 | 46 |
| 6 | pyridine | toluene | 2.0:2.0:2.0 | 36 |
| 7 | pyridine | THF | 2.0:2.0:2.0 | NR |
| 8 | pyridine | CH$_3$CN | 2.0:2.0:2.0 | trace |
| 9 | pyridine | DCM | 1.5:2.0:2.5 | 99(92)[b] |

Reaction conditions: 1a (0.2 mmol), $Tf_2O$ (X equiv), base (Y equiv) in solvent (1.0 mL) for 10 min, then PhOH (Z equiv) for 30 min. [a]Yield was determined by $^1H$ NMR on the crude reaction mixture using 1,3,5-trimethylbenzene as an internal standard. [b]Isolated yield.

c. Exploration of Reaction Scope

With the optimized reaction conditions in hand, the scope of the reaction was explored with diverse dialkyl phosphonates 1, demonstrating efficient substrates to form mixed alkyl aryl phosphonates 3a-3x (Scheme 2). Different substituents on the benzyl group were well tolerated (86-94% yields) (Scheme 2, 3a-3g). Phosphonates with aliphatic substituents 1h-1j are also suitable substrates for this reaction to provide alkyl-substituted mixed phosphonates 3h-3j in 85-90% yields. In addition, phenyl phosphonates 1k-1n with different alkoxy substituents MeO, EtO, i-PrO, and n-BuO were examined, and they afforded the corresponding mixed phosphonates 3k-3n in 81-93% yields. In line with the hypothesis of favoring electron-rich substituents on the phosphonate motif for the activation with $Tf_2O$, the electronic effects of the phenyl substituents on the phosphonates have significant influence on the product yield: for example, an electron-deficient phosphonate 1o with a p-nitro phenyl substituent provided the product 3o in 28% yield (Scheme 2). This reaction shows broad compatibility with a diverse array of substrates bearing halide, allylic, vinyl, alkyne, and diene groups (Scheme 2, 3p-3v). A heteroaromatic phosphonate was also efficiently transformed to the desired mixed phosphonate 3w in 83% yield. Importantly, the synthesis of O-ethyl O-, S-diphenyl phosphorothioate 3x known as a classical antibacterial agent (Kazuo et al. JP 48018461 B 19730606, 1973) was demonstrated by this system with 81% yield.

Next, the scope was investigated with respect to phenol derivatives. The reaction tolerates both electron-donating groups (Me, MeO) and electron-deficient substituents (Br, I, NO$_2$, CF$_3$) on the phenyl ring, providing the desired products in high yields (Scheme 2, 4a-4h). Ortho-, para-substituted dichlorophenol was a suitable substrate for this transformation to afford 4i in 77% yield. In contrast, having bulky groups on 2-, 6-positions on phenols significantly reduced the product yields (Scheme 2, 4k-4l). As compared to initial experimental results with no pre-activation process, polycyclic aromatic alcohols such as 1-naphthol, 2-naphthol, and quinolin-6-ol proved to be suitable substrates under the optimized reaction conditions, affording the mixed phosphonates 4n-4p in 70-87% yields. In addition, this method tolerates a wide range of functional groups (e.g., ester, carbonate, allyl, azo, and acrylate) on the phenol (Scheme 2, 4q-4u). Especially, the reaction of 1a with cholesterol-derived phenol proceeded efficiently to give 4v as a phosphonylated cholesteryl ester derivative bearing a biologically important mixed phosphonate scaffold in 84% yield (Scheme 2, 4v).

With a demonstration of aryloxylation of phosphonates with various phenol derivatives, the reactivity of aliphatic alcohols under the same reaction conditions was explored (Scheme 2). It was found that various alcohols such as 1° alcohols and 2° alcohol were all efficiently coupled with dialkylphosphonates to provide mixed phosphonates 5a-5h in moderate to high yields.

SCHEME 2.

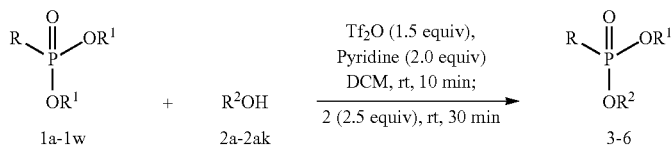

-continued
Phosphonates
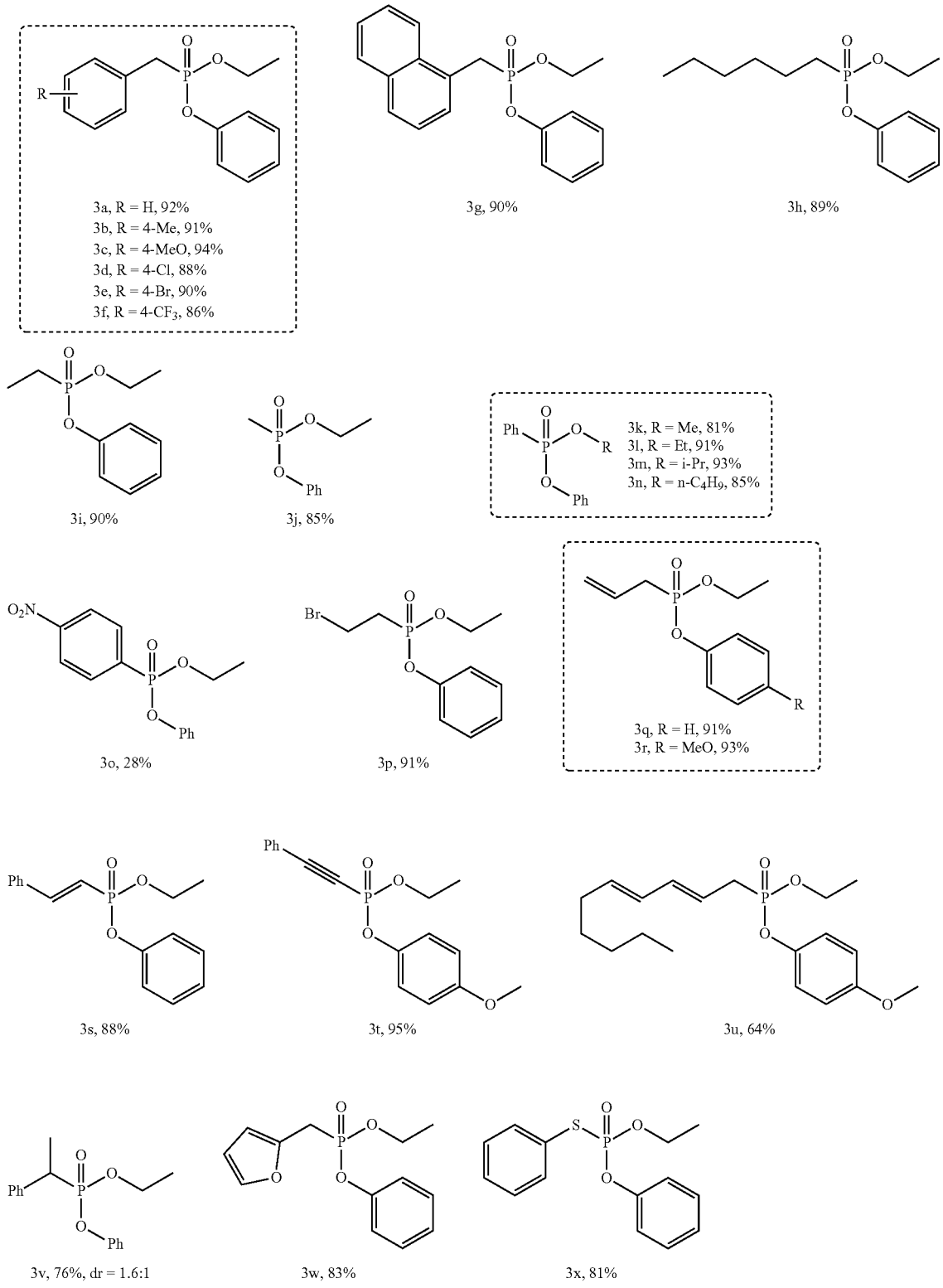

Aryl Alcohols
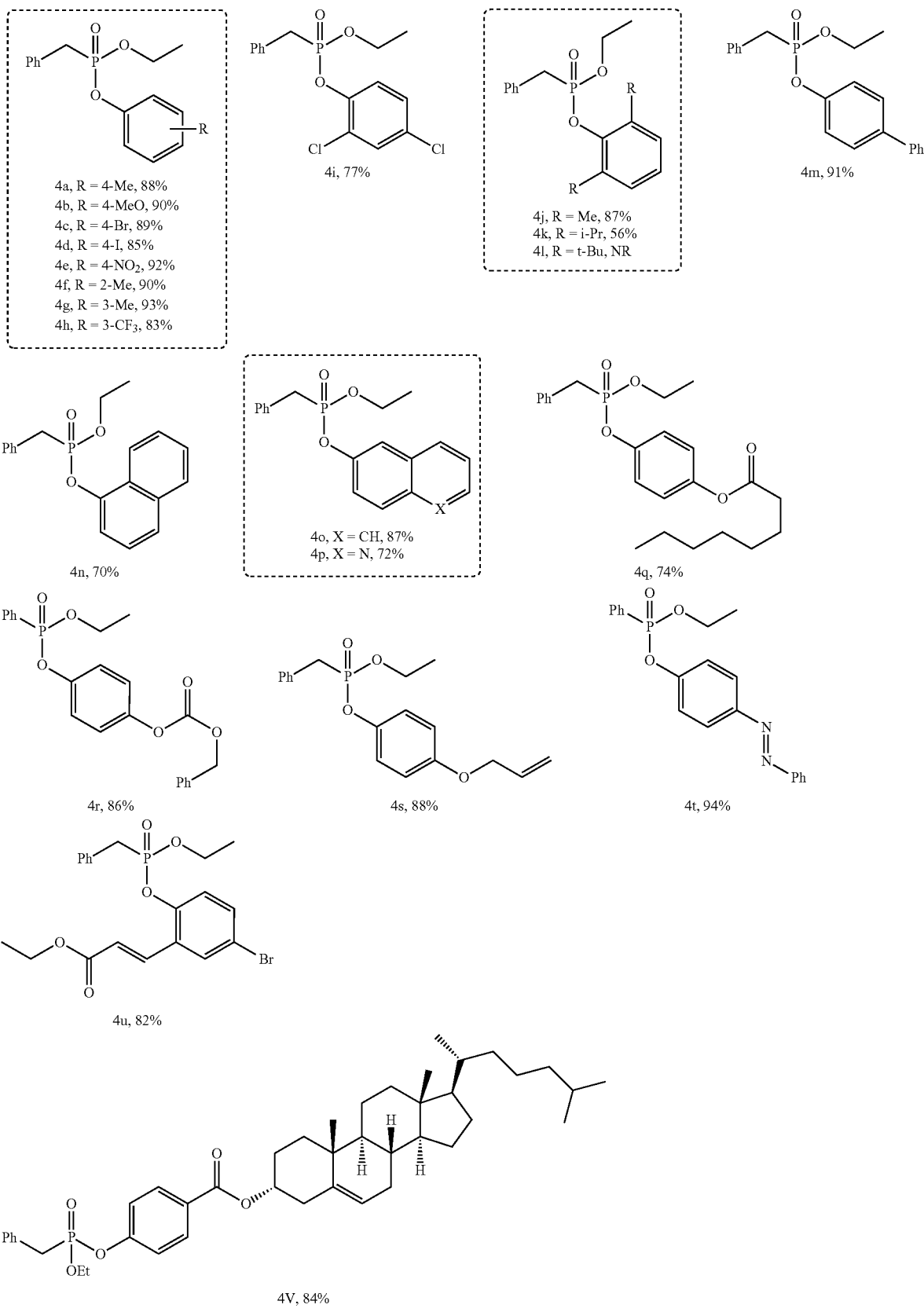

Aliphatic Alcohols

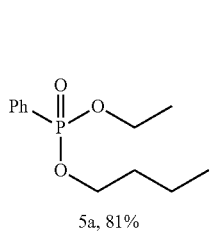
5a, 81%

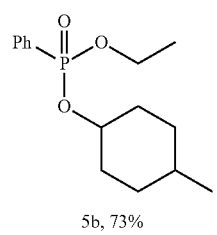
5b, 73%

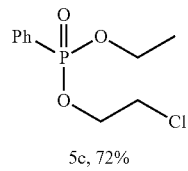
5c, 72%

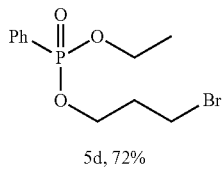
5d, 72%

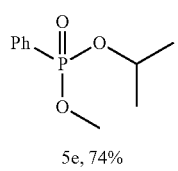
5e, 74%

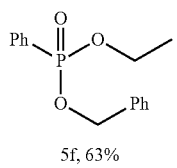
5f, 63%

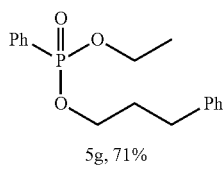
5g, 71%

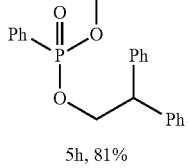
5h, 81%

Natural Compounds

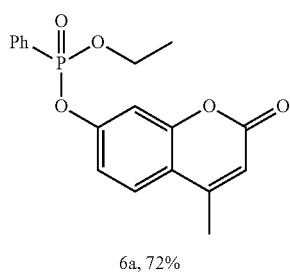
6a, 72%
from coumarins

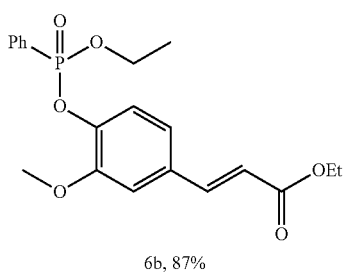
6b, 87%
from ethyl ferulate

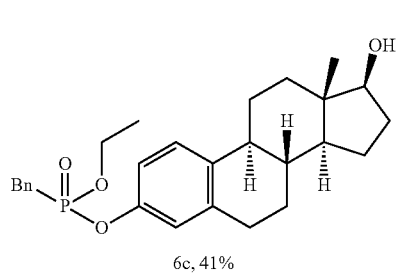
6c, 41%
from estradiol

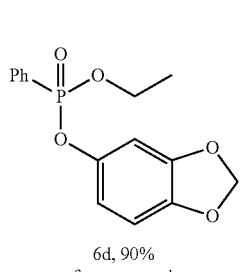
6d, 90%
from sesamol

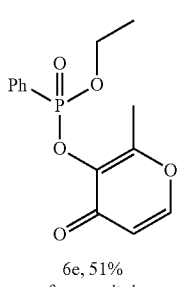
6e, 51%
from maltol

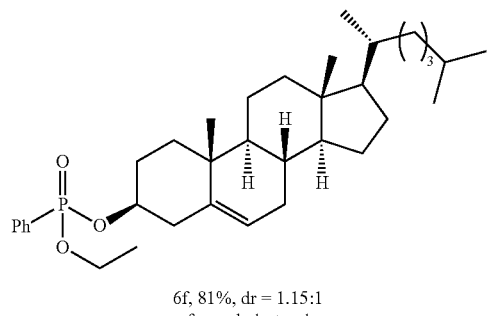
6f, 81%, dr = 1.15:1
from cholesterol

Next, late-stage phosphonylation of various natural products was investigated to demonstrate functionalization of bioactive small molecules (Scheme 2). The phosphonylation reaction of natural compounds such as coumarin 2af, ferulate 2ag, and estradiol 2ah exhibited good functional group tolerance (e.g., ester, acrylate, ether, and hydroxyl group) and provided the corresponding products in moderate to high yields (Scheme 2, 6a-6c). It is worth mentioning that this protocol shows an excellent chemoselectivity with estradiol 2ah bearing both aryl alcohol and aliphatic alcohol, providing only 6c with 41% yield. In addition, sesamol 2ai afforded the corresponding mixed phosphonate 6d in excellent yield (90% yield). An enol nucleophile of maltol was also a suitable coupling partner for this transformation to furnish the desired mixed phosphonate 6e in 51% yield. Finally, aliphatic alcohol-containing natural product cholesterol 2ak was subjected to the standard reaction conditions, and the target mixed phosphonate product 6f (Kalek et al. (2008) *Org. Lett.* 10: 4637) was isolated with 81% yield.

d. Potential Applications to Pharmaceuticals and Organic Synthesis

To demonstrate the potential application of this synthetic protocol to pharmaceuticals and organic synthesis, a larger-scale reaction of 11 (1.07 g, 5.0 mmol) with 2a was performed, which afforded the target mixed phosphonate 31 (1.26 g) in 96% yield along with 52% recovery of the phenol 2a. 2-Hydroxybenzonitrile 2al was also a suitable substrate and generated a functionalized phosphonate 7a (87% yield), which is a key precursor for meta-C—H activation of the benzene ring to give multi-substituted benzene compounds 7aa (Scheme 3, a; Bera et al. (2016) *ACS Catal.* 6: 3575; Bag et al. (2017) *Angew. Chem. Int. Ed.* 56: 12538; Ange. Chem. 129: 12712). Next, the aryloxylation protocol was applied to the synthesis of a key intermediate of butyrophilin ligand prodrug 7bb reported by the Wiemer group. The transformation achieved one step synthesis of 7b from 1x and 2o and enables higher yield (84%) in short reaction time (40 min) (Scheme 3, b; Foust et al. (2017) *ACS Med. Chem. Lett.* 8:

914). Finally, a mixed phosphonate 7c, a key intermediate of polymer immobilized enzyme inhibitors 7cc, was also successfully synthesized in 87% yield from 1y and 2f (Scheme 3, c; Reetz et al. (2002) *Tetrahedron* 58: 8465).

SCHEME 3A-C.

a) direct meta-C—H functionalization

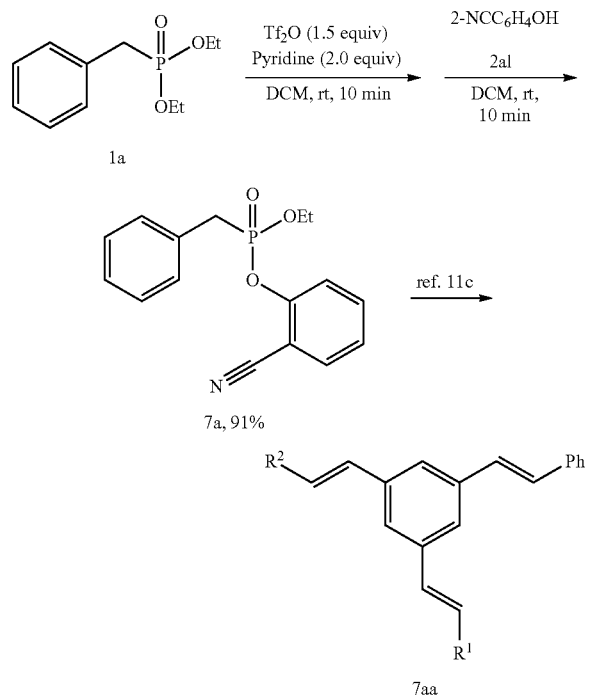

b) synthesis of butyrophilin ligand prodrug

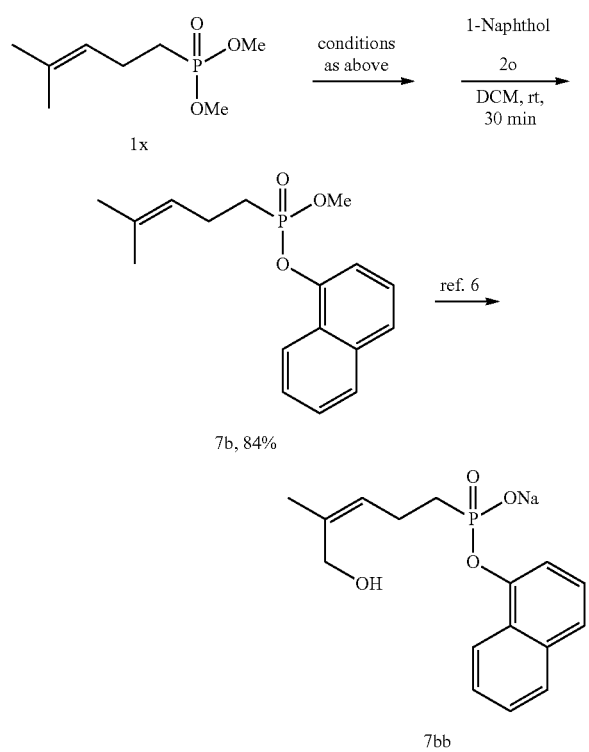

c) synthesis of enzyme inhibitors

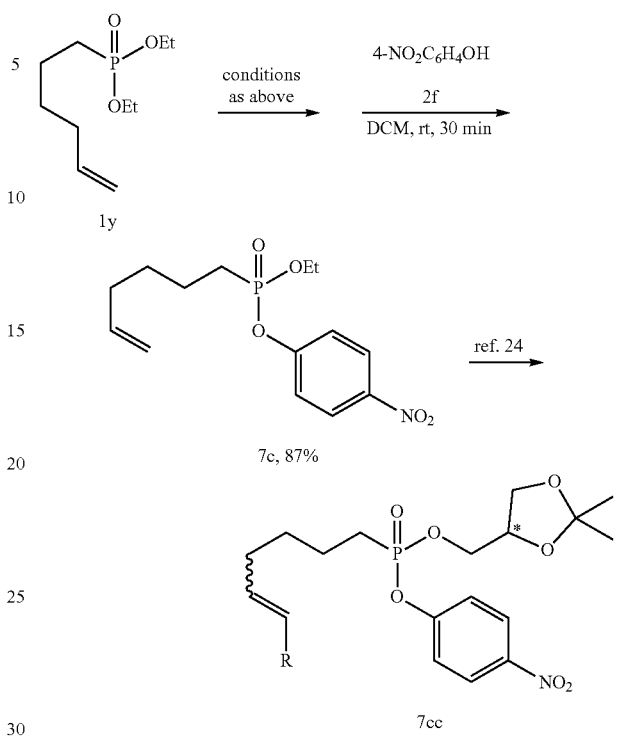

e. In Situ NMR Study of the Mechanism of Aryloxylation of Phosphonates

Figure 4:
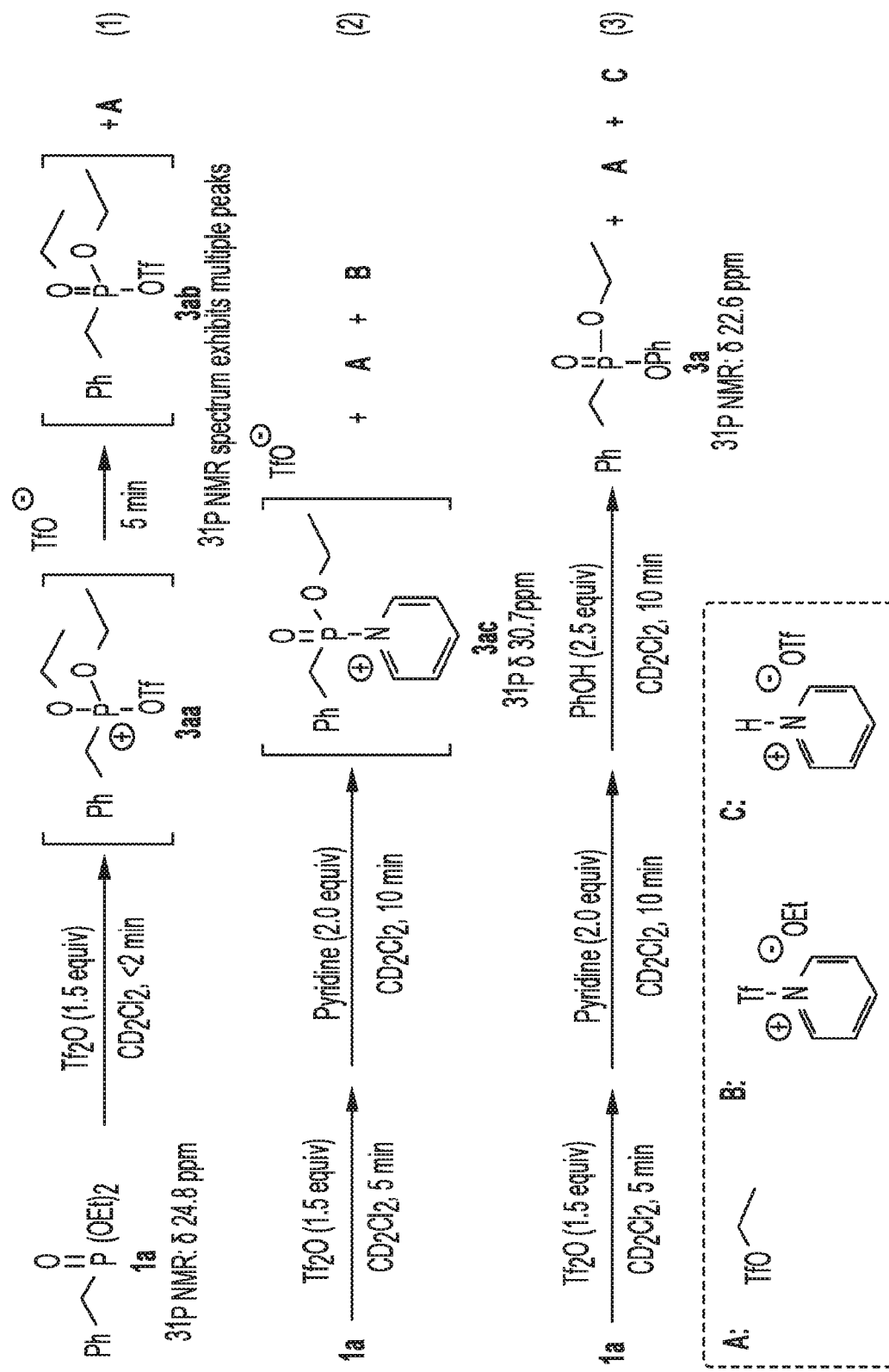
FIG. 4 shows representative $^1$H NMR spectra of the reaction mixtures of equations (1)-(3).
Figure 4:
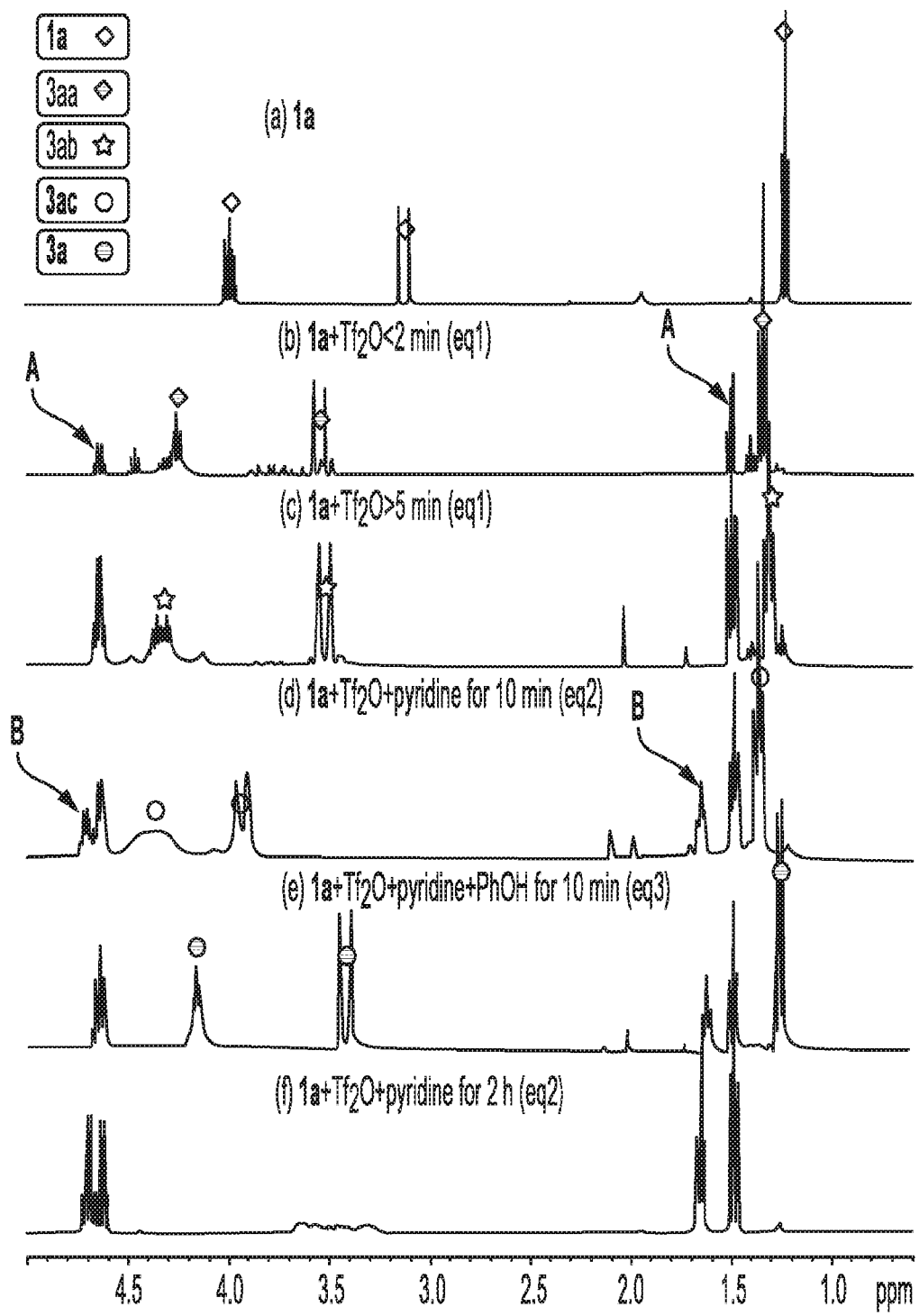

It was initially proposed that a highly reactive P-species such as the intermediate III (FIG. 3) could be generated in the reaction process. To gain evidence for the formation of the intermediate III and to understand a plausible mechanism, in situ NMR studies of the reaction of diethyl benzylphosphonate 1a and phenol 2a with $Tf_2O$ and pyridine were performed (FIG. 4). When $TfO_2$ was added to 1a, peaks corresponding to 1a (FIG. 4, spectrum a) disappeared rapidly within 2 min. and three new major peaks (diamond marks) appeared (FIG. 4, spectrum b). It was proposed that these signals should belong to phosphonium 3aa based on the peak ratios and relative chemical shifts as well as the J-values of the benzylic and methylene protons, which were the same as those in 1a. The corresponding $^1H$ NMR spectra showed that phosphonium intermediate 3aa is quickly converted into the intermediate 3ab (star marks) within 5 min. (FIG. 4, spectrum c; Dahl (1982) *Tetrahedron Lett.* 23: 1493-1496). Intermediate 3ab, however, failed to give the desired mixed phosphonate product when it was directly treated with phenol 2a, implying that 3ab is not a highly reactive intermediate toward aryloxylation reaction of phosphonates. Interestingly, a number of new peaks appeared on the $^1H$ NMR spectra after the addition of pyridine, accompanied by precipitation in the NMR tube. With this observation and a chemical shift of 30.7 ppm in the $^{31}P$ NMR spectrum, it was suggested that a phosphoryl pyridin-1-ium salt 3ac (hollow circles) is formed (FIG. 4, spectrum d). In fact, mixed phosphonate 3a (filled circles) was formed when phenol 2a was introduced to intermediate 3ac (FIG. 4, spectrum e). Phosphoryl pyridine-1-ium 3ac is not only highly reactive but also sensitive. When the crude mixture of 3ae was kept at rt for 2 h, 3ae was completely decomposed to ethyl triflate A and pyridinium salt B, as clearly presented on the $^1$H NMR spectra (FIG. 4, spectrum f).

f. Proposed Mechanism Based on the NMR Study

Based on the NMR study, a plausible mechanism is proposed (Scheme 4, path a). The terminal oxygen of the phosponate $^{18}$O-1a attacks the Tf$_2$O to furnish a phospho- nium intermediate I. Next, TfO-substituted phosphonate II and ethyl triflate by-product are generated by attacking the triflate anion on the carbon atom of the alkoxy group of intermediate I. Then, the pyridine nucleophile attacks intermediate II to form a highly reactive electrophilic phosphorous species of phosphoryl pyridin-1-ium III (Hendsbee et al. (2012) Angew. Chem. Int. Ed. 51: 10836; Huynh et al. (2007) J. Am. Chem. Soc. 128: 5930; Cui et al. (2017) Inorganica Chimica Acta 460: 2). Finally, intermediate III is transformed to mixed phosphonate 3a by substitution reaction with hydroxyl nucleophile 2a (Weiss et al. (2008) J. Am. Chem. Soc. 130: 4610; Fujioka et al. (2006) J. Am. Chem. Soc. 128: 5930; Quesnel et al. (2016) Chem. Sci. 7: 295). An alternative mechanism is also described (Scheme 4, path b).

The bridging oxygen of 1a attacks the Tf$_2$O, resulting in the formation of intermediate Ia. The triflate anion then attacks the carbon atom activated by the positively charged oxygen atom in Ia to form the TfO-substituted phosphonate IIa. Then, the intermediate IIa is converted to the mixed phosphonate product $^{18}$O-3a via intermediate IIIa by following the remaining same mechanistic steps of path a.

SCHEME 4.

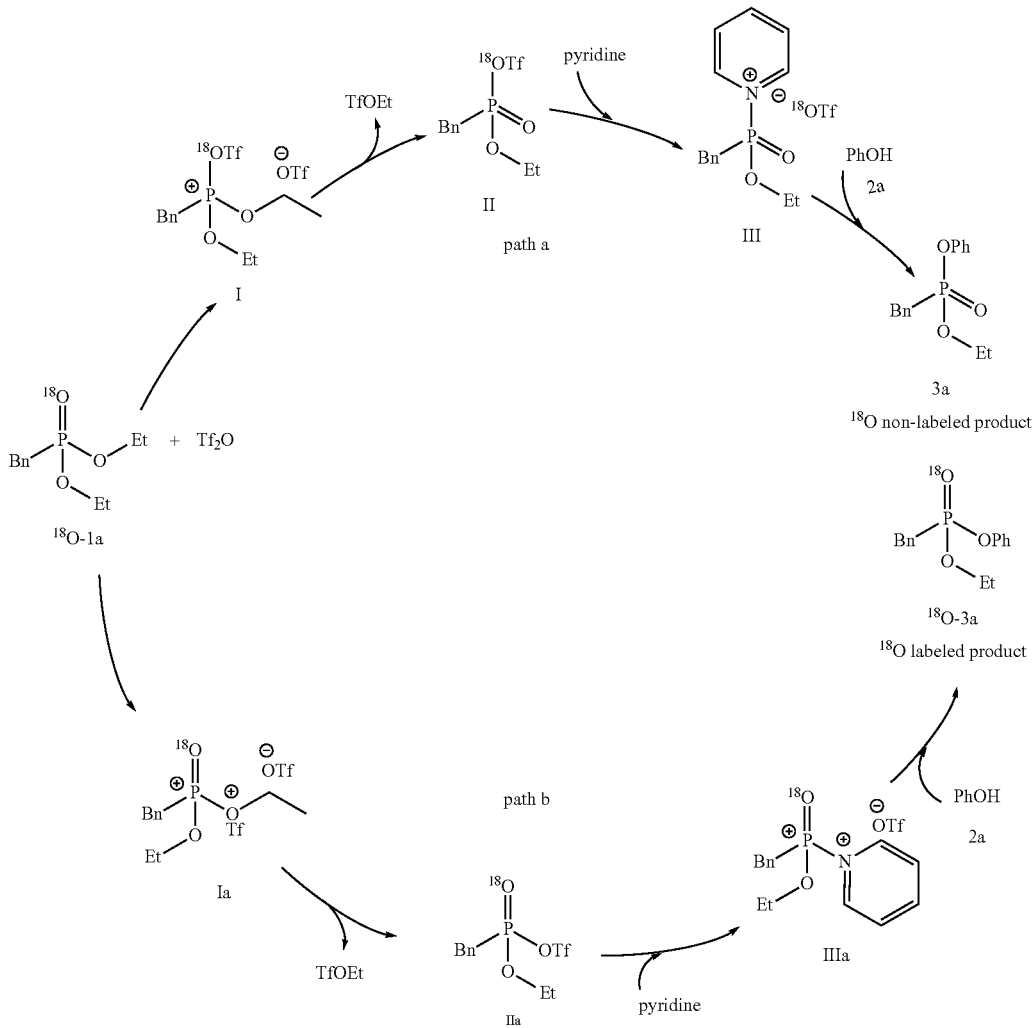

Nevertheless, there are two important mechanistic aspects that need to be considered rigorously. First, what type of substitution reactions (S$_N$1 versus S$_N$2) take place to transform the intermediate I to II? Second, which oxygen atom (terminal oxygen, path a versus internal oxygen, path b) is activated by Tf$_2$O? To take these into account, isopropyl methyl phenylphosphonate 5e was employed under the optimized reaction conditions, and only the isopropyl group was substituted to give 3k (Scheme 5, a). Therefore, it was proposed that this substitution reaction might follow an S$_N$1-type mechanism. Next, to address the activation process of the phosphonate with Tf$_2$O, a 1:1 mixture of diethyl phenylphosphonate 11 and diethyl (4-nitrophenyl)phosphonate 1y was treated with phenol 2a under the standard reaction conditions. Only 1l was converted into the mixed phosphonate 3l with 88% yield and unreacted 1y was recovered with 83% (Scheme 5, b). This outcome generated in 83% yield when $^{18}$O-1l dialkyl phosphonate was employed (Scheme 5, c; Blazewska (2014) *J. Org. Chem.* 79: 408), which strongly supports that this transformation should follow the proposed mechanism of path α shown in Scheme 4.

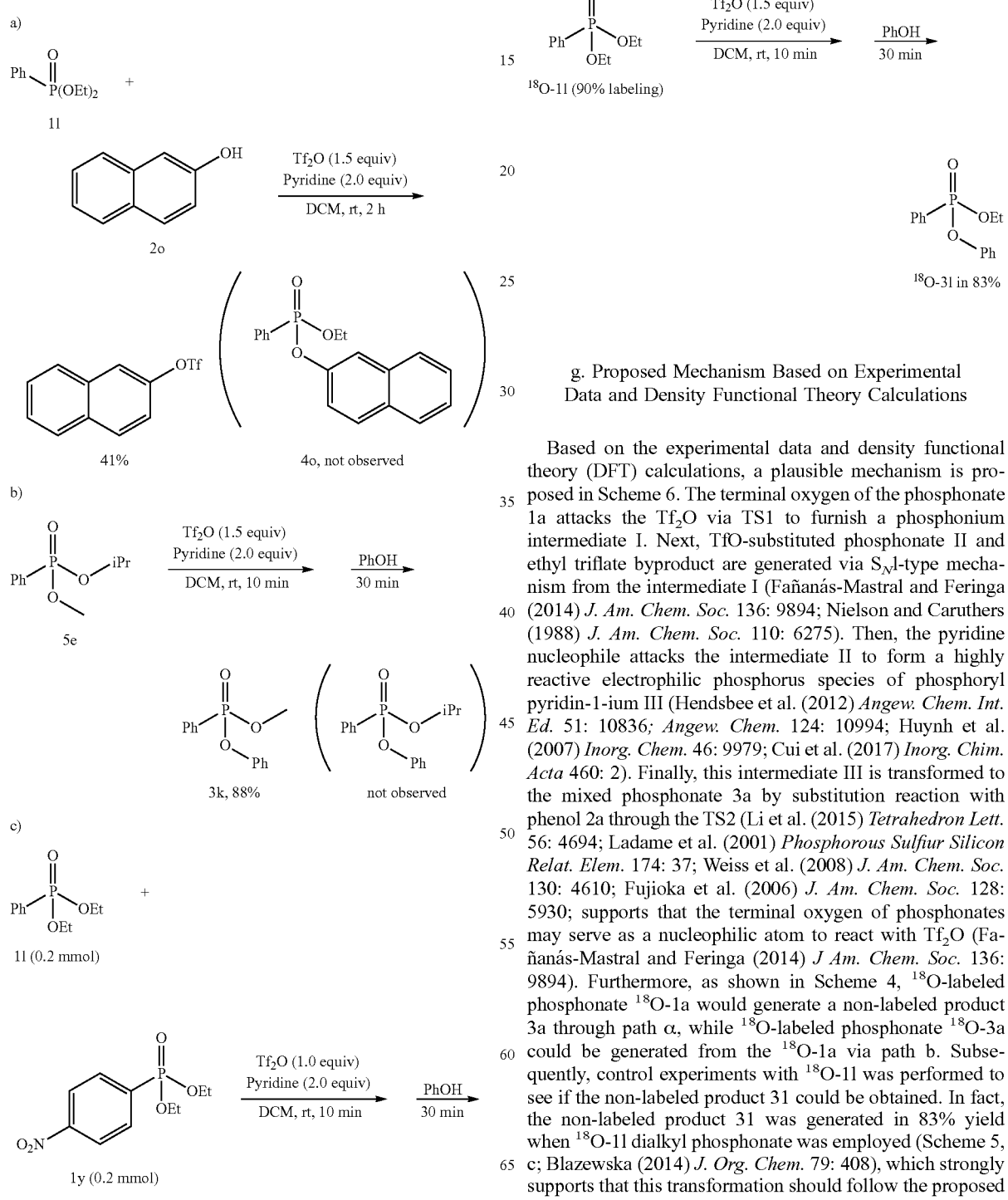

g. Proposed Mechanism Based on Experimental Data and Density Functional Theory Calculations Based on the experimental data and density functional theory (DFT) calculations, a plausible mechanism is proposed in Scheme 6. The terminal oxygen of the phosphonate 1a attacks the Tf$_2$O via TS1 to furnish a phosphonium intermediate I. Next, TfO-substituted phosphonate II and ethyl triflate byproduct are generated via S$_N$1-type mechanism from the intermediate I (Fañanás-Mastral and Feringa (2014) *J. Am. Chem. Soc.* 136: 9894; Nielson and Caruthers (1988) *J. Am. Chem. Soc.* 110: 6275). Then, the pyridine nucleophile attacks the intermediate II to form a highly reactive electrophilic phosphorus species of phosphoryl pyridin-1-ium III (Hendsbee et al. (2012) *Angew. Chem. Int. Ed.* 51: 10836; *Angew. Chem.* 124: 10994; Huynh et al. (2007) *Inorg. Chem.* 46: 9979; Cui et al. (2017) *Inorg. Chim. Acta* 460: 2). Finally, this intermediate III is transformed to the mixed phosphonate 3a by substitution reaction with phenol 2a through the TS2 (Li et al. (2015) *Tetrahedron Lett.* 56: 4694; Ladame et al. (2001) *Phosphorous Sulfiur Silicon Relat. Elem.* 174: 37; Weiss et al. (2008) *J. Am. Chem. Soc.* 130: 4610; Fujioka et al. (2006) *J. Am. Chem. Soc.* 128: 5930; supports that the terminal oxygen of phosphonates may serve as a nucleophilic atom to react with Tf$_2$O (Fañanás-Mastral and Feringa (2014) *J Am. Chem. Soc.* 136: 9894). Furthermore, as shown in Scheme 4, $^{18}$O-labeled phosphonate $^{18}$O-1a would generate a non-labeled product 3a through path α, while $^{18}$O-labeled phosphonate $^{18}$O-3a could be generated from the $^{18}$O-1a via path b. Subsequently, control experiments with $^{18}$O-1l was performed to see if the non-labeled product 3l could be obtained. In fact, the non-labeled product 3l was generated in 83% yield when $^{18}$O-1l dialkyl phosphonate was employed (Scheme 5, c; Blazewska (2014) *J. Org. Chem.* 79: 408), which strongly supports that this transformation should follow the proposed mechanism of path α shown in Scheme 4.

SCHEME 5A-C.

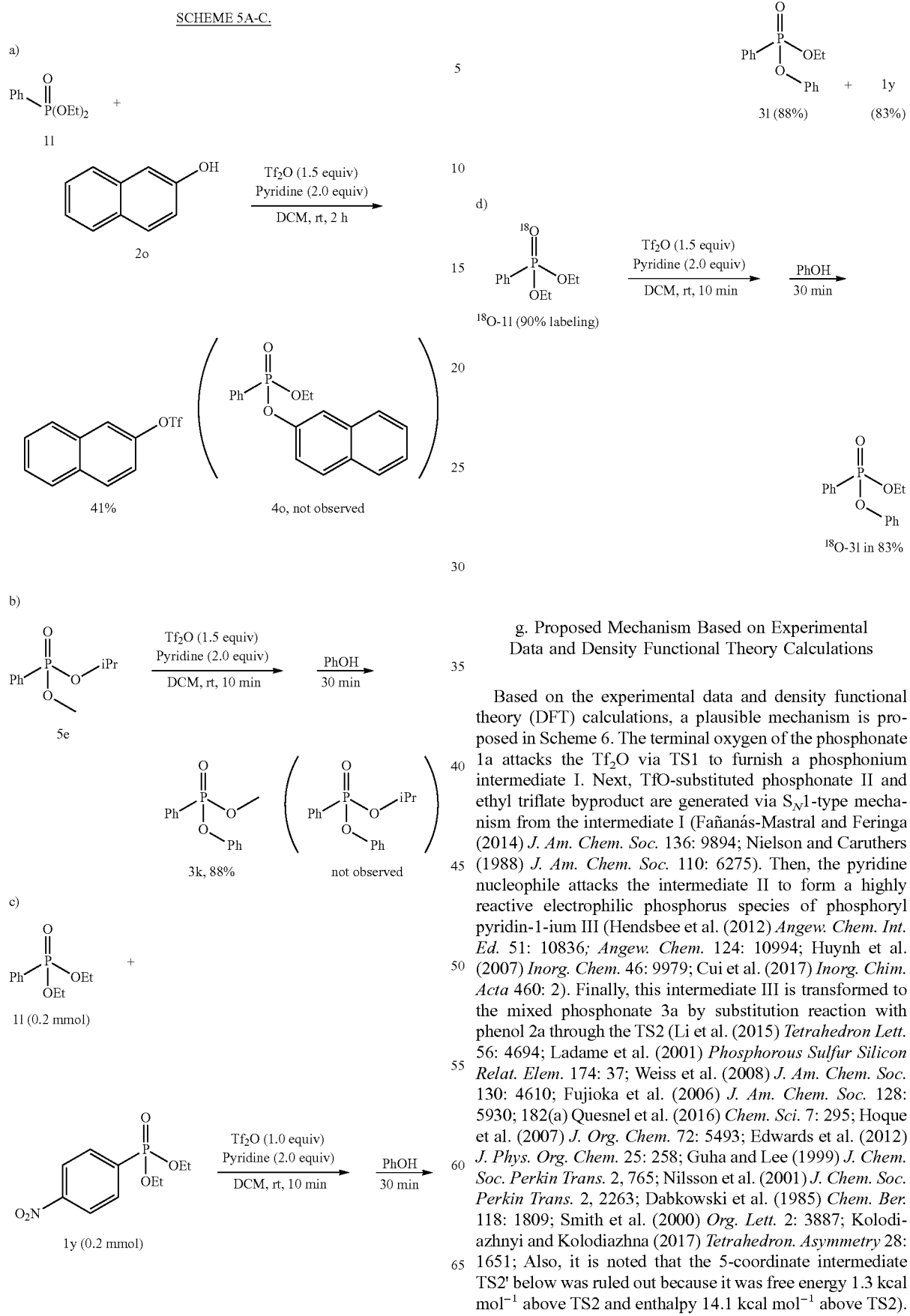

g. Proposed Mechanism Based on Experimental Data and Density Functional Theory Calculations Based on the experimental data and density functional theory (DFT) calculations, a plausible mechanism is proposed in Scheme 6. The terminal oxygen of the phosphonate 1a attacks the $Tf_2O$ via TS1 to furnish a phosphonium intermediate I. Next, TfO-substituted phosphonate II and ethyl triflate byproduct are generated via $S_N1$-type mechanism from the intermediate I (Fañanás-Mastral and Feringa (2014) *J. Am. Chem. Soc.* 136: 9894; Nielson and Caruthers (1988) *J. Am. Chem. Soc.* 110: 6275). Then, the pyridine nucleophile attacks the intermediate II to form a highly reactive electrophilic phosphorus species of phosphoryl pyridin-1-ium III (Hendsbee et al. (2012) *Angew. Chem. Int. Ed.* 51: 10836; *Angew. Chem.* 124: 10994; Huynh et al. (2007) *Inorg. Chem.* 46: 9979; Cui et al. (2017) *Inorg. Chim. Acta* 460: 2). Finally, this intermediate III is transformed to the mixed phosphonate 3a by substitution reaction with phenol 2a through the TS2 (Li et al. (2015) *Tetrahedron Lett.* 56: 4694; Ladame et al. (2001) *Phosphorous Sulfur Silicon Relat. Elem.* 174: 37; Weiss et al. (2008) *J. Am. Chem. Soc.* 130: 4610; Fujioka et al. (2006) *J. Am. Chem. Soc.* 128: 5930; 182(a) Quesnel et al. (2016) *Chem. Sci.* 7: 295; Hoque et al. (2007) *J. Org. Chem.* 72: 5493; Edwards et al. (2012) *J. Phys. Org. Chem.* 25: 258; Guha and Lee (1999) *J. Chem. Soc. Perkin Trans.* 2, 765; Nilsson et al. (2001) *J. Chem. Soc. Perkin Trans.* 2, 2263; Dabkowski et al. (1985) *Chem. Ber.* 118: 1809; Smith et al. (2000) *Org. Lett.* 2: 3887; Kolodiazhnyi and Kolodiazhna (2017) *Tetrahedron. Asymmetry* 28: 1651; Also, it is noted that the 5-coordinate intermediate TS2' below was ruled out because it was free energy 1.3 kcal $mol^{-1}$ above TS2 and enthalpy 14.1 kcal $mol^{-1}$ above TS2).

SCHEME 6.

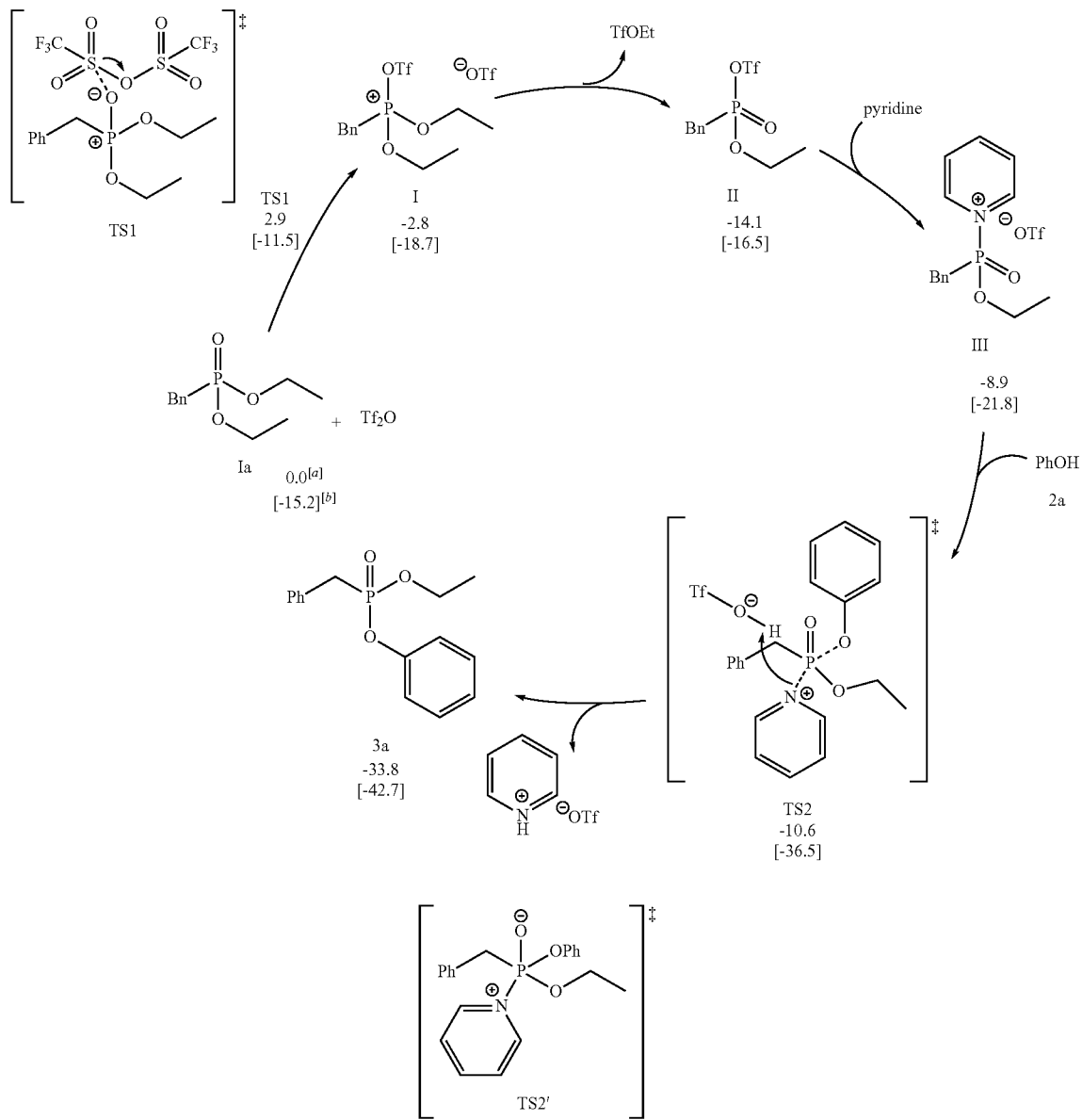

In summary, a mild, efficient, direct aryloxylation/alkyloxylation of dialkyl phosphonates for the synthesis of mixed phosphonates has been developed. This synthetic transformation enabled the synthesis of a wide range of functional mixed phosphonates without the use of metal or chloride reagents. In this chemistry, it was demonstrated that a phosphoryl pyridin-1-ium, a highly electrophilic P-species of powerful phosphonylation reagent for the synthesis of mixed phosphonates, can be generated from dialkyl phosphonates with $Tf_2O$/pyridine. The synthetic utility of this transformation was demonstrated by the synthesis of key intermediates of bioactive compounds (butyrophilin ligand prodrug and enzyme inhibitors) and the late-stage phosphonylation of natural compounds.

3. Synthesis of Mixed Phosphates and Phosphinates a. Optimization of Reaction Conditions To test the hypothesis, triethyl phosphate 1a' and phenol 2a' were used as model substrates to optimize the reaction conditions (Table 2). Gratifyingly, the desired phenyl phosphate 3a' was generated in 96% yield by NMR when our previous optimized reaction conditions for mixed phosphonate was employed (Table 2, entry 1). Further control experiments revealed that the optimized reaction conditions need 2 equivalents of phenol 2a', providing the target compound with 92% isolated yield (Table 2, entries 2-6). Evaluation of other bases such as lutidine, DMAP, DABCO, and DBU provided no target products (Table 2, entries 7-10).

TABLE 2

Tf₂O (X equiv), Base (Y equiv), DCM, rt, 10 min; 2a (Z equiv), rt, 30 min $EtO-P(=O)(OEt)(OEt)$ (1a) + PhOH (2a) → $PhO-P(=O)(OEt)(OEt)$ (3a)

| entry | base | X:Y:Z | yield (%)[a] |
|---|---|---|---|
| 1 | pyridine | 1.5:2.0:2.5 | 96 |
| 2 | pyridine | 1.5:2.0:2.0 | 99(92)[b] |
| 3 | pyridine | 1.5:2.0:1.5 | 43 |
| 4 | pyridine | 2.0:2.0:2.0 | 92 |
| 5 | pyridine | 1.5:1.1:2.0 | 80 |
| 6 | pyridine | 1.5:1.5:2.0 | 70 |
| 7 | lutidine | 1.5:2.0:2.0 | —[c] |
| 8 | DMAP | 1.5:2.0:2.0 | —[c] |
| 9 | DABCO | 1.5:2.0:2.0 | —[c] |
| 10 | DBU | 1.5:2.0:2.0 | —[c] |

Reaction conditions: 1a' (0.2 mmol), Tf₂O (X equiv), base (Y equiv) in solvent (1.0 mL) for 10 min, then 2a' (Z equiv) for 30 min. [a]Yield was determined by ¹H NMR on the crude reaction mixture using 1,3,5-trimethylbenzene as an internal standard. [b]Isolated yield. [c]Major product was PhOTf.

b. Exploration of Reaction Scope

With the optimized reaction conditions in hand, the scope of this reaction was explored with phosphates 1' and diverse arenol nucleophiles 2' to synthesize phosphate derivatives 3'. To demonstrate scalability of this reaction, a gram-scale reaction of 1a' (1.09 g, 6.0 mmol) with 2a' was performed first, which afforded the target phosphonate product 3a' (1.24 g) in 90% yield (Scheme 7, 3a'). Generally, the electronic effects of substituents on the phenyl ring have a negligible effect on this transformation. The reaction tolerates various phenols with diverse substituents (Me, MeO, Br, I, NO₂, Ph) and polycyclic aromatic alcohols such as 1-naphthol and 2-naphthol, providing the desired aryl phosphates with 71-91% yields (Scheme 7, 3b'-3k'). However, a bulky nucleophile such as 2,6-di-isopropyl phenol reduced the reactivity and provided the target product 3m' with 53% yield due to steric hindrance. On the other hand, a sterically bulky phosphate electrophile, triisopropyl phosphate 1b', afforded the corresponding diisopropyl phosphate 3n' in 73% yield (Scheme 7, 3n').

Next, the late-stage phosphorylation of various natural products was investigated. The phosphorylation of quinol, coumarin, sesamol, and ferulate demonstrated good functional group tolerance (e.g., carbonate, ester, ether, and acrylate), yielding the corresponding products in high yields (Scheme 7, 3o'-3r'). Importantly, the reaction of 1a' with a cholesterol-derived phenol provided a phosphorylated cholesteryl ester 3s' with a biologically important phosphate moiety in 76% yield (Scheme 7, 3s'). Furthermore, the reactivity of other nucleophiles was evaluated under the standard reaction conditions (Scheme 7, 3t'-3z'). Both primary and secondary aliphatic alcohols were also efficiently coupled with the phosphate 1a' to yield alkyl phosphates 3t'-3v' in 49-87% yields. Finally, it was demonstrated that amine and thiol nucleophiles can be employed in this transformation to provide the azaphosphates 3w'-3z' and thiophosphate 3aa' in acceptable to moderate yields (Scheme 7).

SCHEME 7.

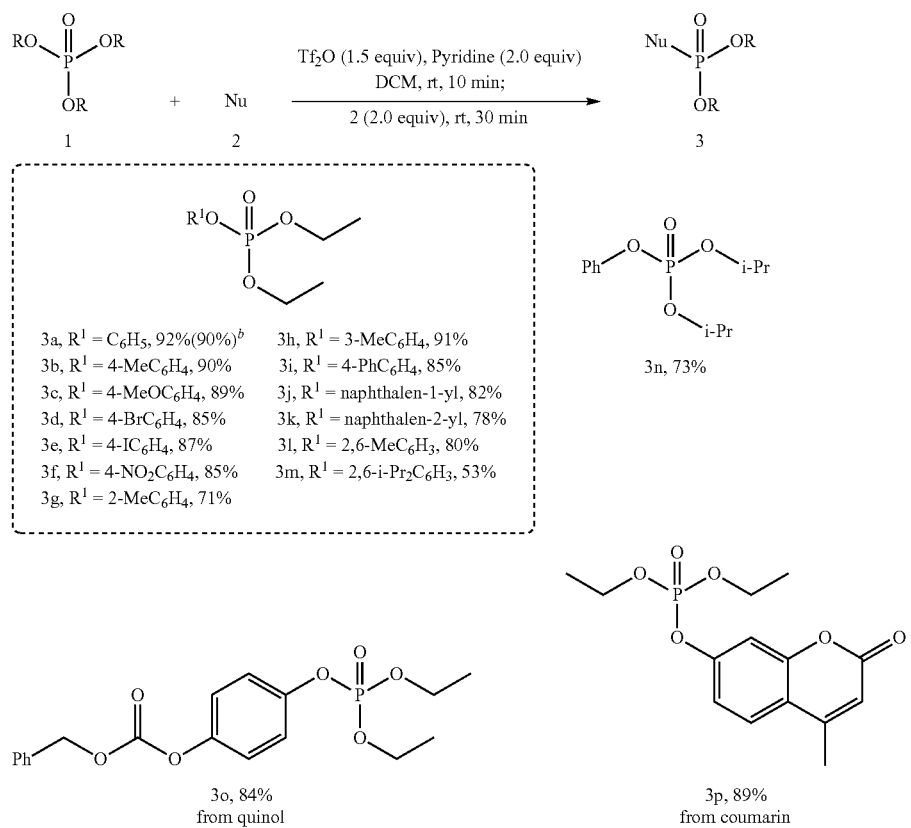

-continued

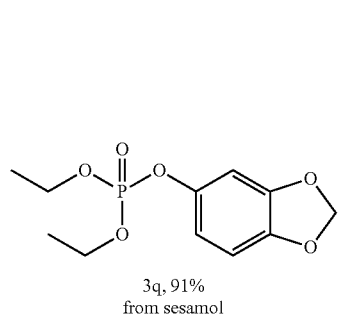

3q, 91%
from sesamol

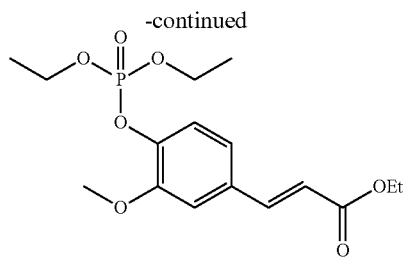

3r, 84%
from ethyl ferulate

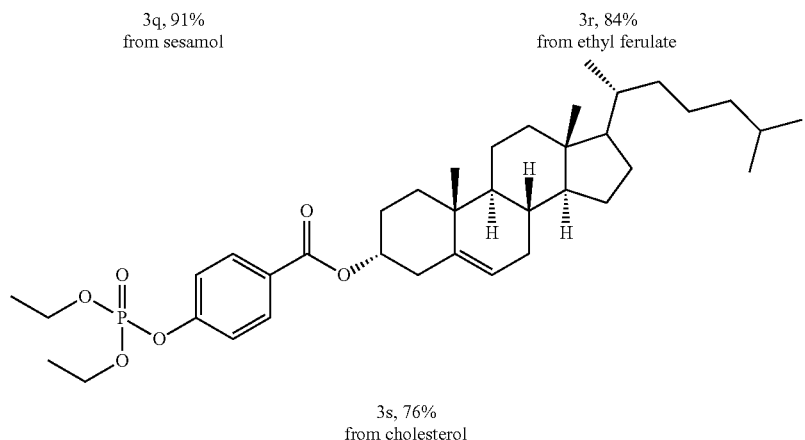

3s, 76%
from cholesterol

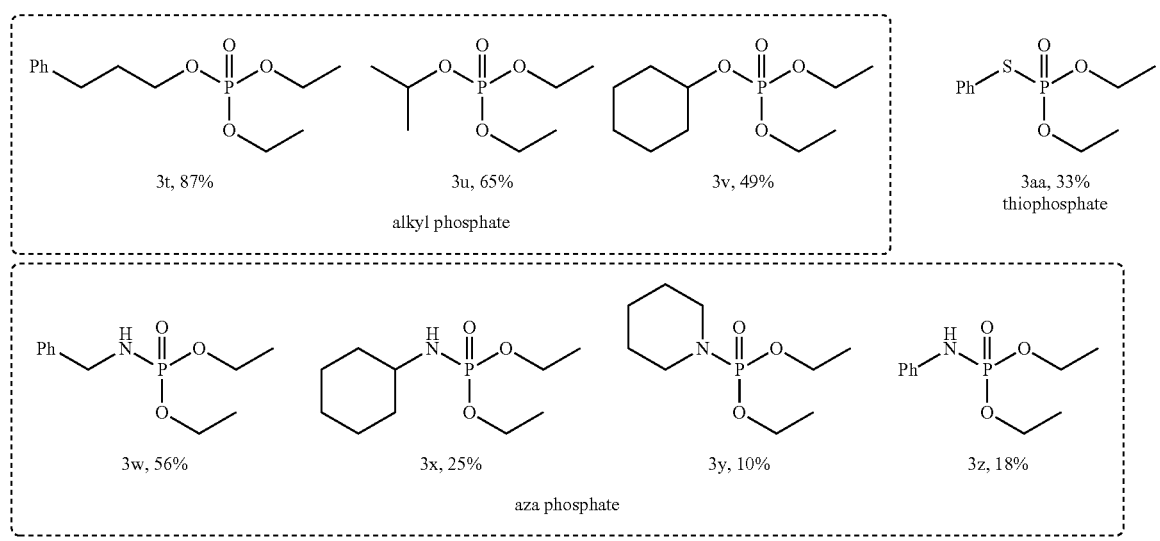

3t, 87%    3u, 65%    3v, 49%    3aa, 33%
                                  thiophosphate
alkyl phosphate 3w, 56%    3x, 25%    3y, 10%    3z, 18%
aza phosphate

[a]Reaction conditions: 1' (0.2 mmol), Tf$_2$O (0.3 mmol), pyridine (0.4 mmol) in DCM (1.0 mL) for 10 min, then 2' (0.4 mmol) for 30 min; Isolated yields were given. [b]A gram-scale experiment with 6.0 mmol of 1a'.

The synthesis of mixed diaryl phosphates from aryl dialkylphosphates is a challenging synthetic transformation in organophosphate chemistry since it requires an exquisite control of reactivity and chemoselectivity to prevent dual substitution reaction of the two alkoxy groups (Takeuchi et al. (1979) *Tetrahedron Lett.* 20: 1231; Blackburn and Ingleson (1980) *J. Chem. Soc., Perkin Trans.* 1, 1150-1153; Chowdhury et al. (2007) *Bioorg. Med. Chem. Lett.* 17: 3745; Koster et al. (1983) *J. Am. Chem. Soc.* 105: 3743; Blackburn and Ingleson (1978) *J. Chem. Soc., Chem. Commun.*, 870-871; Cooke and Gerrard (1955) *J. Chem. Soc.*, 1978-1982; Sevrain et al. (2017) *Beilstein J. Org. Chem.* 13: 2186). Hence, a selective synthesis of mixed diaryl phosphates from aryl dialkylphosphates was explored as shown in Scheme 8. Phenyl phosphate 3a' was used as a starting material and it was efficiently coupled with arenols bearing different substituents such as methyl, halo, CN, CF$_3$, and aryl groups to afford the corresponding mixed diarylphosphates 4a'-4g' in 74-88% yields. 1-naphthol and 2-naphthol were also proved to be suitable substrates under the standard reaction conditions, providing the mixed diarylphosphates 4h' and 4i' in 73% and 85% yields, respectively. In addition, a natural compound sesamol also furnished the corresponding mixed diaryl phosphate 4j' in 81% yield. Furthermore, this reaction tolerates an azo functional group on a phenyl ring, which generated the desired product 4k' in high yield (87%).

SCHEME 8.

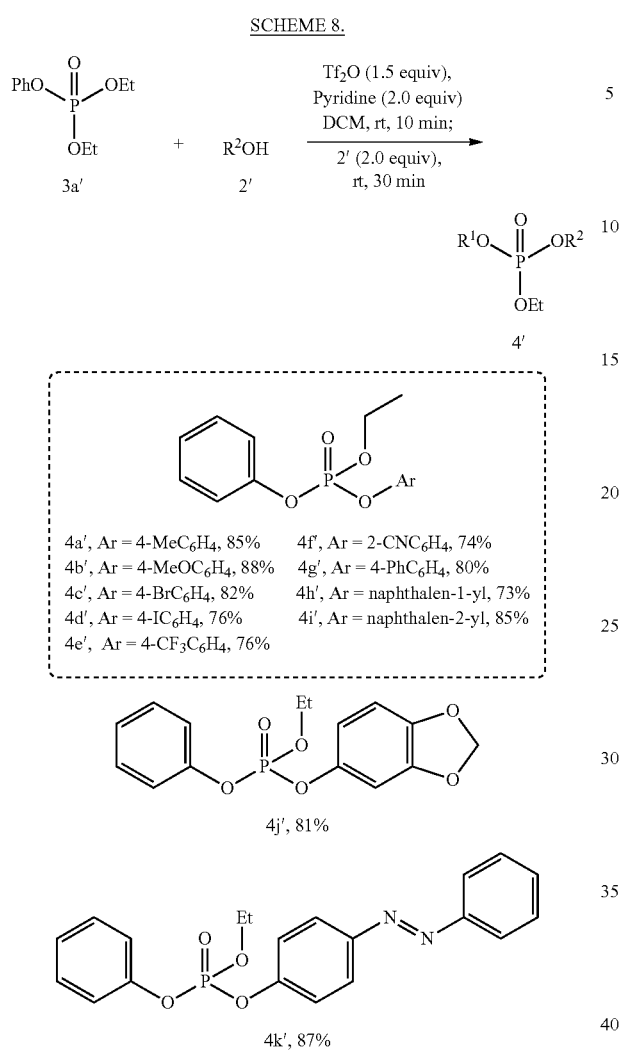

4a', Ar = 4-MeC$_6$H$_4$, 85%   4f', Ar = 2-CNC$_6$H$_4$, 74%
4b', Ar = 4-MeOC$_6$H$_4$, 88%   4g', Ar = 4-PhC$_6$H$_4$, 80%
4c', Ar = 4-BrC$_6$H$_4$, 82%   4h', Ar = naphthalen-1-yl, 73%
4d', Ar = 4-IC$_6$H$_4$, 76%   4i', Ar = naphthalen-2-yl, 85%
4e', Ar = 4-CF$_3$C$_6$H$_4$, 76%

4j', 81%

4k', 87%

Finally, this synthetic protocol has been successfully applied for the conversion of an alkylphosphinate to an arylphosphinate (Nora and Gyorgy (2014) Curr. Org. Chem. 18: 2673; Virieux et al. (2015) Top. Curr. Chem. 360: 39), demonstrating a general activating procedure of all three different oxygen-containing pentavalent phosphorus compounds (phosphates, phosphonates (Huang et al. (2018) Angew. Chem. Int. Ed. 57: 6624), and phosphinates). When diphenyl ethylphosphinate 1c' was treated with p-cresol, the target arylphosphinate 5a' was obtained in 74% yield (Scheme 9).

SCHEME 9.

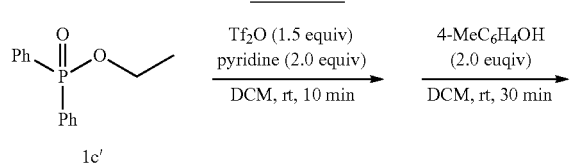

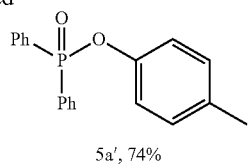

5a', 74% c. Continuous Flow System for Phosphate Synthesis

Figure 5:
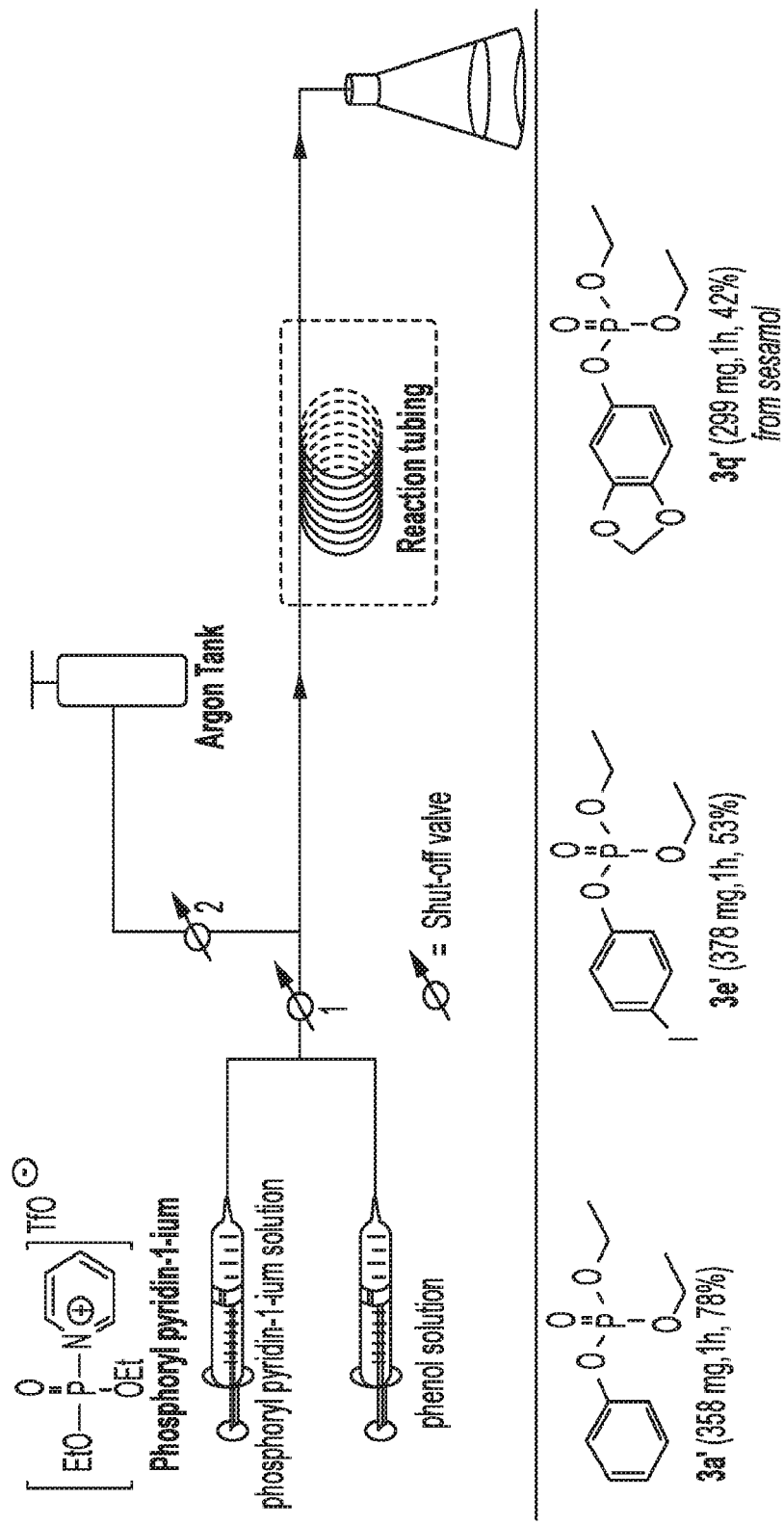
FIG. 5 shows a representative schematic illustrating the use of a continuous flow system for phosphate synthesis.

With the potential application of this versatile synthetic transformation (short reaction time, high tolerance of functional groups, and mild reaction conditions) to chemical enterprise, the development of a continuous flow synthesis system was explored to further demonstrate the synthetic utility of this methodology (Xiong et al. (2015) ACS Catal. 5: 537; Whitesides (2006) Nature 442: 368; Dudukovic et al. (1999) Chem. Eng. Sci. 54: 1975). While enzymatic synthesis of phosphorylated compounds via continuous-flow reactor has been reported (Babich et al. (2013) Int. J. Chem., 5; Babich et al. (2012) Chem. Eur. J. 18: 6604), chemical synthesis of phosphorus compounds using flow chemistry is underdeveloped. Hence, an aryloxylation reaction was conducted to test amenability in a continuous-flow reactor as described in FIG. 5. This continuous-flow procedure efficiently furnished the desired aryl phosphate 3a' in 78% yield. In addition, a natural compound sesamol can also afford the corresponding phosphate 3q' in moderate yield (42% yield) under this continuous-flow system.

In summary, a new synthetic strategy for the activation of pentavalent organophosphorus compounds (phosphate, phosphinate) in which a phosphoryl pyridin-1-ium intermediate is generated in situ from a phosphate with Tf$_2$O/pyridine has been developed. This electrophilic P-species efficiently undergoes nucleophilic substitution reaction with various nucleophiles (aliphatic alcohols, arenols, amines, and thiols) to provide functional phosphate compounds under metal-free reaction conditions. The synthetic utility of this phosphorylation has been demonstrated by late-stage phosphorylation of natural compounds. In addition, a continuous flow system for the synthesis of phosphates has been demonstrated. Further studies on the development of efficient synthesis of functional phosphorus compounds based on the in situ generated P-species especially for improving the product yields of azaphosphates and thiophosphates are underway.

4. Synthesis of Mixed Thiophosphates and Thiophosphates a. Optimization of Reaction Conditions

A summary of the reaction conditions explored with respect to thiophosphate analogs is shown in Table 3 below.

TABLE 3
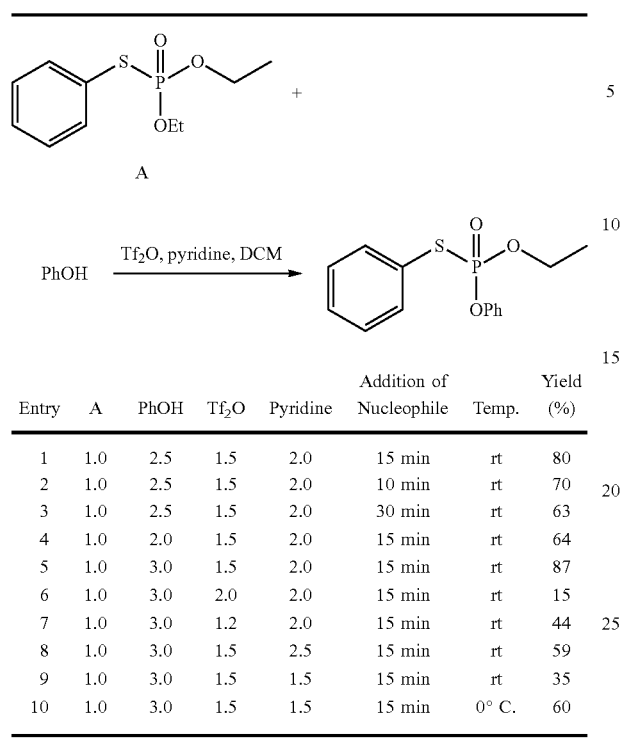
| Entry | A | PhOH | Tf$_2$O | Pyridine | Addition of Nucleophile | Temp. | Yield (%) |
|---|---|---|---|---|---|---|---|
| 1 | 1.0 | 2.5 | 1.5 | 2.0 | 15 min | rt | 80 |
| 2 | 1.0 | 2.5 | 1.5 | 2.0 | 10 min | rt | 70 |
| 3 | 1.0 | 2.5 | 1.5 | 2.0 | 30 min | rt | 63 |
| 4 | 1.0 | 2.0 | 1.5 | 2.0 | 15 min | rt | 64 |
| 5 | 1.0 | 3.0 | 1.5 | 2.0 | 15 min | rt | 87 |
| 6 | 1.0 | 3.0 | 2.0 | 2.0 | 15 min | rt | 15 |
| 7 | 1.0 | 3.0 | 1.2 | 2.0 | 15 min | rt | 44 |
| 8 | 1.0 | 3.0 | 1.5 | 2.5 | 15 min | rt | 59 |
| 9 | 1.0 | 3.0 | 1.5 | 1.5 | 15 min | rt | 35 |
| 10 | 1.0 | 3.0 | 1.5 | 1.5 | 15 min | 0° C. | 60 |
b. Exploration of Reaction Scope
The scope of the reaction was explored with a variety of electrophiles (Scheme 10) and nucleophiles (Scheme 11).
SCHEME 10.
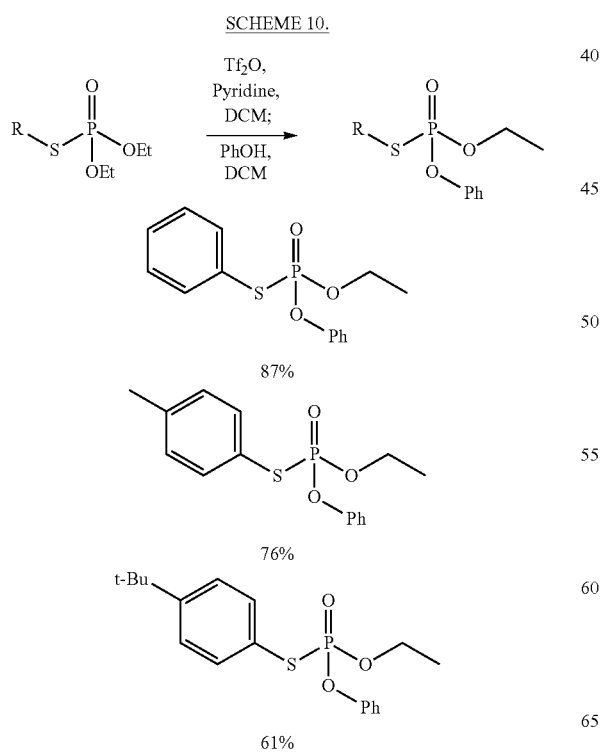
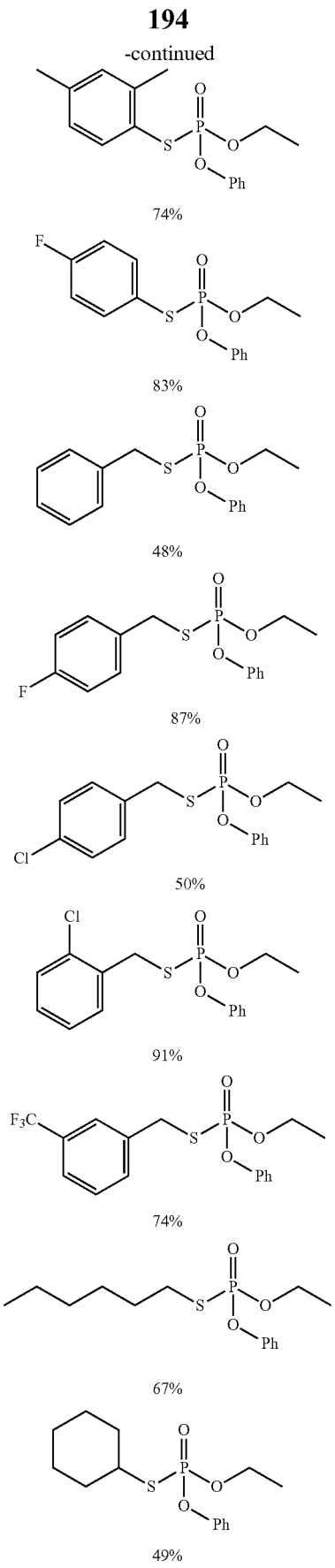

SCHEME 11.

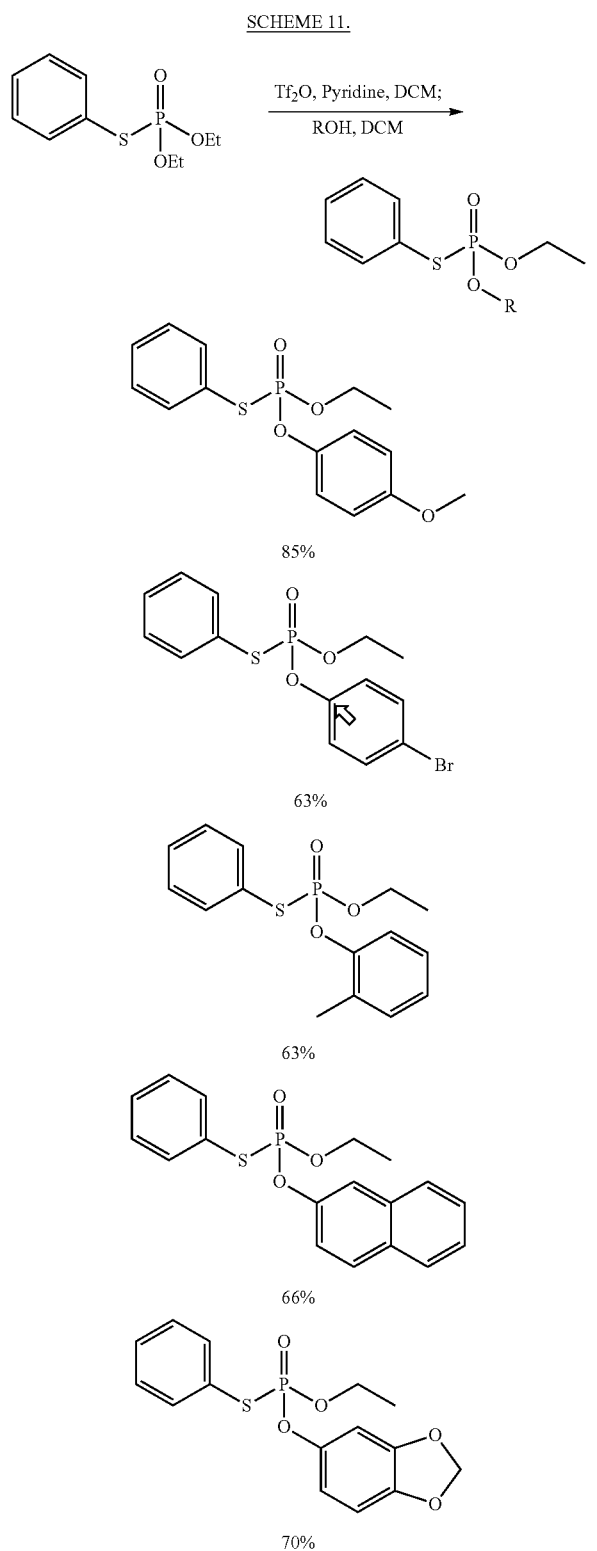

85%

63%

63%

66%

70%

5. Selective Dealkylation of Phosphates

The selective dealkylation of phosphates is illustrated in Scheme 12 below.

SCHEME 12.

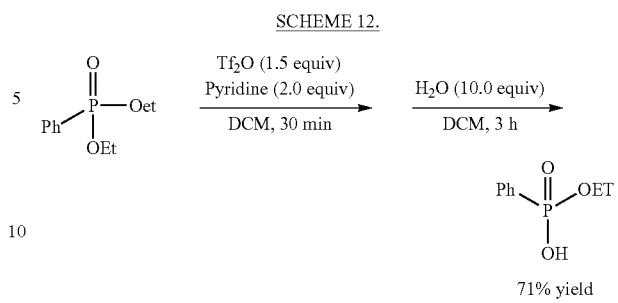

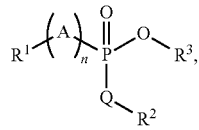

71% yield

It will be apparent to those skilled in the art that various modifications and variations can be made in the present invention without departing from the scope or spirit of the invention. Other aspects of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of making a compound having a structure represented by a formula:

$$R^1 \left( A \right)_n \overset{O}{\underset{Q-R^2}{P}} O-R^3,$$

wherein n is 0 or 1;
wherein A is selected from O, S, $NR^{20}$, and $CHR^{21}$;
  wherein $R^{20}$, when present, is selected from hydrogen and methyl;
  wherein $R^{21}$, when present, is selected from hydrogen and methyl;
wherein Q is selected from O, S, and $NR^{22}$;
  wherein $R^{22}$, when present, is selected from hydrogen and C1-C8 alkyl;
wherein $R^1$ is selected from C1-C8 alkyl, C2-C10 alkenyl, C1-C8 haloalkyl, C3-C6 cycloalkyl, (C1-C4 alkyl)$Ar^1$, (C2-C4 alkenyl)$Ar^1$, —(C2-C4 alkynyl)$Ar^1$, $Ar^1$, and a structure represented by a formula selected from:

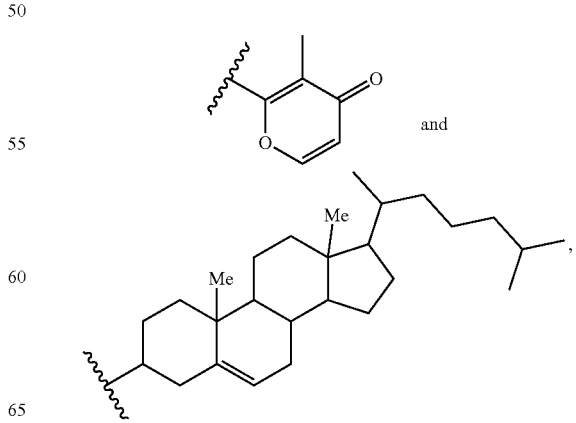

and wherein the C3-C6 cycloalkyl, when present, is substituted with 0 or 1 C1-C4 alkyl group;

wherein $Ar^1$, when present, is selected from aryl and heteroaryl and is substituted with 0, 1, 2, or 3 groups independently selected from halogen, —$NO_2$, —CN, —OH, —SH, —$NH_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —$OCO_2R^{30}$, —$CO_2R^{30}$, —(C1-C4 alkyl)$CO_2R^{30}$, —(C2-C4 alkenyl)$CO_2R^{30}$, —(C=O)(C1-C4 alkyl), —(S=O)(C1-C4 alkyl), —$SO_2$(C1-C4 alkyl), —(C=O)$NR^{31a}R^{31b}$, —$SO_2NR^{31a}R^{31b}$, —O(C=O)$NR^{31a}R^{31b}$, —$NHSO_2NR^{31a}R^{31b}$, —NH(C=O)$NR^{31a}R^{31b}$, and —N=$NR^{32}$;

wherein $R^{30}$, when present, is selected from hydrogen, C1-C8 alkyl, —(C1-C4 alkyl)phenyl, phenyl, and a structure represented by a formula:

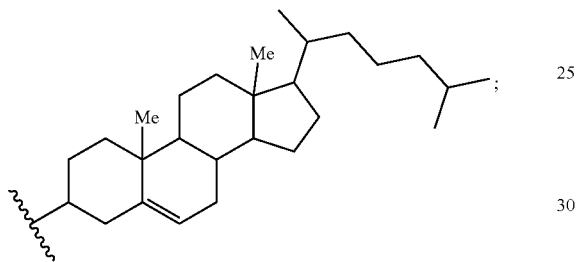

wherein each of $R^{31a}$ and $R^{31b}$, when present, is independently selected from hydrogen, C1-C8 alkyl, —(C1-C4 alkyl)phenyl, and phenyl;

wherein $R^{32}$, when present, is selected from hydrogen, C1-C4 alkyl, and phenyl;

or wherein each of $R^1$ and $R^{20}$, when present, are optionally covalently bonded together and, together with the intermediate carbon atoms, comprise a 3- to 6-membered heterocycloalkyl;

wherein $R^2$ is selected from hydrogen, C1-C8 alkyl substituted with 0-1 phenyl groups, C2-C10 alkenyl, C1-C8 haloalkyl, C3-C6 cycloalkyl, —(C1-C4 alkyl)$Ar^2$, —(C2-C4 alkenyl)$Ar^2$, —(C2-C4 alkynyl)$Ar^2$, $Ar^2$, and a structure represented by a formula selected from:

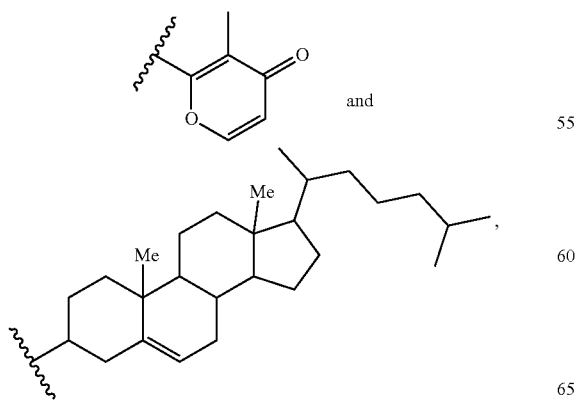

and wherein the C3-C6 cycloalkyl, when present, is substituted with 0 or 1 C1-C4 alkyl groups;

wherein $Ar^2$, when present, is selected from aryl and heteroaryl and is substituted with 0, 1, 2, or 3 groups independently selected from halogen, —$NO_2$, —CN, —OH, —SH, —$NH_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —$OCO_2R^{33}$, —$CO_2R^{33}$, —(C1-C4 alkyl)$CO_2R^{33}$, —(C2-C4 alkenyl)$CO_2R^{33}$, —(C=O)(C1-C4 alkyl), —(S=O)(C1-C4 alkyl), —$SO_2$(C1-C4 alkyl), —(C=O)$NR^{34a}R^{34b}$, —$SO_2NR^{34a}R^{34b}$, —O(C=O)$NR^{34a}R^{34b}$, —$NHSO_2NR^{34a}R^{34b}$, —NH(C=O)$NR^{34a}R^{34b}$, and —N=$NR^{35}$;

wherein $R^{33}$ when present, is selected from hydrogen, C1-C8 alkyl, —(C1-C4 alkyl)phenyl, phenyl, and a structure represented by a formula:

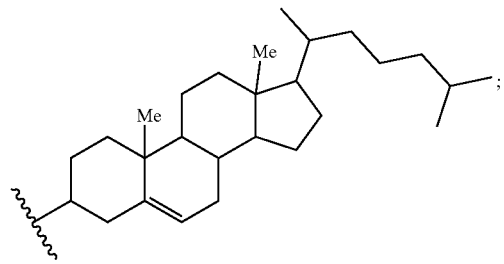 [SMILES: *C1CCC2(C)C(=CCC3C2CCC2(C)C(C(C)CCCC(C)C)CCC32)C1]

wherein each of $R^{34a}$ and $R^{34b}$, when present, is independently selected from hydrogen, C1-C8 alkyl, —(C1-C4 alkyl)phenyl, and phenyl;

wherein $R^{35}$, when present, is selected from hydrogen, C1-C4 alkyl, and phenyl; and wherein $R^3$ is C1-C4 alkyl, or a salt thereof, the method comprising the step of reacting a phosphonate derivative having a structure represented by a formula:

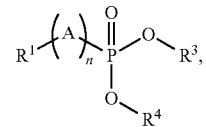

wherein $R^4$ is C1-C4 alkyl,
provided that $R^2$ and $R^4$ are different,
or a salt thereof, with a nucleophile having a structure represented by a formula:

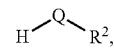

in the presence of an activating agent, wherein the activating agent is selected from triflic anhydride, mesyl chloride, tosyl chloride, oxalyl chloride, thionyl chloride, acetic anhydride, benzoic anhydride, and trifluoroacetic anhydride, and a base.

2. The method of claim 1, wherein the compound has a structure represented by a formula:

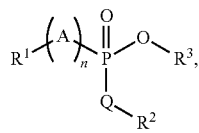

wherein n is 0 or 1;
wherein A is selected from O, S, and CHR$^{21}$;
  wherein R$^{21}$, when present, is selected from hydrogen and methyl;
wherein Q is selected from O, S, and NR$^{22}$;
  wherein R$^{22}$, when present, is selected from hydrogen and C1-C8 alkyl;
wherein R$^1$ is selected from —(C1-C4 alkyl)Ar$^1$ and Ar$^1$;
  wherein Ar$^1$, when present, is selected from aryl and heteroaryl and is substituted with 0, 1, 2, or 3 groups independently selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO$_2$R$^{30}$, —CO$_2$R$^{30}$, —(C1-C4 alkyl)CO$_2$R$^{30}$, —(C2-C4 alkenyl)CO$_2$R$^{30}$, —(C=O)(C1-C4 alkyl), —(S=O)(C1-C4 alkyl), —SO$_2$(C1-C4 alkyl), —(C=O)NR$^{31a}$R$^{31b}$, —SO$_2$NR$^{31a}$R$^{31b}$, —O(C=O)NR$^{31a}$R$^{31b}$, —NHSO$_2$NR$^{31a}$R$^{31b}$, —NH(C=O)NR$^{31a}$R$^{31b}$, and —N=NR$^{32}$;
    wherein R$^{30}$, when present, is selected from hydrogen, C1-C8 alkyl, —(C1-C4 alkyl)phenyl, phenyl, and a structure represented by a formula:

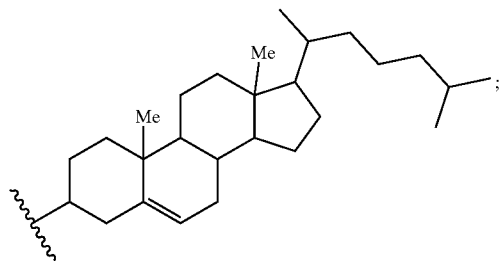 [SMILES: *C1CCC2(C)C(=CCC3C2CCC2(C)C(C(C)CCCC(C)C)CCC32)C1]

wherein each of R$^{31a}$ and R$^{31b}$, when present, is independently selected from hydrogen, C1-C8 alkyl, —(C1-C4 alkyl)phenyl, and phenyl;
    wherein R$^{32}$, when present, is selected from hydrogen, C1-C4 alkyl, and phenyl;
wherein R$^2$ is selected from —(C1-C4 alkyl)Ar$^2$ and Ar$^2$;
  wherein Ar$^2$, when present, is selected from aryl and heteroaryl and is substituted with 0, 1, 2, or 3 groups independently selected from halogen, —NO$_2$, —CN, —OH, —SH, —NH$_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO$_2$R$^{33}$, —CO$_2$R$^{33}$, —(C1-C4 alkyl)CO$_2$R$^{33}$, —(C2-C4 alkenyl)CO$_2$R$^{33}$, —(C=O)(C1-C4 alkyl), —(S=O)(C1-C4 alkyl), —SO$_2$(C1-C4 alkyl), —(C=O)NR$^{34a}$R$^{34b}$, —SO$_2$NR$^{34a}$R$^{34b}$, —O(C=O)NR$^{34a}$R$^{3th}$, —NHSO$_2$NR$^{34a}$R$^{34b}$, —NH(C=O)NR$^{34a}$R$^{34b}$, and —N=NR$^{35}$;
    wherein R$^{33}$, when present, is selected from hydrogen, C1-C8 alkyl, —(C1-C4 alkyl)phenyl, phenyl, and a structure represented by a formula:

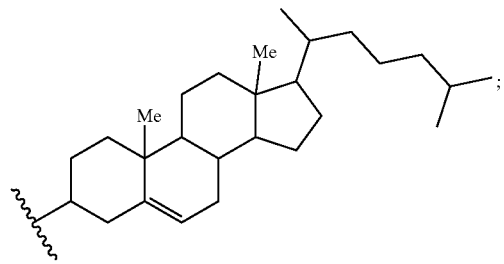 [SMILES: *C1CCC2(C)C(=CCC3C2CCC2(C)C(C(C)CCCC(C)C)CCC32)C1]

wherein each of R$^{34a}$ and R$^{34b}$, when present, is independently selected from hydrogen, C1-C8 alkyl, —(C1-C4 alkyl)phenyl, and phenyl;
    wherein R$^{35}$, when present, is selected from hydrogen, C1-C4 alkyl, and phenyl; and
wherein R$^3$ is C1-C4 alkyl.

3. The method of claim 1, wherein the compound is selected from:

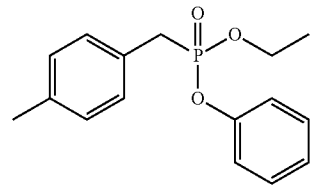

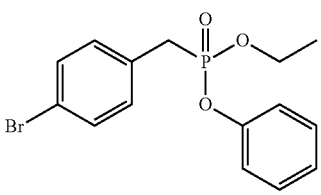

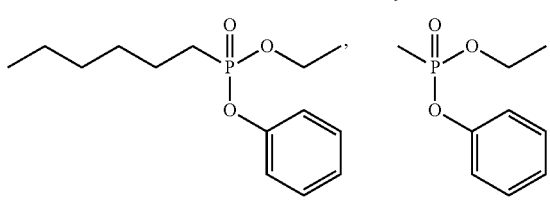

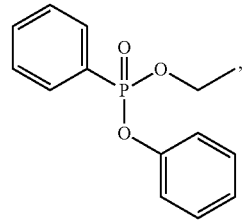

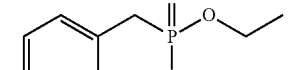
4. The method of claim 1, wherein the compound is selected from:
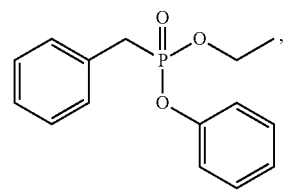
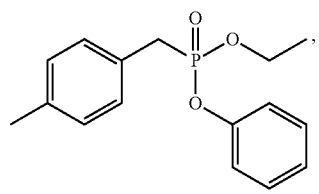
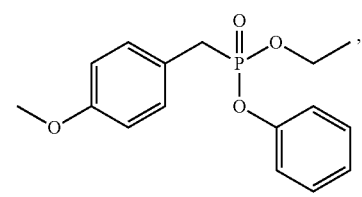
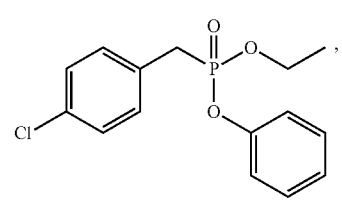
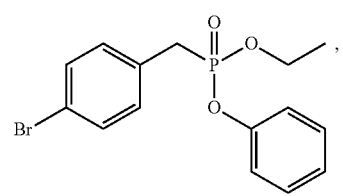
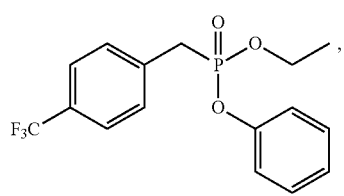

-continued
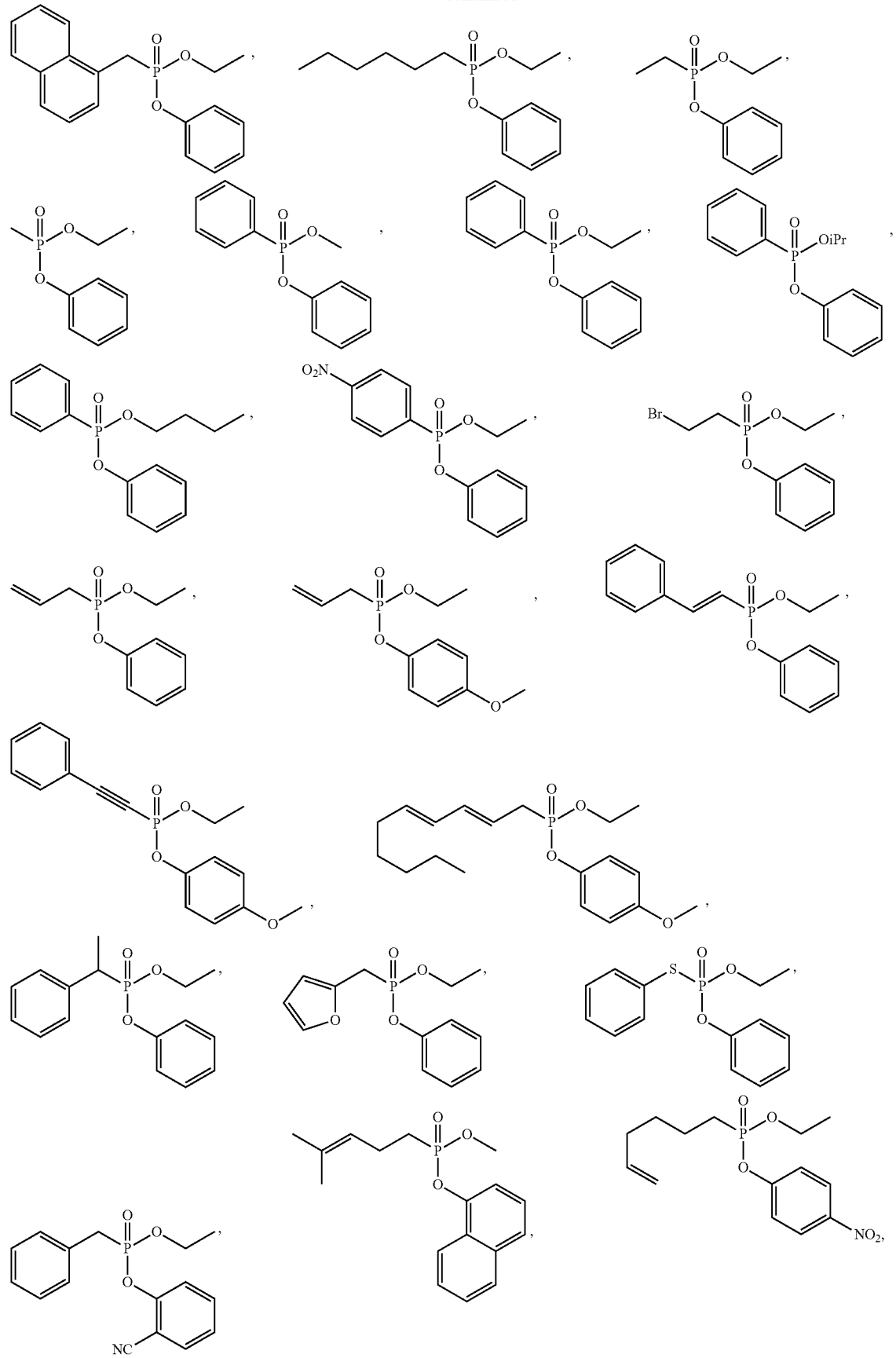

205
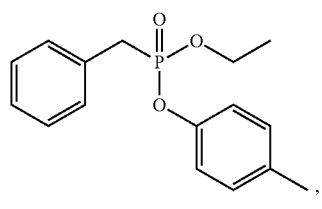
,
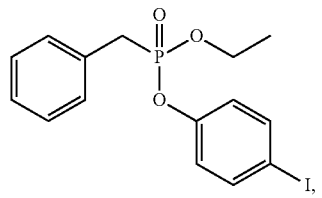
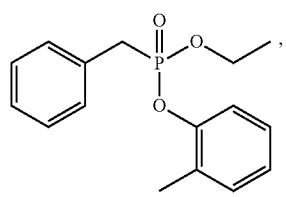
,
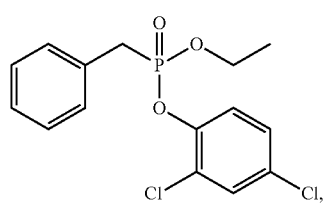
,
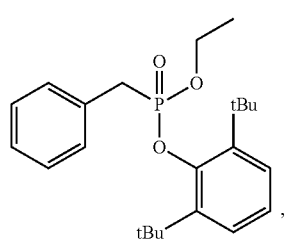
,
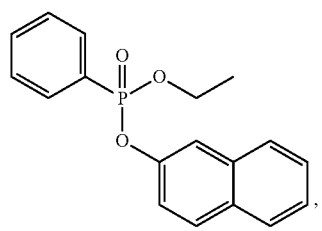
,
-continued
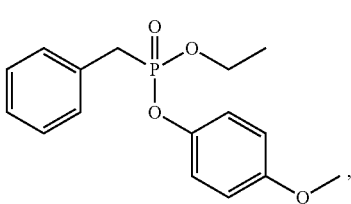
,
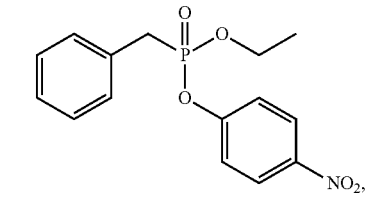
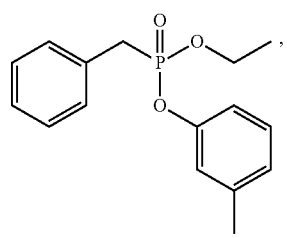
,
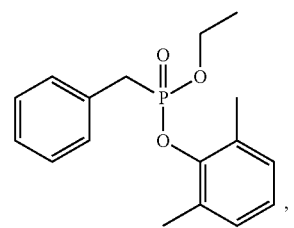
,
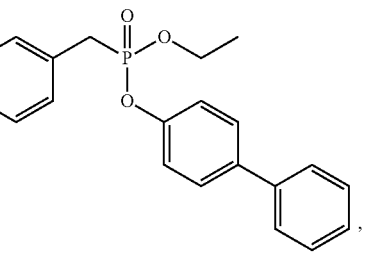
,
206
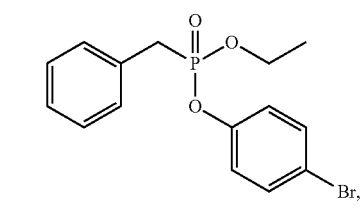
,
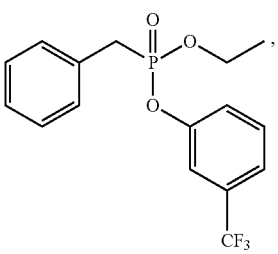
,
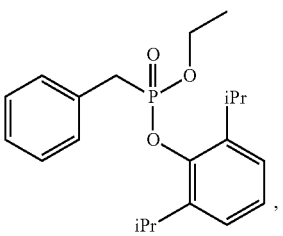
,
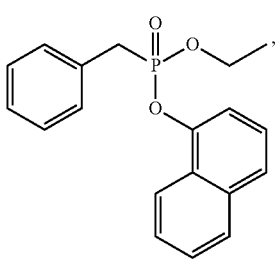
,
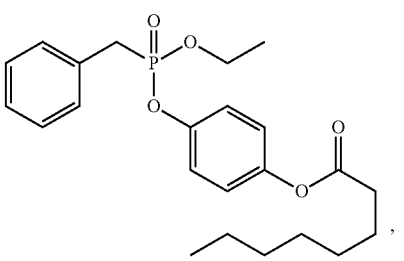
, -continued
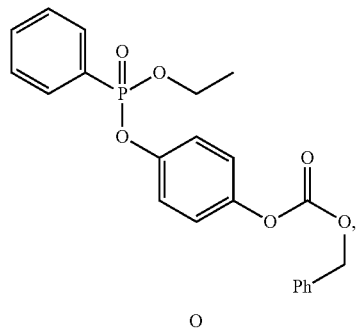
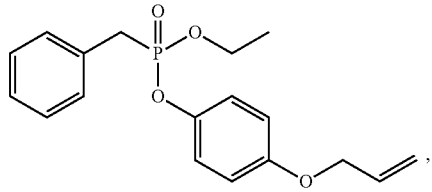
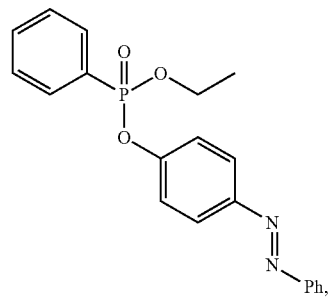
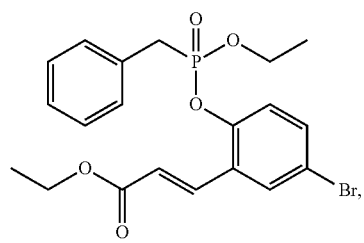
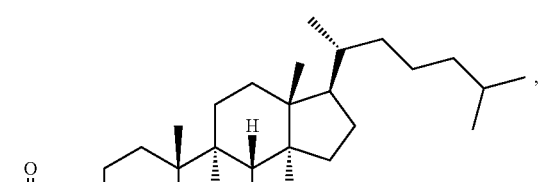
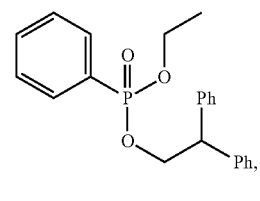
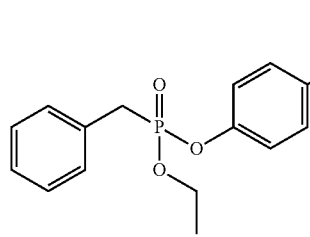
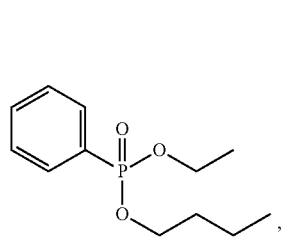
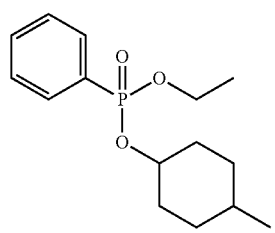
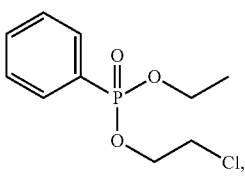
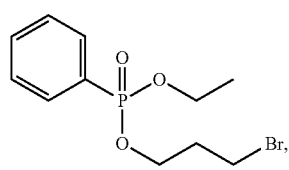
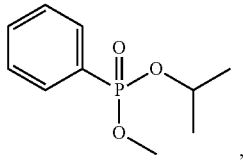
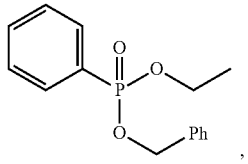

-continued
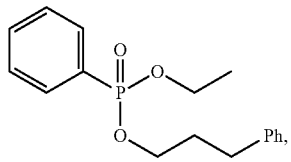
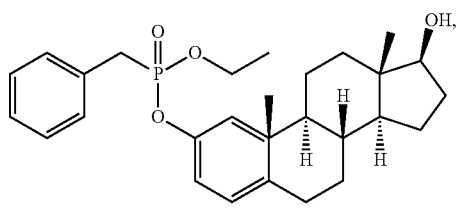
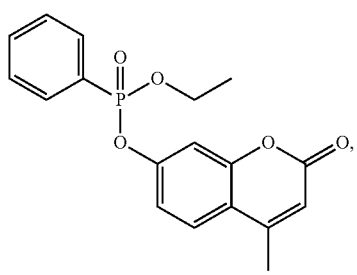
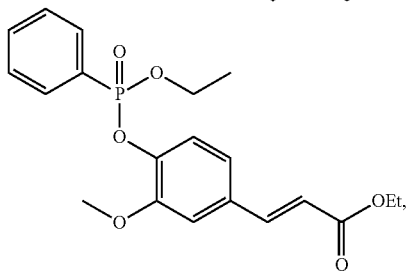
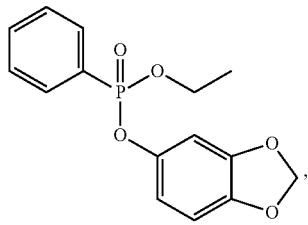
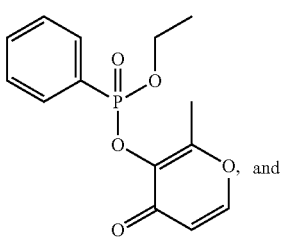 and
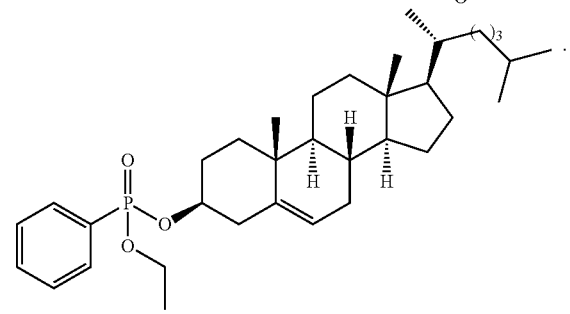
5. The method of claim 1, wherein the compound is selected from:
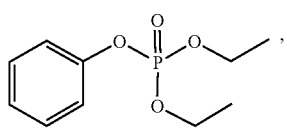, 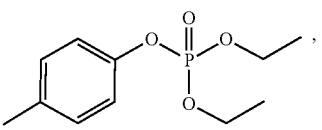, 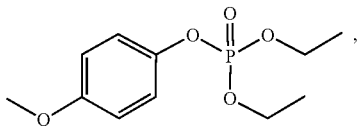,
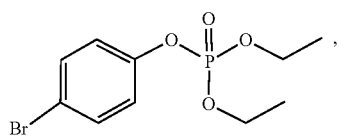, 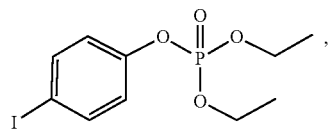, 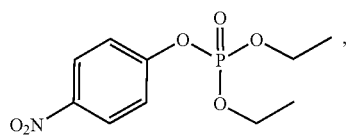,

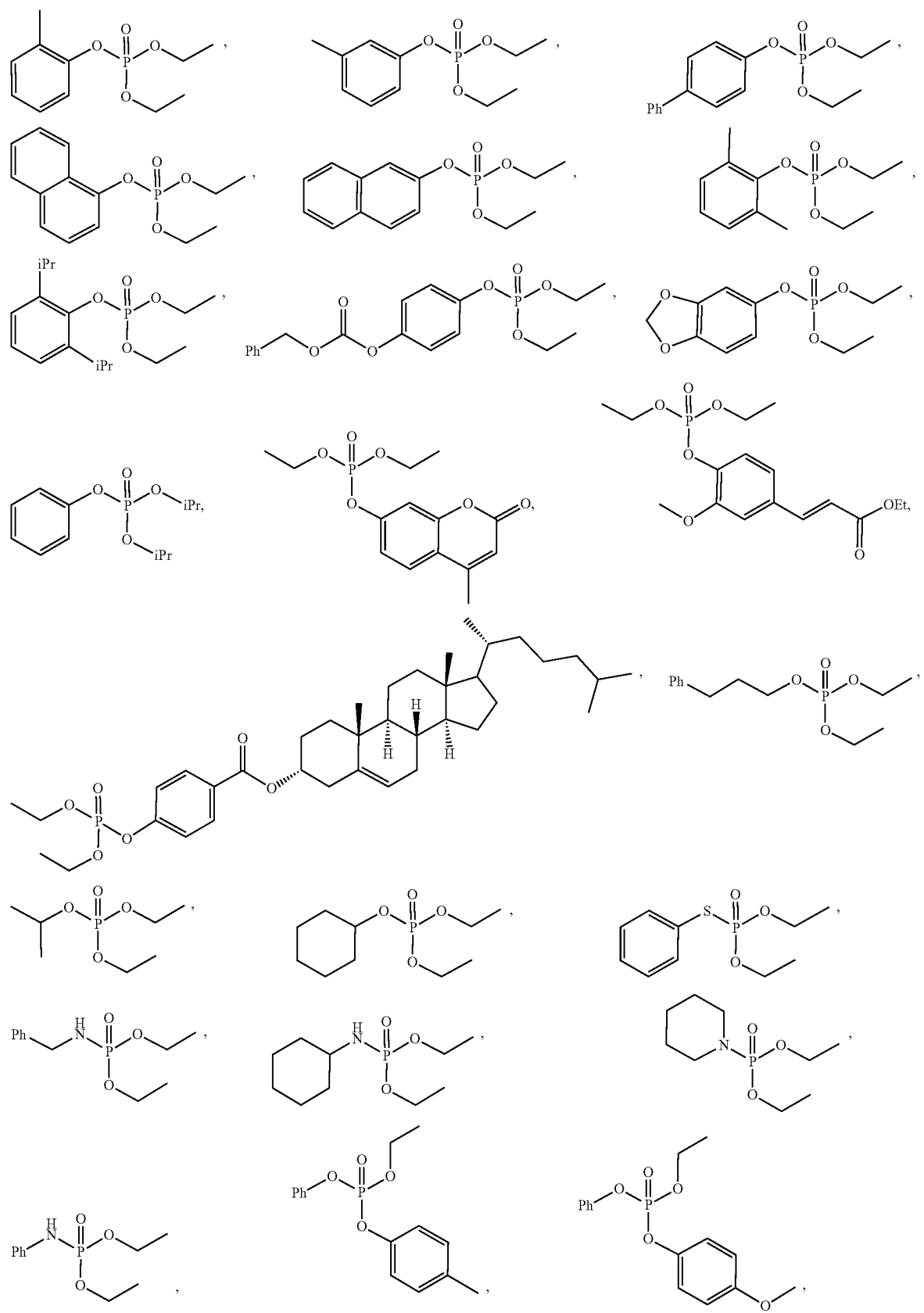

213
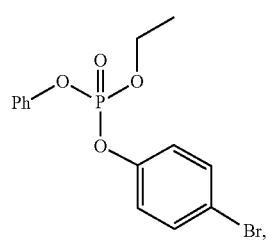
-continued
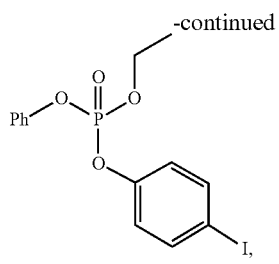
214
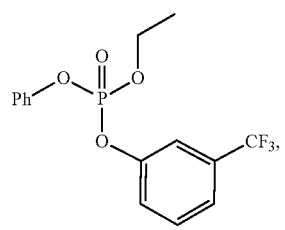
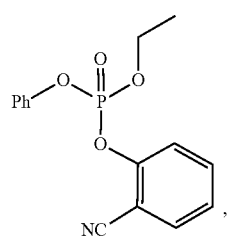
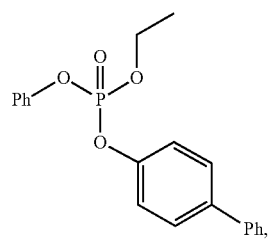
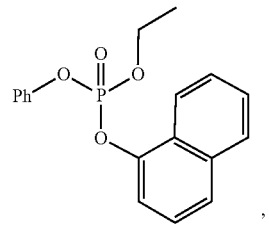
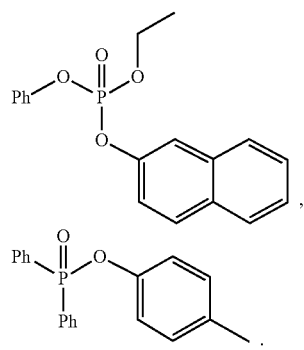
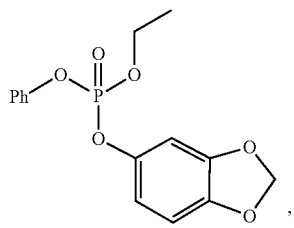
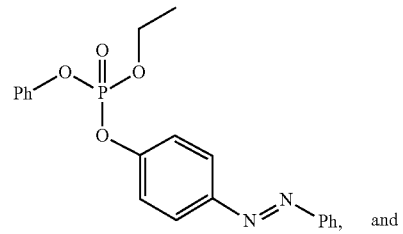 and
6. The method of claim 1, wherein the compound is selected from:
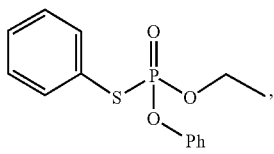
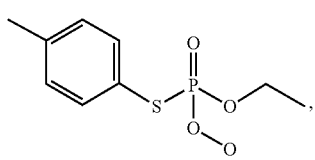
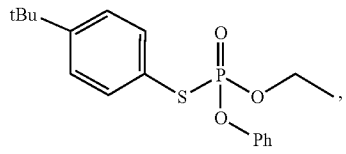
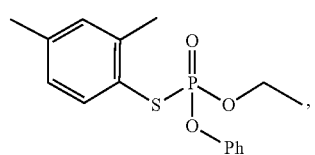
-continued
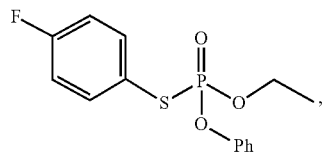
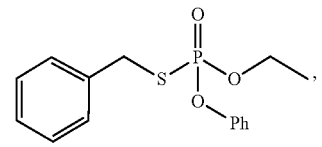
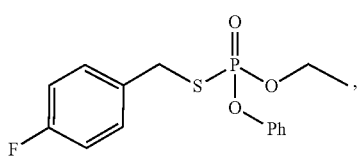
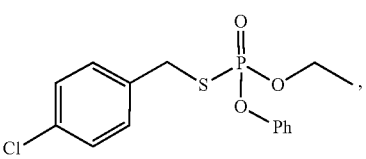

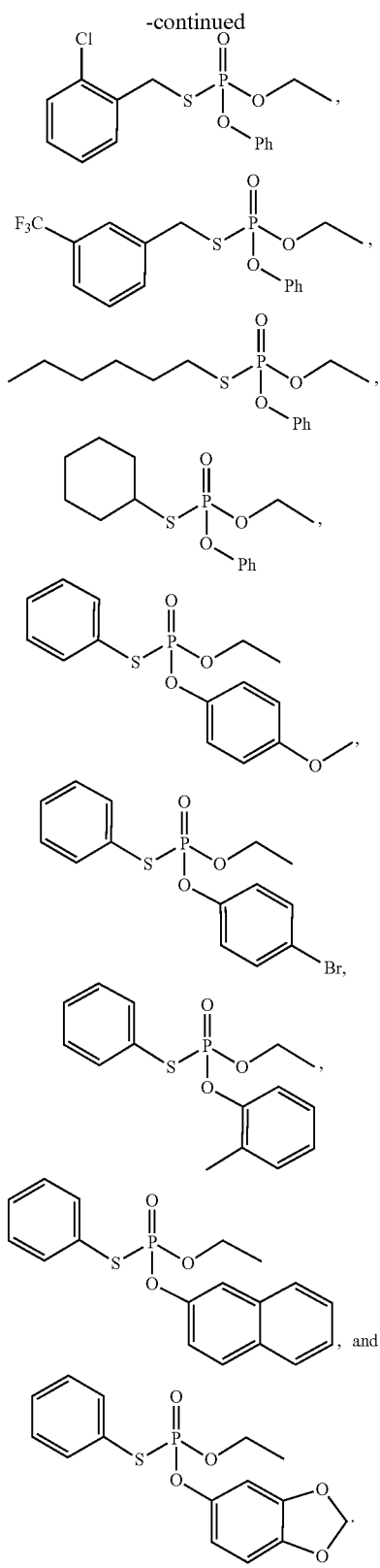

7. The method of claim 1, wherein the activating agent is triflic anhydride.

8. The method of claim 1, wherein the base is pyridine.

9. A method of making a compound having a structure represented by a formula:

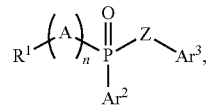

wherein n is 0 or 1;

wherein A is selected from O, S, $NR^{20}$, and $CHR^{21}$;

wherein $R^{20}$, when present, is selected from hydrogen and methyl;

wherein $R^{21}$, when present, is selected from hydrogen and methyl;

wherein Z is selected from O, S, and $NR^{23}$;

wherein $R^{23}$, when present, is selected from hydrogen and methyl;

wherein $R^1$ is selected from C1-C8 alkyl, C2-C10 alkenyl, C1-C8 haloalkyl, C3-C6 cycloalkyl, —(C1-C4 alkyl)$Ar^1$, —(C2-C4 alkenyl)$Ar^1$, —(C2-C4 alkynyl)$Ar^1$, $Ar^1$, and a structure represented by a formula selected from:

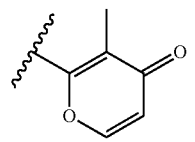

and

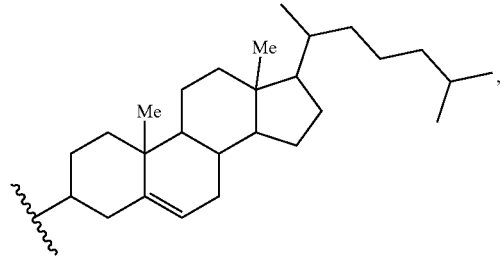

and wherein the C3-C6 cycloalkyl, when present, is substituted with 0 or 1 C1-C4 alkyl group;

wherein $Ar^1$, when present, is selected from aryl and heteroaryl and is substituted with 0, 1, 2, or 3 groups independently selected from halogen, —$NO_2$, —CN, —OH, —SH, —$NH_2$, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —$OCO_2R^{30}$, —$CO_2R^{30}$, —(C1-C4 alkyl)$CO_2R^{30}$, —(C2-C4 alkenyl)$CO_2R^{33}$, —(C=O)(C1-C4 alkyl), —(S=O)(C1-C4 alkyl), —$SO_2$(C1-C4 alkyl), —(C=O)$NR^{31a}R^{31b}$, —$SO_2NR^{31a}R^{31b}$, —O(C=O)$NR^{31a}R^{31b}$, —$NHSO_2NR^{31a}R^{31b}$, —NH(C=O)$NR^{31a}R^{31b}$, and —N=$NR^{32}$;

wherein $R^{30}$, when present, is selected from hydrogen, C1-C8 alkyl, —(C1-C4 alkyl)phenyl, phenyl, and a structure represented by a formula:

217

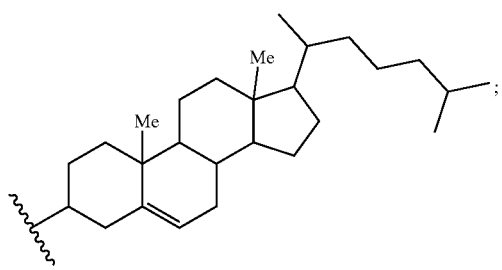 [SMILES: *C1CCC2(C)C(=CCC3C2CCC2(C)C(C(C)CCCC(C)C)CCC32)C1]

wherein each of R³¹ᵃ and R³¹ᵇ, when present, is independently selected from hydrogen, C1-C8 alkyl, —(C1-C4 alkyl)phenyl, and phenyl;

wherein R³², when present, is selected from hydrogen, C1-C4 alkyl, and phenyl;

or wherein each of R¹ and R²⁰, when present, are optionally covalently bonded together and, together with the intermediate carbon atoms, comprise a 3- to 6-membered heterocycloalkyl;

wherein Ar² is selected from aryl and heteroaryl and is substituted with 0, 1, 2, or 3 groups independently selected from halogen, —NO₂, —CN, —OH, —SH, —NH₂, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO₂R³³, —CO₂R³³, —(C1-C4 alkyl)CO₂R³³, —(C2-C4 alkenyl)CO₂R³³, —(C=O)(C1-C4 alkyl), —(S=O)(C1-C4 alkyl), —SO₂(C1-C4 alkyl), —(C=O)NR³⁴ᵃR³⁴ᵇ, —SO₂NR³⁴ᵃR³⁴ᵇ, —O(C=O)NR³⁴ᵃR³⁴ᵇ, —NHSO₂NR³⁴ᵃR³⁴ᵇ, —NH(C=O)NR³⁴ᵃR³⁴ᵇ, and —N=NR³⁵;

wherein R³³, when present, is selected from hydrogen, C1-C8 alkyl, —(C1-C4 alkyl)phenyl, phenyl, and a structure represented by a formula:

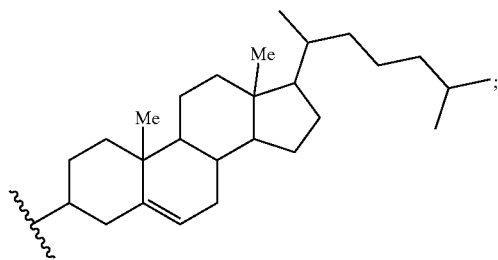 [SMILES: *C1CCC2(C)C(=CCC3C2CCC2(C)C(C(C)CCCC(C)C)CCC32)C1]

wherein each of R³⁴ᵃ and R³⁴ᵇ, when present, is independently selected from hydrogen, C1-C8 alkyl, —(C1-C4 alkyl)phenyl, and phenyl;

wherein R³⁵, when present, is selected from hydrogen, C1-C4 alkyl, and phenyl;

wherein Ar³ is selected from aryl and heteroaryl and is substituted with 0, 1, 2, or 3 groups independently selected from halogen, —NO₂, —CN, —OH, —SH, —NH₂, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl),

218

—OCO₂R³⁶, —CO₂R³⁶, —(C1-C4 alkyl)CO₂R³⁶, —(C2-C4 alkenyl)CO₂R³⁶, —(C=O)(C1-C4 alkyl), —(S=O)(C1-C4 alkyl), —SO₂(C1-C4 alkyl), —(C=O)NR³⁷ᵃR³⁷ᵇ, —SO₂NR³⁷ᵃR³⁷ᵇ, —O(C=O)NR³⁷ᵃR³⁷ᵇ, —NHSO₂NR³⁷ᵃR³⁷ᵇ, —NH(C=O)NR³⁷ᵃR³⁷ᵇ, and —N=NR³⁸;

wherein R³⁶, when present, is selected from hydrogen, C1-C8 alkyl, —(C1-C4 alkyl)phenyl, phenyl, and a structure represented by a formula:

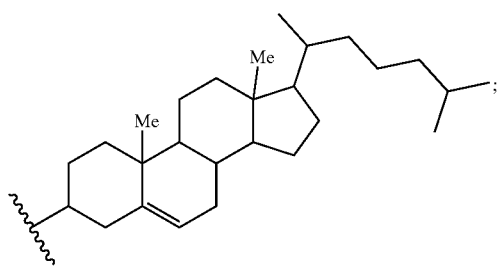 [SMILES: *C1CCC2(C)C(=CCC3C2CCC2(C)C(C(C)CCCC(C)C)CCC32)C1]

wherein each of R³⁷ᵃ and R³⁷ᵇ, when present, is independently selected from hydrogen, C1-C8 alkyl, —(C1-C4 alkyl)phenyl, and phenyl;

wherein R³⁸, when present, is selected from hydrogen, C1-C4 alkyl, and phenyl, or a salt thereof, the method comprising the step of reacting a phosphinate derivative having a structure represented by a formula:

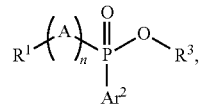

wherein R³ is C1-C4 alkyl, or a salt thereof, with a nucleophile having a structure represented by a formula:

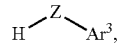

in the presence of an activating agent, wherein the activating agent is selected from triflic anhydride, mesyl chloride, tosyl chloride, oxalyl chloride, thionyl chloride, acetic anhydride, benzoic anhydride, and trifluoroacetic anhydride, and a base.

10. The method of claim 9, wherein the compound has a structure represented by a formula:

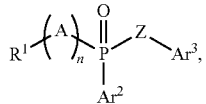

wherein n is 0 or 1;

wherein A is selected from O, S, and CHR²¹;
  wherein R²¹, when present, is selected from hydrogen and methyl;

wherein Z is selected from O, S, and NR²³;
  wherein R²³, when present, is selected from hydrogen and methyl;

wherein R¹ is selected from —(C1-C4 alkyl)Ar¹ and Ar¹;

wherein Ar², when present, is selected from aryl and heteroaryl and is substituted with 0, 1, 2, or 3 groups independently selected from halogen, —NO₂, —CN, —OH, —SH, —NH₂, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO₂R³⁰, —CO₂R³⁰, —(C1-C4 alkyl)CO₂R³⁰, —(C2-C4 alkenyl)CO₂R³³, —(C=O)(C1-C4 alkyl), —(S=O)(C1-C4 alkyl), —SO₂(C1-C4 alkyl), —(C=O)NR³¹ᵃR³¹ᵇ, —SO₂NR³¹ᵃR³¹ᵇ, —O(C=O)NR³¹ᵃR³¹ᵇ, —NHSO₂NR³¹ᵃR³¹ʰ, —NH(C=O)NR³¹ᵃR³¹ᵇ, and —N=NR³²;

wherein R³⁰, when present, is selected from hydrogen, C1-C8 alkyl, —(C1-C4 alkyl)phenyl, phenyl, and a structure represented by a formula:

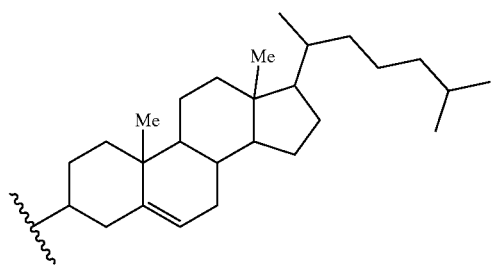

wherein each of R³¹ᵃ and R³¹ᵇ, when present, is independently selected from hydrogen, C1-C8 alkyl, —(C1-C4 alkyl)phenyl, and phenyl;

wherein R³², when present, is selected from hydrogen, C1-C4 alkyl, and phenyl;

wherein Ar², when present, is selected from aryl and heteroaryl and is substituted with 0, 1, 2, or 3 groups independently selected from halogen, —NO₂, —CN, —OH, —SH, —NH₂, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO₂R³³, —CO₂R³³, —(C1-C4 alkyl)CO₂R³³, —(C2-C4 alkenyl)CO₂R³³, —(C=O)(C1-C4 alkyl), —(S=O)(C1-C4 alkyl), —SO₂(C1-C4 alkyl), —(C=O)NR³⁴ᵃR³⁴ᵇ, —SO₂NR³⁴ᵃR³⁴ᵇ, —O(C=O)NR³⁴ᵃR³⁴ᵇ, —NHSO₂NR³⁴ᵃR³⁴ᵇ, —NH(C=O)NR³⁴ᵃR³⁴ᵇ, and —N=NR³⁵;

wherein R³³, when present, is selected from hydrogen, C1-C8 alkyl, —(C1-C4 alkyl)phenyl, phenyl, and a structure represented by a formula:

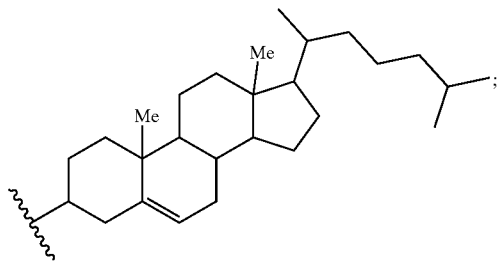 [SMILES: *C1CCC2(C)C(=CCC3C2CCC2(C)C(C(C)CCCC(C)C)CCC32)C1]

wherein each of R³⁴ᵃ and R³⁴ᵇ, when present, is independently selected from hydrogen, C1-C8 alkyl, —(C1-C4 alkyl)phenyl, and phenyl;

wherein R³⁵, when present, is selected from hydrogen, C1-C4 alkyl, and phenyl; and wherein Ar³ is selected from aryl and heteroaryl and is substituted with 0, 1, 2, or 3 groups independently selected from halogen, —NO₂, —CN, —OH, —SH, —NH₂, C1-C4 alkyl, C2-C4 alkenyl, C2-C4 alkynyl, C1-C4 haloalkyl, C1-C4 cyanoalkyl, C1-C4 hydroxyalkyl, C1-C4 haloalkoxy, C1-C4 alkoxy, C1-C4 thioalkyl, C1-C4 alkyl(C1-C4 alkoxy), C1-C4 aminoalkyl, C1-C4 alkylamino, (C1-C4)(C1-C4) dialkylamino, C3-C7 cycloalkyl, C6-C10 aryl, —O(C2-C4 alkenyl), —OCO₂R³⁶, —CO₂R³⁶, —(C1-C4 alkyl)CO₂R³⁶, —(C2-C4 alkenyl)CO₂R³⁶, —(C=O)(C1-C4 alkyl), —(S=O)(C1-C4 alkyl), —SO₂(C1-C4 alkyl), —(C=O)NR³⁷ᵃR³⁷ᵇ, —SO₂NR³⁷ᵃR³⁷ᵇ, —O(C=O)NR³⁷ᵃR³⁷ᵇ, —NHSO₂NR³⁷ᵃR³⁷ᵇ, —NH(C=O)NR³⁷ᵃR³⁷ᵇ, and —N=NR³⁸;

wherein R³⁶, when present, is selected from hydrogen, C1-C8 alkyl, —(C1-C4 alkyl)phenyl, phenyl, and a structure represented by a formula:

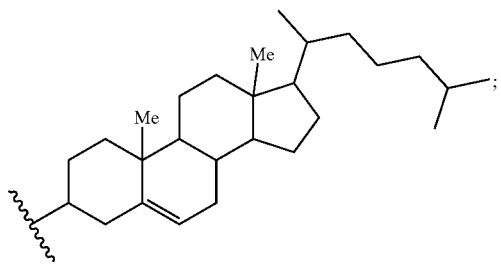 [SMILES: *C1CCC2(C)C(=CCC3C2CCC2(C)C(C(C)CCCC(C)C)CCC32)C1]

wherein each of R³⁷ᵃ and R³⁷ᵇ, when present, is independently selected from hydrogen, C1-C8 alkyl, —(C1-C4 alkyl)phenyl, and phenyl;

wherein R³⁸, when present, is selected from hydrogen, C1-C4 alkyl, and phenyl.

11. The method of claim 9, wherein the compound is:

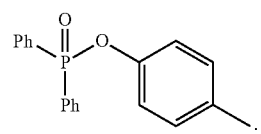

12. The method of claim 9, wherein the activating agent is triflic anhydride.

13. The method of claim 9, wherein the base is pyridine.

* * * * *